(12) United States Patent
Taveras et al.

(10) Patent No.: US 7,691,856 B2
(45) Date of Patent: Apr. 6, 2010

(54) THIADIAZOLEDIOXIDES AND THIADIAZOLEOXIDES AS CXC- AND CC-CHEMOKINE RECEPTOR LIGANDS

(75) Inventors: Arthur G. Taveras, Southborough, MA (US); Jianhua Chao, Pompton Lakes, NJ (US); Purakkattle J. Biju, Piscataway, NJ (US); Younong Yu, East Brunswick, NJ (US); Cynthia J. Aki, Livingston, NJ (US); J. Robert Merritt, Ewing, NJ (US); Ge Li, Shanghai (CN); John J. Baldwin, Gwynedd Valley, PA (US); Gaifa Lai, Monmouth Junction, NJ (US); Minglang Wu, Monmouth Junction, NJ (US); Evan A. Hecker, Austin, TX (US)

(73) Assignees: Schering Corporation, Kenilworth, NJ (US); Pharmacopeia, Inc., Cranbury, NJ (US)

( * ) Notice: Subject to any disclaimer, the term of this patent is extended or adjusted under 35 U.S.C. 154(b) by 92 days.

(21) Appl. No.: 11/651,128

(22) Filed: Jan. 9, 2007

(65) Prior Publication Data
US 2007/0264230 A1    Nov. 15, 2007

Related U.S. Application Data

(63) Continuation of application No. 10/680,393, filed on Oct. 7, 2003, now abandoned.

(60) Provisional application No. 60/417,371, filed on Oct. 9, 2002.

(51) Int. Cl.
*A61K 31/496* (2006.01)
*A61K 31/4453* (2006.01)
*A61K 31/5355* (2006.01)
*C07D 285/06* (2006.01)
*C07D 417/14* (2006.01)

(52) U.S. Cl. .............. 514/236.2; 514/254.03; 514/326; 544/134; 544/367; 546/209; 548/135

(58) Field of Classification Search .............. 514/236.2, 514/254.03, 326; 544/134, 367; 546/209; 548/135
See application file for complete search history.

(56) References Cited

U.S. PATENT DOCUMENTS

| 3,115,495 A | 12/1963 | Wright |
| 3,115,496 A | 12/1963 | Wright |
| 4,170,588 A | 10/1979 | Hegenberg et al. |
| 4,394,508 A | 7/1983 | Crenshaw et al. |
| 4,497,810 A | 2/1985 | Hoffman |
| 4,510,309 A | 4/1985 | Crenshaw et al. |
| 4,532,246 A | 7/1985 | Ife |
| 4,532,252 A | 7/1985 | Sach |
| 4,562,184 A | 12/1985 | Baldwin et al. |
| 4,607,106 A | 8/1986 | Ife |
| 4,639,523 A | 1/1987 | Nohara et al. |
| 4,640,926 A | 2/1987 | Sach |
| 4,659,725 A | 4/1987 | Ife |
| 4,663,331 A | 5/1987 | Brown et al. |
| 4,732,980 A | 3/1988 | Brown et al. |
| 4,863,936 A | 9/1989 | Sach |
| 5,206,252 A | 4/1993 | Butera et al. |
| 5,354,763 A | 10/1994 | Butera et al. |
| 5,397,790 A | 3/1995 | Butera et al. |
| 5,401,753 A | 3/1995 | Butera et al. |
| 5,403,853 A | 4/1995 | Butera et al. |
| 5,466,712 A | 11/1995 | Butera et al. |
| 5,494,925 A | 2/1996 | Court et al. |
| 5,506,252 A | 4/1996 | Butera et al. |
| 5,532,245 A | 7/1996 | Butera et al. |
| 5,550,139 A | 8/1996 | Groutas |
| 5,840,764 A | 11/1998 | Quagliato et al. |
| 5,958,957 A | 9/1999 | Andersen et al. |
| 5,972,978 A | 10/1999 | Andersen et al. |
| 6,063,800 A | 5/2000 | Andersen et al. |
| 6,080,770 A | 6/2000 | Andersen et al. |
| 6,300,325 B1 | 10/2001 | Widdowson et al. |

(Continued)

FOREIGN PATENT DOCUMENTS

DE          33 09 655 A1    9/1984

(Continued)

OTHER PUBLICATIONS esp@cenet Document, "1,2,5-Thiadiazole-1-oxides and 1,1-dioxides, process for their preparation and their use as medicaments" (for DE33 09 655 which is attached to said esp document).

(Continued)

*Primary Examiner*—Taofiq A Solola
(74) *Attorney, Agent, or Firm*—Henry C. Jeanette

(57) ABSTRACT

Disclosed are novel compounds of the formula:

(IA)

$$\underset{H \quad H}{\overset{(O)_g}{\underset{B\diagdown N \diagup \diagdown N \diagup A}{N=\overset{\Vert}{S}=N}}}$$

and the pharmaceutically acceptable salts and solvates thereof. Examples of groups comprising Substituent A include heteroaryl, aryl, heterocycloalkyl, cycloalkyl, aryl, alkynyl, alkenyl, aminoalkyl, alkyl or amino. Examples of groups comprising Substituent B include aryl and heteroaryl. Also disclosed is a method of treating a chemokine mediated diseases, such as, cancer, angiogenisis, angiogenic ocular diseases, pulmonary diseases, multiple sclerosis, rheumatoid arthritis, osteoarthritis, stroke and cardiac reperfusion injury, acute pain, acute and chronic inflammatory pain, and neuropathic pain using a compound of formula IA.

67 Claims, No Drawings

U.S. PATENT DOCUMENTS

| | | | |
|---|---|---|---|
| 6,376,555 | B1 | 4/2002 | Butera et al. |
| 6,420,396 | B1 | 7/2002 | Albers et al. |
| 6,878,709 | B2 | 4/2005 | Taveras et al. |
| 6,903,131 | B2 | 6/2005 | Taveras et al. |
| 7,132,445 | B2 | 11/2006 | Taveras et al. |
| 2001/0018447 | A1 | 8/2001 | Widdowson et al. |
| 2003/0204085 | A1 | 10/2003 | Taveras et al. |
| 2004/0034229 | A1 | 2/2004 | Taveras et al. |
| 2004/0053953 | A1 | 3/2004 | Taveras et al. |
| 2004/0186142 | A1 | 9/2004 | Taveras et al. |
| 2006/0025453 | A1 | 2/2006 | Taveras et al. |
| 2006/0223864 | A1 | 10/2006 | Biju et al. |

FOREIGN PATENT DOCUMENTS

| | | |
|---|---|---|
| EP | 0 040 696 A2 | 12/1981 |
| EP | 0 067 436 | 12/1982 |
| EP | 0 099 121 A2 | 1/1984 |
| EP | 0 275 997 A | 7/1988 |
| EP | 0 376 079 A | 7/1990 |
| EP | 0 796 243 B1 | 9/1997 |
| GB | 1186096 | 4/1970 |
| GB | 2124622 A | 2/1984 |
| GB | 2132190 A | 7/1984 |
| WO | WO 94/29277 | 12/1994 |
| WO | WO 95/14005 | 5/1995 |
| WO | WO 96/14300 | 5/1996 |
| WO | WO 96/15103 | 5/1996 |
| WO | WO 98/33763 | 8/1998 |
| WO | WO 00/20378 | 4/2000 |
| WO | WO 00/21927 A | 4/2000 |
| WO | WO 00/35855 | 6/2000 |
| WO | WO 00/35864 | 6/2000 |
| WO | WO 00/73260 A1 | 12/2000 |
| WO | WO 00/76501 | 12/2000 |
| WO | WO 01/28987 | 4/2001 |
| WO | WO 01/29000 A2 | 4/2001 |
| WO | WO 01/64208 A1 | 9/2001 |
| WO | WO 01/64691 A1 | 9/2001 |
| WO | WO 01/68569 A2 | 9/2001 |
| WO | WO 01/92202 A1 | 12/2001 |
| WO | WO 02/057230 | 7/2002 |
| WO | WO 02/067919 | 9/2002 |
| WO | WO 02/076926 A | 10/2002 |
| WO | WO 02/083624 A1 | 10/2002 |
| WO | WO 03/031440 A1 | 4/2003 |
| WO | WO 03/057676 A1 | 7/2003 |
| WO | WO 03/080053 A1 | 10/2003 |
| WO | WO 2004/033440 | 4/2004 |

OTHER PUBLICATIONS

Chemical Abstract 66:18527 for Maahs, Guenther, et al., "Syntheses and derivatives of squaric acid," *Angewandte Chemie* 78(20):927-31 (1966) (which is attached to said abstract).

Chemical Abstract 87:134383 for Augustin, Manfred, et al., "Disubstitution in 2,3-dichloromaleimides" *Zeitschrift Fuer Chemie* 17(6):215-216 (1977) (which is attached to said abstract).

Chemical Abstract No. 87:151727 for Ehrhardt, Heinz, et al., "Amides and thioamides of squaric acid: syntheses and reactions," *Chemische Berichte* 110(7):2506-23 (1977) (which is attached to said abstract).

Chemical Abstract 102:24633 for Stegelmeier, Hartmut, et al., "1, 2,5-Thiadiazole-1-oxide and 1,1 -dioxides and their use as pharmaceuticals" (for DE3309655 (reference AP)).

Chemical Abstract 104:129517 for Gruenefeld, Johann, at al., "Reactions of squaric acid with carbodiimides," *Archiv der Pharmazie* 318(12):1062-70 (1985) (which is attached to said abstract).

Chemical Abstract No. 122:160745 for Tillack, Annegret, at at., "Asymmetric catalysis. IV. Hydrosilylation of acetophenone with pyrroline-2,5-dione modified [Rh(COD)C1]2 catalyst," *Journal of Organometallic Chemistry* 482:85-91 (1994) (which is attached to said abstract).

Chemical Abstract No. 125:300482 for Chen, Yizhao, et al., "Reaction of dibutyl oxosquarate with aromatic primary amines," *Sichuan Daxue Xuebao, Ziran Kexueban* 33(2)182-186 (1996) (which is attached to said abstract).

Chemical Abstract No. 130:222994 for Chen, Yi-Zhao, et al., "Synthesis of asymmetric aryl-substituted amides of squaric acid and asymmetric isosquarylium amides," *Hechen Huaxue* 6(4):383-392 (1998) (which is attached to said abstract).

Chemical Abstract No. 383164-82-7 1,2,5-Oxadiazole-3, 4-diamine, N, N'—bias [3-(trifluoromethyl) phenyl].- (9CI), Chemical Libaray.

Chemcial Abstracts No. 2004:79464 For Wang, et al., Synthesis of N,N'—bias(3-chlorophenyl)-3,4-diaminofurazan, Hanneng Cailiao (2003), 11(4), 213-214, 218.

Butera, John A., et al., "Design and SAR of Novel Potassium Channel Openers Targeted for Urge Urinary Incontinence, 1. N-Cyanoguanidine Bioisosteres Possessing in Vivo Bladder Selectivity," *J. Med. Chem.* 43:1187-1202 (2000).

Coburn, Michael, D., "Picrylamino-substituted Heterocycles, II. Furazans (1,2)", *Journal of Heterocyclic Chemistry*, 5(1): 83-87 (1968).

Davis, Peter D., et al., "Inhibitors of protein kinase C 1. 2,3-Bisarylmaleimides," *J. Med. Chem.* 35:177-184 (1992).

Hanaineh-Abdelnour, Leila, et al., "Some synthetic applications of 2,3-Dichloro-N-phenylmaleimide: A Novel Synthesis of 2-Phenylpyrrolo[3,4-b]quinoxaline-1,3-diones. I," *Tetrahedron* 55:11859-11870 (1999).

Hoffman, Jacob M., et al., "Conformational Requirements of Histamine $H_2$-Receptor Inhibitors: Structure-Activity Study of Phenylene Analogues Related to Cimetidine and Tiotidine," *Journal of Medicinal Chemistry* 26(2):140-44 (1983).

Karady, Sandor, at al., "1,2,5-Thiadiazole-1-Oxides.I.Synthesis and Reactions of Alkoxy and Alkythio Analogs," *Heterocycles* 16(9):1561-4 (1981).

Martinez, Ana, et al., "Synthesis of Nonsymmetrically 3,4-Disubstituted 1,2,5-Thiadiazole Dioxides," *Journal of Heterocyclic Chemistry* 35(2):297-300 (1998).

Neuse, Eberhard W., et al., "Poly(squaryl amides)" *Polymer* 15:339-45 (1974).

Patent Abstracts of Japan, vol. 018, No. 361 (c-1222), Jul. 7, 1994 and JP 06 092915A, Apr. 5, 1994 abstract.

Schostarez, Heinrich J., et al., "Cyanoguanidine Bioisosteres in Potassium Channel Openers: evaluation of 3,4-Disubstituted-1,2,5-Thiadiazole-1-Oxides," *Bioorganic & Medicinal Chemistry Letters* 6(18):2187-92 (1996).

Sorba, et al., "Potential Histamine $H_2$-Receptor Antagonists Synthesis, structure and activity of a few open models related to classical $H_2$-antagonists", Drug Research 39(9): 1092-1096 (1989).

Wen, Richard Y., et al., "The Chemistry of 1,2,5-Thiadiazoles. II. 3,4-Disubstituted Derivatives of 1,2,5-Thiadiazole 1,1-Dioxide," *J. Org. Chem.* 40(19):2743-8 (1975).

Zhou, Hai-Bing, et al., "Design, synthesis and structure of new chiral squaric acid monoaminoalcohols and diaminoalcohols and their use as catalysts in asymmetric reduction of ketones and diketones," *Tetrahedron* 57:9325-9333 (2001).

THIADIAZOLEDIOXIDES AND
THIADIAZOLEOXIDES AS CXC- AND
CC-CHEMOKINE RECEPTOR LIGANDS

REFERENCE TO RELATED APPLICATION APPLICATIONS

This Application is a continuation of U.S. application Ser. No. 10/680393 filed Oct. 7, 2003 now abandoned which in turn claims the benefit of U.S. Provisional Application Ser. No. 60/417,371 filed Oct. 9, 2002.

FIELD OF THE INVENTION

The present invention relates to novel substituted thiadiazoledioxide and thiadiazolemonooxide compounds, pharmaceutical compositions containing the compounds, and the use of the compounds and formulations in treating CXC and CC-chemokine-mediated diseases.

BACKGROUND OF THE INVENTION

Chemokines are chemotactic cytokines that are released by a wide variety of cells to attract macrophages, T-cells, eosinophils, basophils, neutrophils and endothelial cells to sites of inflammation and tumor growth. There are two main classes of chemokines, the CXC-chemokines and the CC-chemokines. The class depends on whether the first two cysteines are separated by a single amino acid (CXC-chemokines) or are adjacent (CC-chemokines). The CXC-chemokines include, but are not limited to, interleukin-8 (IL-8), neutrophil-activating protein-1 (NAP-1), neutrophil-activating protein-2 (NAP-2), GROα, GROβ, GROγ, ENA-78, GCP-2, IP-10, MIG and PF4. CC chemokines include, but are not limited to, RANTES, MIP-1α, MIP-2β, monocyte chemotactic protein-1 (MCP-1), MCP-2, MCP-3, CCL19, CCL21 and eotaxin. Individual members of the chemokine families are known to be bound by at least one chemokine receptor, with CXC-chemokines generally bound by members of the CXCR class of receptors, and CC-chemokines by members of the CCR class of receptors. For example, IL-8 is bound by the CXCR-1 and CXCR-2 receptors.

Since CXC-chemokines promote the accumulation and activation of neutrophils, these chemokines have been implicated in a wide range of acute and chronic inflammatory disorders including psoriasis and rheumatoid arthritis. Baggiolini et al., FEBS Lett. 307, 97 (1992); Miller et al., Crit. Rev. Immunol. 12, 17 (1992); Oppenheim et al., Annu. Fev. Immunol. 9, 617 (1991); Seitz et al., J. Clin. Invest. 87, 463 (1991); Miller et al., Am. Rev. Respir. Dis. 146, 427 (1992); Donnely et al., Lancet 341, 643 (1993).

ELRCXC chemokines including IL-8, GROα, GROβ, GROγ, NAP-2, and ENA-78 (Strieter et al. 1995 JBC 270 p. 27348-57) have also been implicated in the induction of tumor angiogenesis (new blood vessel growth). All of these chemokines are believed to exert their actions by binding to the 7 transmembrane G-protein coupled receptor CXCR2 (also known as IL-8RB), while IL-8 also binds CXCR1 (also known as IL-8RA). Thus, their angiogenic activity is due to their binding to and activation of CXCR2, and possible CXCR1 for IL-8, expressed on the surface of vascular endothelial cells (ECs) in surrounding vessels.

Many different types of tumors have been shown to produce ELRCXC chemokines and their production has been correlated with a more aggressive phenotype (Inoue et al. 2000 Clin Cancer Res 6 p. 2104-2119) and poor prognosis (Yoneda et. al. 1998 J Nat Cancer Inst 90 p. 447-454). Chemokines are potent chemotactic factors and the ELRCXC chemokines have been shown to induce EC chemotaxis. Thus, these chemokines probably induce chemotaxis of endothelial cells toward their site of production in the tumor. This may be a critical step in the induction of angiogenesis by the tumor. Inhibitors of CXCR2 or dual inhibitors of CXCR2 and CXCR1 will inhibit the angiogenic activity of the ELRCXC chemokines and therefore block the growth of the tumor. This anti-tumor activity has been demonstrated for antibodies to IL-8 (Arenberg et al. 1996 J Clin Invest 97 p. 2792-2802), ENA-78 (Arenberg et al. 1998 J Clin Invest 102 p. 465-72), and GROα (Haghnegahdar et al. J. Leukoc Biology 2000 67 p. 53-62).

Many tumor cells have also been shown to express CXCR2 and thus tumor cells may also stimulate their own growth when they secrete ELRCXC chemokines. Thus, along with decreasing angiogenesis, inhibitors of CXCR2 may directly inhibit the growth of tumor cells.

Hence, the CXC-chemokine receptors represent promising targets for the development of novel anti-inflammatory and anti-tumor agents.

There remains a need for compounds that are capable of modulating activity at CXC-chemokine receptors. For example, conditions associated with an increase in IL-8 production (which is responsible for chemotaxis of neutrophil and T-cell subsets into the inflammatory site and growth of tumors) would benefit by compounds that are inhibitors of IL-8 receptor binding.

SUMMARY OF THE INVENTION

This invention provides novel compounds of formula IA:

$$\text{(IA)}$$

and the pharmaceutically acceptable salts (e.g., sodium or calcium) and solvates thereof, wherein A and B are defined below.

This invention also provides a method of treating a chemokine mediated disease in a patient in need of such treatment comprising administering to said patient an effective amount of at least one compound (usually 1) of formula IA, or a pharmaceutically acceptable salt or solvate thereof.

This invention also provides a method of treating a CXCR1 and/or CXCR2 mediated disease in a patient in need of such treatment comprising administering to said patient an effective amount of at least one compound (usually 1) of formula IA, or a pharmaceutically acceptable salt or solvate thereof.

This invention also provides a method of treating a CCR7 mediated disease in a patient in need of such treatment comprising administering to said patient an effective amount of at least one compound (usually 1) of formula IA, or a pharmaceutically acceptable salt or solvate thereof.

This invention also provides a method of treating cancer in a patient in need of such treatment comprising administering to said patient an effective amount of at least one (usually 1) compound of formula IA, or a pharmaceutically acceptable salt or solvate thereof.

This invention also provides a method of treating Kaposi's sarcoma, melanoma, gastric carcinoma, and non-small cell carcinoma in a patient in need of such treatment comprising administering to said patient an effective amount of at least one (usually 1) compound of formula IA, or a pharmaceutically acceptable salt or solvate thereof.

This invention also provides a method of treating melanoma, gastric carcinoma, and non-small cell carcinoma in a patient in need of such treatment comprising administering to said patient an effective amount of at least one (usually 1) compound of formula IA, or a pharmaceutically acceptable salt or solvate thereof.

This invention also provides a method of treating cancer in a patient in need of such treatment comprising administering to said patient an effective amount of at least one (usually 1) compound of formula IA, or a pharmaceutically acceptable salt or solvate thereof, in combination with at least one anticancer agent selected from the group consisting of: (a) microtubule affecting agents, (b) antineoplastic agents, (c) anti-angiogenesis agents, or (d) VEGF receptor kinase inhibitors, (e) antibodies against the VEGF receptor, (f) interferon, and g) radiation. The compound of formula IA can be administered concurrently or sequentially with the anticancer agent.

This invention also provides a method of treating cancer in a patient in need of such treatment comprising administering to said patient at least one (usually 1) compound of formula IA, or a pharmaceutically acceptable salt or solvate thereof, in combination with at least one (usually 1) antineoplastic agent selected from the group consisting of: gemcitabine, paclitaxel (Taxol®), 5-Fluorourcil (5-FU), cyclophosphamide (Cytoxan®), temozolomide, and Vincristine.

This invention also provides a method of treating cancer in a patient in need of such treatment comprising administering to said patient an effective amount of at least one (usually 1) compound of formula IA, or a pharmaceutically acceptable salt or solvate thereof, concurrently or sequentially with microtubule affecting agent, e.g., paclitaxel.

This invention also provides a method treating cancer in a patient in need of such treatment comprising administering to said patient a therapeutically effective amount of: (a) at least one (usually 1) compound of formula IA, or a pharmaceutically acceptable salt or solvate thereof, concurrently or sequentially with (b) at least one (usually 1) agent selected from the group consisting of: (1) antineoplastic agents, (2) microtubule affecting agents, and (3) anti-angiogenesis agents.

This invention also provides a method of inhibiting angiogenesis in a patient in need of such treatment comprising administering to said patient an effective amount of at least one (usually 1) compound of formula IA, or a pharmaceutically acceptable salt or solvate thereof.

This invention also provides a method of treating angiogenic ocular disease (e.g., ocular inflammation, retinopathy of prematurity, diabetic retinopathy, macular degeneration with the wet type preferred and corneal neovascularization) in a patient in need of such treatment comprising administering to said patient an effective amount of at least one (usually 1) compound of formula IA, or a pharmaceutically acceptable salt or solvate thereof.

This invention also provides a method of treating a chemokine mediated (e.g., CXCR1 and/or CXCR2, or CCR7) disease or condition selected from the group consisting of: acute pain, acute inflammation, chronic inflammation, rheumatoid arthritis, acute inflammatory pain, chronic inflammatory pain, neuropathic pain, psoriasis, atopic dermatitis, asthma, COPD, adult respiratory disease, arthritis, inflammatory bowel disease, Crohn's disease, ulcerative colitis, septic shock, endotoxic shock, gram negative sepsis, toxic shock syndrome, stroke, cardiac reperfusion injury, renal reperfusion injury, glomerulonephritis, thrombosis, Alzheimer's disease, graft vs. host reaction (i.e., graft vs. host disease), allograft rejections (e.g., acute allograft rejection, and chronic allograft rejection), malaria, acute respiratory distress syndrome, delayed type hypersensitivity reaction, atherosclerosis, cerebral ischemia, cardiac ischemia, osteoarthritis, multiple sclerosis, restinosis, angiogenesis, osteoporosis, gingivitis, respiratory viruses, herpes viruses, hepatitis viruses, HIV, Kaposi's sarcoma associated virus (i.e., Kaposi's sarcoma), meningitis, cystic fibrosis, pre-term labor, cough, pruritis, multi-organ dysfunction, trauma, strains, sprains, contusions, psoriatic arthritis, herpes, encephalitis, CNS vasculitis, traumatic brain injury, CNS tumors, subarachnoid hemorrhage, post surgical trauma, interstitial pneumonitis, hypersensitivity, crystal induced arthritis, acute pancreatitis, chronic pancreatitis, acute alcoholic hepatitis, necrotizing enterocolitis, chronic sinusitis, angiogenic ocular disease, ocular inflammation, retinopathy of prematurity, diabetic retinopathy, macular degeneration with the wet type preferred, corneal neovascularization, polymyositis, vasculitis, acne, gastric ulcers, duodenal ulcers, celiac disease, esophagitis, glossitis, airflow obstruction, airway hyperresponsiveness (i.e., airway hyperreactivity), bronchiectasis, bronchiolitis, bronchiolitis obliterans (i.e., bronchiolitis obliterans syndrome), chronic bronchitis, cor pulmonae, dyspnea, emphysema, hypercapnea, hyperinflation, hypoxemia, hyperoxia-induced inflammations, hypoxia, surgical lung volume reduction, pulmonary fibrosis, pulmonary hypertension, right ventricular hypertrophy, peritonitis associated with continuous ambulatory peritoneal dialysis (CAPD), granulocytic ehrlichiosis, sarcoidosis, small airway disease, ventilation-perfusion mismatching, wheeze, colds, gout, alcoholic liver disease, lupus, burn therapy (i.e., the treatment of burns), periodontitis, cancer, transplant reperfusion injury, early transplantation rejection (e.g., acute allograft rejection), airway hyperreactivity, allergic contact dermatitis, allergic rhinitis, alopecia areata, antiphospholipid syndromes, aplastic anemia, autoimmune deafness (including, for example, Meniere's disease), autoimmune hemolytic syndromes, autoimmune hepatitis, autoimmune neuropathy, autoimmune ovarian failure, autoimmune orchitis, autoimmune thrombocytopenia, bullous pemphigoid, chronic allograft vasculopathy, chronic inflammatory demyelinating polyneuropathy, cirrhosis, cor pneumoniae, cryoglobulinemia, dermatomyositis, diabetes, drug-induced autoimmunity, epidermolysis bullosa acquisita, endometriosis, fibrotic diseases, gastritis, Goodpasture's syndrome, Graves' disease, Gullain-Barre disease, Hashimoto's thyroiditis, hepatitis-associated autoimmunity, HIV-related autoimmune syndromes and hematologic disorders, hypophytis, idiopathic thrombocytic pupura, interstitial cystitis, juvenile arthritis, Langerhans' cell histiocytitis, lichen planus, metal-induced autoimmunity, myasthenia gravis, myelodysplastic syndromes, myocarditis (including viral myocarditis), myositis, Neuropathies (including, for example, IgA neuropathy, membranous neuropathy and idiopathic neuropathy), nephritic syndrome, optic neuritis, pancreatitis, paroxysmal nocturnal hemoglobulinemia, pemphigus, polymyalgia, post-infectious autoimmunity, primary biliary cirrhosis, reactive arthritis, ankylosing spondylitis, Raynaud's phenomenon, Reiter's syndrome, reperfusion injury, scleritis, scleroderma, secondary hematologic manifestation of autoimmune diseases (such as, for example, anemias), silicone implant associated autoimmune disease, Sjogren's syndrome, systemic lupus erythematosus, thrombocytopenia, transverse myelitis, tubulointerstitial nephritis, uveitis, vasculitis syndromes (such as, for example, giant cell arteritis, Behcet's disease and Wegener's granulomatosis), and Vitiligo in a patient in need of such treatment comprising administering to said patient an effective amount of at least one compound (usually 1) of formula IA, or a pharmaceutically acceptable salt or solvate thereof.

This invention also provides a method of treating a CXCR1 and/or a CXCR2 mediated disease or condition selected from the group consisting of: acute pain, acute inflammation, chronic inflammation, rheumatoid arthritis, acute inflammatory pain, chronic inflammatory pain, neuropathic pain, psoriasis, atopic dermatitis, asthma, COPD, adult respiratory disease, arthritis, inflammatory bowel disease, Crohn's disease, ulcerative colitis, septic shock, endotoxic shock, gram negative sepsis, toxic shock syndrome, stroke, cardiac reperfusion injury, renal reperfusion injury, glomerulonephritis, thrombosis, Alzheimer's disease, graft vs. host reaction (i.e., graft vs. host disease), allograft rejections (e.g., acute allograft rejection, and chronic allograft rejection), malaria, acute respiratory distress syndrome, delayed type hypersensitivity reaction, atherosclerosis, cerebral ischemia, cardiac ischemia, osteoarthritis, multiple sclerosis, restinosis, angiogenesis, osteoporosis, gingivitis, respiratory viruses, herpes viruses, hepatitis viruses, HIV, Kaposi's sarcoma associated virus (i.e., Kaposi's sarcoma), meningitis, cystic fibrosis, preterm labor, cough, pruritus, multi-organ dysfunction, trauma, strains, sprains, contusions, psoriatic arthritis, herpes, encephalitis, CNS vasculitis, traumatic brain injury, CNS tumors, subarachnoid hemorrhage, post surgical trauma, interstitial pneumonitis, hypersensitivity, crystal induced arthritis, acute pancreatitis, chronic pancreatitis, acute alcoholic hepatitis, necrotizing enterocolitis, chronic sinusitis, angiogenic ocular disease, ocular inflammation, retinopathy of prematurity, diabetic retinopathy, macular degeneration with the wet type preferred, corneal neovascularization, polymyositis, vasculitis, acne, gastric ulcers, duodenal ulcers, celiac disease, esophagitis, glossitis, airflow obstruction, airway hyperresponsiveness (i.e., airway hyperreactivity), bronchiectasis, bronchiolitis, bronchiolitis obliterans, chronic bronchitis, cor pulmonae, dyspnea, emphysema, hypercapnea, hyperinflation, hypoxemia, hyperoxia-induced inflammations, hypoxia, surgical lung volume reduction, pulmonary fibrosis, pulmonary hypertension, right ventricular hypertrophy, peritonitis associated with continuous ambulatory peritoneal dialysis (CAPD), granulocytic ehrlichiosis, sarcoidosis, small airway disease, ventilation-perfusion mismatching, wheeze, colds, gout, alcoholic liver disease, lupus, burn therapy (i.e., the treatment of burns), periodontitis, cancer, transplant reperfusion injury, early transplantation rejection (e.g., acute allograft rejection) in a patient in need of such treatment comprising administering to said patient an effective amount of at least one compound (usually 1) of formula IA, or a pharmaceutically acceptable salt or solvate thereof.

This invention also provides a method of treating a CCR7 mediated disease or condition selected from the group consisting of: acute inflammation, chronic inflammation, acute inflammatory pain, acute pain, chronic inflammatory pain, neuropathic pain, acute allograft rejection, acute respiratory distress syndrome, adult respiratory disease, airway hyperreactivity, allergic contact dermatitis, allergic rhinitis, alopecia areata, alzheimer's disease, angiogenic ocular disease, antiphospholipid syndromes, aplastic anemia, asthma, atherosclerosis, atopic dermatitis, autoimmune deafness (including, for example, Meniere's disease), autoimmune hemolytic syndromes, autoimmune hepatitis, autoimmune neuropathy, autoimmune ovarian failure, autoimmune orchitis, autoimmune thrombocytopenia, bronchiolitis, bronchiolitis obliterans syndrome, bullous pemphigoid, burn therapy (i.e., the treatment of burns), cancer, cerebral ischemia, cardiac ischemia, chronic allograft rejection, chronic allograft vasculopathy, chronic bronchitis, chronic inflammatory demyelinating polyneuropathy, chronic sinusitis, cirrhosis, CNS vasculitis, COPD, Cor pneumoniae, Crohn's disease, cryoglobulinemia, crystal-induced arthritis, delayed-type hypersensitivity reactions, dermatomyositis, diabetes, diabetic retinopathy, drug-induced autoimmunity, dyspnea, emphysema, epidermolysis bullosa acquisita, endometriosis, fibrotic diseases, gastritis, glomerulonephritis, Goodpasture's syndrome, graft vs host disease, Graves' disease, Gullain-Barre disease, Hashimoto's thyroiditis, hepatitis-associated autoimmunity, HIV-related autoimmune syndromes and hematologic disorders, hyperoxia-induced inflammation, hypercapnea, hyperinflation, hypophytis, hypoxia, idiopathic thrombocytic pupura, inflammatory bowel diseases, interstitial cystitis, interstitial pneumonitis, juvenile arthritis, Langerhans' cell histiocytitis, lichen planus, metal-induced autoimmunity, multiple sclerosis, myasthenia gravis, myelodysplastic syndromes, myocarditis including viral myocarditis, myositis, neuropathies (including, for example, IgA neuropathy, membranous neuropathy and idiopathic neuropathy), nephritic syndrome, ocular inflammation, optic neuritis, osteoarthritis, pancreatitis, paroxysmal nocturnal hemoglobulinemia, pemphigus, polymyalgia, polymyositis, post-infectious autoimmunity, pulmonary fibrosis, primary biliary cirrhosis, psoriasis, pruritis, rheumatoid arthritis, reactive arthritis, ankylosing spondylitis, psoriatic arthritis, Raynaud's phenomenon, Reiter's syndrome, reperfusion injury, restenosis, sarcoidosis, scleritis, scleroderma, secondary hematologic manifestation of autoimmune diseases (such as, for example, anemias), silicone implant associated autoimmune disease, Sjogren's syndrome, systemic lupus erythematosus, thrombocytopenia, thrombosis, transverse myelitis, tubulointerstitial nephritis, ulcerative colitis, uveitis, vasculitis and vasculitis syndromes (such as, for example, giant cell arteritis, Behcet's disease and Wegener's granulomatosis), and vitiligo in a patient in need of such treatment comprising administering to said patient an effective amount of at least one compound (usually 1) of formula IA, or a pharmaceutically acceptable salt or solvate thereof.

This invention also provides a method of treating a chemokine (e.g., a CXC, or a CC chemokine) mediated disease in a patient in need of such treatment comprising administering to said patient at least one (usually 1) compound of formula IA, or a pharmaceutically acceptable salt or solvate thereof, in combination with at least one (usually 1) other medicament (e.g., a drug, agent or therapeutic) useful for the treatment of chemokine mediated diseases.

This invention also provides a method of treating a chemokine mediated disease in a patient in need of such treatment comprising administering to said patient at least one (usually 1) compound of formula IA, or a pharmaceutically acceptable salt or solvate thereof, in combination with at least one (usually 1) other medicament (e.g., a drug, agent or therapeutic) selected from the group consisting of:
 a) disease modifying antirheumatic drugs;
 b) nonsteroidal antiinflammatory drugs;
 c) COX-2 selective inhibitors;
 d) COX-1 inhibitors;
 e) immunosuppressives;
 f) steroids;
 g) biological response modifiers; and
 h) other anti-inflammatory agents or therapeutics useful for the treatment of chemokine mediated diseases.

This invention also provides a method of treating a pulmonary disease (e.g., COPD, asthma or cystic fibrosis) in a patient in need of such treatment comprising administering to said patient a therapeutically effective amount of at least one compound (usually 1) of formula IA, or a pharmaceutically acceptable salt or solvate thereof, in combination with at least one (usually 1) compound selected from the group consisting of: glucocorticoids, 5-lipoxygenase inhibitors, β-2 adrenoceptor agonists, muscarinic M1 antagonists, muscarinic M3 antagonists, muscarinic M2 agonists, NK3 antagonists, LTB4 antagonists, cysteinyl leukotriene antagonists, bronchodilators, PDE4 inhibitors, PDE inhibitors, elastase inhibitors, MMP inhibitors, phospholipase A2 inhibitors, phospholipase D inhibitors, histamine H1 antagonists, histamine H3 antagonists, dopamine agonists, adenosine A2 agonists, NK1 and NK2 antagonists, GABA-b agonists, nociceptin agonists, expectorants, mucolytic agents, decongestants, antioxidants, anti-IL-8 anti-bodies, anti-IL-5 antibodies, anti-IgE antibodies, anti-TNF antibodies, IL-10, adhesion molecule inhibitors, and growth hormones.

This invention also provides a method of treating multiple sclerosis in a patient in need of such treatment comprising administering to said patient, a therapeutically effective amount of at least one (usually 1) compound of formula IA, or a pharmaceutically acceptable salt or solvate thereof, in combination with at least one compound selected from the group consisting of glatiramer acetate, glucocorticoids, methotrexate, azothioprine, mitoxantrone, chemokine inhibitors, and CB2-selective inhibitors.

This invention also provides a method of treating multiple sclerosis in a patient in need of such treatment comprising administering to said patient a therapeutically effective amount of at least one (usually 1) compound of formula IA, or a pharmaceutically acceptable salt or solvate thereof, in combination with at least one compound selected from the group consisting of: methotrexate, cyclosporin, leflunimide, sulfasalazine, β-methasone, β-interferon, glatiramer acetate, prednisone, etonercept, and infliximab.

This invention also provides a method of treating rheumatoid arthritis in a patient in need of such treatment comprising administering to said patient a therapeutically effective amount of at least one (usually one) compound of formula IA, or a pharmaceutically acceptable salt or solvate thereof.

This invention also provides a method of treating rheumatoid arthritis in a patient in need of such treatment comprising administering to said patient a therapeutically effective amount of at least one (usually 1) compound of formula IA, or a pharmaceutically acceptable salt or solvate thereof, in combination with at least one compound selected from the group consisting of COX-2 inhibitors, COX inhibitors, immunosuppressives (e.g., methotrexate, cyclosporin, leflunimide and sulfasalazine), steroids (e.g., betamethasone, cortisone and dexamethasone), PDE IV inhibitors, anti-TNF-α compounds, MMP inhibitors, glucocorticoids, chemokine inhibitors, CB2-selective inhibitors, and other classes of compounds indicated for the treatment of rheumatoid arthritis.

This invention also provides a method of treating stroke and cardiac reperfusion injury in a patient in need of such treatment comprising administering to said patient a therapeutically effective amount of at least one compound (usually 1) of formula IA, or a pharmaceutically acceptable salt or solvate thereof, in combination with at least one compound selected from the group consisting of thrombolitics (e.g., tenecteplase, TPA, alteplase), antiplatelet agents (e.g., gpIIb/IIIa), antagonists (e.g., abciximab and eftiifbatide), anticoagulants (e.g., heparin), and other compounds indicated for the treatment of rheumatoid arthritis.

This invention also provides a method of treating stroke and cardiac reperfusion injury in a patient in need of such treatment comprising administering to said patient a therapeutically effective amount of at least one (usually 1) compound of formula IA, or a pharmaceutically acceptable salt or solvate thereof, in combination with at least one compound selected from the group consisting of tenecteplase, TPA, alteplase, abciximab, eftiifbatide, and heparin.

This invention also provides a method of treating psoriasis in a patient in need of such treatment comprising administering to said patient a therapeutically effective amount of at least one (usually 1) compound of formula IA, or a pharmaceutically acceptable salt or solvate thereof, in combination with at least one compound selected from the group consisting of immunosuppressives (e.g., methotrexate, cyclosporin, leflunimide and sulfasalazine), steroids (e.g., β-methasone) and anti-TNF-α compounds (e.g., etonercept and infliximab).

This invention also provides a method of treating COPD in a patient in need of such treatment comprising administering to said patient a therapeutically effective amount of at least one (usually one) compound of formula IA, or a pharmaceutically acceptable salt or solvate thereof.

This invention also provides a method of treating acute pain in a patient in need of such treatment comprising administering to said patient a therapeutically effective amount of at least one (usually one) compound of formula IA, or a pharmaceutically acceptable salt or solvate thereof.

This invention also provides a method of treating acute inflammatory pain in a patient in need of such treatment comprising administering to said patient a therapeutically effective amount of at least one (usually one) compound of formula IA, or a pharmaceutically acceptable salt or solvate thereof.

This invention also provides a method of treating chronic inflammatory pain in a patient in need of such treatment comprising administering to said patient a therapeutically effective amount of at least one (usually one) compound of formula IA, or a pharmaceutically acceptable salt or solvate thereof.

This invention also provides a method of treating neropathic pain in a patient in need of such treatment comprising administering to said patient a therapeutically effective amount of at least one (usually one) compound of formula IA, or a pharmaceutically acceptable salt or solvate thereof.

This invention also provides a method of treating arthritis in a patient in need of such treatment comprising administering to said patient a therapeutically effective amount of at least one (usually one) compound of formula IA, or a pharmaceutically acceptable salt or solvate thereof.

This invention also provides a method of treating osteoarthritis in a patient in need of such treatment comprising administering to said patient a therapeutically effective amount of at least one (usually one) compound of formula IA, or a pharmaceutically acceptable salt or solvate thereof.

This invention also provides a pharmaceutical composition comprising at least one (e.g., 1-3, usually 1) compound of formula IA, or a pharmaceutically acceptable salt or solvate thereof, and a pharmaceutically acceptable carrier.

This invention also provides a pharmaceutical composition comprising at least one (e.g., 1-3, usually 1) compound of formula IA, or a pharmaceutically acceptable salt or solvate thereof, and at least one (e.g., 1-3, usually 1) other agent, medicament, antibody and/or inhibitor disclosed above, and a pharmaceutically acceptable carrier.

DETAILED DESCRIPTION OF THE INVENTION

When any variable occurs more than one time in any moiety, its definition on each occurrence is independent of its definition at every other occurrence. Also, combinations of substituents and/or variables are permissible only if such combinations result in stable compounds.

Unless indicated otherwise, the following definitions apply throughout the present specification and claims. These definitions apply regardless of whether a term is used by itself or in combination with other terms. For example, the definition of "alkyl" also applies to the "alkyl" portion of "alkoxy".

"An effective amount" means a therapeutically acceptable amount (i.e., that amount which provides the desired therapeutic effective).

"At least one" means one or more (e.g., 1-3, 1-2, or 1).

"Bu" represents butyl.

"Bn" represents benzyl.

"Composition" includes a product comprising the specified ingredients in the specified amounts, as well as any product that results, directly or indirectly, from combination of the specified ingredients in the specified amounts.

"Et" represents ethyl.

"In combination with" as used to describe the administration of a compound of formula IA with other medicaments in the methods of treatment of this invention, means that the compounds of formula IA and the other medicaments are administered sequentially or concurrently in separate dosage forms, or are administered concurrently in the same dosage form.

"Mammal" includes a human being, and preferably means a human being.

"Patient" includes both human and other mammals, preferably human.

"Ph", as used in the structures herein, represents phenyl.

"Pr" represents propyl.

"Prodrug" represents compounds that are rapidly transformed in vivo to the parent compound of the above formula, for example, by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

"Alkyl" means a straight or branched saturated hydrocarbon chain having 1 to 20 carbon atoms, preferably 1 to 12 carbon atoms, more preferably 1 to 6 carbon atoms.

"Alkoxy" means an alkyl-O— group wherein alkyl is as defined above. Non-limiting examples of alkoxy groups include: methoxy, ethoxy, n-propoxy, iso-propoxy and n-butoxy. The bond to the parent moiety is through the ether oxygen.

"Alkenyl" means a straight or branched aliphatic hydrocarbon group having at least one carbon-carbon double bond, and 2 to 20 carbon atoms, preferably 2 to 12 carbon atoms, and more preferably 2 to 6 carbon atoms. Non-limiting examples of alkenyl groups include: ethenyl, propenyl, n-butenyl, 3-methylbut-2-enyl, n-pentenyl, octenyl and decenyl.

"Alkynyl" means a straight or branched aliphatic hydrocarbon group having at least one carbon-carbon triple bond, and 2 to 15 carbon atoms, preferably 2 to 12 carbon atoms, and more preferably 2 to 4 carbon atoms. Non-limiting examples of alkynyl groups include ethynyl, propynyl, 2-butynyl, 3-methylbutynyl, n-pentynyl, and decynyl.

"Aryl" means an aromatic monocyclic or multicyclic ring system, wherein at is least one ring is aromatic, comprising about 6 to about 14 carbon atoms, and preferably about 6 to about 10 carbon atoms. Non-limiting examples of suitable aryl groups include: phenyl, naphthyl, indenyl, tetrahydronaphthyl, indanyl, anthracenyl, and fluorenyl.

"Arylalkyl" means an aryl group, as defined above, bound to an alkyl group, as defined above, wherein the alkyl group is bound to the parent moiety. Non-limiting examples of suitable arylalkyl groups include benzyl, phenethyl and naphthleneylmethyl.

"Bn" represents benzyl.

"Cycloalkyl" means saturated carbocyclic rings having 3 to 10 (e.g., 3 to 7) carbon atoms, preferably 5 to 10 carbon atoms, and more preferably 5 to 7 carbon atoms, and having one to three rings. Non-limiting examples of cycloalkyl groups include: cyclopropyl, cyclopentyl, cyclohexyl, cycloheptyl, norbornyl, and adamantyl.

"Cycloalkylalkyl" means a cycloalkyl group bound to the parent moiety through an alkyl group. Non-limiting examples include: cyclopropylmethyl and cyclohexylmethyl.

"Cycloalkenyl" means a non-aromatic mono or multicyclic ring system comprising 3 to 10 carbon atoms, and preferably 5 to 10 carbon atoms, and having at least one carbon-carbon double bond. Preferred cycloalkenyl rings have 5 to 7 carbon atoms. Non-limiting examples of cycloalkyl groups include cyclopentenyl, cyclohexenyl, cycloheptenyl, and norbornenyl.

"Et" represents ethyl.

"Halo" means fluoro, chloro, bromo, or iodo groups. Preferred are fluoro, chloro or bromo, and more preferred are fluoro and chloro.

"Halogen" means fluorine, chlorine, bromine, or iodine. Preferred are fluorine, chlorine or bromine, and more preferred are fluorine and chlorine.

"Haloalkyl" means an alkyl group as defined above wherein one or more hydrogen atoms on the alkyl is replaced by a halo group defined above.

"Heterocyclyl" or "heterocyclic" or "heterocycloalkyl" means a non-aromatic saturated monocyclic or multicyclic ring system (i.e., a saturated carbocyclic ring or ring system) comprising 3 to 10 ring atoms (e.g., 3 to 7 ring atoms), preferably 5 to 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls have 5 to 6 ring atoms. The prefix aza, oxa or thia before the heterocyclyl root name means that at least a nitrogen, oxygen or sulfur atom, respectively, is present as a ring atom. The nitrogen or sulfur atom of the heterocyclyl can be optionally oxidized to the corresponding N-oxide, S-oxide or S,S-dioxide. Non-limiting examples of monocyclic heterocyclyl rings include: piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, and tetrahydrothiopyranyl.

The term heterocyclic acidic functional group is intended to include groups such as, pyrrole, imidazole, triazole, tetrazole, and the like.

"Heteroaryl" means an aromatic monocyclic or multicyclic ring system comprising 5 to 14 ring atoms, preferably 5 to 10 ring atoms, in which one or more of the ring atoms is an element other than carbon, for example nitrogen, oxygen or sulfur, alone or in combination. Preferred heteroaryls contain 5 to 6 ring atoms. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of heteroaryls include: pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, and benzothiazolyl.

"Heteroarylalkyl" means a heteroaryl group, as defined above, bound to an alkyl group, as defined above, where the bond to the parent moiety is through the alkyl group.

N-oxides can form on a tertiary nitrogen present in an R substituent, or on =N— in a heteroaryl ring substituent and are included in the compounds of formula IA.

As well known in the art, a bond drawn from a particular atom wherein no moiety is depicted at the terminal end of the bond indicates a methyl group bound through that bond to the atom. For example:

The compounds of this invention are represented by formula IA:

(IA)

and the pharmaceutically acceptable salts (e.g., sodium or calcium salt) and solvates thereof, wherein:

A is selected from the group consisting of:

(1)

-continued

-continued wherein the above rings of said A groups are substituted with 1 to 6 substituents each independently selected from the group consisting of: $R^9$ groups;

-continued wherein one or both of the above rings of said A groups are substituted with 1 to 6 substituents each independently selected from the group consisting of: R⁹ groups;

wherein the above phenyl rings of said A groups are substituted with 1 to 3 substituents each independently selected from the group consisting of: R⁹ groups; and (5)

B is selected from the group consisting of

-continued

[chemical structures shown]

n is 0 to 6;

p is 1 to 5;

X is O, $NR^{18}$, or S;

Z is 1 to 3;

$R^2$ is selected from the group consisting of: hydrogen, OH, —C(O)OH, —SH, —$SO_2NR^{13}R^{14}$, —NHC(O)$R^{13}$, —$NHSO_2NR^{13}R^{14}$, —$NHSO_2R^{13}$, —$NR^{13}R^{14}$, —C(O)$NR^{13}R^{14}$, —C(O)$NHOR^{13}$, —C(O)$NR^{13}OH$, —$S(O_2)OH$, —OC(O)$R^{13}$, an unsubstituted heterocyclic acidic functional group, and a substituted heterocyclic acidic functional group; wherein there are 1 to 6 substituents on said substituted heterocyclic acidic functional group each substituent being independently selected from the group consisting of: $R^9$ groups;

each $R^3$ and $R^4$ is independently selected from the group consisting of: hydrogen, cyano, halogen, alkyl, cycloalkyl substituted with 1 to 4 alkyl groups (preferably $C_1$ to $C_6$ alkyl groups) wherein each alkyl group is independently selected, unsubstituted cycloalkyl, alkoxy, —OH, —$CF_3$, —$OCF_3$, —$NO_2$, —C(O)$R^{13}$, —C(O)$OR^{13}$, —C(O)$NHR^{17}$, —C(O)$NR^{13}R^{14}$, —$SO_{(t)}NR^{13}R^{14}$, —$SO_{(t)}R^{13}$, —C(O)$NR^{13}OR^{14}$, unsubstituted or substituted aryl, unsubstituted or substituted heteroaryl,

[chemical structures shown]

wherein there are 1 to 6 substituents on said substituted aryl group and each substituent is independently selected from the group consisting of: $R^9$ groups; and wherein there are 1 to 6 substituents on said substituted heteroaryl group and each substituent is independently selected from the group consisting of: $R^9$ groups; or $R^3$ is and $R^4$ taken together with the carbons atoms to which they are bonded to in the phenyl B substituent

[chemical structure shown]

form a fused ring of the formula:

[chemical structures shown]

(preferably $Z^1$) wherein $Z^1$ or $Z^2$ is an unsubstituted or substituted saturated heterocyclic ring (preferably a 4 to 7 membered heterocyclic ring), said ring $Z^1$ or $Z^2$ optionally containing one additional heteroatom selected from the group consisting of: O, S and $NR^{18}$; wherein there are 1 to 3 substituents on said ring $Z^1$ or $Z^2$, and each substituent is independently selected from the group consisting of: alkyl, aryl, hydroxy, hydroxyalkyl, alkoxy, alkoxyalkyl, arylalkyl, fluoroalkyl, cycloalkyl, cycloalkylalkyl, heteroaryl, heteroarylalkyl, amino, —C(O)$OR^{15}$, —C(O)$NR^{15}R^{16}$, —$SO_tNR^{15}R^{16}$, —C(O)$R^{15}$, —$SO_2R^{15}$ provided that $R^{15}$ is not H, —NHC(O)$NR^{15}R^{16}$, —NHC(O)$OR^{15}$, halogen, and a heterocycloalkenyl group (i.e., a heterocyclic group that has at least one, and preferably one, double bond in a ring, e.g.,

[chemical structure shown]

examples of the fused ring moiety include, but are not limited to:

[chemical structure shown]

each $R^5$ and $R^6$ are the same or different and are independently selected from the group consisting of hydrogen, halogen, alkyl, alkoxy, —$CF_3$, —$OCF_3$, —$NO_2$, —C(O)$R^{13}$, —C(O)$OR^{13}$, —C(O)$NR^{13}R^{14}$, —$SO_{(t)}NR^{13}R^{14}$, —C(O)$NR^{13}OR^{14}$, cyano, unsubstituted or substituted aryl, and unsubstituted or substituted heteroaryl group; wherein there are 1 to 6 substituents on said substituted aryl group and each substituent is independently selected from the group consisting of: $R^9$ groups; and wherein there are 1 to 6 substituents on said substituted heteroaryl group and each substituent is independently selected from the group consisting of: $R^9$ groups;

each $R^7$ and $R^8$ is independently selected from the group consisting of: H, unsubstituted or substituted alkyl, unsubstituted or substituted aryl, unsubstituted or substituted heteroaryl, unsubstituted or substituted arylalkyl, unsubstituted or substituted heteroarylalkyl, unsubstituted or substituted cycloalkyl, unsubstituted or substituted cycloalkylalkyl, —$CO_2R^{13}$, —$CONR^{13}R^{14}$, alkynyl, alkenyl, and cycloalkenyl; and wherein there are one or more (e.g., 1 to 6) substituents on said substituted $R^7$ and $R^8$ groups, wherein each substitutent is independently selected from the group consisting of:

a) halogen,
b) —$CF_3$,
c) —$COR^{13}$,
d) —$OR^{13}$,
e) —$NR^{13}R^{14}$,
f) —$NO_2$,
g) —CN,
h) —$SO_2OR^{13}$,
i) —$Si(alkyl)_3$, wherein each alkyl is independently selected,
j) —$Si(aryl)_3$, wherein each alkyl is independently selected,
k) —$(R^{13})_2R^{14}Si$, wherein each $R^{13}$ is independently selected,
l) —$CO_2R^{13}$,
m) —$C(O)NR^{13}R^{14}$,
n) —$SO_2NR^{13}R^{14}$,
o) —$SO_2R^{13}$,
p) —$OC(O)R^{13}$,
q) —$OC(O)NR^{13}R^{14}$,
r) —$NR^{13}C(O)R^{14}$, and
s) —$NR^{13}CO_2R^{14}$;

(fluoroalkyl is one non-limiting example of an alkyl group that is substituted with halogen);

$R^{8a}$ is selected from the group consisting of: hydrogen, alkyl, cycloalkyl and cycloalkylalkyl;

each $R^9$ is independently selected from the group consisting of:

a) —$R^{13}$,
b) halogen,
c) —$CF_3$,
d) —$COR^{13}$,
e) —$OR^{13}$,
f) —$NR^{13}R^{14}$,
g) —$NO_2$,
h) —CN,
i) —$SO_2R^{13}$,
j) —$SO_2NR^{13}R^{14}$,
k) —$NR^{13}COR^{14}$,
l) —$CONR^{13}R^{14}$,
m) —$NR^{13}CO_2R^{14}$,
n) —$CO_2R^{13}$,
o)

p) alkyl substituted with one or more (e.g., one) —OH groups (e.g., —$(CH_2)_qOH$, wherein q is 1-6, usually 1 to 2, and preferably 1), q) alkyl substituted with one or more (e.g., one) —$NR^{13}R^{14}$ group (e.g., —$(CH_2)_qNR^{13}R^{14}$, wherein q is 1-6, usually 1 to 2, and preferably 1), and r) —$N(R^{13})SO_2R^{14}$ (e.g., $R^{13}$ is H and $R^{14}$ is alkyl, such as methyl);

each $R^{10}$ and $R^{11}$ is independently selected from the group consisting of $R^{13}$, (e.g., hydrogen and alkyl (e.g., $C_1$ to $C_6$ alkyl, such as methyl)), halogen, —$CF_3$, —$OCF_3$, —$NR^{13}R^{14}$, —$NR^{13}C(O)NR^{13}R^{14}$, —OH, —$C(O)OR^{13}$, —SH, —$SO_{(t)}NR^{13}R^{14}$, —$SO_2R^{13}$, —$NHC(O)R^{13}$, —$NHSO_2NR^{13}R^{14}$, —$NHSO_2R^{13}$, —$C(O)NR^{13}R^{14}$, —$C(O)NR^{13}OR^{14}$, —$OC(O)R^{13}$ and cyano;

$R^{12}$ is selected from the group consisting of: hydrogen, —$C(O)OR^{13}$, unsubstituted or substituted aryl, unsubstituted or substituted heteroaryl, unsubstituted or substituted arylalkyl, unsubstituted or substituted cycloalkyl, unsubstituted or substituted alkyl, unsubstituted or substituted cycloalkylalkyl, and unsubstituted or substituted heteroarylalkyl group; wherein there are 1 to 6 substituents on the substituted $R^{12}$ groups and each substituent is independently selected from the group consisting of: $R^9$ groups;

each $R^{13}$ and $R^{14}$ is independently selected from the group consisting of: H, unsubstituted or substituted alkyl, unsubstituted or substituted aryl, unsubstituted or substituted heteroaryl, unsubstituted or substituted arylalkyl, unsubstituted or substituted heteroarylalkyl, unsubstituted or substituted cycloalkyl, unsubstituted or substituted cycloalkylalkyl, unsubstituted or substituted heterocyclic, unsubstituted or substituted fluoroalkyl, and unsubstituted or substituted heterocycloalkylalkyl (wherein "heterocyloalkyl" means heterocyclic); wherein there are 1 to 6 substituents on said substituted $R^{13}$ and $R^{14}$ groups and each substituent is independently selected from the group consisting of: alkyl, —$CF_3$, —OH, alkoxy, aryl, arylalkyl, fluoroalkyl, cycloalkyl, cycloalkylalkyl, heteroaryl, heteroarylalkyl, —$N(R^{40})_2$, —$C(O)OR^{15}$, —$C(O)NR^{15}R^{16}$, —$S(O)_tNR^{15}R^{16}$, —$C(O)R^{15}$, —$SO_2R^{15}$ provided that $R^{15}$ is not H, halogen, and —$NHC(O)NR^{15}R^{16}$; or $R^{13}$ and $R^{14}$ taken together with the nitrogen they are attached to in the groups —$C(O)NR^{13}R^{14}$ and —$SO_2NR^{13}R^{14}$ form an unsubstituted or substituted saturated heterocyclic ring (preferably a 3 to 7 membered heterocyclic ring), said ring optionally containing one additional heteroatom selected from the group consisting of: O, S and $NR^{18}$; wherein there are 1 to 3 substituents on the substituted cyclized $R^{13}$ and $R^{14}$ groups (i.e., there is 1 to 3 substituents on the ring formed when the $R^{13}$ and $R^{14}$ groups are taken together with the nitrogen to which they are bound) and each substituent is independently selected from the group consisting of: alkyl, aryl, hydroxy, hydroxyalkyl, alkoxy, alkoxyalkyl, arylalkyl, fluoroalkyl, cycloalkyl, cycloalkylalkyl, heteroaryl, heteroarylalkyl, amino, —$C(O)OR^{15}$, —$C(O)NR^{15}R^{16}$, —$SO_tNR^{15}R^{16}$, —$C(O)R^{15}$, —$SO_2R^{15}$ provided that $R^{15}$ is not H, —$NHC(O)NR^{15}R^{16}$, —$NHC(O)OR^{15}$, halogen, and a heterocycloalkenyl group (i.e., a heterocyclic group that has at least one, and preferably one, double bond in a ring, e.g., each $R^{15}$ and $R^{16}$ is independently selected from the group consisting of: H, alkyl, aryl, arylalkyl, cycloalkyl and heteroaryl;

$R^{17}$ is selected from the group consisting of: $-SO_2$alkyl, $-SO_2$aryl, $-SO_2$cycloalkyl, and $-SO_2$heteroaryl;

$R^{18}$ is selected from the group consisting of: H, alkyl, aryl, heteroaryl, $-C(O)R^{19}$, $-SO_2R^{19}$ and $-C(O)NR^{19}R^{20}$;

each $R^{19}$ and $R^{20}$ is independently selected from the group consisting of: alkyl, aryl and heteroaryl;

$R^{30}$ is selected from the group consisting of: alkyl, cycloalkyl, $-CN$, $-NO_2$, or $-SO_2R^{15}$ provided that $R^{15}$ is not H;

each $R^{31}$ is independently selected from the group consisting of: unsubstituted alkyl, unsubstituted or substituted aryl, unsubstituted or substituted heteroaryl and unsubstituted or substituted cycloalkyl; wherein there are 1 to 6 substituents on said substituted $R^{31}$ groups and each substituent is independently selected from the group consisting of: alkyl, halogen and $-CF_3$;

each $R^{40}$ is independently selected from the group consisting of: H, alkyl and cycloalkyl;

g is 1 or 2 (preferably 1); and t is 0, 1 or 2.

For compounds of formula IA, when $R^3$ is $-SO_{(t)}NR^{13}R^{14}$ (e.g., $-SO_2NR^{13}R^{14}$), preferably $R^{13}$ and $R^{14}$ are independently selected from the group consisting of: H and alkyl (e.g., methyl, ethyl, isopropyl and t-butyl). Examples include, but are not limited to (1) $-SO_2NH_2$ and (2) $-SO_2NR^{13}R^{14}$ wherein $R^{13}$ and $R^{14}$ are the same or different alkyl group (e.g., methyl, ethyl, isopropyl and t-butyl), e.g., the same alkyl group, such as, for example $-SO_2N(CH_3)_2$.

For compounds of formula IA, when $R^3$ is $-C(O)NR^{13}R^{14}$, preferably $R^{13}$ and $R^{14}$ are independently selected from the group consisting of: H and alkyl (e.g., methyl, ethyl, isopropyl and t-butyl). Examples include, but are not limited to $-C(O)NR^{13}R^{14}$ wherein each $R^{13}$ and $R^{14}$ are the same or different alkyl group, e.g., the same alkyl group, such as, for example $-C(O)N(CH_3)_2$.

For the compounds of formula IA substituent A is preferably selected from the group consisting of:

unsubstituted or substituted:

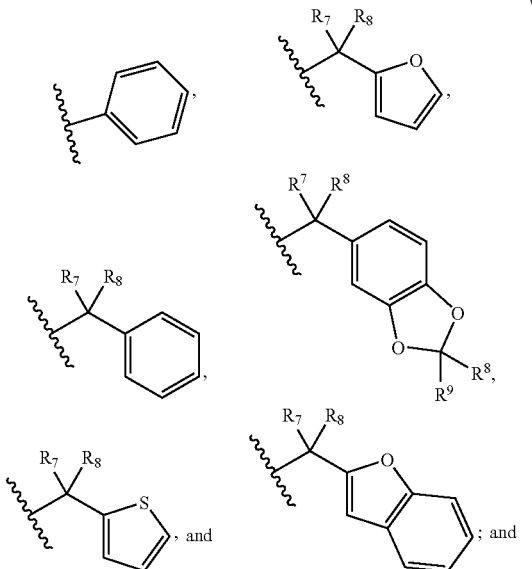

(1)

wherein all substitutents are as defined for formula IA.

For the compounds of formula IA substituent A is most preferably:

(2)

wherein the furan ring is unsubstituted or substituted with 1 or 2 alkyl groups (e.g., $C_1$ to $C_3$ alkyl groups) wherein each alkyl group is independently selected, $R^7$ is selected from the group consisting of: $-CF_3$, alkyl (e.g., $C_1$ to $C_4$ alkyl) and cycloalkyl (e.g., cyclopropyl), and $R^8$ is H. More preferably the furan ring is substituted.

For the compounds of formula IA substituent A is even more preferably:

wherein the furan ring is unsubstituted or substituted with 1 or 2 alkyl groups independently selected from the group consisting of methyl, ethyl and isopropyl, $R^7$ is selected from the group consisting of: $-CF_3$, ethyl, isopropyl, t-butyl and cyclopropyl, and $R^8$ is H. Still more preferably the furan ring is substituted.

For the compounds of formula IA substituent A is even yet more preferably:

wherein the furan ring is substituted with 1 or 2 alkyl groups independently selected from the group consisting of methyl, ethyl and isopropyl, $R^7$ is selected from the group consisting of: ethyl, isopropyl and t-butyl, and $R^8$ is H.

Examples of substituent A in formula IA include, but are not limited to:

-continued

Substituent A in formula IA is most preferably selected from the group consisting of:

and

-continued

Substituent A in formula IA is more preferably selected from the group consisting of:

Substituent A in formula IA is even more preferably selected from the group consisting of:

Substituent B in formula IA is preferably selected from the group consisting of:

[chemical structures: substituted phenyl with R2-R6, thiophene with R2, R3, R11, and pyrazole with R2, R3, R12]

wherein all substituents are as defined for formula IA.

Substituent B in formula IA is most preferably selected from the group consisting of:

[chemical structures: N,N-dimethylbenzamide with OH; cyanophenol; bromo-N,N-dimethylbenzamide with OH; trifluoromethyl-N,N-dimethylbenzamide with OH; chloro-sulfonamide phenol; N-methyl thiophene carboxamide with OH; N,N-dimethylsulfonamide thiophene with OH; N,N-diethylsulfonamide thiophene with OH]

Substituent B in Formula IA is more preferably selected from the group consisting of:

[chemical structures: N,N-dimethylbenzamide with OH; cyanophenol; bromo-N,N-dimethylbenzamide with OH; trifluoromethyl-N,N-dimethylbenzamide with OH; chloro-sulfonamide phenol]

Substituent B in Formula IA is even more preferably selected from the group consisting of:

[chemical structures: N,N-dimethylbenzamide with OH; bromo-N,N-dimethylbenzamide with OH; trifluoromethyl-N,N-dimethylbenzamide with OH]

-continued

[chemical structures: N-methylpiperazine carbonyl phenol; nitrophenol]

Substituent B in Formula IA is still even more preferably selected from the group consisting of:

An embodiment of the present invention is directed to a method of treating an chemokine mediated disease in a patient in need of such treatment (e.g., a mammal, preferably a human being) comprising administering to said patient a therapeutically effective amount of at least one (e.g., 1-3, and usually one) compound of formula IA, or a pharmaceutically acceptable salt or solvate thereof.

Examples of chemokine mediated (e.g., CXCR1 and/or CXCR2, or CCR7) diseases or conditions include but are not limited to: acute pain, acute inflammation, chronic inflammation, rheumatoid arthritis, acute inflammatory pain, chronic inflammatory pain, neuropathic pain, psoriasis, atopic dermatitis, asthma, COPD, adult respiratory disease, arthritis, inflammatory bowel disease, Crohn's disease, ulcerative colitis, septic shock, endotoxic shock, gram negative sepsis, toxic shock syndrome, stroke, cardiac reperfusion injury, renal reperfusion injury, glomerulonephritis, thrombosis, Alzheimers disease, graft vs. host reaction (i.e., graft vs. host disease), allograft rejections (e.g., acute allograft rejection, and chronic allograft rejection), malaria, acute respiratory distress syndrome, delayed type hypersensitivity reaction, atherosclerosis, cerebral ischemia, cardiac ischemia, osteoarthritis, multiple sclerosis, restinosis, angiogenesis, osteoporosis, gingivitis, respiratory viruses, herpes viruses, hepatitis viruses, HIV, Kaposi's sarcoma associated virus (i.e., Kaposi's sarcoma), meningitis, cystic fibrosis, pre-term labor, cough, pruritis, multi-organ dysfunction, trauma, strains, sprains, contusions, psoriatic arthritis, herpes, encephalitis, CNS vasculitis, traumatic brain injury, CNS tumors, subarachnoid hemorrhage, post surgical trauma, interstitial pneumonitis, hypersensitivity, crystal induced arthritis, acute pancreatitis, chronic pancreatitis, acute alcoholic hepatitis, necrotizing enterocolitis, chronic sinusitis, angiogenic ocular disease, ocular inflammation, retinopathy of prematurity, diabetic retinopathy, macular degeneration with the wet type preferred, corneal neovascularization, polymyositis, vasculitis, acne, gastric ulcers, duodenal ulcers, celiac disease, esophagitis, glossitis, airflow obstruction, airway hyperresponsiveness (i.e., airway hyperreactivity), bronchiectasis, bronchiolitis, bronchiolitis obliterans, chronic bronchitis, cor pulmonae, dyspnea, emphysema, hypercapnea, hyperinflation, hypoxemia, hyperoxia-induced inflammations, hypoxia, surgical lung volume reduction, pulmonary fibrosis, pulmonary hypertension, right ventricular hypertrophy, peritonitis associated with continuous ambulatory peritoneal dialysis (CAPD), granulocytic ehrlichiosis, sarcoidosis, small airway disease, ventilation-perfusion mismatching, wheeze, colds, gout, alcoholic liver disease, lupus, burn therapy (i.e., the treatment of burns), periodontitis, cancer, transplant reperfusion injury, early transplantation rejection (e.g., acute allograft rejection), airway hyperreactivity, allergic contact dermatitis, allergic rhinitis, alopecia areata, antiphospholipid syndromes, aplastic anemia, autoimmune deafness (including, for example, Meniere's disease), autoimmune hemolytic syndromes, autoimmune hepatitis, autoimmune neuropathy, autoimmune ovarian failure, autoimmune orchitis, autoimmune thrombocytopenia, bullous pemphigoid, chronic allograft vasculopathy, chronic inflammatory demyelinating polyneuropathy, cirrhosis, cor pneumoniae, cryoglobulinemia, dermatomyositis, diabetes, drug-induced autoimmunity, epidermolysis bullosa acquisita, endometriosis, fibrotic diseases, gastritis, Goodpasture's syndrome, Graves' disease, Gullain-Barre disease, Hashimoto's thyroiditis, hepatitis-associated autoimmunity, HIV-related autoimmune syndromes and hematologic disorders, hypophytis, idiopathic thrombocytic pupura, interstitial cystitis, juvenile arthritis, Langerhans' cell histiocytitis, lichen planus, metal-induced autoimmunity, myasthenia gravis, myelodysplastic syndromes, myocarditis (including viral myocarditis), myositis, Neuropathies (including, for example, IgA neuropathy, membranous neuropathy and idiopathic neuropathy), nephritic syndrome, optic neuritis, pancreatitis, paroxysmal nocturnal hemoglobulinemia, pemphigus, polymyalgia, post-infectious autoimmunity, primary biliary cirrhosis, reactive arthritis, ankylosing spondylitis, Raynaud's phenomenon, Reiter's syndrome, reperfusion injury, scleritis, scleroderma, secondary hematologic manifestation of autoimmune diseases (such as, for example, anemias), silicone implant associated autoimmune disease, Sjogren's syndrome, systemic lupus erythematosus, thrombocytopenia, transverse myelitis, tubulointerstitial nephritis, uveitis, vasculitis syndromes (such as, for example, giant cell arteritis, Behcet's disease and Wegener's granulomatosis), and Vitiligo.

Examples of CXCR1 and/or CXCR2 mediated diseases or conditions include but are not limited to: acute pain, acute inflammation, chronic inflammation, rheumatoid arthritis, acute inflammatory pain, chronic inflammatory pain, neuropathic pain, psoriasis, atopic dermatitis, asthma, COPD, adult respiratory disease, arthritis, inflammatory bowel disease, Crohn's disease, ulcerative colitis, septic shock, endotoxic shock, gram negative sepsis, toxic shock syndrome, stroke, cardiac reperfusion injury, renal reperfusion injury, glomerulonephritis, thrombosis, Alzheimer's disease, graft vs. host reaction (i.e., graft vs. host disease), allograft rejections (e.g., acute allograft rejection, and chronic allograft rejection), malaria, acute respiratory distress syndrome, delayed type hypersensitivity reaction, atherosclerosis, cerebral ischemia, cardiac ischemia, osteoarthritis, multiple sclerosis, restinosis, angiogenesis, osteoporosis, gingivitis, respiratory viruses, herpes viruses, hepatitis viruses, HIV, Kaposi's sarcoma associated virus (i.e., Kaposi's sarcoma), meningitis, cystic fibrosis, pre-term labor, cough, pruritis, multi-organ dysfunction, trauma, strains, sprains, contusions, psoriatic arthritis, herpes, encephalitis, CNS vasculitis, traumatic brain injury, CNS tumors, subarachnoid hemorrhage, post surgical trauma, interstitial pneumonitis, hypersensitivity, crystal induced arthritis, acute pancreatitis, chronic pancreatitis, acute alcoholic hepatitis, necrotizing enterocolitis, chronic sinusitis, angiogenic ocular disease, ocular inflammation, retinopathy of prematurity, diabetic retinopathy, macular degeneration with the wet type preferred, corneal neovascularization, polymyositis, vasculitis, acne, gastric ulcers, duodenal ulcers, celiac disease, esophagitis, glossitis, airflow obstruction, airway hyperresponsiveness (i.e., airway hyperreactivity), bronchiectasis, bronchiolitis, bronchiolitis obliterans, chronic bronchitis, cor pulmonae, dyspnea, emphysema, hypercapnea, hyperinflation, hypoxemia, hyperoxia-induced inflammations, hypoxia, surgical lung volume reduction, pulmonary fibrosis, pulmonary hypertension, right ventricular hypertrophy, peritonitis associated with continuous ambulatory peritoneal dialysis (CAPD), granulocytic ehrlichiosis, sarcoidosis, small airway disease, ventilation-perfusion mismatching, wheeze, colds, gout, alcoholic liver disease, lupus, burn therapy (i.e., the treatment of burns), periodontitis, cancer, transplant reperfusion injury, early transplantation rejection (e.g., acute allograft rejection).

Examples of CCR7 mediated diseases or conditions include, but are not limited to: acute inflammation, chronic inflammation, acute inflammatory pain, acute pain, chronic inflammatory pain, neuropathic pain, acute allograft rejection, acute respiratory distress syndrome, adult respiratory disease, airway hyperreactivity, allergic contact dermatitis, allergic rhinitis, alopecia areata, alzheimer's disease, angiogenic ocular disease, antiphospholipid syndromes, aplastic anemia, asthma, atherosclerosis, atopic dermatitis, autoimmune deafness (including, for example, Meniere's disease), autoimmune hemolytic syndromes, autoimmune hepatitis, autoimmune neuropathy, autoimmune ovarian failure, autoimmune orchitis, autoimmune thrombocytopenia, bronchiolitis, bronchiolitis obliterans syndrome, bullous pemphigoid, burn therapy (i.e., the treatment of burns), cancer, cerebral ischemia, cardiac ischemia, chronic allograft rejection, chronic allograft vasculopathy, chronic bronchitis, chronic inflammatory demyelinating polyneuropathy, chronic sinusitis, cirrhosis, CNS vasculitis, COPD, Cor pneumoniae, Crohn's disease, cryoglobulinemia, crystal-induced arthritis, delayed-type hypersensitivity reactions, dermatomyositis, diabetes, diabetic retinopathy, drug-induced autoimmunity, dyspnea, emphysema, epidermolysis bullosa acquisita, endometriosis, fibrotic diseases, gastritis, glomerulonephritis, Goodpasture's syndrome, graft vs host disease, Graves' disease, Gullain-Barre disease, Hashimoto's thyroiditis, hepatitis-associated autoimmunity, HIV-related autoimmune syndromes and hematologic disorders, hyperoxia-induced inflammation, hypercapnea, hyperinflation, hypophytis, hypoxia, idiopathic thrombocytic pupura, inflammatory bowel diseases, interstitial cystitis, interstitial pneumonitis, juvenile arthritis, Langerhans' cell histiocytitis, lichen planus, metal-induced autoimmunity, multiple sclerosis, myasthenia gravis, myelodysplastic syndromes, myocarditis including viral myocarditis, myositis, neuropathies (including, for example, IgA neuropathy, membranous neuropathy and idiopathic neuropathy), nephritic syndrome, ocular inflammation, optic neuritis, osteoarthritis, pancreatitis, paroxysmal nocturnal hemoglobulinemia, pemphigus, polymyalgia, polymyositis, post-infectious autoimmunity, pulmonary fibrosis, primary biliary cirrhosis, psoriasis, pruritis, rheumatoid arthritis, reactive arthritis, ankylosing spondylitis, psoriatic arthritis, Raynaud's phenomenon, Reiter's syndrome, reperfusion injury, restenosis, sarcoidosis, scleritis, scleroderma, secondary hematologic manifestation of autoimmune diseases (such as, for example, anemias), silicone implant associated autoimmune disease, Sjogren's syndrome, systemic lupus erythematosus, thrombocytopenia, thrombosis, transverse myelitis, tubulointerstitial nephritis, ulcerative colitis, uveitis, vasculitis and vasculitis syndromes (such as, for example, giant cell arteritis, Behcet's disease and Wegener's granulomatosis), and vitiligo.

Another embodiment of this invention is directed to a method of treating a CXCR1 and/or CXCR2 mediated disease, as described above, in a patient in need of such treatment comprising administering to said patient an effective amount of a compound selected from the group consisting of the final compounds of Examples 56, 201.1, 201.9, and the pharmaceutically acceptable salts and solvates thereof.

Another embodiment of this invention is directed to a method of treating a CCR7 mediated disease, as described above, in a patient in need of such treatment comprising administering to said patient an effective amount of a compound selected from the group consisting of the final compounds of Examples 2065, 2066, 2105, 2106, and the pharmaceutically acceptable salts and solvates thereof.

Another embodiment of this invention is directed to a method of treating Kaposi's sarcoma, melanoma, gastric carcinoma, and non-small cell carcinoma in a patient in need of such treatment comprising administering to said patient an effective amount of at least one (e.g., 1-3, usually 1) compound of formula IA, or a pharmaceutically acceptable salt or solvate thereof.

Another embodiment of this invention is directed to a method of treating melanoma, gastric carcinoma, and non-small cell carcinoma in a patient in need of such treatment comprising administering to said patient an effective amount of at least one (e.g., 1-3, usually 1) compound of formula IA, or a pharmaceutically acceptable salt or solvate thereof.

Another embodiment of the present invention is directed to a method of treating cancer in a patient (e.g., a mammal, such as a human being) in need of such treatment, comprising administering to said patient, concurrently or sequentially, a therapeutically effective amount of (a) at least one (e.g., 1-3, and usually one) compound of formula IA, or a pharmaceutically acceptable salt or solvate thereof, and (b) at least one (e.g., 1, 2 or 3) anticancer agent selected from the group consisting of: (1) microtubule affecting agents, (2) antineoplastic agents, (3) anti-angiogenesis agents, (4) VEGF receptor kinase inhibitors, (5) antibodies against the VEGF receptor, (6) interferon, and (7) radiation.

In further embodiments of this invention that are directed to the treatment of cancer, at least one (e.g., 1-3, and usually one) compound of formula IA, or a pharmaceutically acceptable salt or solvate thereof, is administered in combination with at least one (e.g., 1 or 2, or 1) antineoplastic agent selected from the group consisting of: gemcitabine, paclitaxel (Taxol®), 5-Fluorouracil (5-FU), cyclophosphamide (Cytoxan®), temozolomide, taxotere and Vincristine.

In another embodiment the present invention provides a method of treating cancer in a patient (e.g., a mammal, such as a human being) in need of such treatment, comprising administering, concurrently or sequentially, an effective amount of (a) at least one (e.g., 1-3, usually 1) compound of formula IA, or a pharmaceutically acceptable salt or solvate thereof, and (b) at least one (e.g., 1-3, usually 1) microtubule affecting agent (e.g., paclitaxel).

In the method of treating a pulmonary disease (e.g., COPD, asthma, or cystic fibrosis), at least one (usually 1) compound of formula IA, or a pharmaceutically acceptable salt or solvate thereof, is administered in combination with at least one compound selected from the group consisting of: glucocorticoids, 5-lipoxygenase inhibitors, β-2 adrenoceptor agonists, muscarinic M1 antagonists, muscarinic M3 antagonists, muscarinic M2 agonists, NK3 antagonists, LTB4 antagonists, cysteinyl leukotriene antagonists, bronchodilators, PDE4 inhibitors, PDE inhibitors, elastase inhibitors, MMP inhibitors, phospholipase A2 inhibitors, phospholipase D inhibitors, histamine H1 antagonists, histamine H3 antagonists, dopamine agonists, adenosine A2 agonists, NK1 and NK2 antagonists, GABA-b agonists, nociceptin agonists, expectorants, mucolytic agents, decongestants, antioxidants, anti-IL-8 anti-bodies, anti-IL-5 antibodies, anti-IgE antibodies, anti-TNF antibodies, IL-10, adhesion molecule inhibitors, and growth hormones. Agents that belong to these classes include, but are not limited to, beclomethasone, mometasone, ciclesonide, budesonide, fluticasone, albuterol, salmeterol, formoterol, loratadine, desloratadine, tiotropium bromide, MSI-ipratropium bromide, montelukast, theophilline, cilomilast, roflumilast, cromolyn, ZD-4407, talnetant, LTB-019, revatropate, pumafentrine, CP-955, AR-C-89855, BAY-19-8004, GW-328267, QAB-149, DNK-333, YM-40461 and TH-9506 or pharmaceutically acceptable formulations thereof.

Representative embodiments of the novel compounds of this invention are described below. The embodiments have been numbered for purposes of reference thereto.

Embodiment No. 1 is directed to the novel compounds of formula IA wherein B is:

and all other substitutents are as defined for of formula IA.

Embodiment No. 2 is directed to the novel compounds of formula IA wherein B is:

and all other substitutents are as defined for of formula IA.

Embodiment No. 3 is directed to the novel compounds of formula IA wherein B is:

and all other substitutents are as defined for of formula IA.

Embodiment No. 4 is directed to the novel compounds of formula IA wherein B is:

and all other substitutents are as defined for of formula IA.

Embodiment No. 5 is directed to the novel compounds of formula IA wherein B is:

and all other substitutents are as defined for of formula IA.

Embodiment No. 6 is directed to the novel compounds of formula IA wherein B is:

and all other substitutents are as defined for of formula IA.

Embodiment No. 7 is directed to the novel compounds of formula IA wherein B is:

and all other substitutents are as defined for of formula IA.

Embodiment No. 8 is directed to the novel compounds of formula IA wherein B is:

and all other substitutents are as defined for of formula IA.

Embodiment No. 9 is directed to the novel compounds of formula IA wherein B is:

and all other substitutents are as defined for of formula IA.

Embodiment No. 10 is directed to the novel compounds of formula IA wherein B is:

and all other substitutents are as defined for of formula IA.

Embodiment No. 11 is directed to the novel compounds of formula IA wherein B is:

and all other substitutents are as defined for of formula IA.

Embodiment No. 12 is directed to the novel compounds of formula IA wherein B is:

and all other substitutents are as defined for of formula IA.

Embodiment No. 13 is directed to the novel compounds of formula IA wherein B is:

and all other substitutents are as defined for of formula IA.

Embodiment No. 14 is directed to the novel compounds of formula IA wherein B is:

and all other substitutents are as defined for of formula IA.

Embodiment No. 15 is directed to the novel compounds of formula IA wherein B is:

and all other substitutents are as defined for of formula IA.

Embodiment No. 16 is directed to the novel compounds of formula IA wherein B is:

and all other substitutents are as defined for of formula IA.

Embodiment No. 17 is directed to the novel compounds of formula IA wherein B is:

and all other substitutents are as defined for of formula IA.

Embodiment No. 18 is directed to the novel compounds of formula IA wherein B is:

and all other substitutents are as defined for of formula IA.

Embodiment No. 19 is directed to compounds of formula IA wherein B is selected from the group consisting of:

(1)

and $R^3$ for this B group is selected from the group consisting of: —C(O)NR$^{13}$R$^{14}$, and all other substituents are as defined for formula IA.

Embodiment No. 20 is directed to compounds of formula IA wherein B is:

and all other substituents are as defined in formula IA.

Embodiment No. 21 is directed to compounds of formula IA wherein B is $R^{13}$ and $R^{14}$ are independently selected from the group consisting of H and alkyl (e.g., methyl, ethyl, isopropyl and t-butyl), and all other substituents are as defined in formula IA.

Embodiment No. 22 is directed to compounds of formula IA wherein B is wherein:
(1) $R^2$ is —OH and all other substituents are as defined in formula IA, or
(2) $R^2$ is —OH, and $R^{13}$ and $R^{14}$ are independently selected from the group, consisting of: H and alkyl (e.g., methyl, ethyl, isopropyl and t-butyl), or
(3) $R^2$ is —OH, and $R^{13}$ and $R^{14}$ are the same or different and alkyl group (e.g., methyl, ethyl, isopropyl and t-butyl), for example the same alkyl group, for example methyl, and
(4) and all other substituents are as defined in formula IA.

Embodiment No. 23 is directed to compounds of formula IA wherein B is $R^3$ is selected from the group consisting of:

and all other substituents are as defined in formula IA.

Embodiment No. 24 is directed to compounds of formula IA wherein B is $R^3$ is selected from the group consisting of:

$R^2$ is —OH, and all other substituents are as defined in formula IA.

Embodiment No. 25 is directed to compounds of formula IA wherein B is:

and all other substituents are as defined in formula IA.

Embodiment No. 26 is directed to compounds of formula IA wherein B is:

$R^2$ is —OH, and all other substituents are as defined in formula IA.

Embodiment No. 27 is directed to compounds of formula IA wherein B is:

[Structure: N(R13)(R14)-C(=O)-phenyl with R2 substituent]

$R^2$ is as defined for compounds of formula IA, $R^{13}$ and $R^{14}$ are independently selected from the group consisting of H and alkyl (e.g., methyl, ethyl, isopropyl and t-butyl), and all other substituents areas defined for compounds of formula IA. For example, $R^{13}$ and $R^{14}$ are the same or different alkyl group. Also, for example, $R^{13}$ and $R^{14}$ are the same alkyl group. Also, for example, $R^{13}$ and $R^{14}$ are methyl.

Embodiment No. 28 is directed to the novel compounds of formula IA wherein B is:

[Structure: N(R13)(R14)-C(=O)-phenyl with R2 substituent]

$R^2$ is —OH, $R^{13}$ and $R^{14}$ are independently selected from the group consisting of H and alkyl (e.g., methyl, ethyl, isopropyl and t-butyl), and all other substituents areas defined for compounds of formula IA. For example, $R^{13}$ and $R^{14}$ are the same or different alkyl group. Also, for example, $R^{13}$ and $R^{14}$ are the same alkyl group. Also, for example, $R^{13}$ and $R^{14}$ are methyl.

Embodiment No. 29 is directed to novel compounds of formula IA wherein B is as described in Embodiment No. 23, $R^4$ is H, $R^5$ is H, $R^6$ is H, and all other substituents are as defined for compounds of formula IA.

Embodiment No. 30 is directed to novel compounds of formula IA wherein B is as described in Embodiment No. 24, $R^4$ is H, $R^5$ is H, $R^6$ is H, and all other substituents areas defined for compounds of formula IA.

Embodiment No. 31 is directed to novel compounds of formula IA wherein B is as described in Embodiments Nos. 21, 22, 25 and 26, except that $R^{13}$ and $R^{14}$ are each methyl, and all other substituents are as defined in formula IA.

Embodiment No. 32 is directed to compounds of formula IA wherein B is:

[Thiophene structure with R11, R3, R2 substituents]

$R^{11}$ is H or methyl (preferably H), and all other substituents are as defined in formula IA.

Embodiment No. 33 is directed to compounds of formula IA wherein B is:

[Thiophene structure with R11, R3, R2 substituents]

$R^2$ is —OH, and all other substituents are as defined in formula IA.

Embodiment No. 34 is directed to compounds of formula IA wherein B is:

[Thiophene structure with R11, R3, R2 substituents]

$R^3$ is —C(O)NR$^{13}$R$^{14}$, and all other substituents are as defined in formula IA.

Embodiment No. 35 is directed to compounds of formula IA wherein B is:

[Thiophene structure with R11, R3, R2 substituents]

$R^3$ is —S(O)$_t$NR$^{13}$R$^{14}$ (e.g., t is 2), and all other substituents are as defined in formula IA.

Embodiment No. 36 is directed to compounds of formula IA wherein B is:

[Thiophene structure with R11, R3, R2 substituents]

$R^2$ is —OH, $R^3$ is —C(O)NR$^{13}$R$^{14}$, and all other substituents are as defined in formula IA.

Embodiment No. 37 of this invention is directed to compounds of formula IA wherein B is:

[Thiophene structure with R11, R3, R2 substituents]

$R^2$ is —OH, and $R^3$ is —S(O)$_t$NR$^{13}$R$^{14}$ (e.g., t is 2), and all other substituents are as defined in formula IA.

Embodiment No. 38 is directed to compounds of formula IA wherein B is:

[structure: thiophene with R$^{11}$, R$^3$, R$^2$ substituents]

R$^2$ is —OH, R$^3$ is —C(O)NR$^{13}$R$^{14}$, R$^{11}$ is H or methyl (preferably H), and all other substituents are as defined in formula IA.

Embodiment No. 39 is directed to compounds of formula IA wherein B is:

[structure: thiophene with R$^{11}$, R$^3$, R$^2$ substituents]

R$^2$ is —OH, R$^3$ is —S(O)$_t$NR$^{13}$R$^{14}$ (e.g., t is 2), R$^{11}$ is H or methyl (preferably H), and all other substituents are as defined in formula IA.

Embodiment No. 40 is directed to compounds of formula IA wherein B is:

[structure: thiophene with R$^{11}$, R$^3$, R$^2$ substituents]

R$^2$ is —OH, R$^3$ is —C(O)NR$^{13}$R$^{14}$, R$^{11}$ is H or methyl (preferably H), and R$^{13}$ and R$^{14}$ are independently selected from the group consisting of: H, alkyl (e.g., methyl, ethyl, isopropyl and t-butyl), unsubstituted cycloalkyl, substituted cycloalkyl, unsubstituted heteroaryl and substituted heteroaryl, and all other substituents are as defined in formula IA. For example, one of R$^{13}$ or R$^{14}$ is alkyl (e.g., methyl). An example of a substituted heteroaryl group is

[structure: isoxazole with methyl group].

Embodiment No. 41 is directed to compounds of formula IA wherein B is:

[structure: thiophene with R$^{11}$, R$^3$, R$^2$ substituents]

R$^2$ is —OH, R$^3$ is —S(O)$_t$NR$^{13}$R$^{14}$ (e.g., t is 2), R$^{11}$ is H or methyl (preferably H), and R$^{13}$ and R$^{14}$ are independently selected from the group consisting of: H, alkyl (e.g., methyl, ethyl, isopropyl, and t-butyl), unsubstituted cycloalkyl, and substituted cycloalkyl, and all other substituents are as defined in formula IA. For example R$^3$ is (1) —SO$_2$NH$_2$ or (2) —SO$_2$NR$^{13}$R$^{14}$ wherein R$^{13}$ and R$^{14}$ are the same or different alkyl group (e.g., methyl, ethyl, isopropyl and t-butyl), e.g., the same alkyl group, such as, for example —SO$_2$N(CH$_3$)$_2$.

Embodiment No. 42 is directed to compounds of formula IA wherein B is:

[structure: thiophene with R$^{11}$, R$^3$, R$^2$ substituents]

R$^{11}$ is H, and all other substituents are as defined in formula IA.

Embodiment No. 43 is directed to compounds of formula IA wherein B is:

[structure: thiophene with R$^{11}$, R$^3$, R$^2$ substituents]

R$^2$ is —OH, and all other substituents are as defined in formula IA.

Embodiment No. 44 is directed to compounds of formula IA wherein B is:

[structure: thiophene with R$^{11}$, R$^3$, R$^2$ substituents]

R$^3$ is —C(O)NR$^{13}$R$^{14}$, and all other substituents are as defined in formula IA.

Embodiment No. 45 is directed to compounds of formula IA wherein B is:

[structure: thiophene with R$^{11}$, R$^3$, R$^2$ substituents]

R$^3$ is —S(O)$_t$NR$^{13}$R$^{14}$ (e.g., t is 2), and all other substituents are as defined in formula IA.

Embodiment No. 46 is directed to compounds of formula IA wherein B is:

[structure: thiophene with R$^{11}$, R$^3$, R$^2$ substituents]

R$^2$ is —OH, R$^3$ is —C(O)NR$^{13}$R$^{14}$, and all other substituents are as defined in formula IA.

Embodiment No. 47 of this invention is directed to compounds of formula IA wherein B is:

$R^2$ is —OH, and $R^3$ is $S(O)_tNR^{13}R^{14}$ (e.g., t is 2), and all other substituents are as defined in formula IA.

Embodiment No. 48 is directed to compounds of formula IA wherein B is:

$R^2$ is —OH, $R^3$ is —C(O)$NR^{13}R^{14}$, $R^{11}$ is H, and all other substituents are as defined in formula IA.

Embodiment No. 49 is directed to compounds of formula IA wherein B is:

$R^2$ is —OH, $R^3$ is —S(O)$_tNR^{13}R^{14}$ (e.g., t is 2), $R^{11}$ is H, and all other substituents are as defined in formula IA.

Embodiment No. 50 is directed to compounds of formula IA wherein B is:

$R^2$ is —OH, $R^3$ is —C(O)$NR^{13}R^{14}$, $R^{11}$ is H, and $R^{13}$ and $R^{14}$ are independently selected from the group consisting of: alkyl, unsubstituted heteroaryl and substituted heteroaryl, and all other substituents are as defined in formula IA. For example, one of $R^{13}$ or $R^{14}$ is alkyl (e.g., methyl). An example of a substituted heteroaryl group is Embodiment No. 51 is directed to compounds of formula IA wherein B is:

$R^2$ is —OH, $R^3$ is —S(O)$_tNR^{13}R^{14}$ (e.g., t is 2), $R^{11}$ is H, $R^{13}$ and $R^{14}$ are independently selected from the group consisting of: H and alkyl (e.g., methyl, ethyl, isopropyl, and t-butyl), and all other substituents are as defined in formula IA. For example $R^3$ is (1) —SO$_2$NH$_2$ and (2) —SO$_2$NR$^{13}$R$^{14}$ wherein $R^{13}$ and $R^{14}$ are the same or different alkyl group (e.g., methyl, ethyl, isopropyl and t-butyl), e.g., the same alkyl group, such as, for example —SO$_2$N(CH$_3$)$_2$.

Embodiment No. 52 is directed to compounds of formula IA wherein substituent B is selected from the group consisting of:

wherein $R^2$ to $R^6$ and $R^{10}$ to $R^{14}$ are as defined above for the compounds of formula IA.

Embodiment No. 53 is directed to compounds of formula IA wherein substituent B in formula is selected from the group consisting of:

-continued $$\text{[thiophene ring with } R^3, R^2, R^{11} \text{ substituents]}$$

wherein

R$^2$ is selected from the group consisting of: H, OH, —NHC(O)R$^{13}$ or and —NHSO$_2$R$^{13}$;

R$^3$ is selected from the group consisting of: —SO$_2$NR$^{13}$R$^{14}$, —NO$_2$, cyano, —C(O)NR$^{13}$R$^{14}$, —SO$_2$R$^{13}$; and —C(O)OR$^{13}$;

R$^4$ is selected from the group consisting of: H, —NO$_2$, cyano, —CH$_3$, halogen, and —CF$_3$;

R$^5$ is selected from the group consisting of: H, —CF$_3$, —NO$_2$, halogen and cyano;

R$^6$ is selected from the group consisting of: —H, alkyl and —CF$_3$;

each R$^{10}$ and R$^{11}$ is independently selected from the group consisting of: R$^{13}$, hydrogen, halogen, —CF$_3$, —NR$^{13}$R$^{14}$, —NR$^{13}$C(O)NR$^{13}$R$^{14}$, —C(O)OR$^{13}$, —SH, —SO$_{(t)}$NR$^{13}$R$^{14}$, —SO$_2$R$^{13}$, —NHC(O)R$^{13}$, —NHSO$_2$NR$^{13}$R$^{14}$, —NHSO$_2$R$^{13}$, —C(O)NR$^{13}$R$^{14}$, —C(O)NR$^{13}$OR$^{14}$, —OC(O)R$^{13}$, —COR$^{13}$, —OR$^{13}$, and cyano;

each R$^{13}$ and R$^{14}$ is independently selected from the group consisting of: H, methyl, ethyl and isopropyl; or R$^{13}$ and R$^{14}$ when taken together with the nitrogen they are attached to in the groups —NR$^{13}$R$^{14}$, —C(O)NR$^{13}$R$^{14}$, —SO$_2$NR$^{13}$R$^{14}$, —OC(O)NR$^{13}$R$^{14}$, —CONR$^{13}$R$^{14}$, —NR$^{13}$C(O)NR$^{13}$R$^{14}$, —SO$_t$NR$^{13}$R$^{14}$, —NHSO$_2$NR$^{13}$R$^{14}$ form an unsubstituted or substituted saturated heterocyclic ring (preferably a 3 to 7 membered ring) optionally having one additional heteroatom selected from the group consisting of: O, S or NR$^{18}$; wherein R$^{18}$ is selected from the group consisting of: H, alkyl, aryl, heteroary, —C(O)R$^{19}$, —SO$_2$R$^{19}$ and —C(O)NR$^{19}$R$^{20}$; wherein each R$^{19}$ and R$^{20}$ is independently selected from the group consisting of: alkyl, aryl and heteroaryl; wherein there are 1 to 3 substituents on the substituted cyclized R$^{13}$ and R$^{14}$ groups (i.e., the substituents on the ring formed when R$^{13}$ and R$^{14}$ are taken together with the nitrogen to which they are bound) and each substituent is independently selected from the group consisting of: alkyl, aryl, hydroxy, hydroxyalkyl, alkoxy, alkoxyalkyl, arylalkyl, fluoroalkyl, cycloalkyl, cycloalkylalkyl, heteroaryl, heteroarylalkyl, amino, —C(O)OR$^{15}$—C(O)NR$^{15}$R$^{16}$, —SO$_t$NR$^{15}$R$^{16}$, —C(O)R$^{15}$, —SO$_2$R$^{15}$ provided that R$^{15}$ is not H, —NHC(O)NR$^{15}$R$^{16}$ and halogen; and wherein each R$^{15}$ and R$^{16}$ is independently selected from the group consisting: of H, alkyl, aryl, arylalkyl, cycloalkyl and heteroaryl.

Embodiment No. 54 is directed to compounds of formula IA wherein substituent B in formula selected from the group consisting of:

$$\text{[benzamide structure with } R^4, R^5, R^6, R^{13}, R^{14}, R^2 \text{ substituents]} \text{ and [thiophene structure with } R^3, R^2, R^{11} \text{ substituents]}$$

wherein:

R$^2$ is selected from the group consisting of: H, OH, —NHC(O)R$^{13}$ and —NHSO$_2$R$^{13}$;

R$^3$ is selected from the group consisting of: —C(O)NR$^{13}$R$^{14}$, —SO$_2$NR$^{13}$R$^{14}$, —NO$_2$, cyano, —SO$_2$R$^{13}$; and —C(O)OR$^{13}$;

R$^4$ is selected from the group consisting of: H, —NO$_2$, cyano, —CH$_3$ or —CF$_3$;

R$^5$ is selected from the group consisting of: H, —CF$_3$, —NO$_2$, halogen and cyano; and R$^6$ is selected from the group consisting of: H, alkyl and —CF$_3$;

R$^{11}$ is selected from the group consisting of: H, halogen and alkyl; and each R$^{13}$ and R$^{14}$ is independently selected from the group consisting of: H, methyl, ethyl and isopropyl; or R$^{13}$ and R$^{14}$ when taken together with the nitrogen they are attached to in the groups —NR$^{13}$R$^{14}$, —C(O)NR$^{13}$R$^{14}$, —SO$_2$NR$^{13}$R$^{14}$, —OC(O)NR$^{13}$R$^{14}$, —CONR$^{13}$R$^{14}$, —NR$^{13}$C(O)NR$^{13}$R$^{14}$, —SO$_t$NR$^{13}$R$^{14}$, —NHSO$_2$NR$^{13}$R$^{14}$ form an unsubstituted or substituted saturated heterocyclic ring (preferably a 3 to 7 membered ring) optionally having one additional heteroatom selected from O, S or NR$^{18}$ wherein R$^{18}$ is selected from H, alkyl, aryl, heteroaryl, —C(O)R$^{19}$, —SO$_2$R$^{19}$ and —C(O)NR$^{19}$R$^{20}$, wherein each R$^{19}$ and R$^{20}$ is independently selected from alkyl, aryl and heteroaryl, wherein there are 1 to 3 substituents on the substituted cyclized R$^{13}$ and R$^{14}$ groups (i.e., on the ring formed when R$^{13}$ and R$^{14}$ are taken together with the nitrogen to which they are bound) and each substituent is independently selected from the group consisting of: alkyl, aryl, hydroxy, hydroxyalkyl, alkoxy, alkoxyalkyl, arylalkyl, fluoroalkyl, cycloalkyl, cycloalkylalkyl, heteroaryl, heteroarylalkyl, amino, —C(O)OR$^{15}$, —C(O)NR$^{15}$R$^{16}$, —SO$_t$NR$^{15}$R$^{16}$, —C(O)R$^{15}$, —SO$_2$R$^{15}$ provided that R$^{15}$ is not H, —NHC(O)NR$^{15}$R$^{16}$ and halogen; and wherein each R$^{15}$ and R$^{16}$ is independently selected from the group consisting of: H, alkyl, aryl, arylalkyl, cycloalkyl and heteroaryl.

Embodiment No. 55 is directed to compounds of formula IA wherein substituent B is selected from the group consisting of:

$$\text{[benzamide structure with } R^4, R^5, R^6, R^{13}, R^{14}, R^2 \text{ substituents]} \text{ and [thiophene structure with } R^3, R^2, R^{11} \text{ substituents]}$$

wherein:

R$^2$ is selected from the group consisting of: H, OH, —NHC(O)R$^{13}$ and —NHSO$_2$R$^{13}$;

R$^3$ is selected from the group consisting of: —C(O)NR$^{13}$R$^{14}$ —SO$_2$NR$^{13}$R$^{14}$, —NO$_2$, cyano, and —SO$_2$R$^{13}$;

R$^4$ is selected from the group consisting of: H, —NO$_2$, cyano, —CH$_3$ or —CF$_3$;

R$^5$ is selected from the group consisting of: H, —CF$_3$, —NO$_2$, halogen and cyano; and R$^6$ is selected from the group consisting of: H, alkyl and —CF$_3$;

R$^{11}$ is selected from the group consisting of: H, halogen and alkyl; and each R$^{13}$ and R$^{14}$ is independently selected from the group consisting of: H, methyl and ethyl.

Embodiment No. 56 is directed to compounds of formula IA wherein substituent B is selected from the group consisting of:

[structures]

wherein:

$R^2$ is —OH;

$R^3$ is selected from the group consisting of: —SO$_2$NR$^{13}$R$^{14}$ and —CONR$^{13}$R$^{14}$;

$R^4$ is selected form the group consisting of: H, —CH$_3$ and —CF$_3$;

$R^5$ is selected from the group consisting of: H and cyano;

$R^6$ is selected from the group consisting of: H, —CH$_3$ and —CF$_3$;

$R^{11}$ is H; and $R^{13}$ and $R^{14}$ are independently selected from the group consisting of H and methyl (e.g., for —SO$_2$NR$^{13}$R$^{14}$ both $R^{13}$ and $R^{14}$ are H, or both $R^{13}$ and $R^{14}$ are methyl, also, for example, for —CONR$^{13}$R$^{14}$ both $R^{13}$ and $R^{14}$ are methyl).

Embodiment No. 57 is directed to compounds of formula IA wherein substituent B is selected from the group consisting of:

[structures]

wherein all substituents are as defined for formula IA.

Embodiment No. 58 is directed to compounds of formula IA wherein substituent B is selected from the group consisting of:

[structures]

Embodiment No. 59 is directed to compounds of formula IA wherein substituent B is selected from the group consisting of:

[structures]

Embodiment No. 60 is directed to compounds of formula IA wherein substituent B is selected from the group consisting of:

Embodiment No. 61 is directed to compounds of formula IA wherein substituent B is selected from the group consisting of:

Embodiment No. 62 is directed to compounds of formula IA wherein substituent B is:

Embodiment No. 63 is directed to compounds of formula IA wherein substituent B is:

Embodiment No. 64 is directed to compounds of formula IA wherein substituent B is:

Embodiment No. 65 is directed to compounds of formula IA wherein: substituent A is selected from the group consisting of:

(a)

wherein the above rings are unsubstituted or substituted, as described for formula IA: and (b)

and wherein in (a) and (b): each $R^7$ and $R^8$ is independently selected from the group consisting of: H, unsubstituted or substituted alkyl, unsubstituted or substituted aryl, unsubstituted or substituted heteroaryl, unsubstituted or substituted arylalkyl, unsubstituted or substituted heteroarylalkyl, unsubstituted or substituted cycloalkyl, unsubstituted or substituted cycloalkylalkyl, —$CO_2R^{13}$, —$CONR^{13}R^{14}$, fluoroalkyl, alkynyl, alkenyl, and cycloalkenyl, wherein said substituents on said $R^7$ and $R^8$ substituted groups are selected from the group consisting of: a) cyano, b) —$CO_2R^{13}$, c) —$C(O)NR^{13}R^{14}$, d) —$SO_2NR^{13}R^{14}$, e) —$NO_2$, f) —$CF_3$, g) —$OR^{13}$, h) —$NR^{13}R^{14}$, i) —$OC(O)R^{13}$, j) —$OC(O)NR^{13}R^{14}$, and k) halogen; and $R^{8a}$ and $R^9$ are as defined in formula IA.

Embodiment No. 66 is directed to compounds of formula IA wherein substituent A is selected from the group consisting of:

(a)

wherein the above rings are unsubstituted, or the above rings are substituted with 1 to 3 substituents independently selected from the group consisting of: halogen, alkyl, cycloalkyl, —$CF_3$, cyano, —$OCH_3$, and —$NO_2$; each $R^7$ and $R^8$ is independently selected from the group consisting of: H, alkyl (e.g., methyl, ethyl, t-butyl, and isopropyl), fluoroalkyl (such as, —$CF_3$ and —$CF_2CH_3$), cycloalkyl (e.g., cyclopropyl, and cyclohexyl), and cycloalkylalkyl (e.g., cyclopropylmethyl); and $R^9$ is selected from the group consisting of: H, halogen, alkyl, cycloalkyl, —$CF_3$, cyano, —$OCH_3$, and —$NO_2$; and (b)

wherein each $R^7$ and $R^8$ is independently selected from the group consisting of: H, alkyl (e.g., methyl, ethyl, t-butyl, and isopropyl), fluoroalkyl (such as, —$CF_3$ and —$CF_2CH_3$), cycloalkyl (e.g., cyclopropyl, and cyclohexyl), and cycloalkylalkyl (e.g., cyclopropylmethyl); wherein $R^{8a}$ is as defined in formula IA, and wherein $R^9$ is selected from the group consisting of: H, halogen, alkyl, cycloalkyl, —$CF_3$, cyano, —$OCH_3$, and —$NO_2$; each $R^7$ and $R^8$ is independently selected from the group consisting of: H, alkyl (e.g., methyl, ethyl, t-butyl, and isopropyl), fluoroalkyl (such as, —$CF_3$ and —$CF_2CH_3$), cycloalkyl (e.g., cyclopropyl, and cyclohexyl), and cycloalkylalkyl (e.g., cyclopropylmethyl).

Embodiment No. 67 is directed to the novel compounds of formula IA wherein substituent A is selected from the group consisting of:

(a)

-continued

[chemical structures shown]

wherein the above rings are unsubstituted, or the above rings are substituted with 1 to 3 substituents independently selected from the group consisting of: H, F, Cl, Br, alkyl, cycloalkyl, and —CF$_3$; R$^7$ is selected from the group consisting of: H, fluoroalkyl, alkyl and cycloalkyl; R$^8$ is selected form the group consisting of: H, alkyl, —CF$_2$CH$_3$ and —CF$_3$; and R$^9$ is selected from the group consisting of: H, F, Cl, Br, alkyl or —CF$_3$; and (b)

[chemical structure shown]

wherein R$^7$ is selected from the group consisting of: H, fluoroalkyl, alkyl and cycloalkyl; R$^8$ is selected form the group consisting of: H, alkyl, —CF$_2$CH$_3$ and —CF$_3$; and R$^{8a}$ is as defined for formula IA.

Embodiment No. 68 is directed to compounds of formula IA wherein substituent A is selected from the group consisting of:

(a)

[chemical structures shown]

wherein the above rings are unsubstituted, or the above rings are substituted with 1 to 3 substituents independently selected from the group consisting of: H, F, Cl, Br, alkyl, cycloalkyl, and —CF$_3$; R$^7$ is selected from the group consisting of: H, —CF$_3$, —CF$_2$CH$_3$, methyl, ethyl, isopropyl, cyclopropyl and t-butyl; and R$^8$ is H; and (b)

[chemical structure shown]

wherein R$^7$ is selected from the group consisting of: H, —CF$_3$, —CF$_2$CH$_3$, methyl, ethyl, isopropyl, cyclopropyl and t-butyl; and R$^8$ is H; and R$^{8a}$ is as defined for formula IA.

Embodiment No. 69 is directed compounds of formula IA wherein substituent A is selected from the group consisting of:

(a)

[chemical structures shown]

-continued (a) and (a)

wherein the above rings are unsubstituted, or the above rings are substituted with 1 to 3 substituents independently selected from the group consisting of: F, Cl, Br, alkyl, cycloalkyl, and —$CF_3$; $R^7$ is selected from the group consisting of: H, —$CF_3$, —$CF_2CH_3$, methyl, ethyl, isopropyl, cyclopropyl and t-butyl; and $R^8$ is H; and (b)

wherein $R^7$ is selected from the group consisting of: H, —$CF_3$, —$CF_2CH_3$, methyl, ethyl, isopropyl, cyclopropyl and t-butyl; and $R^8$ is H; and $R^{8a}$ is as defined for formula IA;

Embodiment No. 70 is directed compounds of formula IA wherein substituent A is selected from the group consisting of:

unsubstituted or substituted:

(1)

, , , ,

, ; and (2)

wherein all substitutents are as defined for formula IA.

Embodiment No. 71 is directed to compounds of formula IA wherein substituent A is selected from the group consisting of:

, , , , , , , , , , , , , ,

-continued

Embodiment No. 72 is directed to compounds of formula IA wherein substituent A is selected from the group consisting of:

-continued

Embodiment No. 73 is directed to compounds of formula IA wherein substituent A is selected from the group consisting of:

Embodiment No. 74 is directed to compounds of formula IA wherein substituent A is selected from the group consisting of:

Embodiment No. 75 is directed to compounds of formula IA wherein substituent A is selected from the group consisting of:

Embodiment No. 76 is directed to compounds of formula IA wherein substituent A is:

[structure]

Embodiment No. 77 is directed to compounds of formula IA wherein substituent A is:

[structure]

Embodiment No. 78 is directed to compounds of formula IA wherein substituent A is:

[structure]

Embodiment No. 79 is directed to compounds of formula IA wherein substituent A is selected from the group consisting of:

[structures], and and substituent B is selected from the group consisting of:

[structure],

-continued

[structures] and .

Embodiment No. 80 is directed to compounds of formula IA wherein substituent A is selected from the group consisting of:

[structures], and

[structure], and substituent B is selected from the group consisting of:

[structures].

Embodiment No. 81 is directed to novel compounds of formula IA wherein g is 1.

Embodiment No. 82 is directed to novel compounds as described in any one of Embodiments Nos. 1-80 wherein g is 1.

Embodiment No. 83 is directed to novel compounds is directed to novel compounds of formula IA wherein g is 2.

Embodiment No. 84 is directed to novel compounds as described in any one of Embodiments Nos. 1-80 wherein g is 2.

Embodiment No. 85 is directed to novel compounds of formula IA wherein B is as described in any one of the Embodiment Nos. 1 to 64, and A is as defined in any one of the Embodiment Nos. 65 to 78.

Embodiment No. 86 is directed to compounds of formula IA wherein B is as described in any one of the Embodiment Nos. 1 to 64, and A is:

and all other substituents are as defined for formula IA.

Embodiment No. 87 is directed to compounds of formula IA wherein B is as described in any one of the Embodiment Nos. 1 to 64, and A is:

wherein $R^7$ is H, and $R^8$ is alkyl (e.g., methyl, ethyl, isopropyl, cyclopropyl and t-butyl), and all other substituents are as defined for formula IA.

Embodiment No. 88 is directed to compounds of formula IA wherein B is as described in any one of the Embodiment Nos. 1 to 64, and A is:

and all other substituents are as defined for formula IA.

Embodiment No. 89 is directed to compounds of formula IA wherein B is as described in any one of the Embodiment Nos. 1 to 64, and A is:

wherein the furan ring is unsubstituted or substituted as described in the definition of A for formula IA, and all other substituents are as defined for formula IA.

Embodiment No. 90 is directed to compounds of formula IA wherein B is described in any one of the Embodiment Nos. 1 to 64, and A is wherein the furan ring is substituted and all other substituents are as defined for formula IA.

Embodiment No. 91 is directed to compounds of formula IA wherein B is as described in any one of the Embodiment Nos. 1 to 64, and A is wherein the furan ring is substituted with at least one (e.g., 1 to 3, or 1 to 2) alkyl group and all other substituents are as defined for formula IA.

Embodiment No. 92 is directed to compounds of formula IA wherein B is as described in any one of the Embodiment Nos. 1 to 64, A is wherein the furan ring is substituted with one alkyl group and all other substituents are as defined for formula IA.

Embodiment No. 93 is directed to compounds of formula IA wherein B is as described in any one of the Embodiment Nos. 1 to 64, and A is wherein the furan ring is substituted with one $C_1$ to $C_3$ alkyl group (e.g., methyl or isopropyl), and all other substituents are as defined for formula IA.

Embodiment No. 94 is directed to novel compounds of formula IA wherein B is as described in any one of the Embodiment Nos. 1 to 64, and A is as defined in any one of the Embodiment Nos. 89 to 93, except that $R^7$ and $R^8$ are the same or different and each is selected from the group consisting of: H and alkyl.

Embodiment No. 95 is directed to novel compounds of formula IA wherein B is as described in any one of the Embodiment Nos. 1 to 64, and A is as defined in any one of the Embodiment Nos. 89 to 93, except that $R^7$ is H, and $R^8$ is alkyl (e.g., ethyl or t-butyl).

Embodiment No. 96 is directed to compounds of formula IA wherein:

(1) substituent A in formula IA is selected from the group consisting of:

(a)

[Structures: various R⁷R⁸-substituted pyridines, pyridine N-oxides, furan, oxazole, thiophene, phenylalkyl, isoxazole, benzodioxole, cyclopropyl, benzofuran]

wherein the above rings are unsubstituted or substituted, as described for formula IA; and (b)

[Structures: R⁷R⁸C(R⁸ᵃ)—, alkynyl R⁷R⁸CH(CH₂)ₙC≡C—R⁹, and alkenyl R⁷R⁸CH(CH₂)ₙCH=CH—R⁹]

and wherein in (a) and (b) above: each $R^7$ and $R^8$ is independently selected from the group consisting of: H, unsubstituted or substituted alkyl, unsubstituted or substituted aryl, unsubstituted or substituted heteroaryl, unsubstituted or substituted arylalkyl, unsubstituted or substituted heteroarylalkyl, unsubstituted or substituted cycloalkyl, unsubstituted or substituted cycloalkylalkyl, —$CO_2R^{13}$, —$CONR^{13}R^{14}$, fluoroalkyl, alkynyl, alkenyl, and cycloalkenyl, wherein said substituents on said $R^7$ and $R^8$ substituted groups are selected from the group consisting of: a) cyano, b) —$CO_2R^{13}$, c) —$C(O)NR^{13}R^{14}$, d) —$SO_2NR^{13}R^{14}$, e) —$NO_2$, f) —$CF_3$, g) —$OR^{13}$, h) —$NR^{13}R^{14}$, is i) —$OC(O)R^{13}$, j) —$OC(O)NR^{13}R^{14}$, and k) halogen; and $R^{8a}$ and $R^9$ are as defined in formula IA; and (2) substituent B in formula IA is selected from the group consisting of:

[Structures: substituted benzamide with R⁴, R⁵, R⁶, R², R¹³, R¹⁴; pyrrole with R³, R¹², R¹⁰, R²; two pyrazoles with R³, R¹², R²; thiophene with R³, R¹¹, R²]

and wherein $R^2$ to $R^6$ and $R^{10}$ to $R^{14}$ are as defined above for the novel compounds of formula IA.

Embodiment No. 97 is directed to compounds of formula IA wherein:

(1) substituent A in formula IA is selected from the group consisting of:

(a)

[Structures: R⁷R⁸-substituted 4-pyridyl, 3-pyridyl, 2-pyridyl, 4-pyridyl N-oxide, 3-pyridyl N-oxide, 2-pyridyl N-oxide]

-continued wherein the above rings are unsubstituted, or the above rings are substituted with 1 to 3 substituents independently selected from the group consisting of: halogen, alkyl, cycloalkyl, —$CF_3$, cyano, —$OCH_3$, and —$NO_2$; each $R^7$ and $R^8$ is independently selected from the group consisting of: H, alkyl (e.g., methyl, ethyl, t-butyl, and isopropyl), fluoroalkyl (such as, —$CF_3$ and —$CF_2CH_3$), cycloalkyl (e.g., cyclopropyl, and cyclohexyl), and cycloalkylalkyl (e.g., cyclopropylmethyl); and $R^9$ is selected from the group consisting of: H, halogen, alkyl, cycloalkyl, —$CF_3$, cyano, —$OCH_3$, and —$NO_2$; and (b)

wherein each $R^7$ and $R^8$ is independently selected from the group consisting of: H, alkyl (e.g., methyl, ethyl, t-butyl, and isopropyl), fluoroalkyl (such as, —$CF_3$ and —$CF_2CH_3$), cycloalkyl (e.g., cyclopropyl, and cyclohexyl), and cycloalkylalkyl (e.g., cyclopropylmethyl); wherein $R^{8a}$ is as defined in formula IA, and wherein $R^9$ is selected from the group consisting of: H, halogen, alkyl, cycloalkyl, —$CF_3$, cyano, —$OCH_3$, and —$NO_2$; each $R^7$ and $R^8$ is independently selected from the group consisting of: H, alkyl (e.g., methyl, ethyl, t-butyl, and isopropyl), fluoroalkyl (such as, —$CF_3$ and —$CF_2CH_3$), cycloalkyl (e.g., cyclopropyl, and cyclohexyl), and cycloalkylalkyl (e.g., cyclopropylmethyl); and (2) substituent B in formula IA is selected from the group consisting of:

wherein
$R^2$ is selected from the group consisting of: H, OH, —NHC(O)$R^{13}$ or and —NHSO$_2R^{13}$;
$R^3$ is selected from the group consisting of: —SO$_2$NR$^{13}$R$^{14}$, —NO$_2$, cyano, —C(O)NR$^{13}$R$^{14}$, —SO$_2$R$^{13}$; and —C(O)OR$^{13}$;
$R^4$ is selected from the group consisting of: H, —NO$_2$, cyano, —CH$_3$, halogen, and —CF$_3$;
$R^5$ is selected from the group consisting of: H, —CF$_3$, —NO$_2$, halogen and cyano;
$R^6$ is selected from the group consisting of: H, alkyl and —CF$_3$;
each $R^{10}$ and $R^{11}$ is independently selected from the group consisting of: $R^{13}$, hydrogen, halogen, —CF$_3$, —NR$^{13}$R$^{14}$, —NR$^{13}$C(O)NR$^{13}$R$^{14}$, —C(O)OR$^{13}$, —SH, —SO$_{(t)}$NR$^{13}$R$^{14}$, —SO$_2$R$^{13}$, —NHC(O)R$^{13}$, —NHSO$_2$NR$^{13}$R$^{14}$, —NHSO$_2$R$^{13}$, —C(O)NR$^{13}$R$^{14}$, —C(O)NR$^{13}$OR$^{14}$, —OC(O)R$^{13}$, —COR$^{13}$, —OR$^{13}$, and cyano;
each $R^{13}$ and $R^{14}$ is independently selected from the group consisting of: H, methyl, ethyl and isopropyl; or
$R^{13}$ and $R^{14}$ when taken together with the nitrogen they are attached to in the groups —NR$^{13}$R$^{14}$, —C(O)NR$^{13}$R$^{14}$, —SO$_2$NR$^{13}$R$^{14}$, —OC(O)NR$^{13}$R$^{14}$, —CONR$^{13}$R$^{14}$, —NR$^{13}$C(O)NR$^{13}$R$^{14}$, —SO$_t$NR$^{13}$R$^{14}$, —NHSO$_2$NR$^{13}$R$^{14}$ form an unsubstituted or substituted saturated heterocyclic ring (preferably a 3 to 7 membered ring) optionally having one additional heteroatom selected from the group consisting of: O, S or NR$^{18}$; wherein $R^{18}$ is selected from the group consisting of: H, alkyl, aryl, heteroaryl, —C(O)R$^{19}$, —SO$_2$R$^{19}$ and —C(O)NR$^{19}$R$^{20}$; wherein each $R^{19}$ and $R^{20}$ is independently selected from the group consisting of: alkyl, aryl and heteroaryl; wherein there are 1 to 3 substituents on the substituted cyclized $R^{13}$ and $R^{14}$ groups (i.e., the substituents on the ring formed when $R^{13}$ and $R^{14}$ are taken together with the nitrogen to which they are bound) and each substituent is independently selected from the group consisting of: alkyl, aryl, hydroxy, hydroxyalkyl, alkoxy, alkoxyalkyl, arylalkyl, fluoroalkyl, cycloalkyl, cycloalkylalkyl, heteroaryl, heteroarylalkyl, amino, —C(O)OR$^{15}$, —C(O)NR$^{15}$R$^{16}$, —SO$_t$NR$^{15}$R$^{16}$, —C(O)R$^{15}$, —SO$_2$R$^{15}$ provided that $R^{15}$ is not H, —NHC(O)NR$^{15}$R$^{16}$ and halogen; and wherein each $R^{15}$ and $R^{16}$ is independently selected from the group consisting: of H, alkyl, aryl, arylalkyl, cycloalkyl and heteroaryl.

Embodiment No. 98 is directed to compounds of formula IA wherein substituent A in formula IA is even more preferably selected from the group consisting of:

(a) [structures shown]

wherein the above rings are unsubstituted, or the above rings are substituted with 1 to 3 substituents independently selected from the group consisting of: H, F, Cl, Br, alkyl, cycloalkyl, and —$CF_3$; $R^7$ is selected from the group consisting of: H, fluoroalkyl, alkyl and cycloalkyl; $R^8$ is selected form the group consisting of: H, alkyl, —$CF_2CH_3$ and —$CF_3$; and $R^9$ is selected from the group consisting of: H, F, Cl, Br, alkyl or —$CF_3$; and (b) [structure shown]

wherein $R^7$ is selected from the group consisting of: H, fluoroalkyl, alkyl and cycloalkyl; $R^8$ is selected form the group consisting of: H, alkyl, —$CF_2CH_3$ and —$CF_3$; and $R^{8a}$ is as defined for formula IA.

Embodiment No. 99 is directed to compounds of formula IA wherein:

(1) substituent A in formula IA is selected from the group consisting of:

(a) [structures shown]

wherein the above rings are unsubstituted, or the above rings are substituted with 1 to 3 substituents independently selected from the group consisting of: H, F, Cl, Br, alkyl, cycloalkyl, and —$CF_3$; $R^7$ is selected from the group consisting of: H, —$CF_3$, —$CF_2CH_3$, methyl, ethyl, isopropyl, cyclopropyl and t-butyl; and $R^8$ is H; and (b) [structure shown]

wherein $R^7$ is selected from the group consisting of: H, —$CF_3$, —$CF_2CH_3$, methyl, ethyl, isopropyl, cyclopropyl and t-butyl; and $R^8$ is H; and $R^{8a}$ is as defined for formula IA.

(2) substituent B in formula IA is selected from the group consisting of:

[structures shown]

wherein:

$R^2$ is selected from the group consisting of: H, OH, —NHC(O)$R^{13}$ and —NHSO$_2R^{13}$;

$R^3$ is selected from the group consisting of: —C(O)NR$^{13}R^{14}$, —SO$_2$NR$^{13}R^{14}$, —NO$_2$, cyano, —SO$_2R^{13}$; and —C(O)OR$^{13}$;

$R^4$ is selected from the group consisting of: H, —NO$_2$, cyano, alkyl (e.g., —CH$_3$ and ethyl), —CF$_3$, and halogen;

$R^5$ is selected from the group consisting of: H, —CF$_3$, —NO$_2$, halogen and cyano; and $R^6$ is selected from the group consisting of: H, alkyl and —CF$_3$;

$R^{11}$ is selected from the group consisting of: H, halogen and alkyl; and each $R^{13}$ and $R^{14}$ is independently selected from the group consisting of: H, methyl, ethyl and isopropyl; or $R^{13}$ and $R^{14}$ when taken together with the nitrogen they are attached to in the groups —NR$^{13}$R$^{14}$, —C(O)NR$^{13}$R$^{14}$, —SO$_2$NR$^{13}$R$^{14}$, —OC(O)NR$^{13}$R$^{14}$, —CONR$^{13}$R$^{14}$, —NR$^{13}$C(O)NR$^{13}$R$^{14}$, —SO$_t$NR$^{13}$R$^{14}$, —NHSO$_2$NR$^{13}$R$^{14}$ form an unsubstituted or substituted saturated heterocyclic ring (preferably a 3 to 7 membered ring) optionally having one additional heteroatom selected from O, S or NR$^{18}$ wherein R$^{18}$ is selected from H, alkyl, aryl, heteroaryl, —C(O)R$^{19}$, —SO$_2$R$^{19}$ and —C(O)NR$^{19}$R$^{20}$, wherein each R$^{19}$ and R$^{20}$ is independently selected from alkyl, aryl and heteroaryl, wherein there are 1 to 3 substituents on the substituted cyclized R$^{13}$ and R$^{14}$ groups (i.e., on the ring formed when R$^{13}$ and R$^{14}$ are taken together with the nitrogen to which they are bound) and each substituent is independently selected from the group consisting of: alkyl, aryl, hydroxy, hydroxyalkyl, alkoxy, alkoxyalkyl, arylalkyl, fluoroalkyl, cycloalkyl, cycloalkylalkyl, heteroaryl, heteroarylalkyl, amino, —C(O)OR$^{15}$, —C(O)NR$^{15}$R$^{16}$, —SO$_t$NR$^{15}$R$^{16}$, —C(O)R$^{15}$, —SO$_2$R$^{15}$ provided that R$^{15}$ is not H, —NHC(O)NR$^{15}$R$^{16}$ and halogen; and wherein each R$^{15}$ and R$^{16}$ is independently selected from the group consisting of: H, alkyl, aryl, arylalkyl, cycloalkyl and heteroaryl.

Embodiment No. 100 is directed to compounds of formula IA wherein:

(1) substituent A in formula IA is selected from the group consisting of:

(a)

wherein the above rings are unsubstituted, or the above rings are substituted with 1 to 3 substituents independently selected from the group consisting of: F, Cl, Br, alkyl, cycloalkyl, and —CF$_3$; R$^7$ is selected from the group consisting of: H, —CF$_3$, —CF$_2$CH$_3$, methyl, ethyl, isopropyl, cyclopropyl and t-butyl; and R$^8$ is H; and (b)

wherein R$^7$ is selected from the group consisting of: H, —CF$_3$, —CF$_2$CH$_3$, methyl, ethyl, isopropyl, cyclopropyl and t-butyl; and R$^8$ is H; and R$^{8a}$ is as defined for formula IA;

(2) substituent B in formula IA is selected from the group consisting of:

wherein:

$R^2$ is selected from the group consisting of: H, OH, —NHC(O)R$^{13}$ and —NHSO$_2$R$^{13}$;

$R^3$ is selected from the group consisting of: —C(O)NR$^{13}$R$^{14}$ —SO$_2$NR$^{13}$R$^{14}$, —NO$_2$, cyano, and —SO$_2$R$^{13}$;

$R^4$ is selected from the group consisting of: H, —NO$_2$, cyano, alkyl (e.g., —CH$_3$ and ethyl), —CF$_3$ and halogen;

$R^5$ is selected from the group consisting of: H, —CF$_3$, —NO$_2$, halogen and cyano; and $R^6$ is selected from the group consisting of: H, alkyl and —CF$_3$;

$R^{11}$ is selected from the group consisting of: H, halogen and alkyl; and each $R^{13}$ and $R^{14}$ is independently selected from the group consisting of: H and unsubstituted alkyl (e.g., methyl and ethyl).

Embodiment No. 101 is directed to compounds of formula IA wherein:

(1) substituent A in formula IA is selected from the group consisting of:

(2) substituent B in formula IA is selected from the group consisting of:

wherein:

R² is —OH;

R³ is selected from the group consisting of: —SO₂NR¹³R¹⁴ and —CONR¹³R¹⁴;

R⁴ is selected form the group consisting of: H. Br, —CH₃, ethyl and —CF₃;

R⁵ is selected from the group consisting of: H and cyano;

R⁶ is selected from the group consisting of: H, —CH₃ and —CF₃;

R¹¹ is H; and

R¹³ and R¹⁴ are independently selected from the group consisting of H and methyl (e.g., for —SO₂NR¹³R¹⁴ both R¹³ and R¹⁴ are H, or both R¹³ and R¹⁴ are methyl, also, for example, for —CONR¹³R¹⁴ both R¹³ and R¹⁴ are methyl).

Embodiment No. 102 is directed to compounds of formula IA wherein substituent A is as defined in Embodiment No. 70 and substituent B is as defined in Embodiment No. 57.

Embodiment No. 103 is directed to compounds of formula IA wherein substituent A is as defined in Embodiment No. 70 and substituent B is as defined in Embodiment No. 58.

Embodiment No. 104 is directed to compounds of formula IA wherein substituent A is as defined in Embodiment No. 70 and substituent B is as defined in Embodiment No. 59.

Embodiment No. 105 is directed to compounds of formula IA wherein substituent A is as defined in Embodiment No. 71 and substituent B is as defined in Embodiment No. 57.

Embodiment No. 106 is directed to compounds of formula IA wherein substituent A is as defined in Embodiment No. 71 and substituent B is as defined in Embodiment No. 58.

Embodiment No. 107 is directed to compounds of formula IA wherein substituent A is as defined in Embodiment No. 71 and substituent B is as defined in Embodiment No. 59.

Embodiment No. 108 is directed to compounds of formula IA wherein substituent A is as defined in Embodiment No. 72 and substituent B is as defined in Embodiment No. 57.

Embodiment No. 109 is directed to compounds of formula IA wherein substituent A is as defined in Embodiment No. 72 and substituent B is as defined in Embodiment No. 58.

Embodiment No. 110 is directed to compounds of formula IA wherein substituent A is as defined in Embodiment No. 72 and substituent B is as defined in Embodiment No. 59.

Embodiment No. 111 is directed to compounds of formula IA wherein substituent A is as defined in Embodiment No. 73 and substituent B is as defined in Embodiment No. 57.

Embodiment No. 112 is directed to compounds of formula IA wherein substituent A is as defined in Embodiment No. 73 and substituent B is as defined in Embodiment No. 58.

Embodiment No. 113 is directed to compounds of formula IA wherein substituent A is as defined in Embodiment No. 73 and substituent B is as defined in Embodiment No. 59.

Embodiment No. 114 is directed to any one of the Embodiment Nos. 1 to 113 wherein the compound of formula IA is a pharmaceutically acceptable salt.

Embodiment No. 115 is directed to any one of the Embodiment Nos. 1 to 113 wherein the compound of formula IA is a sodium salt.

Embodiment No. 116 is directed to any one of the Embodiment Nos. 1 to 113 wherein the compound of formula IA is a calcium salt.

Embodiment No. 117 is directed to a pharmaceutically acceptable salt of any one of the representative compounds of this invention that are described below.

Embodiment No. 118 is directed to a sodium salt of any one of the representative compounds described below.

Embodiment No. 119 is directed to a calcium salt of any one of the representative compounds described below.

Embodiment No. 120 is directed to a pharmaceutical composition comprising at least one (e.g., 1 to 3, usually 1) compound of formula IA as described in any one of Embodiment Nos. 1 to 119 in combination with a pharmaceutically acceptable carrier (or diluent). When more than one compound is used each compound is independently selected from the group consisting of Embodiment Nos. 1 to 119.

Embodiment No. 121 is directed to a method of treating any one of the diseases described herein (i.e., the chemokine mediated diseases) comprising administering to a patient in need of such treatment an effective amount (e.g., a therapeutically effective amount) of a compound of formula IA as described in any one of the Embodiment Nos. 1 to 119.

Embodiment No. 122 is directed to a method of treating any one of the diseases described herein (i.e., the chemokine mediated diseases) comprising administering to a patient in need of such treatment an effective amount (e.g., a therapeutically effective amount) of the pharmaceutical composition described in Embodiment No. 120.

Embodiment No. 123 is directed to a method of treating rheumatoid arthritis in a patient in need of such treatment comprising administering to said patient a therapeutically effective amount of at least one (usually one) compound from any of Embodiment Nos. 1 to 119. When more than one compound is used each compound is independently selected from the group consisting of Embodiment Nos. 1 to 119.

Embodiment No. 124 is directed to a method of treating rheumatoid arthritis in a patient in need of such treatment comprising administering to said patient a therapeutically effective amount of the pharmaceutical composition described in Embodiment No. 120.

Embodiment No. 125 is directed to a method of treating rheumatoid arthritis in a patient in need of such treatment comprising administering to said patient a therapeutically effective amount of at least one (usually 1) compound from any of Embodiment Nos. 1 to 119 in combination with at least one compound selected from the group consisting of COX-2 inhibitors, COX inhibitors, immunosuppressives (e.g., methotrexate, cyclosporin, leflunimide and sulfasalazine), steroids (e.g., betamethasone, cortisone and dexamethasone), PDE IV inhibitors, anti-TNF-α compounds, MMP inhibitors, glucocorticoids, chemokine inhibitors, CB2-selective inhibitors, and other classes of compounds indicated for the treatment of rheumatoid arthritis. When more than one compound of Embodiment Nos. 1 to 119 is used, each compound is independently selected from said Embodiment Numbers.

Embodiment No. 126 is directed to a method of treating rheumatoid arthritis in a patient in need of such treatment comprising administering to said patient a therapeutically effective amount of the pharmaceutical composition described in Embodiment 120 in combination with at least one compound selected from the group consisting of COX-2 inhibitors, COX inhibitors, immunosuppressives (e.g., methotrexate, cyclosporin, leflunimide and sulfasalazine), steroids (e.g., betamethasone, cortisone and dexamethasone), PDE IV inhibitors, anti-TNF-α compounds, MMP inhibitors, glucocorticoids, chemokine inhibitors, CB2-selective inhibitors, and other classes of compounds indicated for the treatment of rheumatoid arthritis.

Embodiment No. 127 is directed to a method of treating COPD in a patient in need of such treatment comprising administering to said patient a therapeutically effective amount of at least one (usually one) compound from any of Embodiment Nos. 1 to 119. When more than one compound is used each compound is independently selected from the group consisting of Embodiment Nos. 1 to 119.

Embodiment No. 128 is directed to a method of treating COPD in a patient in need of such treatment comprising administering to said patient a therapeutically effective amount of the pharmaceutical composition described in Embodiment 120.

Embodiment No. 129 is directed to a method of treating acute pain in a patient in need of such treatment comprising administering to said patient a therapeutically effective amount of at least one (usually one) compound from any of Embodiment Nos. 1 to 119. When more than one compound is used each compound is independently selected from the group consisting of Embodiment Nos. 1 to 119.

Embodiment No. 130 is directed to a method of treating acute pain in a patient in need of such treatment comprising administering to said patient a therapeutically effective amount of the pharmaceutical composition described in Embodiment No. 120.

Embodiment No. 131 is directed to a method of treating acute inflammatory pain in a patient in need of such treatment comprising administering to said patient a therapeutically effective amount of at least one (usually one) compound from any of Embodiment Nos. 1 to 119. When more than one compound is used each compound is independently selected from the group consisting of Embodiment Nos. 1 to 119.

Embodiment No. 132 is directed to a method of treating acute inflammatory pain in a patient in need of such treatment comprising administering to said patient a therapeutically effective amount of the pharmaceutical composition described in Embodiment No. 120.

Embodiment No. 133 is directed to a method of treating chronic inflammatory pain in a patient in need of such treatment comprising administering to said patient a therapeutically effective amount of at least one (usually one) compound from any of Embodiment Nos. 1 to 119. When more than one compound is used each compound is independently selected from the group consisting of Embodiment Nos. 1 to 119.

Embodiment No. 134 is directed to a method of treating chronic inflammatory pain in a patient in need of such treatment comprising administering to said patient a therapeutically effective amount of the pharmaceutical composition described in Embodiment No. 120.

Embodiment No. 135 is directed to a method of treating neuropathic pain in a patient in need of such treatment comprising administering to said patient a therapeutically effective amount of at least one (usually one) compound from any of Embodiment Nos. 1 to 119. When more than one compound is used each compound is independently selected from the group consisting of Embodiment Nos. 1 to 119.

Embodiment No. 136 is directed to a method of treating neuropathic pain in a patient in need of such treatment comprising administering to said patient a therapeutically effective amount of the pharmaceutical composition described in Embodiment No. 120.

Embodiment No. 137 is directed to a method of treating arthritis in a patient in need of such treatment comprising administering to said patient a therapeutically effective amount of at least one (usually one) compound from any of Embodiment Nos. 1 to 119. When more than one compound is used each compound is independently selected from the group consisting of Embodiment Nos. 1 to 119.

Embodiment No. 138 is directed to a method of treating arthritis in a patient in need of such treatment comprising administering to said patient a therapeutically effective amount of the pharmaceutical composition described in Embodiment No. 120.

Embodiment No. 139 is directed to a method of treating osteoarthritis in a patient in need of such treatment comprising administering to said patient a therapeutically effective amount of at least one (usually one) compound from any of Embodiment Nos. 1 to 119. When more than one compound is used each compound is independently selected from the group consisting of Embodiment Nos. 1 to 119.

Embodiment No. 140 is directed to a method of treating osteoarthritis in a patient in need of such treatment comprising administering to said patient a therapeutically effective amount of the pharmaceutical composition described in Embodiment No. 120.

Representative compounds of the invention include but are not limited to:

-continued

-continued

-continued

-continued

-continued

-continued

-continued

99

-continued

100

-continued the pharmaceutically acceptable salts thereof, and the pharmaceutically acceptable solvates thereof.

Preferred compounds of this invention are selected from the group consisting of:

-continued

-continued 107 108
-continued -continued

-continued

-continued

-continued the pharmaceutically acceptable salts thereof, and the pharmaceutically acceptable solvates thereof.

Most preferred compounds of this invention are selected from the group consisting of:

-continued

-continued

-continued

-continued the pharmaceutically acceptable salts thereof, and the pharmaceutically acceptable solvates thereof.

-continued

-continued (a12), (a13), (a14), (a15), (a16), (a17), (a18), (a19), (a20), (a21), (a22)

(a23), (a24), (a25), (a26), (a27), (a28), (a29), (a30), (a31), (a32)

(a33), (a34), (a35), (a36), (a37), (a38), (a39), (a40), (a41), (a41a)

the pharmaceutically acceptable salts, and the pharmaceutically acceptable solvates thereof.

An embodiment of this invention is directed to compounds of formula IA selected from the group consisting of compounds of the formula:

-continued (a28), (a29), (a30), (a31), (a32), (a33), (a34), (a35), (a36), (a37)

-continued the pharmaceutically acceptable salts thereof, and the pharmaceutically acceptable solvates thereof.

Certain compounds of the invention may exist in different stereoisomeric forms (e.g., enantiomers, diastereoisomers and atropisomers). The invention contemplates all such stereoisomers both in pure form and in admixture, including racemic mixtures. Isomers can be prepared using conventional methods.

Certain compounds will be acidic in nature, e.g. those compounds which possess a carboxyl or phenolic hydroxyl group. These compounds may form pharmaceutically acceptable salts. Examples of such salts may include sodium, potassium, calcium, aluminum, gold and silver salts. Also contemplated are salts formed with pharmaceutically acceptable amines such as ammonia, alkyl amines, hydroxyalkylamines, N-methylglucamine and the like.

Certain basic compounds also form pharmaceutically acceptable salts, e.g., acid addition salts. For example, the pyrido-nitrogen atoms may form salts with strong acid, while compounds having basic substituents such as amino groups also form salts with weaker acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those skilled in the art. The salts are prepared by contacting the free base form with a sufficient amount of the desired acid to produce a salt in the conventional manner. The free base forms may be regenerated by treating the salt with a suitable dilute aqueous base solution such as dilute aqueous NaOH, potassium carbonate, ammonia and sodium bicarbonate. The free base forms differ from their respective salt forms somewhat in certain physical properties, such as solubility in polar solvents, but the acid and base salts are otherwise equivalent to their respective free base forms for purposes of the invention.

All such acid and base salts are intended to be pharmaceutically acceptable salts within the scope of the invention and all acid and base salts are considered equivalent to the free forms of the corresponding compounds for purposes of the invention.

Compounds of formula IA can exist in unsolvated and solvated forms, including hydrated forms. In general, the solvated forms, with pharmaceutically acceptable solvents such as water, ethanol and the like, are equivalent to the unsolvated forms for the purposes of this invention.

This invention also includes Prodrugs of the novel compounds of this invention. The term "prodrug," as used herein, represents compounds which are rapidly transformed in vivo to the parent compound of the above formula, for example, by hydrolysis in blood. A thorough discussion is provided in T.

Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

This invention also includes the compounds of this invention in isolated and pure form.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington: The Science and Practice of Pharmacy, $20^{th}$ Edition, (2000), Lippincott Williams & Wilkins, Baltimore, Md.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal composition can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 0.01 mg to about 1000 mg, preferably from about 0.01 mg to about 750 mg, more preferably from about 0.01 mg to about 500 mg, and most preferably from about 0.01 mg to about 250 mg, according to the particular application.

The actual dosage employed may be varied depending upon the requirements of the patient and the severity of the condition being treated. Determination of the proper dosage regimen for a particular situation is within the skill of the art. For convenience, the total dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 0.04 mg/day to about 4000 mg/day, in two to four divided doses.

Classes of compounds that can be used as the chemotherapeutic agent (antineoplastic agent) include: alkylating agents, antimetabolites, natural products and their derivatives, hormones and steroids (including synthetic analogs), and synthetics. Examples of compounds within these classes are given below.

Alkylating agents (including nitrogen mustards, ethylenimine derivatives, alkyl sulfonates, nitrosoureas and triazenes): Uracil mustard, Chlormethine, Cyclophosphamide (Cytoxan®), Ifosfamide, Melphalan, Chlorambucil, Pipobroman, Triethylene-melamine, Triethylenethiophosphoramine, Busulfan, Carmustine, Lomustine, Streptozocin, Dacarbazine, and Temozolomide.

Antimetabolites (including folic acid antagonists, pyrimidine analogs, purine analogs and adenosine deaminase inhibitors): Methotrexate, 5-Fluorouracil, Floxuridine, Cytarabine, 6-Mercaptopurine, 6-Thioguanine, Fludarabine phosphate, Pentostatine, and Gemcitabine.

Natural products and their derivatives (including vinca alkaloids, antitumor antibiotics, enzymes, lymphokines and epipodophyllotoxins): Vinblastine, Vincristine, Vindesine, Bleomycin, Dactinomycin, Daunomubicin, Doxorubicin, Epirubicin, Idarubicin, paclitaxel (paclitaxel is commercially available as Taxol® and is described in more detail below in the subsection entitled "Microtubule Affecting Agents"), Mithramycin, Deoxyco-formycin, Mitomycin-C, L-Asparaginase, Interferons (especially IFN-a), Etoposide, and Teniposide.

Hormones and steroids (including synthetic analogs): 17α-Ethinylestradiol, Diethylstilbestrol, Testosterone, Prednisone, Fluoxymesterone, Dromostanolone propionate, Testolactone, Megestrolacetate, Tamoxifen, Methylprednisolone, Methyl-testosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, Zoladex.

Synthetics (including inorganic complexes such as platinum coordination complexes): Cisplatin, Carboplatin, Hydroxyurea, Amsacrine, Procarbazine, Mitotane, Mitoxantrone, Levamisole, and Hexamethylmelamine.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR), e.g., 2002 edition (Medical Economics Company, Montvale, N.J. 07645-1742, USA); the disclosure of which is incorporated herein by reference thereto.

As used herein, a microtubule affecting agent is a compound that interferes with cellular mitosis, i.e., having an anti-mitotic effect, by affecting microtubule formation and/or action. Such agents can be, for instance, microtubule stabilizing agents or agents that disrupt microtubule formation.

Microtubule affecting agents useful in the invention are well known to those of skill in the art and include, but are not limited to allocolchicine (NSC 406042), Halichondrin B (NSC 609395), colchicine (NSC 757), colchicine derivatives (e.g., NSC 33410), dolastatin 10 (NSC 376128), maytansine (NSC 153858), rhizoxin (NSC 332598), paclitaxel (Taxol®, NSC 125973), Taxol® derivatives (e.g., derivatives (e.g., NSC 608832), thiocolchicine (NSC 361792), trityl cysteine (NSC 83265), vinblastine sulfate (NSC 49842), vincristine sulfate (NSC 67574), epothilone A, epothilone, and discodermolide (see Service, (1996) *Science,* 274:2009) estramustine, nocodazole, MAP4, and the like. Examples of such agents are also described in the scientific and patent literature, see, e.g., Bulinski (1997) *J. Cell Sci.* 110:3055-3064; Panda (1997) *Proc. Natl. Acad. Sci. USA* 94:10560-10564; Muhiradt (1997) *Cancer Res.* 57:3344-3346; Nicolaou (1997) *Nature* 387:268-272; Vasquez (1997) *Mol. Biol. Cell.* 8:973-985; Panda (1996) *J. Biol. Chem.* 271:29807-29812.

Particularly preferred agents are compounds with paclitaxel-like activity. These include, but are not limited to paclitaxel and paclitaxel derivatives (paclitaxel-like compounds) and analogues. Paclitaxel and its derivatives are available commercially. In addition, methods of making paclitaxel and paclitaxel derivatives and analogues are well known to those of skill in the art (see, e.g., U.S. Pat. Nos. 5,569,729; 5,565,478; 5,530,020; 5,527,924; 5,508,447; 5,489,589; 5,488,116; 5,484,809; 5,478,854; 5,478,736; 5,475,120; 5,468,769; 5,461,169; 5,440,057; 5,422,364; 5,411,984; 5,405,972; and 5,296,506).

More specifically, the term "paclitaxel" as used herein refers to the drug commercially available as Taxol® (NSC number: 125973). Taxol® inhibits eukaryotic cell replication by enhancing polymerization of tubulin moieties into stabilized microtubule bundles that are unable to reorganize into the proper structures for mitosis. Of the many available chemotherapeutic drugs, paclitaxel has generated interest because of its efficacy in clinical trials against drug-refractory tumors, including ovarian and mammary gland tumors (Hawkins (1992) *Oncology,* 6: 17-23, Horwitz (1992) *Trends Pharmacol. Sci.* 13: 134-146, Rowinsky (1990) *J. Natl. Canc. Inst.* 82: 1247-1259).

Additional microtubule affecting agents can be assessed using one of many such assays known in the art, e.g., a semiautomated assay which measures the tubulin-polymerizing activity of paclitaxel analogs in combination with a cellular assay to measure the potential of these compounds to block cells in mitosis (see Lopes (1997) *Cancer Chemother. Pharmacol.* 41:37-47).

Generally, activity of a test compound is determined by contacting a cell with that compound and determining whether or not the cell cycle is disrupted, in particular, through the inhibition of a mitotic event. Such inhibition may be mediated by disruption of the mitotic apparatus, e.g., disruption of normal spindle formation. Cells in which mitosis is interrupted may be characterized by altered morphology (e.g., microtubule compaction, increased chromosome number, etc.).

Compounds with possible tubulin polymerization activity can be screened in vitro. In a preferred embodiment, the compounds are screened against cultured WR21 cells (derived from line 69-2 wap-ras mice) for inhibition of proliferation and/or for altered cellular morphology, in particular for microtubule compaction. In vivo screening of positive-testing compounds can then be performed using nude mice bearing the WR21 tumor cells. Detailed protocols for this screening method are described by Porter (1995) *Lab. Anim. Sci.,* 45(2):145-150.

Other methods of screening compounds for desired activity are well known to those of skill in the art. Typically such assays involve assays for inhibition of microtubule assembly and/or disassembly. Assays for microtubule assembly are described, for example, by Gaskin et al. (1974) *J. Molec. Biol.,* 89: 737-758. U.S. Pat. No. 5,569,720 also provides in vitro and in vivo assays for compounds with paclitaxel-like activity.

Methods for the safe and effective administration of the above-mentioned microtubule affecting agents are known to those skilled in the art. In addition, their administration is described in the standard literature. For example, the administration of many of the chemotherapeutic agents is described in the "Physicians' Desk Reference" (PDR), e.g., 1996 edition (Medical Economics Company, Montvale, N.J. 07645-1742, USA); the disclosure of which is incorporated herein by reference thereto.

The amount and frequency of administration of the compounds of formula IA and the chemotherapeutic agents and/or radiation therapy will be regulated according to the judgment of the attending clinician (physician) considering such factors as age, condition and size of the patient as well as severity of the disease being treated. A dosage regimen of the compound of formula IA can be oral administration of from 10 mg to 2000 mg/day, preferably 10 to 1000 mg/day, more preferably 50 to 600 mg/day, in two to four (preferably two) divided doses, to block tumor growth. Intermittant therapy (e.g., one week out of three weeks or three out of four weeks) may also be used.

The chemotherapeutic agent and/or radiation therapy can be administered according to therapeutic protocols well known in the art. It will be apparent to those skilled in the art that the administration of the chemotherapeutic agent and/or radiation therapy can be varied depending on the disease being treated and the known effects of the chemotherapeutic agent and/or radiation therapy on that disease. Also, in accordance with the knowledge of the skilled clinician, the therapeutic protocols (e.g., dosage amounts and times of administration) can be varied in view of the observed effects of the administered therapeutic agents (i.e., antineoplastic agent or radiation) on the patient, and in view of the observed responses of the disease to the administered therapeutic agents.

In the methods of this invention, a compound of formula IA is administered concurrently or sequentially with a chemotherapeutic agent and/or radiation. Thus, it is not necessary that, for example, the chemotherapeutic agent and the compound of formula IA, or the radiation and the compound of formula IA, should be administered simultaneously or essentially simultaneously. The advantage of a simultaneous or essentially simultaneous administration is well within the determination of the skilled clinician.

Also, in general, the compound of formula IA and the chemotherapeutic agent do not have to be administered in the same pharmaceutical composition, and may, because of different physical and chemical characteristics, have to be administered by different routes. For example, the compound of formula IA may be administered orally to generate and maintain good blood levels thereof, while the chemotherapeutic agent may be administered intravenously. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

The particular choice of a compound of formula IA, and chemotherapeutic agent and/or radiation will depend upon the diagnosis of the attending physicians and their judgement of the condition of the patient and the appropriate treatment protocol.

The compound of formula IA, and chemotherapeutic agent and/or radiation may be administered concurrently (e.g., simultaneously, essentially simultaneously or within the same treatment protocol) or sequentially, depending upon the nature of the proliferative disease, the condition of the patient, and the actual choice of chemotherapeutic agent and/or radiation to be administered in conjunction (i.e., within a single treatment protocol) with the compound of formula or IA.

If the compound of formula IA, and the chemotherapeutic agent and/or radiation are not administered simultaneously or essentially simultaneously, then the initial order of administration of the compound of formula IA, and the chemotherapeutic agent and/or radiation, may not be important. Thus, the compound of formula IA may be administered first, followed by the administration of the chemotherapeutic agent and/or radiation; or the chemotherapeutic agent and/or radiation may be administered first, followed by the administration of the compound of formula IA. This alternate administration may be repeated during a single treatment protocol. The determination of the order of administration, and the number of repetitions of administration of each therapeutic agent during a treatment protocol, is well within the knowledge of the skilled physician after evaluation of the disease being treated and the condition of the patient.

For example, the chemotherapeutic agent and/or radiation may be administered first, especially if it is a cytotoxic agent, and then the treatment continued with the administration of the compound of formula IA followed, where determined advantageous, by the administration of the chemotherapeutic agent and/or radiation, and so on until the treatment protocol is complete.

Thus, in accordance with experience and knowledge, the practicing physician can modify each protocol for the administration of a component (therapeutic agent—i.e., the compound of formula IA, chemotherapeutic agent or radiation) of the treatment according to the individual patient's needs, as the treatment proceeds.

The attending clinician, in judging whether treatment is effective at the dosage administered, will consider the general well-being of the patient as well as more definite signs such as relief of disease-related symptoms, inhibition of tumor growth, actual shrinkage of the tumor, or inhibition of metastasis. Size of the tumor can be measured by standard methods such as radio-logical studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment.

BIOLOGICAL EXAMPLES

The compounds of the present invention are useful in the treatment of CXC-chemokine mediated conditions and diseases. This utility is manifested in their ability to inhibit IL-8 and GRO-α chemokine as demonstrated by the following in vitro assays.

Receptor Binding Assays:

CXCR1 SPA Assay

For each well of a 96 well plate, a reaction mixture of 10 µg hCXCR1-CHO overexpressing membranes (Biosignal) and 200 µg/well WGA-SPA beads (Amersham) in 100 µl was prepared in CXCR1 assay buffer (25 mM HEPES, pH 7.8, 2 mM $CaCl_2$, 1 mM $MgCl_2$, 125 mM NaCl, 0.1% BSA) (Sigma). A 0.4 nM stock of ligand, [125I]-IL-8 (NEN) was prepared in the CXCR1 assay buffer. 20× stock solutions of test compounds were prepared in DMSO (Sigma). A 6× stock solution of IL-8 (R&D) was prepared in CXCR2 assay buffer. The above solutions were added to a 96-well assay plate (PerkinElmer) as follows: 10 µl test compound or DMSO, 40 µl CXCR1 assay buffer or IL-8 stock, 100 µl of reaction mixture, 50 µl of ligand stock (Final [Ligand]=0.1 nM). The assay plates were shaken for 5 minutes on plate shaker, then incubated for 8 hours before cpm/well were determined in Microbeta Trilux counter (PerkinElmer). % Inhibition of Total binding-NSB (250 nM IL-8) was determined for $IC_{50}$ values.

Alternative CXCR1 SPA Assay

Protocol using CXCR1-expressing membranes from Biosignal Packard

For each 50 µl reaction, a working stock of 0.25 µg/µl hCXCR1-CHO over-expressing membranes with a specific activity of 0.05 pmol/mg (Biosignal Packard) and 25 µg/µl WGA-SPA beads (Perkin Elmer Life Sciences) was prepared in CXCR1 assay buffer (25 mM HEPES, pH 7.8, 0.1 mM $CaCl_2$, 1 mM $MgCl_2$, 100 mM NaCl) (Sigma). This mixture was incubated on ice for 30 minutes and then centrifuged at 2500 rpm for 5 minutes. The beads and membranes were resuspended in CXCR1 assay buffer to the same concentrations as in the original mixture. A 0.125 nM stock of ligand, [$^{125}$I]-IL-8 (Perkin Elmer Life Sciences), was prepared in the CXCR1 assay buffer. Test compounds were first serially diluted by half-logs in DMSO (Sigma) and then diluted 20-fold in CXCR1 assay buffer. The above solutions were added to a Corning NBS (non-binding surface) 96-well assay plate as follows: 20 µl test compound or 5% DMSO (final [DMSO]=2%), 20 µl of membranes and SPA bead mixture (Final [membrane]=5 µg/reaction; Final [SPA bead]=500 µg/reaction), 10 µl of ligand stock (Final [$^{125}$I-IL-8]=0.025 nM). The assay plates were incubated for 4 hours before cpm/well were determined in a Microbeta Trilux counter (Perkin Elmer Life Sciences). $IC_{50}$ values were quantified using nonlinear regression analysis in GraphPad Prism.

Alternative CXCR1 SPA Assay

Protocol Using CXCR1-Expressing Membranes from Euroscreen

For each 50 µl reaction, a working stock of 0.025 µg/µl hCXCR1-CHO over-expressing membranes with a specific activity of 3.47 pmol/mg (Euroscreen) and 5 µg/µl WGA-SPA beads (Perkin Elmer Life Sciences) was prepared in CXCR1 assay buffer (25 mM HEPES, pH 7.8, 2.0 mM $CaCl_2$, 1 mM $MgCl_2$, 125 mM NaCl) (Sigma). This mixture was incubated on ice for 5 minutes. A 0.125 nM stock of ligand, [$^{125}$I]-IL-8 (Perkin Elmer Life Sciences), was prepared in the CXCR1 assay buffer. Test compounds were first serially diluted by half-logs in DMSO (Sigma) and then diluted 13.3-fold in CXCR1 assay buffer. The above solutions were added to a Corning NBS (non-binding surface) 96-well assay plate as follows: 20 µl test compound or 7.5% DMSO (final [DMSO]= 3%), 20 µl of membranes and SPA bead mixture (Final [membrane]=0.5 µg/reaction; Final [SPA bead]=100 µg/reaction), 10 µl of ligand stock (Final [$^{125}$I-IL-8]=0.025 nM). The assay plates were incubated for 4 hours before cpm/well were determined in a Microbeta Trilux counter (Perkin Elmer Life Sciences). $IC_{50}$ values were quantified using nonlinear regression analysis in GraphPad Prism.

For the CXCR1 assay, compounds of this invention had an $IC_{50}$ of <20 µM. Most preferred compounds (a1) to (a21) had a $K_i$ within the range of 4 nM to 3000 nM. The compound of Example 56 (i.e., (a9)) had a $K_i$ of 4 nM, the compound of Example 201.1 (i.e., (a20)) had a $K_i$ of 123 nM, and the compound of Example 201.9 (i.e., (a21)) had a $K_i$ of 50 nM.

CXCR2 SPA Assay

For each well of a 96 well plate, a reaction mixture of 4 µg hCXCR2-CHO overexpressing membranes (Biosignal) and 200 μg/well WGA-SPA beads (Amersham) in 100 μl was prepared in CXCR2 assay buffer (25 mM HEPES, pH 7.4, 2 mM CaCl$_2$, 1 mM MgCl$_2$). A 0.4 nM stock of ligand, [125I]-IL-8 (NEN), was prepared in the CXCR2 assay buffer. 20× stock solutions of test compounds were prepared in DMSO (Sigma). A 6× stock solution of GRO-α (R&D) was prepared in CXCR2 assay buffer. The above solutions were added to a 96-well assay plate (PerkinElmer or Corning) as follows: 10 μl test compound or DMSO, 40 ul CXCR2 assay buffer or GRO-α stock, 100 μl of reaction mixture, 50 μl of ligand stock (Final [Ligand]=0.1 nM). When 40× stock solutions of test compounds in DMSO were prepared, then the above protocol was used except instead 5 μl test compound or DMSO and 45 μl CXCR2 assay buffer were used. The assay plates were shaken for 5 minutes on a plate shaker, then incubated for 2-8 hours before cpm/well were determined in Microbeta Trilux counter (PerkinElmer). % Inhibition of total binding minus non-specific binding (250 nM Gro-α or 50 μM antagonist) was determined and IC50 values calculated. Compounds of this invention had an IC$_{50}$ of <5 μM.

Alternative CXCR2 SPA Assay

Protocol Using the CXCR2 50 μl Assay

For each 50 μl reaction, a working stock of 0.031 μg/μl hCXCR2-CHO over-expressing membranes with a specific activity of 0.4 pmol/mg (Biosignal Packard) and 2.5 μg/μl WGA-SPA beads (Perkin Elmer Life Sciences) was prepared in CXCR2 assay buffer (25 mM HEPES, pH 7.4, 2.0 mM CaCl$_2$, 1 mM MgCl$_2$) (Sigma). This mixture was incubated on ice for 5 minutes. A 0.50 nM stock of ligand, [$^{125}$I]-IL-8 (Perkin Elmer Life Sciences), was prepared in the CXCR2 assay buffer. Test compounds were first serially diluted by half-logs in DMSO (Sigma) and then diluted 13.3-fold in CXCR2 assay buffer. The above solutions were added to a Corning NBS (non-binding surface) 96-well assay plate as follows: 20 μl test compound or 7.5% DMSO (final [DMSO]= 3%), 20 μl of membranes and SPA bead mixture (final [membrane]=0.625 μg/reaction; final [SPA bead]=50 μg/reaction), 10 μl of ligand stock (final [$^{125}$I-IL-8]=0.10 nM). The assay plates were incubated for 2 hours before cpm/well were determined in a Microbeta Trilux counter (Perkin Elmer Life Sciences). IC$_{50}$ values were quantified using nonlinear regression analysis in GraphPad Prism.

Alternative CXCR2 SPA Assay

Protocol Using the CXCR2 200 μl Assay

For each 200 μl reaction, a working stock of 0.02 μg/μl hCXCR2-CHO over-expressing membranes with a specific activity of 0.6 pmol/mg (Biosignal Packard) and 2 μg/μl WGA-SPA beads (Perkin Elmer Life Sciences) was prepared in CXCR2 assay buffer (25 mM HEPES, pH 7.4, 2.0 mM CaCl$_2$, 1 mM MgCl$_2$) (Sigma). This mixture was incubated on ice for 5 minutes. A 0.40 nM stock of ligand, [$^{125}$I]-IL-8 (Perkin Elmer Life Sciences), was prepared in the CXCR2 assay buffer. Test compounds were first serially diluted by half-logs in DMSO (Sigma) and then diluted 20-fold in CXCR2 assay buffer. The above solutions were added to a Corning NBS (non-binding surface) 96-well assay plate as follows: 50 μl test compound or 10% DMSO (final [DMSO]= 2.5%), 100 μl of membranes and SPA bead mixture (final [membrane]=2 μg/reaction; final [SPA bead]=200 μg/reaction), 50 μl of ligand stock (final [$^{125}$I-IL-8]=0.10 nM). The assay plates were incubated for 2 hours before cpm/well were determined in a Microbeta Trilux counter (Perkin Elmer Life Sciences). IC$_{50}$ values were quantified using nonlinear regression analysis in GraphPad Prism.

For the CXCR2 assay, most preferred compounds (a1) to (a21) had a K$_i$ within the range of 2 nM to 36 nM. The compound of Example 56 (i.e., (a9)) had a K$_i$ of 7 nM, the compound of Example 201.1 (i.e., (a20)) had a K$_i$ of 3.5 nM, and the compound of Example 201.9 (i.e., (a21)) had a K$_i$ of 2.7 nM.

Calcium Fluorescence Assay (FLIPR)

HEK 293 cells stably transfected with hCXCR2 and Gαi/q were plated at 10,000 cells per well in a Poly-D-Lysine Black/Clear plate (Becton Dickinson) and incubated 48 hours at 5% CO$_2$, 37° C. The cultures were then incubated with 4 mM fluo-4, AM (Molecular Probes) in Dye Loading Buffer (1% FBS, HBSS w. Ca & Mg, 20 mM HEPES (Cellgro), 2.5 mM Probenicid (Sigma) for 1 hour. The cultures were washed with wash buffer (HBSS w Ca, & Mg, 20 mM HEPES, Probenicid (2.5 mM)) three times, then 100 μl/well wash buffer was added.

During incubation, compounds were prepared as 4× stocks in 0.4% DMSO (Sigma) and wash buffer and added to their respective wells in the first addition plate. IL-8 or GRO-α (R&D Systems) concentrations were prepared 4× in wash buffer+0.1% BSA and added to their respective wells in second addition plate.

Culture plate and both addition plates were then placed in the FLIPR imaging system to determine change in calcium fluorescence upon addition of compound and then ligand. Briefly, 50 μl of compound solutions or DMSO solution was added to respective wells and change in calcium fluorescence measured by the FLIPR for 1 minute. After a 3 minute incubation within the instrument, 50 μl of ligand was then added and the change in calcium fluorescence measured by the FLIPR instrument for 1 minute. The area under each stimulation curve was determined and values used to determine % Stimulation by compound (agonist) and % Inhibition of Total Calcium response to ligand (0.3 nM IL-8 or GRO-α) for IC50 values of the test compounds.

Chemotaxis Assays for 293-CXCR2

A chemotaxis assay is setup using Fluorblok inserts (Falcon) for 293-CXCR2 cells (HEK-293 cells overexpressing human CXCR2). The standard protocol used at present is as follows:

1. Inserts are coated with collagen IV (2 ug/ml) for 2 hrs at 37° C.
2. The collagen is removed and inserts are allowed to air dry overnight.
3. Cells are labeled with 10 uM calcein AM (Molecular Probes) for 2 hrs. Labeling is done in complete media with 2% FBS.
4. Dilutions of compound are made in minimal media (0.1% BSA) and placed inside the insert which is positioned inside the well of a 24 well plate. Within the well is IL-8 at a concentration of 0.25 nM in minimal media. Cells are washed and resuspended in minimal media and placed inside the insert at a concentration of 50,000 cells per insert.
5. Plate is incubated for 2 hrs and inserts are removed and placed in a new 24 well. Fluorescence is detected at excitation=485 nM and emission=530 nM.

Cytotoxicity Assays

A cytotoxicity assay for CXCR2 compounds is conducted on 293-CXCR2 cells. Concentrations of compounds are tested for toxicity at high concentrations to determine if they may be used for further evaluation in binding and cell based assays. The protocol is as follows:

1. 293-CXCR2 cells are plated overnight at a concentration of 5000 cells per well in complete media.
2. Dilutions of compound are made in minimal media w/0.1% BSA. Complete media is poured off and the dilutions of compound are added. Plates are incubated for 4, 24 and 48 hrs. Cells are labeled with 10 uM calcein AM for 15 minutes to determine cell viability. Detection method is the same as above.

Soft Agar Assay 10,000 SKMEL-5 cells/well are placed in a mixture of 1.2% agar and complete media with various dilutions of compound. Final concentration of agar is 0.6%. After 21 days viable cell colonies are stained with a solution of MTT (1 mg/ml in PBS). Plates are then scanned to determine colony number and size. IC$_{50}$ is determined by comparing total area vs. compound concentration.

CCR7 Membrane Preparation.

Ba/F3-CCR7 membranes were prepared as previously described (Hipkin et al., *J. Biol. Chem.*, 272, 1997, 13869-76). Cells were pelleted by centrifugation, incubated in homogenization buffer (10 mM Tris-HCl, 5 mM EDTA, 3 mM EGTA, pH 7.6) and 1 µM PMSF for 30 min. on ice. The cells were then lysed with a Dounce homogenizer using stirrer type RZR3 polytron homogenizer (Caframo, Wiarton, Ont.) with 12 strokes at 900 RPM. The intact cells and nuclei were removed by centrifugation at 500×g for 5 min. The cell membranes in the supernatant were then pelleted by centrifugation at 100,000×g for 30 min. The membranes were then resuspended in glygly buffer (20 mM glycylglycine, 1 mM MgCl$_2$, 250 mM sucrose, pH 7.2), aliquoted, quick frozen and stored at −80° C.

CCR7 [$^{35}$S]GTPγS Exchange Assay.

The exchange of guanosine 5'-[γ-$^{35}$S]triphospate ([$^{35}$S]GTPγS, triethylammonium salt; specific activity 1250 Ci/mmol; NEN Boston, Mass.) was measured using a scintillation proximity assay (SPA) as previously described (Cox, et. al., *Mol. Pharmacol.*, 59, 2001, 707-15). For each assay point, 2 µg of membrane was preincubated for 30 min at room temperature with 200 µg wheat germ agglutinin-coated SPA beads (WGA-SPA; Amersham, Arlington Heights, Ill.) in SPA binding buffer (50 mM HEPES, 10 mM MgCl$_2$, 1 mM EDTA, 100 mM NaCl, 0.1% BSA, pH 7.6). The beads and membranes were transferred to a 96-well Isoplate (Wallac, Gaithersburg, Md.) and incubated with 10 µM guanosine 5'-diphosphate (GDP) in the presence or absence of 2 nM MIP-30 and/or compounds for 60 min at room temperature. The incubation continued for another 60 min. following the addition of 0.1 nM [$^{35}$S]GTPγS. Membrane-bound [$^{35}$S]GTPγS was measured using a 1450 Microbeta Trilux counter (Wallac, Gaithersburg, Md.).

There were compounds of this invention that had an EC$_{50}$ of <10 µM. The compound of Example 2065 had an EC$_{50}$ of 13 nM, the compound of Example 2066 had an EC$_{50}$ of 16 nM, the compound of Example 2105 had an EC$_{50}$ of 3 nM, and the compound of Example 2106 had an EC$_{50}$ of 12 nM.

Compounds of formula IA may be produced by processes known to those skilled in the art, in the following reaction schemes, and in the preparations and examples below.

A general procedure for the preparation of compounds of formula IA is as follows:

Compounds of this invention are prepared by condensing an amine (either A-NH$_2$ or B—NH$_2$) with dimethoxythiadiazoledioxide to give the monomethoxy-thiadiazoledioxide intermediate. Subsequent condensation of this intermediate with the commercially available or prepared amine (either A-NH$_2$ or B—NH$_2$) provides the desired chemokine antagonist.

Thiadiazoleoxide compounds are prepared similarly starting with dimethoxythiadiazoleoxide. Sequential condensation with amine A-NH$_2$ or B—NH$_2$ as described above provides the desired antagonist.

The invention disclosed herein is exemplified by the following preparations and examples which should not be construed to limit the scope of the disclosure. Alternative mechanistic pathways and analogous structures may be apparent to those skilled in the art.

Preparative Example 1

3-Nitrosalicylic acid (500 mg, 2.7 mmol), DCC (563 mg) and ethyl acetate (10 mL) were combined and stirred for 10 min. (R)-(–)-2-pyrrolidinemethanol (0.27 mL) was added and the resulting suspension was stirred at room temperature overnight. The solid was filtered and the filtrate washed with 1N NaOH. The aqueous phase was acidified and extracted with EtOAc. The resulting organic phase was dried over anhydrous MgSO$_4$, filtered and concentrated in vacuo. Purification of the residue by preparative plate chromatography (silica gel, 5% MeOH/CH$_2$Cl$_2$ saturated with AcOH) gave the product (338 mg, 46%, MH$^+$=267).

Preparative Example 2

Step A

3-Nitrosalicylic acid (9.2 g), bromotripyrrolidinophosphonium hexafluorophosphate (PyBroP, 23 g) and N,N-diisopropylethylamine (DIEA, 26 mL) in anhydrous CH$_2$Cl$_2$ (125 mL) were combined and stirred at 25° C. for 30 min. (R)-(+)-3-pyrrolidinol (8.7 g) in CH$_2$Cl$_2$ (25 mL) was added over 25 min and the resulting suspension was stirred at room temperature overnight. The mixture was extracted with 1M NaOH (aq) and the organic phase was discarded. The aqueous phase was acidified with 1M HCl (aq), extracted with EtOAc, dried over anhydrous Na$_2$SO$_4$, filtered and concentrated in vacuo to afford the crude product (7 g) which was used without further purification.

Step B

The crude product from Step A above was stirred with 10% Pd/C (0.7 g) in MeOH (100 mL) under a hydrogen gas atmosphere overnight. The reaction mixture was filtered through celite, the filtrate concentrated in vacuo, and the resulting residue purified by column chromatography (silica gel, 10% MeOH/CH$_2$Cl$_2$ saturated with NH$_4$OH) to give the product (2.5 g, 41%, MH+=223).

Preparative Example 2.1

To N—BOC-3-(amino)piperidine (0.5 g) dissolved in CH$_2$Cl$_2$ (10 mL) was added benzylisocyanate (3 mmol). After stirring for 2 hrs, amine scavenger resin (1.9 mmol) was added and the mixture was stirred overnight, filtered, the resin back-washed with CH$_2$Cl$_2$ and methanol, and the organics concentrated in vacuo. Stirring of the crude material in 4N HCl/dioxane (40 mL) for 2.5 hrs before concentrating in vacuo gave the title compound (41%, MH+=369).

Preparative Example 2.2-2.6

Following the procedures set forth in Preparative Example 2.1 but using the isocyanate (or chloroformate) indicated in the Table below, the amines were obtained and used without further purification.

| Prep Ex. | Amine | Isocyanate | Amine |
|---|---|---|---|
| 2.2 | H$_2$N-piperidine-NH | cyclopentyl-NCO | cyclopentyl-NH-C(O)-NH-piperidine-NH |
| 2.3 | H$_2$N-piperidine-NH | phenyl-NCO | phenyl-NH-C(O)-NH-piperidine-NH |

| Prep Ex. | Amine | Isocyanate | Amine |
|---|---|---|---|
| 2.4 | H₂N-(3-aminopiperidine) | ethyl-NCO | ethyl-NHC(O)NH-(3-piperidinyl) |
| 2.5 | H₂N-(3-aminopiperidine) | benzyl chloroformate analog (CH₂-O-C(O)-Cl) | ethoxycarbonylamino-(3-piperidinyl) |
| 2.6 | H₂N-(3-aminopyrrolidine) | ethyl-NCO | ethyl-NHC(O)NH-(3-pyrrolidinyl) |

Preparative Example 2.7

To N—BOC-3-(amino)piperidine (5 mmol) dissolved in CH$_2$Cl$_2$ (30 mL) was added trifluoromethanesulfonic anhydride (5 mmol) and the mixture was stirred overnight. The mixture was concentrated in vacuo, diluted with CH$_2$Cl$_2$ (10 mL) and treated with trifluoroacetic acid (10 mL). After stirring for 2 hr, the mixture was concentrated in vacuo to give the title compound (43%, MH+=233.1).

Preparative Example 2.8

Step A

3-Nitrosalicylic acid (5 mmol) and N-hydroxysuccinimide (5 mmol) were added to a solution of 2% DMF/CH$_2$Cl$_2$, followed by DCC (5 mmol). After stirring for 2 hr, the mixture was filtered and concentrated in vacuo and the residue used directly in Step B.

Step B

The product from Step A above was suspended in DMF and to this was added morpholino-2-carboxylic acid HCl (5 mmol) in CH$_2$Cl$_2$ (10 mL)/DMF (5 mL) and diisopropylethylamine (10 mmol). The mixture was stirred overnight, filtered, basified with 1N NaOH (50 mL), washed with CH$_2$Cl$_2$, acidified with 5N HCl and extracted with EtOAc. The organic phase was dried over Na$_2$SO$_4$, filtered and concentrated in vacuo to give the desired compound which was used directly in Step C (MH+=296).

Step C

Following a similar procedure as in Preparative Example 2 Step B, but using the product from Step B above, the title compound was obtained (23%, MH+=267).

Preparative Example 2.9

Step A

2-Piperazinecarboxylic acid and 2-chloro-1,3-pyrimidine were stirred with triethylamine and MeOH. After stirring overnight at reflux, the mixture was filtered and concentrated in vacuo to give the desired compound which was used directly in Step B (MH+=209).

Step B

Following a similar procedure as Preparative Example 2.8, Step B except using the product from Preparative Example 2.9 Step A above, the desired compound was obtained (41%, MH+=374).

Step C

Following a similar procedure as in Preparative Example 2, Step B, but using the product from Step B above, the desired compound was obtained (99%, MH+=344).

Preparative Example 2.10

Step A

Following a similar procedure as Preparative Example 2.8, Step A except using 3-nitrobenzoic acid, the desired compound was obtained and used directly in Step B.

Step B

Following a similar procedure as Preparative Example 2.8, Step B except using the products from Preparative Example 2.9, Step A and Preparative Example 2.10, Step A, the desired compound was obtained (86%).

Step C

Following a similar procedure as in Preparative Example 2, Step B, but using the product from Step B above, the desired compound was obtained (67%, MH+=331).

Preparative Example 2.11

Step A

N-Benzylpiperidone (2 g, HCl salt, hydrate) was stirred with THF (20 mL), concentrated to dryness, and placed under high vac. The residue was diluted in THF (20 mL), and methyllithium was added (2.5 eq of 1.6N in $Et_2O$) via syringe. After stirring for 3 hr, the mixture was concentrated in vacuo, diluted with water, extracted with $CH_2Cl_2$, and dried over $Na_2SO_4$. Filtration and concentrating in vacuo gave the desired product (50%, MH+=205).

Step B

Following a similar procedure as in Preparative Example 2, Step B, but using the product from Step A above, the title compound was obtained (95%, MH+=116).

Preparative Example 2.12

Step A

To N-benzyl-N-methylamine (20 mmol) dissolved in acetone (50 mL) was added concentrated HCl (20 mmol), paraformaldehyde (30 mmol) and 2-propanol (2 mL). After stirring at reflux overnight, the mixture was concentrated in vacuo, diluted with water, basified to pH 14 and extracted with ether. The organic phase was dried over $Na_2SO_4$, filtered and concentrated in vacuo to give the desired product (98%) which was used directly in Step B.

Step B

The product from Step A above (500 mg) was dissolved in MeOH (20 mL) and to this was added $NaBH_4$ (50 mg). After stirring for 10 min, the solution was concentrated in vacuo to give the desired compound which was used directly in Step C without purification.

Step C

The product from Step B above was diluted with MeOH (20 mL) and to this was added AcOH (0.1 mL), a catalytic amount of Pd/C (10%) and the mixture stirred under $H_2$ atmosphere (balloon) overnight. The mixture was filtered, 4N HCl in dioxane (1 mL) was added, and the mixture was concentrated in vacuo to give the desired compound that was used directly without purification.

Preparative Example 2.13

Step A

Following a similar procedure as Preparative Example 2, Step A except using methyl glycinate, the desired ester was obtained. The mixture was poured into 200 mL of 1N NaOH, then extracted with dichloromethane. The pH was adjusted to 1 and NaCl was added until saturation. After several hours, the resulting precipitate was filtered and washed with cold water to give the desired product (42%).

Step B

Following a similar procedure as in Preparative Example 2 Step B, but using the product from Step A above, the title compound was obtained (95%).

Preparative Example 2.14

Step A

Following a similar procedure as in Preparative Example 2.13, Step A except using methyl N-methylglycinate, the desired product was obtained (18%).

Step B

Following a similar procedure as in Preparative Example 2, Step B, but using the product from Step A above, the title compound was obtained (95%, MH+=225).

Preparative Example 2.16

The above n-oxide (2 g) was combined with $H_2NMe/H_2O$ (15 cm$^3$) and heated to 140° C. overnight. Potassium carbonate (1.3 g) added and the mixture concentrated in vacuo. Extraction with EtOH and concentration of the filtrate in vacuo gave 1.56 g of crude amine (MH+=125).

Preparative Example 3-10.50

Following the procedures set forth in Preparative Examples 1-2 but using the carboxylic acid, amine, and coupling agent [DCC (Prep. Ex. 1) or PyBrop (Prep. Ex. 2)] listed in the Table below, the indicated amide products were obtained and used without further purification.

| Prep Ex. | Carboxylic acid | Amine | Product 1. Coupling Agent 2. % yield 3. MH+ |
|---|---|---|---|
| 3 | 3-nitro-2-hydroxybenzoic acid | dimethylamine | N,N-dimethyl-3-nitro-2-hydroxybenzamide<br>1. PyBrop<br>2. 87, 86<br>3. 181 |
| 4 | 3-nitro-2-hydroxybenzoic acid | N-methylisopropylamine | N-isopropyl-N-methyl-3-amino-2-hydroxybenzamide<br>1. PyBroP<br>2. 49<br>3. 209 |
| 5 | 3-nitro-2-hydroxybenzoic acid | $NH_3$ | 3-amino-2-hydroxybenzamide<br>1. PyBroP<br>2. 95<br>3. 153 |
| 6 | 3-nitro-2-hydroxybenzoic acid | $CH_3NH_2$ | N-methyl-3-amino-2-hydroxybenzamide<br>1. PyBroP<br>2. 83<br>3. 167 |
| 7 | 3-nitro-2-hydroxybenzoic acid | morpholine | (3-amino-2-hydroxyphenyl)(morpholino)methanone<br>1. PyBroP<br>2. 76<br>3. 223 |

-continued

| Prep Ex. | Carboxylic acid | Amine | Product<br>1. Coupling Agent<br>2. % yield<br>3. MH+ |
|---|---|---|---|
| 8 | 3-nitro-2-hydroxy-benzoic acid (HO₂C, NO₂, OH) | 3-hydroxyazetidine | 1-(3-amino-2-hydroxybenzoyl)-3-hydroxyazetidine<br>1. PyBroP<br>2. 65, 53<br>3. 209 |
| 9 | 3-nitro-2-hydroxy-benzoic acid | pyrrolidine | (3-amino-2-hydroxyphenyl)(pyrrolidin-1-yl)methanone<br>1. PyBroP<br>2. 59, 69<br>3. 207 |
| 10 | 3-nitro-2-hydroxy-benzoic acid | (3R)-3-(hydroxymethyl)pyrrolidine | (3-amino-2-hydroxyphenyl)[(3R)-3-(hydroxymethyl)pyrrolidin-1-yl]methanone<br>1. PyBroP<br>2. 49, 86<br>3. 237 |
| 10.1 | 3-nitro-2-hydroxy-benzoic acid | cyclopropylamine | 3-amino-N-cyclopropyl-2-hydroxybenzamide<br>1. PyBroP<br>2. 30, 88<br>3. 193 |
| 10.2 | 3-nitro-2-hydroxy-benzoic acid | isopropylamine | 3-amino-2-hydroxy-N-isopropylbenzamide<br>1. PyBroP<br>2. 26, 87<br>3. 195 |
| 10.3 | 3-nitro-2-hydroxy-benzoic acid | n-butylamine | 3-amino-N-butyl-2-hydroxybenzamide<br>1. PyBroP<br>2. 38<br>3. 209 |

-continued

| Prep Ex. | Carboxylic acid | Amine | Product 1. Coupling Agent 2. % yield 3. MH+ |
|---|---|---|---|
| 10.4 | 3-nitro-2-hydroxy-benzoic acid | isobutylamine | N-isobutyl 3-amino-2-hydroxybenzamide<br>1. PyBroP<br>2. 29<br>3. 209 |
| 10.5 | 3-nitro-2-hydroxy-benzoic acid | 3-pentylamine | N-(pentan-3-yl) 3-amino-2-hydroxybenzamide<br>1. PyBroP<br>2. 38<br>3. 223 |
| 10.6 | 3-nitro-2-hydroxy-benzoic acid | 2.7 N-(piperidin-3-yl)trifluoromethanesulfonamide | 1. PyBroP<br>2. 32, 99<br>3. 367, 9 |
| 10.7 | 3-nitro-2-hydroxy-benzoic acid | 3-hydroxypiperidine | 1. PyBroP<br>2. 35, 99<br>3. 237 |
| 10.8 | 3-nitro-2-hydroxy-benzoic acid | thiazolidine-4-carboxylic acid | 1. DCC<br>2. 30, 99<br>3. 269 |

-continued

| Prep Ex. | Carboxylic acid | Amine | Product 1. Coupling Agent 2. % yield 3. MH+ |
|---|---|---|---|
| 10.9 | HO₂C-C₆H₃(NO₂)(OH) | 2.11 3-methyl-3-hydroxypiperidine | 1. PyBroP 2. 58, 95 3. 233.1 |
| 10.10 | HO₂C-C₆H₃(NO₂)(OH) | 2.12 4-(methylamino)-2-butanol | 1. PyBroP 2. 42, 95 3. 238.9 |
| 10.13 | HO₂C-C₆H₃(NO₂)(OH) | 2.4 N-ethyl-N'-(piperidin-3-yl)urea | 1. PyBroP 2. 51, 95 3. 307 |
| 10.14 | HO₂C-C₆H₃(NO₂)(OH) | 2.2 N-cyclopentyl-N'-(piperidin-3-yl)urea | 1. PyBroP 2. 55 3. 347 |
| 10.15 | HO₂C-C₆H₃(NO₂)(OH) | 2.1 N-benzyl-N'-(piperidin-3-yl)urea | 1. PyBroP 2. 41 3. 369.1 |
| 10.16 | HO₂C-C₆H₃(NO₂)(OH) | 2.3 N-phenyl-N'-(piperidin-3-yl)urea | 1. PyBroP 2. 56 3. 354.9 |

-continued

| Prep Ex. | Carboxylic acid | Amine | Product
1. Coupling Agent
2. % yield
3. MH+ |
|---|---|---|---|
| 10.17 | 3-nitro salicylic acid | 2.5 ethyl (piperidin-3-yl)carbamate | 1. PyBroP
2. 56
3. 308 |
| 10.18 | 3-nitro salicylic acid | 12.4 (morpholin-2-yl)methanol | 1. PyBroP
2. 10, 95
3. 252.9 |
| 10.19 | 3-nitro salicylic acid | N-methylcyclohexylamine | 1. PyBroP
2. 42, 95
3. 249 |
| 10.20 | 3-nitro salicylic acid | 2-(piperidin-2-yl)ethanol | 1. PyBroP
2. 15, 95
3. 264.9 |

-continued

| Prep Ex. | Carboxylic acid | Amine | Product 1. Coupling Agent 2. % yield 3. MH+ |
|---|---|---|---|
| 10.21 | HO₂C—(3-NO₂, 2-OH-phenyl) | (R)-HO-CH₂-CH(NH₂)-Ph | 3-amino-2-hydroxy-N-[(1R)-2-hydroxy-1-phenylethyl]benzamide<br>1. PyBroP<br>2. 64, 95<br>3. 273 |
| 10.22 | HO₂C—(3-NO₂, 2-OH-phenyl) | 3-HO-C₆H₄-NH-Et | 3-amino-N-ethyl-2-hydroxy-N-(3-hydroxyphenyl)benzamide<br>1. PyBroP<br>2. 45, 95<br>3. 273 |
| 10.23 | HO₂C—(3-NO₂, 2-OH-phenyl) | tBuO-CO-CH₂-CH₂-NH₂ | tert-butyl 3-(3-amino-2-hydroxybenzamido)propanoate<br>1. PyBroP<br>2. 44, 95<br>3. 281 |
| 10.24 | HO₂C—(3-NO₂, 2-OH-phenyl) | 3-pyridyl-CH₂-NH-Me | 3-amino-2-hydroxy-N-methyl-N-(pyridin-3-ylmethyl)benzamide<br>1. PyBroP<br>2. 41, 95<br>3. 281.1 |

-continued

| Prep Ex. | Carboxylic acid | Amine | Product 1. Coupling Agent 2. % yield 3. MH+ |
|---|---|---|---|
| 10.25 | 3-nitrosalicylic acid | N-methylbenzylamine | 3-amino-2-hydroxy-N-benzyl-N-methylbenzamide 1. PyBroP 2. 48, 95 3. 257 |
| 10.26 | 3-nitrosalicylic acid | 3-piperidine | (3-aminopiperidin-1-yl)(3-amino-2-hydroxyphenyl)methanone 1. DCC 2. 15, 99 3. 235 |
| 10.28 | 3-nitrosalicylic acid | (S)-prolinol | 1. PyBroP 2. 52, 95 3. 237.1 |
| 10.29 | 3-nitrosalicylic acid | 2-(methylamino)phenol | 1. PyBroP 2. 31, 95 3. 259.1 |
| 10.30 | 3-nitrosalicylic acid | 2-(hydroxymethyl)piperidine | 1. PyBroP 2. 54, 95 3. 250.9 |

-continued

| Prep Ex. | Carboxylic acid | Amine | Product 1. Coupling Agent 2. % yield 3. MH+ |
|---|---|---|---|
| 10.31 | 3-nitrosalicylic acid | 2-(methylamino)ethanol | 3-amino-2-hydroxy-N-(2-hydroxyethyl)-N-methylbenzamide<br>1. PyBroP<br>2. 64, 95<br>3. 210.9 |
| 10.32 | 3-nitrosalicylic acid | ethanolamine | 3-amino-2-hydroxy-N-(2-hydroxyethyl)benzamide<br>1. PyBroP<br>2. 47, 95<br>3. 197 |
| 10.33 | 3-nitrosalicylic acid | 2-anilinoethanol | 3-amino-2-hydroxy-N-(2-hydroxyethyl)-N-phenylbenzamide<br>1. PyBroP<br>2. 47, 95<br>3. 273 |
| 10.34 | 3-nitrosalicylic acid | 4-hydroxypiperidine | (3-amino-2-hydroxyphenyl)(4-hydroxypiperidin-1-yl)methanone<br>1. PyBroP<br>2. 51, 95<br>3. 237.1 |
| 10.35 | 3-nitrosalicylic acid | sarcosinamide | 2-(3-amino-2-hydroxy-N-methylbenzamido)acetamide<br>1. PyBroP<br>2. 60, 90<br>3. 224 |

-continued

| Prep Ex. | Carboxylic acid | Amine | Product 1. Coupling Agent 2. % yield 3. MH+ |
|---|---|---|---|
| 10.36 | 3-nitrosalicylic acid | MeNHCH2C(O)NMe2 | 3-amino-2-hydroxy-N-methyl-N-(dimethylcarbamoylmethyl)benzamide<br>1. PyBroP<br>2. 65, 99<br>3. 252 |
| 10.37 | 3-nitrosalicylic acid | MeNHCH2CO2Me | 3-amino-2-hydroxy-N-methyl-N-(methoxycarbonylmethyl)benzamide<br>1. PyBroP<br>2. 58, 99<br>3. 239 |
| 10.38 | 3-nitrosalicylic acid | piperidine | (3-amino-2-hydroxyphenyl)(piperidin-1-yl)methanone<br>1. PyBroP<br>2. 35, 99<br>3. 221.1 |
| 10.39 | 3-nitrosalicylic acid | azepane | (3-amino-2-hydroxyphenyl)(azepan-1-yl)methanone<br>1. PyBroP<br>2. 42, 99<br>3. 235.2 |
| 10.40 | 3-nitrosalicylic acid | ethyl piperidine-3-carboxylate | ethyl 1-(3-amino-2-hydroxybenzoyl)piperidine-3-carboxylate<br>1. DCC<br>2. 32, 99<br>3. 293.1 |

-continued

| Prep Ex. | Carboxylic acid | Amine | Product 1. Coupling Agent 2. % yield 3. MH+ |
|---|---|---|---|
| 10.41 | 3-nitrosalicylic acid | (3R)-3-hydroxypyrrolidine | 1. PyBroP<br>2. 45, 99<br>3. 223.1 |
| 10.42 | 3-nitrosalicylic acid | 3-(hydroxymethyl)piperidine | 1. PyBroP<br>2. 55, 81<br>3. 251.1 |
| 10.43 | 3-nitrosalicylic acid | 2-(ethylamino)ethanol | 1. PyBroP<br>2. 68, 66<br>3. 224.9 |
| 10.44 | 3-nitrosalicylic acid | diethanolamine | 1. PyBroP<br>2. 68, 66<br>3. 241.1 |
| 10.45 | 3-nitrosalicylic acid | 12.3 | 1. PyBroP<br>2. 44, 40<br>3. 295 |

-continued

| Prep Ex. | Carboxylic acid | Amine | Product 1. Coupling Agent 2. % yield 3. MH+ |
|---|---|---|---|
| 10.46 | HO2C, OH, NO2 (3-nitro salicylic acid) | piperidine-2-carboxylic acid (HO-C(=O) on piperidine NH) | amide product<br>1. DCC<br>2. 37, 81<br>3. 265 |
| 10.47 | HO2C, OH, NO2 | 1-ethyl-3-(pyrrolidin-3-yl)urea | amide product<br>1. PyBroP<br>2. 71, 95<br>3. 293.1 |
| 10.48 | HO2C, OH, NO2 | 5-amino-tetrazole | amide product<br>1. PyBroP<br>2. 35, 99<br>3. 220.9 |
| 10.49 | HO2C, OH, NO2 | tert-butylamine | amide product<br>1. DCC<br>2. 16, 99<br>3. 209.0 |
| 10.50 | HO2C, OH, NO2 | piperidine-3-carboxamide | amide product<br>1. DCC<br>2. 18, 99<br>3. 264.0 |

Preparative Example 10.55

Alternative Procedure for Preparative Example 3

Step A

To the nitrosalicylic acid (3 g) dissolved dichloromethane (150 mL) at room temperature was added oxalyl chloride (4.3 mL) and DMF (0.01 eq.). After stirring for one day the mixture was concentrated in a vacuum to give a semi solid which was used directly in step B.

Step B

To the material from step A diluted in dichloromethane (50 mL) and cooled to 0° C. was added dimethyl amine in THF (2N solution, 24.6 mL) and triethylamine (4 eq.). After stirring for 24 hours at room temperature the mixture was concentrated in vacuo, diluted with 1M sodium hydroxide (30 mL) and after a half hour was washed with dichloromethane. The aqueous phase was acidified with 6M HCl (aq), extracted with dichloromethane and the organic phase was washed with water, dried over $Na_2SO_4$ and concentrated to give the title compound (3.2 g, 93%).

Step C

A mixture of the product from step B above (6 g), 10% Pd/C (0.6 g), and EtOH (80 mL) was stirred in a parr shaker under hydrogen (40 psi) at room temperature for 2 days. Filtration through celite and concentration in vacuo afforded the title product (5.1 g, 99%, MH$^+$=181).

Preparative Example 11

Step A

Following a similar procedure as in Preparative Example 1 except using dimethylamine (2M in THF, 33 mL) and 5-methylsalicylic acid (5 g), the desired product was prepared (6.5 g).

Step B

Nitric acid (0.8 mL) in $H_2SO_4$ was added to a cooled (−20° C.) suspension of the product from Step A above (3 g) in $H_2SO_4$ (25 mL). The mixture was treated with 50% NaOH (aq) dropwise, extracted with $CH_2Cl_2$, dried over anhydrous $MgSO_4$, filtered and concentrated in vacuo to give the product as a crude solid (2.1 g, 44%, MH$^+$=225).

Step C

The product was prepared in the same manner as described in Step B of Preparative Example 2 (0.7 g, 99%, MH$^+$=195).

Preparative Example 11.1

Preparative Example 11.10

Step A
Following the procedure set forth in Preparative Example 1, but using N-hydroxysuccinimide and 2% DMF in CH$_2$Cl$_2$, the desired amide was obtained (33%, MH+=297).

Step B
Following the procedure set forth in Preparative Example 2, Step B, the amine was prepared (99%, MH+=267).

Preparative Example 11.11-11.18

Following the procedures set forth in Preparative Examples 11.11 but using the carboxylic acid, amine, and coupling agent DCC indicated, the indicated amide products were obtained and used without further purification.

Step A
The above amine was reacted with the acid using the procedure set forth in Preparative Example 2, Step A to yield the desired amide (54%).

Step B
Na$_2$S$_2$O$_4$ (1.22 g) was dissolved in water (4 ml) followed by the addition of NH$_3$/H$_2$O (300 ul). The solution was then added to the product from Step A (200 mg) in dioxane (4 ml) and stirred for 30 min. The crude material was purified via flash column chromatography (CH$_2$Cl$_2$/MeOH, 20:1) to give 100 mg of product (56%, MH+=251).

Preparative Example 11.2

Following the procedures set forth in Preparative Example 11.1, Steps A and B, but using N-methylmethoxylamine, the title compound was obtained (86%, MH+=181).

| Prep Ex. | Carboxylic acid | Amine | Product | 1. % Yield 2. MH$^+$ |
|---|---|---|---|---|
| 11.11 | | | | 1. 45, 92 2. 310.0 |
| 11.12 | | | | 1. 45, 92 2. 247.2 |
| 11.13 | | | | 1. 85, 85 2. 251.1 |

-continued

| Prep Ex. | Carboxylic acid | Amine | Product | 1. % Yield 2. MH+ |
|---|---|---|---|---|
| 11.14 | 3-nitrosalicylic acid | 1-amino-2-propanol | N-(2-hydroxypropyl) 3-amino-2-hydroxybenzamide | 1. 99, 92 2. 211.1 |
| 11.15 | 3-nitrosalicylic acid | piperidine-4-carboxylic acid | 1-(3-amino-2-hydroxybenzoyl)piperidine-4-carboxylic acid | 1. 48, 84 2. 265 |
| 11.16 | 3-nitrosalicylic acid | N,N,N'-trimethylethylenediamine | 3-amino-N-(2-(dimethylamino)ethyl)-2-hydroxy-N-methylbenzamide | 1. 78, 91 2. 238.1 |
| 11.17 | 3-nitrosalicylic acid | piperidine-3-carboxylic acid | 1-(3-amino-2-hydroxybenzoyl)piperidine-3-carboxylic acid | 1. 67, 90 2. 265.1 |
| 11.18 | 3-nitrosalicylic acid | morpholine-2-carboxylic acid | 4-(3-amino-2-hydroxybenzoyl)morpholine-2-carboxylic acid | 1. 28, 99 2. 267 |

Preparative Example 12

Step A

Following a similar procedure as described in Preparative Example 2 Step A except using dimethylamine in place of R-(+)-3-pyrrolidinol, the desired product was prepared.

Step B

The product from step A above (8 g) was combined with iodine (9.7 g), silver sulfate (11.9 g), EtOH (200 mL) and water (20 mL) and stirred overnight. Filtration, concentration of the filtrate, re-dissolution in $CH_2Cl_2$ and washing with 1M HCl (aq) gave an organic solution which was dried over anhydrous $MgSO_4$, filtered and concentrated in vacuo to afford the product (7.3 g, 57%, $MH^+$=337).

Step C

The product from Step B above (3.1 g) was combined with DMF (50 mL) and MeI (0.6 mL). NaH (60% in mineral oil, 0.4 g) was added portionwise and the mixture was stirred overnight. Concentration in vacuo afforded a residue which was diluted with $CH_2Cl_2$, washed with 1M NaOH (aq), dried over anhydrous $MgSO_4$, filtered and concentrated in vacuo. Purification through a silica gel column (EtOAc/Hex, 1:1) gave the desired compound (1.3 g, 41%, $MH^+$=351).

Step D

The product from Step D above (200 mg), $Zn(CN)_2$ (132 mg), $Pd(PPh_3)_4$ (130 mg) and DMF (5 mL) were heated at 80° C. for 48 hrs, then cooled to room temperature and diluted with EtOAc and 2M $NH_4OH$. After shaking well, the organic extract was dried over anhydrous $MgSO_4$, filtered, concentrated in vacuo and purified by preparative plate chromatography (Silica, EtOAc/Hex, 1:1) to give the desired compound (62 mg, 44%, $MH^+$=250).

Step E $BBr_3$ (1.3 mL, 1M in $CH_2Cl_2$) was added to a $CH_2Cl_2$ solution (5 mL) of the product from step D above (160 mg) and stirred for 30 min. The mixture was diluted with water, extracted with $CH_2Cl_2$, dried over anhydrous $MgSO_4$, filtered, and concentrated in vacuo to give the desired compound (158 mg, $MH^+$=236).

Step F

A mixture of the product from step E above (160 mg), platinum oxide (83%, 19 mg), and EtOH (20 mL) was stirred under hydrogen (2540 psi) for 1.5 hr. Filtration through celite and concentration in vacuo afforded the product (165 mg, $MH^+$=206).

Preparative Example 12.1

Step A

Following a similar procedure as in Preparative Example 2, Step A except using 3-(methylaminomethyl)pyridine and 3-nitrosalicylic acid, the desired compound was prepared (41%).

Step B

The compound from Step A above (0.3 g) was diluted with chloroform (15 mL) and stirred with mCPBA (0.4 g) for 2 hr. Purification by column chromatography (silica, 10% MeOH/ $CH_2Cl_2$) gave the pyridyl N-oxide (0.32 g, 100%, $MH^+$=303.9).

Step C

Following a similar procedure as in Preparative Example 11.1, Step B, but using the product from Step B above, the desired compound was obtained (15%, MH+=274).

Preparative Example 12.2

Step A

3-Nitrosalicylic acid (4 g) in MeOH (100 mL) and concentrated $H_2SO_4$ (1 mL) were stirred at reflux overnight, concentrated in vacuo, diluted with $CH_2Cl_2$, and dried over $Na_2SO_4$.

Purification by column chromatography (silica, 5% MeOH/CH₂Cl₂) gave the methyl ester (2.8 g, 65%).

Step B

Following a similar procedure as in Preparative Example 2, Step B, but using the product from Step A above, the desired compound was obtained (95%, MH+=167.9).

Preparative Example 12.3

To morpholine-2-carboxilic acid (200 mg) in EtOH (41 mL) at 0° C. was added acetyl chloride (3 mL) and the mixture was stirred at reflux overnight. Concentration in vacuo, dilution with CH₂Cl₂ and washing with NaHCO₃ (aq) gave the title compound (99%, MH⁺=160.1).

Preparative Example 12.4

To N-Boc morpholine-2-carboxylic acid (2 g) in THF (5 ml) at 0° C. was added a solution of borane.THF complex (1N, 10.38 ml) and the mixture was stirred for 30 min at 0° C., and for 2 hr at room temperature. Water (200 ml) was added to the reaction and the mixture extracted with CH₂Cl₂, dried with Na₂SO₄, and concentrated in vacuo to give 490 mg of product (26%). The product was then stirred in 4N HCl/dioxane to give the amine salt.

Preparative Example 13

Step A

Following a similar procedure as in Preparative Example 1 except using dimethylamine (2M in THF, 50 mL) and 4-methylsalicylic acid (15 g), the desired compound was prepared (6.3 g, 35%).

Step B

The product from Step A above (1.5 g) was combined with iodine (2.1 g), NaHCO₃ (1.1 g), EtOH (40 mL) and water (10 mL) and stirred overnight. Filtration, concentration of the filtrate, re-dissolution in CH₂Cl₂ and washing with 1M HCl (aq) gave an organic solution which was dried over anhydrous MgSO₄, filtered and concentrated in vacuo. Purification by flash column chromatography (silica gel, 0.5-0.7% MeOH/CH₂Cl₂) gave the product (0.5 g, 20%, MH⁺=306).

Step C

Nitric acid (3.8 mL) in AcOH (10 mL) was added to the product from Step B above (0.8 g) and the mixture was stirred for 40 min. The mixture was diluted with water and extracted with CH₂Cl₂, dried over anhydrous MgSO₄, filtered and concentrated in vacuo to give the product as an orange solid (0.8 g, 92%, MH⁺=351).

Step D

A mixture of the product from step C above (800 mg), 10% Pd/C (100 mg), and EtOH/MeOH (40 mL) was stirred in a parr shaker under hydrogen (45 psi) for 1.5 hr. Filtration through celite and concentration in vacuo afforded the title product after purification by preparative plate chromatography (Silica, 10% MeOH/CH₂Cl₂, saturated with NH₄OH) to give the product (92 mg, 22%, MH⁺=195).

Preparative Example 13.1

Step A

Following a similar procedure as in Preparative Example 2, Step A except using dimethylamine (2M in THF, 23 ml) and 5-bromosalicylic acid (5 g), the desired compound was prepared (4.2 g, 75%, MH+=244).

Step B

Nitric acid (10 ml) in AcOH (100 ml) was added to the product from Step A above (2 g) and the mixture was stirred for 20 min. The mixture was diluted with water and extracted with CH$_2$Cl$_2$, dried over anhydrous MgSO$_4$, filtered and concentrated in vacuo to give the product as a yellow solid (1.9 g, 80%, MH+=289).

Step C

The product from Step B above (1.9 g) was partially dissolved in EtOH (50 ml). Conc HCl in EtOH (5 ml in 40 ml), followed by SnCl$_2$.2H$_2$O (5.74 g) was added and stirred at room temperature overnight. The crude reaction was concentrated in vacuo, diluted with CH$_2$Cl$_2$ and washed with NaHCO$_3$, dried over anhydrous MgSO$_4$, filtered and concentrated in vacuo to give the product as a solid (185 mg, 9%, MH+=259).

Preparative Example 13.2

Step A

Following a similar procedure as in Preparative Example 2, Step A, except using dimethylamine (2M in THF, 29 ml) and 5-chlorosalicylic acid (5 g), the desired compound was prepared (4.5 g, 78%, MH+=200).

Step B

Nitric acid (10 ml) in AcOH (100 ml) was added to the product from Step A above (2 g) and the mixture was stirred for 20 min. The mixture was diluted with water and extracted with CH$_2$Cl$_2$, dried over anhydrous MgSO$_4$, filtered and concentrated in vacuo to give the product as a solid (2.2 g, 88%, MH+=245).

Step C

The product from Step B above (2.2 g) was partially dissolved in EtOH (50 ml). Conc HCl in EtOH (5 ml in 40 ml), followed by SnCl$_2$.2H$_2$O (7.011 g) was added and stirred at room temperature overnight. The crude reaction was concentrated in vacuo, diluted with CH$_2$Cl$_2$ and neutralized with NaOH. The entire emulsion was filtered though celite, the layers were separated and the organic layer was dried over anhydrous MgSO$_4$, filtered and concentrated in vacuo to give a solid (540 mg, 22%, MH+=215).

Preparative Example 13.3

Step A

3-Nitrosalicylic acid (10 g), PyBroP (20.52 g), and DIEA (28 ml) in anhydrous $CH_2Cl_2$ (200 ml) were combined and stirred at room temperature for 10 min. Dimethylamine (2M in THF, 55 ml) was added and let the reaction stir over the weekend. The mixture was extracted with 1N NaOH (aq) and the organic phase was discarded. The aqueous phase was acidified with 1N HCl (aq), extracted with $CH_2Cl_2$, dried over anhydrous $MgSO_4$, filtered and concentrated in vacuo. The oil was taken up in ether and a solid crashed out, triterated in ether to give 4.45 g of a solid (39%, MH+=211).

Step B

The product from Step A (2.99 g), $K_2CO_3$ (9.82 g), and iodomethane (8.84 ml) were combined in acetone and heated to reflux overnight. The reaction was filtered and concentrated in vacuo. The oil was taken up in $CH_2Cl_2$ and washed with 1N NaOH, dried over anhydrous $MgSO_4$, filtered and concentrated in vacuo to give 3.3 g of an oil (99%, MH+=225).

Step C

The crude product from Step B (3.3 g) was stirred with 10% Pd/C (350 mg) in EtOH (50 ml) under a hydrogen gas atmosphere at 20 psi overnight. The reaction mixture was filtered through celite and the filtrate was concentrated in vacuo to give 2.34 g of a solid (85%, MH+=195).

Step D

The product from Step C (469 mg) was dissolved in AcOH (6 ml). 1.95M $Br_2$ in AcOH (1.23 ml) was added dropwise to the reaction and the mixture was stirred at room temperature for 1 hour. 50% NaOH was added to the reaction at 0° C. and the mixture was extracted with $CH_2Cl_2$, dried over anhydrous $MgSO_4$, filtered and concentrated in vacuo. The crude mixture was purified by preparative plate chromatography (Silica, 5% MeOH/$CH_2Cl_2$) to give the desired product (298 mg, 23%, MH+=273).

Step E $BBr_3$ (2.14 ml, 1M in $CH_2Cl_2$) was added to a $CH_2Cl_2$ solution (8 ml) of the product from Step D above (290 mg) and stirred overnight. A solid formed and was filtered, taken up in MeOH/$CH_2Cl_2$ and purified by preparative plate chromatography (Silica, 5% MeOH/$CH_2Cl_2$) to give the desired product (137 mg, 49%, MH+=259).

Preparative Example 13.4

Step A

To the product from Preparative Example 13.3 Step D (200 mg) was added phenylboronic acid (98 mg), $PdCl_2(PPh_3)_2$ (51 mg), and $Na_2CO_3$ (155 mg) in THF/$H_2O$ (4 ml/1 ml). The solution was heated at 80° C. overnight. EtOAc was added to reaction and washed with 1N NaOH. The organic layer was dried over anhydrous $MgSO_4$, filtered and concentrated in vacuo. The crude mixture was purified by preparative plate chromatography (5% MeOH/$CH_2Cl_2$) to give 128 mg of an oil (65%, MH+=271).

Step B

Following a similar procedure as in Preparative Example 13.3 Step E and using the product from Step A above, the desired compound was prepared (0.1 g, 69%, MH+=257.1).

Preparative Examples 13.5-13.7

Following the procedures set forth in Preparative Example 13.4 but using the boronic acid indicated in the Table below, the amine products were obtained.

| Prep Ex. | Boronic Acid | Product | 1. Yield (%) 2. NH+ |
|---|---|---|---|
| 13.5 | | | 1. 15% 2. 258 |

| Prep Ex. | Boronic Acid | Product | 1. Yield (%) 2. NH+ |
|---|---|---|---|
| 13.6 | 3-CF3-C6H4-B(OH)2 | biaryl with CF3, N,N-dimethyl amide, OH, NH2 | 1. 32% 2. 325 |
| 13.7 | 4-F3C-C6H4-B(OH)2 | biaryl with CF3 (para), N,N-dimethyl amide, OH, NH2 | 1. 18% 2. 325 |

Preparative Example 13.8

Step A

2-Cyanophenol (500 mg), sodium azide (819 mg), and triethylamine hydrochloride (1.73 g) were combined in anhydrous toluene and heated to 99° C. overnight. After the reaction cooled down, product was extracted with $H_2O$. Aqueous layer was acidified with conc. HCl dropwise giving a precipitate, which was filtered to give the product (597 mg, 87%, MH+=163).

Step B

Nitric acid (0.034 ml) in AcOH (5 ml) was added to the product from Step A above (100 mg) in AcOH and the mixture was allowed to stir for 1 hr. $CH_2Cl_2$ and $H_2O$ were added to reaction. The organic layer was dried over anhydrous $MgSO_4$, filtered and concentrated in vacuo to give an oil. Trituration in ether gave the product as a solid (12 mg, 9%, MH+=208).

Step C

The product from step C (56 mg) was stirred with 10% Pd/C (20 mg) in EtOH/MeOH (15 ml) under a hydrogen gas atmosphere overnight. The reaction mixture was filtered through celite, the filtrate was concentrated in vacuo to give 29 mg of a solid (62%, MH+=178).

Preparative Example 13.9

The amine was prepared following the procedure disclosed in WO 01/68570, the disclosure of which is incorporated herein by reference thereto:

Preparative Example 13.10

The amine was prepared following the procedure disclosed in WO 01/68570, the disclosure of which is incorporated herein by reference thereto.

Preparative Example 13.11

Step A

Following the procedure described in Preparative Example 88.2, Step A, the ketone was prepared (6.4 g, 36%).

Step B

To a solution of ketone (1 g) and 2-R-methylbenzylamine (0.73 ml) in anhydrous toluene (20 ml) was added 1N TiCl$_4$ in toluene (3 ml) at room temperature for 1.5 hrs. The precipitate was filtered and the filtrate was concentrated in vacuo and purified via flash column chromatography (Hex/EtOAc, 18/1) to give 800 mg of product (71%).

Step C

The imine from above (760 mg) and DBU (800 ul) were stirred without solvent for 4 hr. The crude reaction was concentrated in vacuo and purified via flash column chromatography (Hex/EtOAc, 8/1) to give 600 mg of product (79%).

Step D

The imine from Step C (560 mg) was dissolved in ether (8 ml). 3N HCl (5 ml) added and let stir at room temperature overnight. The ether layer was separated and concentrated in vacuo to give 400 mg of the amine hydrochloride product (93%).

Preparative Example 13.12

The title compound was prepared similarly as in Preparative Example 13.11, but using the 2-S-methylbenzylamine instead of 2-R-methylbenzylamine (69%).

Preparative Example 13.13

Step A

At room temperature, CsF (60 mg) was added to a mixture of furfuraldehyde (1.3 ml) and TMS-CF$_3$ (2.5 g) and stirred at room temperature (24 h) and refluxed for another 12 h. 3N HCl (40 ml) was added and after 4 hr, the mixture was extracted with ether, washed with brine, dried over MgSO$_4$, and concentrated in vacuo to give the product (2.6 g, 100%).

Step B

To a solution of alcohol from above (2.6 g) in CH$_2$Cl$_2$ at room temperature was added Dess-Martin reagent (10 g) portionwise and 1 drop of water. After stirring for 3 hr at room temperature, 10% Na$_2$S$_2$O$_3$ (60 ml) was added and after stirring overnight, the solid was filtered off and the filtrate was extracted with CH$_2$Cl$_2$. The organic layer was washed with saturated sodium bicarbonate, dried with MgSO$_4$, filtered and concentrated in vacuo. Ether/hexane (1:2; 30 ml) was added to the residue, filtered, and filtrate concentrated in vacuo to give the product (2 g, 78%).

Step C

Following the procedures described in Preparative Example 13.11, Steps B, C and D, the amine salt was prepared.

Preparative Examples 13.15-13.17

Following the procedure set forth in Preparative Example 13.13, but using the prepared or commercially available aldehydes, the optically pure amine products in the Table below were obtained.

| Prep Ex. | Aldehyde | Amine | Product | Yield (%) |
|---|---|---|---|---|
| 13.15 | 34.12 (4-chloro-furan-2-carbaldehyde) | (S)-1-phenylethylamine | ClH·H₂N-CH(CF₃)-(4-chloro-furan-2-yl) | 20 |
| 13.16 | 4-bromo-furan-2-carbaldehyde | (S)-1-phenylethylamine | ClH·H₂N-CH(CF₃)-(4-bromo-furan-2-yl) | 31 |
| 13.17 | benzo[1,3]dioxole-5-carbaldehyde | (S)-1-phenylethylamine | ClH·H₂N-CH(CF₃)-(benzo[1,3]dioxol-5-yl) | 66 |
| 13.17A | 34.8 (4-isopropyl-furan-2-carbaldehyde) | H₂N-CH(CF₃)-(4-isopropyl-furan-2-yl) | ClH·H₂N-CH(CF₃)-(4-isopropyl-furan-2-yl) | 38 |
| 13.17B | 4-tert-butyl-furan-2-carbaldehyde | H₂N-CH(CF₃)-(4-tert-butyl-furan-2-yl) | ClHH₂N-CH(CF₃)-(4-tert-butyl-furan-2-yl) | 31 |

Preparative Example 13.18

The title compound was prepared from trifluorophenylketone according to the procedures described in Preparative Example 13.11, Steps B, C, and D (68%).

Preparative Example 13.19

Step A

Methyl-3-hydroxy-4-bromo-2-thiophenecarboxylate (10.0 g, 42.2 mmol) was dissolved in 250 mL of acetone. Potassium carbonate (30.0 g, 217.4 mmol) was added followed by a solution of iodomethane (14.5 mL, 233.0 mmol). The mixture was heated to reflux and continued for 6 h. After cooled to room temperature, the mixture was filtered, the solid material was rinsed with acetone (~200 mL). The filtrate and rinsing were concentrated under reduced pressure to a solid, further dried on high vacuum, yielding 13.7 g (100%) of methyl-3-methoxy-4-bromo-2-thiophenecarboxylate ($MH^+$=251.0).

Step B

Methyl-3-methoxy-4-bromo-2-thiophenecarboxylate (13.7 g), available from step A, was dissolved in 75 mL of THF, and added with a 1.0 M sodium hydroxide aqueous solution (65 mL, 65.0 mmol). The mixture was stirred at room temperature for 24 h. A 1.0 M hydrogen chloride aqueous solution was added dropwise to the mixture until pH was approximately 2. The acidic mixture was extracted with $CH_2Cl_2$ (100 mL×2, 50 mL). The combined organic extracts were washed with brine (40 mL), dried with $Na_2SO_4$, and concentrated under reduced pressure to a solid, 10.0 g (100%, over two steps) of 3-methoxy-4-bromo-2-thiophenecarboxylic acid ($MH^+$=237.0).

Step C

To a stirred solution of 3-methoxy-4-bromo-2-thiophenecarboxylic acid (6.5 g, 27.4 mmol) in 140 mL of $CH_2Cl_2$, obtained from step B, was added bromo-tripyrrolidinophosphonium hexafluorophosphate (PyBrop, 12.8 g, 27.5 mmol), a 2.0 M solution of dimethyl amine in THF (34.5 mL, 69.0 mmol), and diisopropylethyl amine (12.0 mL, 68.7 mmol). After 3 d, the mixture was diluted with 100 mL of $CH_2Cl_2$, and washed with a 1.0 M sodium hydroxide aqueous solution (30 mL×3) and brine (30 mL). The organic solution was dried with $Na_2SO_4$, filtered, and concentrated to an oil. This crude oil product was purified by flash column chromatography, eluting with $CH_2Cl_2$-hexanes (1:1, v/v). Removal of solvents afforded a solid, further dried on high vacuum, yielding 6.76 g (93%) of N,N'-dimethyl-3-methoxy-4-bromo-2-thiophenecarboxamide ($MH$+=265.0, M+2=266.1).

Step D

An oven dried three-neck round bottom flask was equipped with a refluxing condenser, charged sequentially with palladium acetate (95 mg, 0.42 mmol), (R)-BINAP (353 mg, 0.57 mmol), cesium carbonate (9.2 g, 28.33 mmol), and N,N'-dimethyl-3-methoxy-4-bromo-2-thiophenecarboxamide (3.74 g, 14.2 mmol, from step C). The solid mixture was flushed with nitrogen. Toluene (95 mL) was added to the solid mixture followed by benzophenone imine (3.6 mL, 21.5 mmol). The mixture was heated to reflux and continued for 10 h. A second batch of palladium acetate (95 mg, 0.42 mmol) and (R)-BINAP (353 mg, 0.57 mmol) in 5 mL of toluene was added. Refluxing was continued for 14 h. The third batch of palladium acetate (30 mg, 0.13 mmol) and (R)-BINAP (88 mg, 0.14 mmol) was added, and reaction continued at 110° C. for 24 h. The mixture was cooled to room temperature, diluted with ether (50 mL), filtered through a layer of Celite, rinsing with ether. The filtrate and rinsing were concentrated under reduced pressure to an oil, which was purified twice by flash column chromatography using $CH_2Cl_2$ and $CH_2Cl_2$-MeOH (200:1) as eluents. Removal of solvents afforded 4.1 g (79%) of the amido-thiophene diphenylimine product as a solid ($MH^+$=365.1).

Step E

To a stirred solution of thiophene imine (5.09 g, 13.97 mmol), obtained from step D, in 140 mL of $CH_2Cl_2$ at −78° C. was added dropwise a 1.0 M solution of boron tribromide in $CH_2Cl_2$. The mixture was stirred for 3 h while the temperature of the cooling bath was increased slowly from −78° C. to −15°

C. 100 mL of H₂O was added, the mixture was stirred at room temperature for 30 min, then the two layers were separated. The organic layer (as A) was extracted with H₂O (30 mL×2). The aqueous layer and aqueous extracts were combined, washed with CH₂Cl₂ (30 mL), and adjusted to pH~8 using a saturated NaHCO₃ aqueous solution. The neutralized aqueous solution was extracted with CH₂Cl₂ (100 mL×3), the extracts were washed with brine, dried with Na₂SO₄, and concentrated under reduced pressure to a light yellow solid, 1.49 g of N,N'-dimethyl-3-hydroxy-4-amino-2-thiophenecarboxamide (first crop). The previous separated organic layer A and organic washing were combined, stirred with 30 mL of a 1.0 M HCl aqueous solution for 1 h. The two layers were separated, the aqueous layer was washed with CH₂Cl₂ (30 mL) and adjusted to pH~8 using a saturated NaHCO₃ aqueous solution, and the separated organic layer and organic washing were combined as organic layer B. The neutralized aqueous solution was extracted with CH₂Cl₂ (30 mL×4), the extracts were washed with brine, dried by Na₂SO₄, and concentrated under reduced pressure to give 0.48 g of a solid as the second crop of the titled product. Organic layer B from above was washed with brine, and concentrated to an oil, which was separated by preparative TLC (CH₂Cl₂-MeOH=50:1) to afford 0.45 g of a solid as the third crop of the titled product. The overall yield of the product, N,N'-dimethyl-3-hydroxy-4-amino-2-thiophenecarboxamide, is 2.32 g (89%) (MH⁺=187.0).

Preparative Example 13.20

[Chemical structures shown]

Step A

To the product from Preparative Example 13.19 Step D (1.56 g) in CH₂Cl₂ (55 ml) was added potassium carbonate (1.8 g) followed by dropwise addition of bromine (0.45 ml). After 5 hr of mixing, water (100 ml) was added to the reaction and the layers were separated. The aqueous layer was extracted with CH₂Cl₂, which was then washed with brine, saturated sodium bicarbonate, and brine again. The organic layer was dried with Na₂SO₄, and concentrated in vacuo. The residue was purified via flash column chromatography (CH₂Cl₂) to yield 1.6 g of product (83%).

Step B

The product from above was reacted in the procedure set forth in Preparative Example 13.19 Step C to give the amine.

Preparative Example 13.21

[Chemical structures shown]

Step A

To the product from Preparative Example 13.20, Step A (300 mg) in THF (7 ml) at −78° C. was added a solution of n-BuLi (1.6M in hexanes, 0.54 ml). After 1 hr, iodomethane (0.42 ml) was added dropwise. After 3 hrs of stirring at −78° C., the reaction was warmed to room temperature overnight. Saturated ammonium chloride and water were added to the reaction and extracted with CH₂Cl₂. The organic layer was washed with saturated sodium bicarbonate and brine, dried over Na₂SO₄, and concentrated in vacuo. The crude product was purified by preparative plate chromatography (CH₂Cl₂-MeOH=70:1 to 50:1) to afford the product (111 mg, 43%).

Step B

The product from above was reacted in the procedure set forth in Preparative Example 13.19, Step E to give the amine.

Preparative Example 13.22

[Chemical structures shown]

Step A
To the product from Preparative Example 13.19 (400 mg), Step D in CH$_2$Cl$_2$-pyridine (14 ml) was added N-chlorosuccinimide (220 mg). The mixture was stirred for 5 hr and then diluted with CH$_2$Cl$_2$ and washed with water, saturated sodium bicarbonate and brine, and concentrated in vacuo. The crude product was purified via preparative plate chromatography (CH$_2$Cl$_2$-MeOH=50:1) to give 180 mg of product (64%).

Step B
The product from above (274 mg) was reacted in the procedure set forth in Preparative Example 13.19, Step E to give the amine (89 mg, 58%).

Preparative Example 13.23

Step A
To a stirred solution of acid (630 mg) from Preparative Example 13.19, Step B in CH$_2$Cl$_2$ (25 ml) was added oxalyl chloride (235 ul) followed by a catalytic amount of DMF (10 ul). The mixture was stirred for 1 hr, then potassium carbonate (1.8 g) was added followed by 3-amino-5-methylisoxazole (443 mg). The reaction stirred overnight and was quenched with water (25 ml). Layers were separated and the organic layer was washed with brine, dried over Na$_2$SO$_4$, and concentrated in vacuo. The crude product was purified by preparative plate chromatography (CH$_2$Cl$_2$) to afford the product (580 mg, 78%, MH+=317, 319).

Step B
The acid from the above (750 mg) step was reacted following the procedure set forth in Preparative Example 13.3, Step B to yield 625 mg of product (80%, MH+=331).

Step C
The product from above was reacted following the procedure set forth in Preparative Example 13.19, Step D to yield 365 mg of product (53%)

Step D
The product from above was reacted following the procedure set forth in Preparative Example 13.19, Step E to give the amine product (MH+=254).

Preparative Example 13.25

Step A
To a solution of 2-methylfuran (1 g) in ether (30 ml) was added n-BuLi (5.32 ml) at −78° C. The reaction was warmed to room temperature and then refluxed at 38° C. for 1 hr. The reaction was cooled back down to −78° C. where the furyl lithium was quenched with trifluorobutyraldehyde and let stir at room temperature overnight. Saturated ammonium chloride added and extracted with ether. Purified via flash column chromatography to yield pure product (2 g, 80%)

Step B
The azide was prepared using the procedure from Preparative Example 75.75, Step B and the alcohol (1 g) from above and carried on crude to Step C below.

Step C

The amine was prepared using the procedure from Preparative Example 75.75, Step C to yield 400 mg of an oil (53%).

Preparative Example 13.26

Step A

Perfluoroiodide (3.6 ml) was condensed at −78° C. Ether (125 ml) was added followed by the methyllithium.lithium-bromide complex (1.5M in ether, 18.4 ml). After 15 min, a solution of 5-methylfuraldehyde (2.5 ml) in ether was added dropwise. The reaction was warmed to −45° C. and let stir for 2 hr. Saturated ammonium chloride (30 ml) and water (30 ml) were added and let stir at room temperature for 1 hr. The layers were separated and the aqueous layer was extracted with $CH_2Cl_2$. The organic layer was washed with brine, dried with $Na_2SO_4$, filtered and concentrated in vacuo to give 5.86 g of product (100%).

Step B

The alcohol from above was reacted to form the azide using the procedure set forth in Preparative Example 75.75 Step B.

Step C

The azide from above was reacted to form the racemic amine using the procedure set forth in Preparative Example 75.75 Step C.

Preparative Example 13.27

Step A

Following the procedure set forth in Preparative Example 13.26, Step A, the alcohol was prepared (100%).

Step B

To a solution of the alcohol (500 mg) from step A above in $CH_2Cl_2$ (20 ml) was added N-methyl-morpholine monohydrate (575 mg) and a catalytic amount of tetrapropyl ammonium perruthenate (76 mg). After 3 hr, the mixture was diluted with is hexane (10 ml) and filtered through a silica pad, rinsing with hexane: $CH_2Cl_2$ (200 ml). The filtrate was concentrated in vacuo to give 350 mg of product (70.7%)

Step C

The ketone (1.19 g) from Step B was dissolved in THF (9.5 ml) and cooled to 0° C. A solution of S-methyl oxazoborolidine (1M in toluene, 1 ml) followed by a solution of borane complexed with dimethylsulfide (9.5 ml, 2 M in THF) was added to the solution. The mixture was stirred at 0° C. for 30 min and continued at room temperature for 5 hr. The mixture was cooled back down to 0° C. and methanol (15 ml) was added dropwise to the mixture. After 30 min, the mixture was concentrated in vacuo to give an oily residue.

The residue was dissolved in $CH_2Cl_2$ and washed with 1N HCl, water, and brine. Dried with $Na_2SO_4$, filtered and concentrated in vacuo. The crude material was purified via flash column chromatography (Hex/$CH_2Cl_2$, 1:1) to afford 1.14 g of an oil (67%).

Step D

The alcohol (1.14 g) from above was reacted to form the azide using the procedure set forth in Preparative Example 75.75 Step B.

Step E

The azide (1.1 g) from above was stirred with 10% Pd/C (280 mg) in EtOH (40 ml) under a hydrogen gas atmosphere overnight. The reaction was filtered through celite, the filtrate was concentrated in vacuo to give 700 mg of product (70%).

Preparative Example 13.28

Step A

To a stirred solution of 1-(2-thienyl)-1-propanone (3 g) in acetic anhydride (6 ml) at 0° C. was added dropwise a solution of fuming nitric acid in acetic acid (2 ml in 10 ml). After 30 min, the reaction was warmed to room temperature and let stir for 5 hrs where a solid precipitated out. Ice was added to the reaction and the solid was filtered. The solid was purified by flash column chromatography (Hex/CH$_2$Cl$_2$, 3:1 and 2:1) to yield 800 mg of desired product (20%).

Step B

The above nitro-thiophene compound (278 mg) was reduced using the procedure set forth in Preparative Example 2, Step B to give 54 mg of product (23%).

Step C

The above amine (395 mg), TEA (1 ml) and methanesulfonylchloride (0.5 ml) were combined in CH$_2$Cl$_2$ (35 ml) and stirred at room temperature for 1 hr. The reaction was quenched with saturated sodium bicarbonate (15 ml). The organic layer was washed with brine, dried over Na$_2$SO$_4$, filtered and concentrated in vacuo to afford product (854 mg, 100%).

Step D

To the above product (854 mg) in THF (25 ml) was added dropwise a solution of tetrabutylammonium fluoride (1M in THF, 2.8 ml). The mixture was stirred overnight, then diluted with CH$_2$Cl$_2$ (30 ml), washed with ammonium chloride and brine, dried over Na$_2$SO$_4$, filtered and concentrated in vacuo to afford product (2.36 g, >100%).

Step E

The ketone (2.36 g) above was reacted via the procedure set forth in Preparative Example 88.2, Step B to yield 547 mg of product (86.6%).

Step F

To the product from step E (310 mg) in dimethoxyethane (12 ml) was added dropwise a solution of LAH (1M in ether, 3.8 ml). The mixture was heated to reflux overnight. The reaction was cooled to room temperature, SiO$_2$ was added as well as water (1 ml) dropwise and let stir for 15 min. The mixture was filtered and the filtrate was concentrated in vacuo. The crude product was purified by preparative plate chromatography (MeOH/CH$_2$Cl$_2$, 15:1) to give the amine product (40 mg, 14%).

Preparative Example 13.29

Step A

To a solution of 3-methoxythiophene (3 g) in dichloromethane (175 mL) at −78° C. was added chlorosulfonic acid (8.5 mL) dropwise. The mixture was stirred for 15 min at −78° C. and 1.5 h at room temp. Afterwards, the mixture was poured carefully into crushed ice, and extracted with dichloromethane. The extracts were washed with brine, dried over magnesium sulfate, filtered through a 1-in silica gel pad. The filtrate was concentrated in vacuo to give the desired compound (4.2 g).

Step B

The product from Step A above (4.5 g) was dissolved in dichloromethane (140 mL) and added with triethylamine (8.8 mL) followed by diethyl amine in THF (2M, 21 mL). The resulting mixture was stirred at room temperature overnight. The mixture was washed with brine and saturated bicarbonate (aq) and brine again, dried over sodium sulfate, filtered through a 1-in silica gel pad. The filtrate was concentrated in vacuo to give the desired compound (4.4 g).

Step C

The product from Step B above (4.3 g) was dissolved in dichloromethane (125 mL) and cooled in a −78° C. bath. A solution of boron tribromide (1.0 M in dichloromethane, 24.3 mL) was added. The mixture was stirred for 4 h while the temperature was increased slowly from −78° C. to 10° C. $H_2O$ was added, the two layers were separated, and the aqueous layer was extracted with dichloro-methane. The combined organic layer and extracts were washed with brine, dried over magnesium sulfate, filtered, and concentrated in vacuo to give 3.96 g of the desired hydroxy-compound.

Step D

The product from step C above (3.96 g) was dissolved in 125 mL of dichloromethane, and added with potassium carbonate (6.6 g) followed by bromine (2 mL). The mixture was stirred for 5 h at room temperature, quenched with 100 mL of $H_2O$. The aqueous mixture was adjusted to pH~5 using a 0.5N hydrogen chloride aqueous solution, and extracted with dichloromethane. The extracts were washed with a 10% $Na_2S_2O_3$ aqueous solution and brine, dried over sodium sulfate, and filtered through a celite pad. The filtrate was concentrated in vacuo to afford 4.2 g of the desired bromo-compound.

Step E

The product from Step D (4.2 g) was dissolved in 100 mL of acetone and added with potassium carbonate (10 g) followed by iodomethane (9 mL). The mixture was heated to reflux and continued for 3.5 h. After cooled to room temperature, the mixture was filtered through a Celite pad. The filtrate was concentrated in vacuo to a dark brown residue, which was purified by flash column chromatography eluting with dichloromethane-hexanes (1:1, v/v) to give 2.7 g of the desired product.

Step F

The product from step E (2.7 g) was converted to the desired imine compound (3 g), following the similar procedure to that of Preparative Example 13.19 step D.

Step G

The imine product from step F (3 g) was dissolved in 80 mL of dichloromethane and cooled in a −78° C. bath. A solution of boron tribromide (1.0 M in dichloromethane, 9.2 mL) was added dropwise. The mixture was stirred for 4.25 h from −78° C. to 5° C. $H_2O$ (50 mL) was added, and the layers were separated. The aqueous layer was extracted with dichloromethane. The organic layer and extracts were combined, washed with brine, and concentrated to an oily residue. The residue was dissolved in 80 mL of methanol, stirred with sodium acetate (1.5 g) and hydroxyamine hydrochloride (0.95 g) at room temperature for 2 h. The mixture was poured into an aqueous mixture of sodium hydroxide (1.0 M aq, 50 mL) and ether (100 mL). The two layers were separated. The aqueous layer was washed with ether three times. The combined ether washings were re-extracted with $H_2O$ once. The aqueous layers were combined, washed once with dichloromethane, adjusted to pH~6 using 3.0 M and 0.5 M hydrogen chloride aqueous solutions, and extracted with dichloromethane. The organic extracts were combined, washed with brine, dried over sodium sulfate, and concentrated in vacuo to give 1.2 g of desired amine compound.

Preparative Examples 13.30-13.32-A

Following the procedures set forth in Example 13.29, but using commercially available amines, hydroxy-aminothiophene products in the Table below were obtained.

| Prep Ex | Amine | Product | Yield (%) MH+ |
|---------|-------|---------|---------------|
| 13.30 | (Bn)$_2$NH | | 10% 375.1 |
| 13.31 | Me(Bn)NH | | 14% 299.0 |
| 13.32 | Et(Bn)NH | | 22% |
| 13.32A | (Et)$_2$NH | | 25% |

Preparative Example 13.33

Step A

2-Chlorosulfonyl-3-methoxy-thiophene (4.0 g, 18.8 mmol), the product from Step A of Preparative Example 13.29 was converted to 3-methoxy-2-ethylbenzylsulfonyl-thiophene (5.5 g, 94%, MH$^+$=312.1) by using ethylbenzyl-amine, following the procedure set forth in Preparative Example 13.29, Step B.

Step B

The product from Step A above (5.5 g, 17.70 mmol) was demethylated following the procedure set forth in Preparative Example 13.29, Step C. The alcohol product was obtained in 4.55 g (87%, MH$^+$=298.0).

Step C

The product from Step B above (4.55 g, 15.30 mmol) was brominated using the procedure set forth in Preparative Example 13.29, Step D. The corresponding bromide was obtained in 4.85 g (84%).

Step D

The bromo-alcohol from Step C above (4.84 g, 12.86 mmol) was methylated using the procedure set forth in Preparative Example 13.29, Step E. The product was obtained in 4.82 g (96%).

Step E

The product from Step D above (4.82 g, 12.36 mmol) was stirred with concentrated sulfuric acid (5 mL) at room temperature to 3 h. Ice water (30 mL) was added to the mixture followed by CH$_2$Cl$_2$ (50 mL). The aqueous mixture was adjusted to pH ~6 using a 1.0 M NaOH aqueous solution. The layers were separated. The aqueous layer was extracted with CH$_2$Cl$_2$ (50 mL×3). The combined organic layers were washed with brine, dried over Na$_2$SO$_4$, and concentrated to a dark brown oil, which was purified by flash column chromatography, eluting with CH$_2$Cl$_2$-hexanes (1:1, v/v). Removal of solvents afforded 3.03 g (82%) of the debenzylated product (M$^+$=300.0, M+2=302.0).

Step F

The product from Step E (1.34 g, 4.45 mmol) was methylated using the procedure set forth in Preparative Example 13.29, Step E. The desired product was obtained in 1.36 g (97%, M$^+$=314.1, M+2=316.0).

Step G

The product from Step F (1.36 g, 4.33 mmol) was converted to imine product (1.06 g, 55%, MH$^+$=415.1) using the procedure set forth in Preparative Example 13.29, Step F.

Step H

The imine product from Step G (1.06 g, 2.56 mmol) was converted to the desired hydroxy-amino thiophene compound (0.26 g, 43%) using the procedure set forth in Preparative Example 13.29, Step G.

Preparative Example 13.34

Step A

2-Chlorosulfonyl-3-methoxy-thiophene (3.8 g, 17.87 mmol), the product from step A of Preparative Example 13.29, was dissolved in 100 mL of CH$_2$Cl$_2$ and 20 mL of pyridine. 3-Amino-5-methyl-isoxazole (3.5 g, 35.68 mmol) was added. The mixture was stirred for 20 h at room temperature, diluted with 100 mL of CH$_2$Cl$_2$, and washed with a 0.5 N HCl aqueous solution (50 mL×2), H$_2$O (50 mL), and brine (50 mL). The organic solution was dried with Na$_2$SO$_4$, and concentrated in vacuo to a brown oil. This oil was dissolved in 100 mL of CH$_2$Cl$_2$, washed again with a 0.5 M HCl aqueous solution (30 mL×3) and brine. After dried over Na$_2$SO$_4$, the organic solution was concentrated in vacuo to a yellow solid, 4.48 g (91%, MH$^+$=275.0) of the desired product.

Step B

The product from Step A above (4.48 g, 16.33 mmol) was dissolved in acetone (100 mL), added with potassium carbonate (5.63 g, 40.80 mmol) and iodomethane (10.1 mL, 163.84 mmol). The mixture was stirred at room temperature for 1.5 h, diluted with 100 mL of hexanes and 50 mL of CH$_2$Cl$_2$, and filtered through a 1-in silica gel pad, rinsing with CH$_2$Cl$_2$. The filtrate was concentrated under reduced pressure to give 4.23 g (90%, MH$^+$=289.0) of the desired product as a light yellow solid.

Step C

To a stirred suspension of sodium hydride (130 mg, 95%, 5.4 mmol) in 8 mL of N,N'-dimethylformamide at room temperature was added ethanethiol (0.45 mL, 6.0 mmol) dropwise. After 5 min, the mixture became a clear solution, and was added to a stirred solution of the product obtained from Step B above (0.45 g, 1.56 mmol) in 2 mL of N,N'-dimethylformamide in a round bottom flask. The flask was sealed with a ground glass stopper, and the mixture was heated at 90-95° C. for 4 h. After cooled to room temperature, the mixture was poured into 20 mL of a 1.0 M NaOH aqueous solution, further rinsed with 20 mL of H$_2$O. The aqueous mixture was washed with diethyl ether (30 mL×2), adjusted to PH~5 using a 0.5 M HCl aqueous solution, and extracted with CH$_2$Cl$_2$ (50 mL×4). The combined extracts were washed with brine, dried (Na$_2$SO$_4$), and concentrated to a dark yellow solution. This was dissolved in 50 mL of ethyl acetate, washed with H$_2$O (30 mL×2) and brine (30 mL), dried over Na$_2$SO$_4$. Evaporation of solvent gave 0.422 g of the alcohol product (99%, MH$^+$=275.0).

Step D

The alcohol obtained from Step C above (0.467 g, 1.70 mmol) was brominated using the procedure set forth in Preparative Example 13.29, Step D, to afford the corresponding bromide in 0.607 g (100%).

Step E

The bromide obtained from Step D above (0.607 g, 1.72 mmol) was methylated using the procedure set forth in Preparative Example 13.29, Step E, to give the desired product in 0.408 g (65%, M$^+$=367, M+2=369.1).

Step F

The product (0.405 g, 1.103 mmol) from Step E above was converted to the imine compound (0.29 g, 56%) using the procedure set forth in Preparative Example 13.29, Step F.

Step G

The imine product obtained from Step F above (0.29 g, 0.61 mmol) was demethylated using the procedure set forth in Step C above to give the corresponding alcohol as a dark yellow oil, which was dissolved in 5 mL methanol and added with sodium acetate (0.12 g, 1.46 mmol) and hydroxyamine hydrochloride (0.075 g, 1.08 mmol). The resulting mixture was stirred at room temperature for 3 h, and poured into 10 mL of 1.0 M NaOH aqueous solution. 30 mL of H$_2$O was used as rinsing and combined to the aqueous layer. The aqueous mixture was washed with diethyl ether (40 mL×3), adjusted to pH ~6 using a 1.0 M HCl aqueous solution, and extracted with ethyl acetate (40 mL×3). The organic extracts were washed with H$_2$O (20 mL×2), brine (20 mL), dried over Na$_2$SO$_4$, and concentrated in vacuo to give 0.112 g of the desired hydroxy-amino thiophene sulfonamide (64%, MH$^+$=290).

Preparative Example 13.35

Step A
To a solution of 2-methyl furan (1.72 g) in ether was added BuLi (8.38 mL) at −78° C. and stirred at room temperature for half an hour. The reaction mixture again cooled to −78° C. and quenched with cyclopropyl amide 1 and stirred for two hours at −78° C. and slowly warmed to room temperature. The reaction mixture stirred for three hours at room temperature and quenched with the addition of saturated ammonium chloride solution. The mixture was taken to a separatory funnel, washed with water, brine and dried over anhydrous sodium sulfate. Filtration and removal of solvent afforded the crude ketone, which was purified by using column chromatography to afford the ketone 3.0 g (87%) as a pale yellow oil.

Step B
To a solution of ketone (1.0 g) in THF (5.0 mL) at 0° C. was added R-methyl oxazoborolidine (1.2 Ml, 1M in toluene) dropwise followed by addition of a solution of borane complexed with dimethyl sulfide (1.85 mL, 2M in THF). The reaction mixture was stirred for 30 minutes at 0° C. and than at room temperature for one hour. The reaction mixture was cooled to 0° C. and MeOH was added carefully. The mixture was stirred for 20 minutes and was concentrated under reduced pressure. The residue was extracted with ether, washed with water, 1M HCl (10 mL), saturated sodium bicarbonate (10.0 mL) water and brine. The organic layer was dried over anhydrous sodium sulfate, filtered and removal of solvent afforded the crude alcohol which was purified by silica gel chromatography to afford the pure alcohol 0.91 g (91%) as yellow oil.

Preparative Example 13.36

Step A
An equimolar mixture of 2-methylfuran (1.0 g) and anhydride (2.6 g) was mixed with $SnCl_4$ (0.05 mL) and heated at 100° C. for 3 hours. After cooling the reaction mixture, water (10 mL) was added, followed by saturated sodium carbonate solution until it becomes alkaline. The reaction mixture was extracted with ether several times and the combined ether layer was washed with water, brine and dried over anhydrous sodium sulfate. Filtration and removal of solvent afforded the crude ketone, which was purified by using silica gel chromatography to afford the ketone 0.9 g (43%) as a yellow oil.

Step B
The step B alcohol was obtained following a similar procedure set forth in the preparative example 13.35 Step B.

Preparative Example 13.37

Step A
To a solution of 5-methyl furan-2-aldehyde (1.0 g) and 3-bromo-3,3-difluoropropene (2.24 g) in DMF (30 mL) was added indium powder (1.66 g) and lithium iodide (50.0 mg). The reaction mixture was stirred over night, diluted with water and extracted with ether. The ether layer was washed with water, brine and purified by silica gel chromatography to afford the pure alcohol 2.8 g (92%).

Preparative Examples 13.38-13.45

Following a similar procedure set forth in Preparative Examples 13.25 and 13.35, and using the indicated Furan and Electrophile, the following Alcohols in the Table below were prepared.

| Prep. ex | Furan | Electrophile | Alcohol | Yield |
|---|---|---|---|---|
| 13.38 | | CHO | | 86% |

-continued

| Prep. ex | Furan | Electrophile | Alcohol | Yield |
|---|---|---|---|---|
| 13.39 | 2-methylfuran | CH₃CHF-COOEt | 1-(5-methylfuran-2-yl)-2-fluoropropan-1-ol | 69% |
| 13.40 | 3-methylfuran | 1-methylcyclopropyl-C(O)-N(Me)OMe | (1-methylcyclopropyl)(4-methylfuran-2-yl)methanol | 84% |
| 13.41 | 3-methylfuran | 1-methylcyclopropyl-C(O)-N(Me)OMe | (1-methylcyclopropyl)(3-methylfuran-2-yl)methanol | 82% |
| 13.42 | 3-methylfuran | CH₃CHF-COOEt | 1-(4-methylfuran-2-yl)-2-fluoropropan-1-ol | 60% |
| 13.43 | 3-methylfuran | CH₃CHF-COOEt | 1-(3-methylfuran-2-yl)-2-fluoropropan-1-ol | 65% |
| 13.44 | 2-methylfuran | CF₂(CH₃)-C(O)-N(Me)OMe | 1-(5-methylfuran-2-yl)-2,2-difluoropropan-1-ol | 82% |
| 13.45 | 2-methylfuran | OHC-CH₂-CF₃ | 1-(5-methylfuran-2-yl)-3,3,3-trifluoropropan-1-ol | 89% |

Preparative Examples 13.50-13.61

Following a similar procedure set forth in Preparative Examples 13.25, and using the indicated Alcohol, the following Amines in the Table below were prepared.

| PREP. EX. | ALCOHOL | AMINE | % YIELD |
|---|---|---|---|
| 13.50 | 13.45 | (structure) | 28% |
| 13.51 | 13.38 | (structure) | 58% |
| 13.52 | 13.36 | (structure) | 69% |
| 13.53 | 13.35 | (structure) | 81% |
| 13.54 | 13.37 | (structure) | 82% |
| 13.55 | 13.39 | (structure) | 45% |
| 13.56 | 13.41 | (structure) | 57% |
| 13.57 | 13.40 | (structure) | 58% |
| 13.58 | 13.44 | (structure) | 54% |
| 13.59 | 13.42 | (structure) | 53% |
| 13.60 | 14.43 | (structure) | 50% |
| 13.61 | 13.37 | (structure) | 82% |

Preparative Example 13.70

Step A
The imine was prepared following the procedure set forth in the preparative example 13.19 from the known bromoester (1.0 g) as a yellow solid, Step A to yield 1.1 g (79%).

Step B
The Step A product (0.6 g) was reacted following the procedure set forth in the preparative example 13.19 to give the amine product 0.19 g (64%).

Step C
The Step B product (1.0 g) was reacted following the procedure set forth in the preparative example 13.19 to give the acid as yellow solid 0.9 g (94%)

Step D
The Step C product (0.35 g) was reacted following the procedure set forth in the preparative example 13.19 to give the amino acid as yellow solid 0.167 g (93%).

Preparative Example 13.71

Following a similar procedure set forth in Preparative Example 13.33 Step E, but using the product from Preparative Example 13.32, the title compound was obtained (121 mg, 69% yield, MH+=223.0).

Preparative Example 14

Step A
3-Nitro-1,2-phenylenediamine (10 g), sodium nitrite (5.4 g) and acetic acid (20 mL) were heated at 60° C. overnight, then concentrated in vacuo, diluted with water and extracted with EtOAc. The product precipitated from the organic phase (5.7 g) as a solid and used directly in step B.

Step B
The product from Step A above (2.8 g) was stirred with 10% Pd/C (0.3 g) in MeOH (75 mL) under a hydrogen gas atmosphere overnight. The reaction mixture was filtered through celite and the filtrate concentrated in vacuo, to give the product (2.2 g, MH+=135).

Preparative Example 15

Step A

N-methyl-4-bromopyrazole-3-carboxylic acid was prepared according to known methods, see: Yu. A. M.; Andreeva, M. A.; Perevalov, V. P.; Stepanov, V. I.; Dubrovskaya, V. A.; and Seraya, V. I. in *Zh. Obs. Khim*, (Journal of General Chemistry of the USSR) 1982, 52, 2592 (and the references cited therein) the disclosure of which is incorporated herein by reference thereto.

Step B

To a solution of N-methyl-4-bromopyrazole-3-carboxylic acid (2.0 g), available from step A, in 65 mL of anhydrous DMF was added bromotripyrrolidinophosphonium hexafluorophosphate (PyBrop, 4.60 g), dimethyl amine (10 mL, 2.0 M in THF) and diisopropylethyl amine (5.2 mL) at 25° C. The mixture was stirred for 26 h, and concentrated under reduced pressure to an oily residue. This residue was treated with a 1.0 M NaOH aqueous solution, and extracted with ethyl acetate (50 mL×4). The organic extracts were combined, washed with brine, and dried with anhydrous $Na_2SO_4$. Removal of solvents yielded an oil, which was purified by preparative thin layer chromatography, eluting with $CH_2Cl_2$-MeOH (20:1), to give 1.09 g of the amide product (48%, $MH^+$=232.0).

Step C

To a solution of the amide (0.67 g), obtained from step B, in 8 mL of concentrated sulfuric acid at 0° C. was added potassium nitrate (1.16 g) in small portions. The cooling bath was removed and the mixture was heated at 110° C. for 6 h. After cooling to 25° C., the mixture was poured into 80 mL of $H_2O$, and an additional 20 mL of $H_2O$ was used as a rinse. The aqueous mixture was extracted with $CH_2Cl_2$ (100 mL×4). The combined extracts were washed with brine (50 mL), sat. $NaHCO_3$ aqueous solution (50 mL), brine (50 mL), and dried with $Na_2SO_4$. Evaporation of solvent gave an oil, which solidified on standing. The crude product was purified by flash column chromatography, eluting with $CH_2Cl_2$-MeOH (1:0, 50:1 and 40:1). Removal of solvents afforded 0.521 g (65%) of the product as a solid ($MH^+$=277.1)

Step D

The product (61 mg) obtained from step C was dissolved in 3 mL of THF. To this solution at −78° C. was added dropwise along the inside wall of the flask a 1.6 M solution of n-butyl lithium in hexane. After 45 min, a solution of methyl borate (0.1 mL) in THF (1.0 mL) was added. After 1.5 h, a solution of acetic acid in THF (0.25 mL, 1:10 v/v) was added to the cold mixture. Stirring was continued for 10 min, and a 30 wt % aqueous hydrogen peroxide solution (0.1 mL) was added. An additional portion of hydrogen peroxide aqueous solution (0.05 mL) was added 20 min later. The cooling bath was removed, and the mixture was stirred at 25° C. for 36 h. The mixture was poured into 30 mL of $H_2O$, and the aqueous mixture was extracted with ethyl acetate (30 mL×4). The extracts were combined, washed with brine (10 mL), 5% $NaHCO_3$ aqueous solution (10 mL) and brine (10 mL). The organic layer was dried with $Na_2SO_4$ and concentrated under reduced pressure to a residue, which was then purified by preparative thin layer chromatography eluting with $CH_2Cl_2$-MeOH (20:1) to give the hydroxylated product (5 mg, 10%, $MH^+$=215.3).

Step E

By treating the hydroxylated product of Step E with $H_2$ under the conditions of 10% palladium on carbon in ethanol, one would obtain the desired hydroxyl-amino compound.

Preparative Example 16

Step A

Following a similar procedure used in Preparative Example 13, Step C except using the known compound, 4-methyl-pyrimidin-5-ol, the product can be prepared.

Step B

Following a similar oxidation procedure used in Preparative Example 15, Step A except using the compound from Step A above, the product can be prepared.

Step C

Following a similar procedure used in Preparative Example 11, Step A except using the compound from Step B above, the product can be prepared.

Step D

Following a similar procedure used in Preparative Example 12, Step F except using the compound from Step C above, the product can be prepared.

Preparative Example 17

Step A
Following a similar procedure used in Preparative Example 11, Step A except using the known 4-hydroxynicotinic acid, the product can be prepared.

Step B
Following a similar procedure used in Preparative Example 13, Step C except using the compound from Step A above, the product can be prepared.

Step C
Following a similar procedure used in Preparative Example 12, Step F except using the compound from Step C above, the product can be prepared.

Preparative Example 18

Step A
Following a similar procedure used in Preparative Example 13, Step C except using the compound from Step A above, the product can be prepared.

Step B
Stirring the compound from Step A above, a suitable Pt or Pd catalyst and EtOH under hydrogen atmosphere (1-4 atm) the product can be prepared.

Preparative Example 19

The amine was prepared following WO 01/68570, the disclosure of which is incorporated herein by reference thereto.

Preparative Example 19.1

The amine was prepared following WO 01/68570, the disclosure of which is incorporated herein by reference thereto.

Preparative Example 20

The title compound was prepared according to the procedure set forth in Preparative Example 1, but instead using 4-nitrosalycilic acid (57%, MH+=181).

Preparative Example 21

The above compound is prepared following the procedure set forth in *The Journal of Organic Chemistry*, 1975, 40(19), 2743-2748, the disclosure of which is incorporated herein by reference thereto.

Preparative Example 22

The compound from Preparative Example 21 (250 mg) and the compound from Preparative Example 3 (252 mg) were

Preparative Example 22.1

3,4-Diethoxy-1,2-5-thiadiazole-1,1-oxide (226 mg, 1.4 mmol) (prepared according to known methods, see: *J. Am. Chem. Soc.*, 1982, p. 1375, the disclosure of which is incorporated herein by reference thereto) was added to 3-amino-2-hydroxy-N,N-dimethylbenzamide (252 mg, 1.4 mmol) in methanol (15 mL). The reaction mixture was stirred overnight. The desired product precipitated and was recovered by filtration. Concentration of the mother liquor to half volume afforded a second batch of precipitated product. Combined batches afforded 293 mg (65% yield) of product with sufficient purity to be used in subsequent steps. $MH^+=346.9$.

Preparative Example 22.2

3,4-Diethoxy-1,2-5-thiadiazole-1,1-oxide (226 mg, 1.4 mmol) (prepared according to known methods, see: *J. Am. Chem. Soc.*, 1982, p. 1375, the disclosure of which is incorporated herein by reference thereto) was added to R-2-phenylpropylamine (0.195 mL, 1.4 mmol) in methanol (15 mL). The reaction mixture was stirred overnight. Evaporation of solvent afforded an amorphous solid (390 mg, 99%) of sufficient purity for use in subsequent steps. $MH^+=279.9$.

Preparative Examples 22.3-22.7

Following a similar procedure set forth in Preparative Example 22.1 but using the commercially available (or prepared amine) indicated in the Table below, the following thiadiazoleoxide intermediates could be obtained.

combined in MeOH (15 ml) and stirred overnight. The reaction was concentrated under vacuo and used crude (450 mg, 99%, MH+=327).

| Ex. | Amine | Product |
|---|---|---|
| 22.6 | | |
| 22.7 | | |

Preparative Examples 22.8-22.38

Following a similar procedure as that set forth in Preparative Example 22.1 but using the commercially available (or prepared amine) indicated in the Table below, the following thiadiazoleoxide intermediates could be obtained.

| Ex. | Amine | Product |
|---|---|---|
| 22.8 | | |
| 22.9 | | |
| 22.10 | | |

-continued

| Ex. | Amine | Product |
|---|---|---|
| 22.16 | | |
| 22.17 | | |
| 22.19 | | |
| 22.20 | | |
| 22.21 | | |
| 22.22 | | |
| 22.23 | | |

-continued

| Ex. | Amine | Product |
|---|---|---|
| 22.24 | | |
| 22.25 | | |
| 22.26 | | |
| 22.27 | | |
| 22.28 | | |
| 22.29 | | |

-continued

| Ex. | Amine | Product |
|---|---|---|
| 22.30 | | |
| 22.31 | | |
| 22.32 | | |
| 22.34 | | |
| 22.36 | | |
| 22.37 | | |
| 22.38 | | |

243

Preparative Examples 22.39-22.51

Following a similar procedure set forth in Preparative Example 22.1 but using the commercially available (or prepared amine) indicated in the Table below, the following thiadiazoleoxide intermediates could be obtained.

| Ex. | Amine | Product |
|---|---|---|
| 22.39 | | |
| 22.40 | | |
| 22.41 | | |
| 22.42 | | |
| 22.43 | | |

-continued

| Ex. | Amine | Product |
|---|---|---|
| 22.44 | | |
| 22.45 | | |
| 22.46 | | |
| 22.47 | | |
| 22.48 | | |
| 22.49 | | |

-continued

| Ex. | Amine | Product |
|---|---|---|
| 22.50 | | |
| 22.51 | | |
| 22.52 | | |
| 22.53 | | |

Preparative Examples 23.1-23.9

Following a similar procedure set forth in Preparative Example 22 but using the commercially available (or prepared amine) indicated in the Table below, the following thiadiazoledioxide intermediates were obtained.

| Ex. | Amine | Product | 1. Yield<br>2. MH+ |
|---|---|---|---|
| 23.1 | | | 1. 99%<br>2. 281.8 |

-continued

| Ex. | Amine | Product | 1. Yield 2. MH+ |
|---|---|---|---|
| 23.2 | | | 1. 99% 2. 327 |
| 23.3 | | | 1. 99% 2. 234.0 |
| 23.4 | | | 1. 99% 2. Not observed |
| 23.5 | | | 1. 99% 2. Not observed |
| 23.6 | | | 1. 99% 2. Not observed |
| 23.7 | | | 1. 99% 2. Not observed |

| Ex. | Amine | Product | 1. Yield 2. MH+ |
|---|---|---|---|
| 23.8 | (structure) | (structure) | 1. 99%  2. 404.9 |
| 23.9 | (structure) | (structure) | 1. 99%  2. Not observed |

Preparative Examples 23.30-23.41

Following a similar procedure set forth in Preparative Example 22 but using the commercially available (or prepared amine) indicated in the Table below, the following thiadiazoledioxide intermediates could be obtained.

| Ex. | Amine | Product |
|---|---|---|
| 23.30 | (structure) | (structure) |
| 23.33 | (structure) | (structure) |
| 23.34 | (structure) | (structure) |

-continued

| Ex. | Amine | Product |
|---|---|---|
| 23.35 | [structure] | [structure] |
| 23.37 | [structure] | [structure] |
| 23.38 | [structure] | [structure] |
| 23.40 | [structure] | [structure] |
| 23.42 | [structure] | [structure] |

Preparative Example 24

[structure] →Step A→ [structure] →Step B→ [structure]

Step A

To a solution of N-protected amino acid (1.5 g, 6.9 mmol) in CH$_2$Cl$_2$ (25 mL) at room temperature was added DIPEA (3.6 mL, 20.7 mmol), and PyBrop (3.4 g, 6.9 mmol) followed by MeNH$_2$ (6.9 mL, 13.8 mmol, 2.0 M in CH$_2$Cl$_2$). The resulting solution was stirred for 18 h at room temperature (until TLC analysis deemed the reaction to be complete). The resulting mixture was washed sequentially with 10% citric acid (3×20 mL), sat. aq. NaHCO$_3$ (3×20 mL), and brine (3×20 mL). The organic layer was dried (Na$_2$SO$_4$), filtered, and concentrated under reduced pressure. The crude product was purified by flash chromatography eluting with CH$_2$Cl$_2$/MeOH (40:1) to afford 1.0 g (63% yield) of a solid.

Step B

To a round bottom charged with the N-protected amide (1.0 g, 4.35 mmol) (from Step A) was added 4N HCl/dioxane (10 mL) and the mixture was stirred at room temperature for 2 h. The mixture was diluted with Et$_2$O (20 mL) and concentrated under reduced pressure. The crude product was treated with Et$_2$O (2×20 mL) and concentrated under reduced pressure to afford 0.72 g (~100% yield) of crude product as the HCl salt. This material was taken on without further purification or characterization.

Preparative Examples 25-33.1

Following the procedure set forth in Preparative Example 24 but using the commercially available N-protected amino acids and amines in the Table below, the amine hydrochloride products were obtained.

| Prep Ex. | Amino acid | Amine | Product | Yield (%) |
|---|---|---|---|---|
| 25 | Boc-Val-OH | NH$_3$ | Val-NH$_2$·HCl | 70 |
| 26 | Boc-Val-OH | H$_2$N-CH$_2$-Ph | Val-NHCH$_2$Ph·HCl | 71 |
| 27 | Boc-Val-OH | H$_2$N-Ph | Val-NHPh·HCl | 66 |
| 28 | Boc-Val-OH | H$_2$N-CH(Et)-Ph | Val-NHCH(Et)Ph·HCl | 65 |
| 29 | Boc-Val-OH | H$_2$N-CH(Me)-Ph (R) | Val-NHCH(Me)Ph·HCl | 90 |
| 30 | Boc-Val-OH | H$_2$N-CH(Me)-Ph (S) | Val-NHCH(Me)Ph·HCl | 68 |
| 31 | Boc-Val-OH | H$_2$N-CH(Me)-Ph | Val-NHCH(Me)Ph·HCl | 68 |
| 32 | Boc-Val-OH | H$_2$N-CH(Et)-Ph | Val-NHCH(Et)Ph·HCl | 97 |

-continued

| Prep Ex. | Amino acid | Amine | Product | Yield (%) |
|---|---|---|---|---|
| 33 | BOC-Val-OH | (R)-1-phenylethylamine | BOC-Val-NH-CH(Ph)-CH₂CH₃ (ClH·H₂N) | 97 |
| 33.1 | BOC-Abu-OH | cyclohexylamine | Abu-NH-cyclohexyl (ClH·H₂N) | 20 |

Preparative Example 33.2

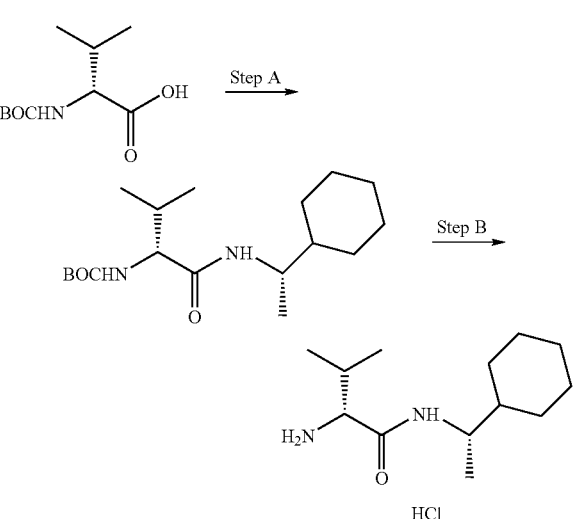

Step A

BOC-valine (45 mg) and PS-carbodiimide (200 mg) were suspended in CH$_2$Cl$_2$ (4 ml). After addition of the CH$_2$Cl$_2$-amine solution (0.138N, 1 ml), the mixture was shaken overnight. The solution was filtered and the resin was washed with more CH$_2$Cl$_2$, and the filtrate was concentrated in vacuo to yield the product, which was carried on directly in Step B.

Step B

The crude material from Step A was dissolved in 4N HCl/dioxane (2.5 ml) and stirred for 2 h. The reaction was concentrated in vacuo to yield the desired amine hydrochloride, which was used directly in the next step.

Preparative Examples 33.3-33.47

If one were to follow the procedure set forth in Example 33.2 but using the commercially available N-protected amino acids in the Table below, one could obtain the amine hydrochloride products in the Table below.

| Prep Ex. | Amino acid | Amine | Product |
|---|---|---|---|
| 33.3 | BOC-Val-OH | 4-biphenylmethylamine | Val-NH-CH₂-(4-biphenyl) · HCl |
| 33.4 | BOC-Val-OH | 4-(1,2,3-thiadiazol-4-yl)benzylamine | Val-NH-CH₂-(4-(1,2,3-thiadiazol-4-yl)phenyl) · HCl |

| Prep Ex. | Amino acid | Amine | Product |
| --- | --- | --- | --- |
| 33.5 | | | |
| 33.6 | | | |
| 33.7 | | | |
| 33.8 | | | |
| 33.9 | | | |
| 33.10 | | | |
| 33.11 | | | |
| 33.12 | | | |

| Prep Ex. | Amino acid | Amine | Product |
|---|---|---|---|
| 33.13 | Boc-Val-OH | 3-(aminomethyl)pyridine | H-Val-NHCH₂-(3-pyridyl) · HCl |
| 33.14 | Boc-Val-OH | 2-phenoxyethylamine | H-Val-NHCH₂CH₂OPh · HCl |
| 33.15 | Boc-Val-OH | phenethylamine | H-Val-NHCH₂CH₂Ph · HCl |
| 33.16 | Boc-Val-OH | 4-(aminomethyl)pyridine | H-Val-NHCH₂-(4-pyridyl) · HCl |
| 33.17 | Boc-Val-OH | 2-methylbenzylamine | H-Val-NHCH₂-(2-methylphenyl) · HCl |
| 33.18 | Boc-Val-OH | (1-phenylpropyl)amine | H-Val-NH-CH(Et)Ph · HCl |
| 19 | Boc-Val-OH | 3-chlorobenzylamine | H-Val-NHCH₂-(3-chlorophenyl) · HCl |
| 33.20 | Boc-Val-OH | α-amino-phenylacetonitrile | H-Val-NH-CH(CN)Ph · HCl |
| 33.21 | Boc-Val-OH | 3,4-dichlorobenzylamine | H-Val-NHCH₂-(3,4-dichlorophenyl) · HCl |

-continued

| Prep Ex. | Amino acid | Amine | Product |
|---|---|---|---|
| 33.22 | Boc-Ala-OH | (S)-1-phenylethylamine | H-Ala-NH-CH(CH₃)Ph · HCl |
| 33.23 | Boc-Val-OH | H-Phg-OMe | H-Val-Phg-OMe · HCl |
| 33.24 | Boc-Val-OH | 2-methoxyethylamine | H-Val-NH-CH₂CH₂-OMe · HCl |
| 33.25 | Boc-Val-OH | 2-(aminomethyl)pyridine | H-Val-NH-CH₂-(2-pyridyl) · HCl |
| 33.26 | Boc-Aib-OH | (S)-1-phenylethylamine | H-Aib-NH-CH(CH₃)Ph · HCl |
| 33.27 | Boc-Val-OH | 4-methoxybenzylamine | H-Val-NH-CH₂-C₆H₄-OMe · HCl |
| 33.28 | Boc-Val-OH | cyclohexylmethylamine | H-Val-NH-CH₂-cyclohexyl · HCl |
| 33.29 | Boc-Val-OH | 4-methylphenethylamine | H-Val-NH-CH₂CH₂-C₆H₄-Me · HCl |
| 33.30 | Boc-Val-OH | (S)-1-(4-nitrophenyl)ethylamine | H-Val-NH-CH(CH₃)-C₆H₄-NO₂ · HCl |

-continued

| Prep Ex. | Amino acid | Amine | Product |
|---|---|---|---|
| 33.31 | Boc-Val-OH | N-methylbenzylamine | H-Val-N(Me)Bn · HCl |
| 33.32 | Boc-Val-OH | (S)-tetrahydrofurfurylamine | H-Val-NH-CH₂-(S)-THF · HCl |
| 33.33 | Boc-Val-OH | 2-aminoindane | H-Val-NH-(2-indanyl) · HCl |
| 33.34 | Boc-Val-OH | 2,5-difluorobenzylamine | H-Val-NH-CH₂-(2,5-diF-C₆H₃) · HCl |
| 33.35 | Boc-Val-OH | 3-(trifluoromethyl)benzylamine | H-Val-NH-CH₂-(3-CF₃-C₆H₄) · HCl |
| 33.36 | Boc-Val-OH | aniline | H-Val-NH-Ph · HCl |
| 33.37 | Boc-Val-OH | furfurylamine | H-Val-NH-CH₂-(2-furyl) · HCl |
| 33.38 | Boc-Phe-OH | (R)-α-methylbenzylamine | H-Phe-NH-CH(Me)-Ph · HCl |
| 33.39 | Boc-Val-OH | (R)-1-cyclohexylethylamine | H-Val-NH-CH(Me)-Cy · HCl |

-continued

| Prep Ex. | Amino acid | Amine | Product |
|---|---|---|---|
| 33.40 | Boc-Val-OH | H₂N-C(CH₃)₂-Ph | H-Val-NH-C(CH₃)₂-Ph · HCl |
| 33.41 | Boc-Phe-OH | H₂N-CH(Et)-Ph | H-Phe-NH-CH(Et)-Ph · HCl |
| 33.42 | Boc-Val-OH | H₂N-CH(CH₃)-C₆H₄-OMe | H-Val-NH-CH(CH₃)-C₆H₄-OMe · HCl |
| 33.43 | Boc-Val-OH | H₂N-CH(CH₃)-Ph | H-Val-NH-CH(CH₃)-Ph · HCl |
| 33.44 | Boc-Val-OH | 1-amino-2-hydroxyindane | H-Val-NH-(2-hydroxyindan-1-yl) · HCl |
| 33.45 | Boc-Val-OH | cyclopropylmethylamine | H-Val-NH-CH₂-cyclopropyl · HCl |
| 33.46 | Boc-Val-OH | H₂N-CH(CH₂OH)-Ph | H-Val-NH-CH(CH₂OH)-Ph · HCl |
| 33.47 | Boc-Val-OH | 1-naphthylamine | H-Val-NH-(1-naphthyl) · HCl |

Preparative Example 34

To a solution of 3-chlorobenzaldehyde (2.0 g, 14.2 mmol) in THF (5 mL) at 0° C. was added LiN(TMS)$_2$ (17.0 ml, 1.0 M in THF) dropwise and the resulting solution was stirred for 20 min. EtMgBr (6.0 mL, 3.0 M in Et$_2$O) was added dropwise and the mixture was refluxed for 24 h. The mixture was cooled to room temperature, poured into saturated aqueous NH$_4$Cl (50 mL), and then extracted with CH$_2$Cl$_2$ (3×50 volumes). The organic layers were combined, concentrated under reduced pressure. The crude residue was stirred with 3 M HCl (25 mL) for 30 min and the aqueous layer was extracted with CH$_2$Cl$_2$ (3×15 mL) and the organic layers were discarded. The aqueous layer was cooled to 0° C. and treated with solid NaOH pellets until pH=10 was attained. The aqueous layer was extracted with CH$_2$Cl$_2$ (3×15 mL) and the organic layers were combined. The organic layer was washed with brine (1×25 mL), dried (Na$_2$SO$_4$), and concentrated under reduced pressure to afford 1.6 g (66% yield) of the crude amine as an oil (MH$^+$ 170). This material was determined to be >90% pure and was used without further purification.

Preparative Example 34.1

The aldehyde (3.5 g) and conc. HCl (20 ml) were combined and stirred overnight at 40° C. The reaction mixture was poured into cold water and extracted with ether, washed with satd. NaHCO$_3$ and brine, dried over anhydrous MgSO$_4$, filtered and concentrated in vacuo to give 1.76 g of product (55%)

Preparative Example 34.2

Chlorine was bubbled into 100 ml of CH$_2$Cl$_2$ at 10° C. The aldehyde (3.73 ml) was charged with 50 ml of CHCl$_3$ and then cooled to 0° C. AlCl$_3$ was added portionwise, followed by the chlorine solution and let stir at room temperature overnight. The reaction was poured into 150 ml of ice and 50 ml of 3N HCl and stirred for 30 min. Organic layer was washed with brine, dried with Na$_2$SO$_4$, and concentrated in vacuo. The crude product was purified via flash column chromatography (Hex/EtOAc 40/1) to yield 1.5 g of pure product.

Preparative Example 34.3

Step A
The ketone (3.25 g) was reacted following the procedure set forth in Preparative Example 88.2, Step B to give the oxime (3.5 g, 99%).

Step B
The product from step A (1.2 g) was stirred with AcOH (3 ml) and Pd/C (10%, 300 mg) in EtOH (40 ml) under a hydrogen atmosphere overnight. The reaction mixture was filtered through celite and the filtrate was concentrated in vacuo. The crude material dissolved in ether and washed with 2N NaOH, organic washed with brine, dried with Na$_2$SO$_4$, and concentrated in vacuo to give product (960 mg, 86%).

Preparative Example 34.4

Step A
To a suspension of NaH (1.45 g) in DMF (25 ml) under a nitrogen atmosphere was added p-bromophenol (5 g) at 0° C. After stirring for 20 min, BrCH$_2$CH(OEt)$_2$ (5.3 ml) was added and the reaction was heated to reflux overnight. The solution was cooled and poured into ice water (80 ml) and extracted with ether. The ether layer was washed with 1N NaOH and brine, dried with MgSO₄, filtered and concentrated in vacuo to give 8.4 g of crude product (100%).

Step B

To a solution of the product from Step A (8.4 g) in benzene (50 ml) was added polyphosphoric acid (10 g). The mixture was heated at reflux for 4 hrs. The reaction was cooled to 0° C. and poured into ice water (80 ml) and extracted with ether. The ether layer was washed with saturated sodium bicarbonate and brine, dried with MgSO₄, filtered and concentrated in vacuo to give 4.9 g of crude product (85%).

Step C

To a solution of the product from Step B (2 g) in ether (20 ml) at −78° C. was added t-BuLi dropwise. After stirring for 20 min, DMF (950 mg) was added dropwise and the mixture was stirred at −25° C. for 3 hrs and then warmed to room temperature overnight. Saturated ammonium chloride was added and the solution was extracted with ether. The ether layer was washed with brine, dried with MgSO₄, filtered and concentrated in vacuo to give 980 mg of crude product (67%).

Step D

To a solution of aldehyde (400 g) in ether (10 ml) was added LiN(TMS)₂ (1M in THF, 3.3 ml) at 0° C. dropwise. The solution was stirred at 0° C. for 30 min and EtMgBr (3M in THF, 1.83 ml) was added dropwise. The reaction was refluxed overnight, cooed to 0° C., quenched with saturated ammonium chloride and extracted with ether. The ether was stirred with 3N HCl (20 ml), then the aqueous layer was basified with NaOH pellets and extracted with ether. The ether layer was washed with brine, dried with MgSO₄, filtered and concentrated in vacuo to give 220 mg of product (46%).

Preparative Example 34.5

Following the procedures set forth in Preparative Example 34.4 Steps A through D, but using m-bromophenol (8 g), both amines were formed and separated by preparative plate chromatography (63-65%, MH+=175).

Preparative Example 34.6

To a solution of 3-methyl-thiophene (5 g) in ether (50 ml) was added dropwise a solution of n-BuLi (1.6M in hexane, 32 ml). The mixture was stirred for 1.5 hr at room temperature. DMF (5.1 ml) was then added and let stir overnight. The mixture was poured into saturated ammonium chloride and extracted with ether. The ether layer was washed with brine, dried with Na₂SO₄, and concentrated in vacuo. The crude product was purified via flash column chromatography (EtOAc/Hex 20:1) to afford 5.27 g of an oil (84%).

Preparative Example 34.7

Step A

To a solution of 4-bromo-2-furaldehyde (4 g) in MeOH (75 ml) was added trimethyl-orthoformate (3.8 ml). A catalytic amount of p-toluene sulfonic acid (195 mg) and the mixture was heated to reflux for 3.5 hr. The reaction was cooled down and potassium carbonate was added. The mixture was filtered through a silica gel pad. The filtrate was concentrated in vacuo, dissolved in $CH_2Cl_2$ and filtered. The filtrate was again concentrated in vacuo to give 4.03 g of product (80%).

Step B

To a solution of the product from Step A (2.02 g) in THF (80 ml) at −78° C. was added dropwise a solution of n-BuLi (2.5M in hexanes, 4.4 ml) and stirred for 1.5 hr. A solution of iodomethane (1.7 ml) was added and let stir for 2.5 hrs at −60° C. The cooling bath was removed and saturated ammonium chloride was added and let stir for 10 min. The layers were separated and the organic layer was washed with brine, dried with $Na_2SO_4$, and concentrated in vacuo to afford 1.34 g of crude product.

Step C

The product from Step B (1.43 g) was dissolved in acetone (50 ml) and treated with a catalytic amount of p-toluene sulfonic acid (80 mg). The mixture was heated to reflux for 2 hr. The reaction was cooled down and solid potassium carbonate was added. The mixture was filtered through a silica gel pad and the filtrate was concentrated in vacuo to give 1.246 g of crude product.

Preparative Example 34.8

Step A

To a stirred solution of potassium t-butoxide (2.5 g) in HMPA (20 ml) was added 2-nitropropane (2 ml) dropwise. After 5 min, a solution of methyl-5-nitro-2-furoate (3.2 g) in HMPA (8 ml) was added to the mixture and stirred for 16 hr. Water was added and the aqueous mixture was extracted with EtOAc. The EtOAc layer was washed with water, dried with $MgSO_4$, filtered and concentrated in vacuo. The crude material was purified by flash column chromatography (Hex/EtOAc, 6:1) to yield 3.6 g of product (90%).

Step B

To a solution of the product from Step A (3.6 g) in toluene (16 ml) was added tributyltin hydride (5.4 ml) followed by AIBN (555 mg). The mixture was heated to 85° C. for 3.5 hr. After cooling, the mixture was separated by flash column chromatography (Hex/EtOAc, 7:1) to afford 2.06 g of product (73%).

Step C

To a solution of product from Step B (2.05 g) in THF (60 ml) at 0° C. was added a solution of LAH (1M in ether, 12.8 ml). The reaction was stirred at room temperature for 30 min. Water and 1M NaOH was added until a precipitate formed, diluted with EtOAc, stirred for 30 min and then filtered through a celite pad. The organic filtrate was concentrated in vacuo to give 1.56 g of product (93%).

Step D

To a solution of product from Step C (2.15 g) in $CH_2Cl_2$ (100 ml) was added Dess-Martin oxidant (7.26 g) in $CH_2Cl_2$ (45 ml) and stirred for 30 min. The mixture was diluted with ether (200 ml). The organic layer was washed with 1N NaOH, water and brine, dried with $MgSO_4$, filtered and concentrated in vacuo to give oil and solid. The material was extracted with ether and filtered. Some solid crystallized out from the filtrate, filtered again, and the filtrate was concentrated in vacuo to give 2.19 g of product.

Preparative Example 34.9

Step A

To a solution of carboxylic acid (5 g) in $CH_2Cl_2$ (400 ml) at 0° C. was added $N(OCH_3)CH_3 \cdot HCl$ (11.5 g), DEC (15.1 g), HOBt (5.3 g) and NMM (43 ml) and stirred for 14 hr. The mixture was diluted with $CH_2Cl_2$ (100 ml) and the organic layer was washed with 10% HCl, saturated sodium bicarbonate and brine, dried with $Na_2SO_4$, and concentrated in vacuo to afford 5.74 g of crude product (85%).

Step B

To a solution of iodoethane (0.56 ml) in ether (5 ml) at −78° C. was added a solution of t-BuLi (1.7M in pentane, 8.3 ml) dropwise. The mixture was warmed to room temperature for 1 hr and transferred to a 100 ml round bottom charged with the product from Step A (1 g) in THF (12 ml) at −78° C. The mixture was stirred at −78° C. for 1 hr and at 0° C. for an additional 2 hr. 1M HCl was added dropwise followed by CH$_2$Cl$_2$. The layers were separated and the organic layer was washed with brine, dried with Na$_2$SO$_4$, and concentrated in vacuo to afford 620 mg of product (76%).

Step C

To a solution of the product from Step B (620 mg) in THF/MeOH (10:1) at 0° C. was added NaBH$_4$ (250 mg) in one portion. The mixture was stirred overnight at 0° C., concentrated in vacuo and the crude material was dissolved in CH$_2$Cl$_2$ and washed with 1N NaOH and brine, dried with Na$_2$SO$_4$, and concentrated in vacuo to afford 510 mg of product.

Step D

The above material was reacted in the procedures set forth in Preparative Example 75.75 Steps B and C to yield 170 mg of amine product (28%).

Preparative Example 34.10

The above amine was made analogous to the procedures set forth in Patent WO96/22997 p. 56 (the disclosure of which is incorporated herein by reference thereto), but using ethylglycine instead of benzylglycine in the DCC coupling.

Preparative Example 34.11

Step A

To the nitro compound (3.14 g) and cyclohexylmethanol (1.14 g) in THF (50 ml) was added PPH$_3$ (4.72 g) and cooled to 0° C. Diisopropylazadicarboxylate (3.15 ml) was added dropwise and let stir overnight. The reaction was concentrated in vacuo and purified via flash column chromatography (Hex/EtOAc, 30:1) to give product (3.3 g), which was carried on directly to the next step.

Step B

To the product from step A (3.3 g) in EtOH (50 ml) was added 10% Pd/C (1.7 g) under a hydrogen atmosphere at 55 psi and let stir overnight. The reaction was filtered through celite and concentrated in vacuo to give 3.2 g of product.

Preparative Example 34.12

Step A

A solution of acid (2 g) in ether (20 ml) was added dropwise to a suspension of LiAlH$_4$ (350 mg) in ether (15 ml) at 0° C. The solution was refluxed for 3 hr and stirred at room temperature overnight. 5% KOH was added and reaction was filtered, extracted with ether, dried with MgSO$_4$, filtered and concentrated in vacuo to give the product (1.46 g, 79%, MH+=166).

Step B

To a solution of alcohol from above (1.46 g) in CH$_2$Cl$_2$ at room temperature was added Dess-Martin reagent (5.6 g) portionwise and one drop of water and let stir over the weekend at room temperature. 10% Na$_2$S$_2$O$_3$ was added and stirred for 20 min, extracted with CH$_2$Cl$_2$, washed with saturated sodium bicarbonate, dried with Na$_2$SO$_4$, and concentrated in vacuo to afford 1.1 g of product (76%).

Preparative Example 34.13

The above compound was prepared according to the procedure set forth in EP 0 555 153 A1 (the disclosure of which is incorporated herein by reference thereto).

Preparative Example 34.14

The aldehyde (500 mg) from above was reacted following the procedure set forth in the Preparative Example 13.4, Step A to yield 372 mg of product (76%).

Preparative Example 34.15-34.16

Following the procedures set forth in Preparative Example 34.8 but using the nitroalkanes indicated in the table below, the aldehydes were prepared.

| PREP. Ex. | NITROALKANE | ALDEHYDE | YIELD (%) |
|---|---|---|---|
| 34.15 | cyclopentyl-CH2-NO2 | 4-cyclopentyl-furan-2-carbaldehyde | 17 |
| 34.16 | cyclohexyl-CH2-NO2 | 4-cyclohexyl-furan-2-carbaldehyde | 21 |

Preparative Example 34.17

Step A

To a stirred suspension of 5-bromo-2-furoic acid (15.0 g, 78.54 mmol) in 225 mL of CH$_2$Cl$_2$ at room temperature was added oxalyl chloride followed by a catalytic amount of N,N'-dimethylforamide. After 1 h, ethanol (20 mL) was added followed by triethylamine (22 mL). Reaction was continued for 15 h. The mixture was concentrated under reduced pressure to a residue, which was extracted with excess volume of hexanes, and hexanes-CH$_2$Cl$_2$ (3:1, v/v). The extracts were filtered, the filtrated was concentrated to a yellow oil, dried on high vacuum, yielding 17.2 g (93%) of the desired ester.

Step B

The ester product obtained from Step A above (17.2 g, 73.18 mmol) was converted to 2-ethyl-4-tertbutyl-5-bromo-furoate (7.9 g, 37%) using the literature procedure: *J. Am. Chem. Soc.*, 1939, 61, 473-478 (the disclosure of which is incorporated herein by reference thereto).

Step C

The ester product obtained from Step B above (7.9 g, 27.13 mol) was reduced to the alcohol (6.32 g) using the procedure set forth in Preparative Example 34.8, Step C.

Step D

The product obtained from Step C above (6.32 g) was dissolved in 140 mL of THF and cooled in a −78° C. bath. A 2.5 M solution of n-butyllithium in hexanes (22 mL, 55.0 mmol) was added dropwise along the side wall of the flask. After 15 min, H$_2$O (~70 mL) was added. Cooling bath was removed, the mixture was stirred for an additional 1 h. Brine (50 mL) and CH$_2$Cl$_2$ (300 mL) were added, the two layers were separated, the aqueous layer was extracted with CH$_2$Cl$_2$ (100 mL), and the combined organic layers ere dried by Na$_2$SO$_4$. Evaporation of solvents afforded 5.33 g (crude) of the debrominated product as a reddish brown oil.

Step E

The alcohol product obtained from Step D above (5.33 g) was oxidized to the corresponding aldehyde (3.06 g, 74% over three steps) using the procedure set forth in Preparative Example 34.8, Step D.

Preparative Example 34.18

Step A

To a stirred solution of cyclopropyl bromide (4.0 mL, 50 mmol) in 120 mL of ether at −78° C. was added dropwise a 1.7M solution of t-butyllithium in pentane (44.5 mL, 75.7 mmol). After 10 min, cooling bath was removed, stirring was continued for 1.5 h. The mixture was cooled again in a −78° C. bath, and 3-furaldehyde (3.5 mL, 41.9 mmol) was added. Reaction was continued for 1 h, and quenched with a saturated NH4Cl aqueous solution. The aqueous mixture was extracted with $CH_2Cl_2$ (100 mL×3). The organic extracts were washed with brine, dried by $Na_2SO_4$, filtered, and concentrated in vacuo to give 5.3 g (91%) of the alcohol product as a yellow oil.

Step B

Chloro trimethylsilane (27.2 mL, 214.2 mmol) was added dropwise to a vigorously stirred suspension of sodium iodide (32 g, 213.5 mmol) in 100 mL of acetonitrile. After 5 min, a solution of the alcohol obtained from Step A above (4.93 g, 35.68 mmol) in 100 mL of acetonitrile was added dropwise. Stirring was continued for 5 min. $H_2O$ (100 mL) was added, the layers were separated, and the aqueous layer was extracted with ether (100 mL×2). The organic layers were combined, washed with a 10% $Na_2S_2O_3$ aqueous solution and brine, and dried over $Na_2SO_4$. Evaporation of solvents gave a dark brown oil, which was filtered through a 5-in silica gel column, eluting with $CH_2Cl_2$-hexanes (1:3.5, v/v). Removal of solvents afforded 4.22 g (47%) of the iodo product as a light yellow oil.

Step C

The iodo-product obtained from Step B above (2.2 g, 8.8 mmol) was dissolved in 60 mL of ether, and stirred in a −78° C. bath. A 1.7 M solution of t-butyllithium in pentane (10.4 mL, 17.7 mmol) was added dropwise. After 20 min, cooling bath was removed. Reaction was continued for 2.5 h, and quenched with $H_2O$ (20 mL). The aqueous mixture was stirred overnight and separated. The aqueous layer was extracted with ether (30 mL). The combined organic layers were washed with brine, dried by $Na_2SO_4$, and filtered through a Celite pad. Removal of solvent gave 1.10 g (100%) of 3-butylfuran as a reddish-yellow oil.

Step D

3-Butylfuran (1.1 g, 8.8 mmol), obtained from Step C above, was dissolved in 60 mL of ether, and stirred in a −78° C. bath. A 1.7 M solution of t-butyllithium in pentane (6.0 mL, 10.2 mmol) was added dropwise along the side wall of the flask. The mixture was stirred for 3 h from −78° C. to 0° C., and continued for 1 h at room temperature. A solution of N,N′-dimethylforamide (1.1 mL, 14.23 mmol) was added. Reaction was continued overnight, and quenched with a saturated $NH_4Cl$ aqueous solution. The two layers were separated, the aqueous layer was extracted with $CH_2Cl_2$ (30 mL×2). The combined organic layers were washed with brine, dried with $Na_2SO_4$, and concentrated to an oil, which was purified by preparative TLC ($CH_2Cl_2$-hexanes=1:1.5, v/v) to give 0.48 g (36%) of the aldehyde (contaminated by some 3-butyl-2-furaldehyde).

Preparative Example 34.19

Step A

3-Ethylfuran was prepared from 3-hydroxymethylfuran according to literature procedure: *J. Org. Chem.*, 1983, 48, 1106-1107 (the disclosure of which is incorporated herein by reference thereto).

Step B

3-Ethylfuran obtained from Step A above was converted to 4-ethyl-2-furaldehyde using the procedure set forth in Preparative Example 34.32, Step D.

Preparative Examples 35-51.20

Following the procedure set forth in Preparative Example 34 but using the commercially available aldehydes and Grignard reagents listed in the Table below, the amine products below were obtained.

| Prep Ex. | Aldehyde | Grignard Reagent | Amine | 1. Yield 2. MH+ |
|---|---|---|---|---|
| 35 | 2-fluorobenzaldehyde | EtMgBr | 1-(2-fluorophenyl)propan-1-amine | 1. 65% 2. 154 |
| 36 | 2-ethoxybenzaldehyde | EtMgBr | 1-(2-ethoxyphenyl)propan-1-amine | 1. 75% 2. 180 |
| 37 | 2-chlorobenzaldehyde | EtMgBr | 1-(2-chlorophenyl)propan-1-amine | 1. 78% 2. 170 |
| 38 | 2-(trifluoromethyl)benzaldehyde | EtMgBr | 1-(2-(trifluoromethyl)phenyl)propan-1-amine | 1. 34% 2. 204 |
| 39 | 2-methylbenzaldehyde | EtMgBr | 1-(2-methylphenyl)propan-1-amine | 1. 68% 2. 150 |
| 40 | 2-(trifluoromethoxy)benzaldehyde | EtMgBr | 1-(2-(trifluoromethoxy)phenyl)propan-1-amine | 1. 40% 2. 220 |
| 41 | 3-fluorobenzaldehyde | EtMgBr | 1-(3-fluorophenyl)propan-1-amine | 1. 73% 2. 154 |
| 42 | 3-(trifluoromethoxy)benzaldehyde | EtMgBr | 1-(3-(trifluoromethoxy)phenyl)propan-1-amine | 1. 52% 2. 220 |
| 43 | benzo[d][1,3]dioxole-5-carbaldehyde | EtMgBr | 1-(benzo[d][1,3]dioxol-5-yl)propan-1-amine | 1. 55% 2. 180 |

-continued

| Prep Ex. | Aldehyde | Grignard Reagent | Amine | 1. Yield<br>2. MH+ |
|---|---|---|---|---|
| 44 | 3-(trifluoromethyl)benzaldehyde | EtMgBr | 1-[3-(trifluoromethyl)phenyl]propan-1-amine | 1. 20%<br>2. 204 |
| 45 | 4-methoxybenzaldehyde | EtMgBr | 1-(4-methoxyphenyl)propan-1-amine | 1. 80%<br>2. 166 |
| 46 | 4-(trifluoromethoxy)benzaldehyde | EtMgBr | 1-[4-(trifluoromethoxy)phenyl]propan-1-amine | 1. 35%<br>2. 220 |
| 47 | benzaldehyde | i-PrMgBr | 2-methyl-1-phenylpropan-1-amine | 1. 20%<br>2. 150 |
| 48 | 3-methoxybenzaldehyde | EtMgBr | 1-(3-methoxyphenyl)propan-1-amine | 1. 77%<br>2. [M − NH$_2$]$^+$ = 149 |
| 49 | 3,5-difluorobenzaldehyde | EtMgBr | 1-(3,5-difluorophenyl)propan-1-amine | 1. 77%<br>2. 172 |
| 50 | 3,5-dimethylbenzaldehyde | EtMgBr | 1-(3,5-dimethylphenyl)propan-1-amine | 1. 78%<br>2. [M − NH$_2$]$^+$ = 147 |
| 51 | pivaldehyde | EtLi | 2,2-dimethylpentan-3-amine | 1. 10%<br>2. 116 |

-continued

| Prep Ex. | Aldehyde | Grignard Reagent | Amine | 1. Yield 2. MH+ |
|---|---|---|---|---|
| 51.2 | 2,3-dihydrobenzofuran-6-carbaldehyde | EtMgBr | 1-(2,3-dihydrobenzofuran-6-yl)propan-1-amine | 1. 37% 2. 161 |
| 51.3 | 2,2-difluorobenzo[d][1,3]dioxole-5-carbaldehyde | EtMgBr | 1-(2,2-difluorobenzo[d][1,3]dioxol-5-yl)propan-1-amine | 1. 63% 2. 216 |
| 51.4 | 3-phenoxybenzaldehyde | EtMgBr | 1-(3-phenoxyphenyl)propan-1-amine | 1. 71% 2. 228 |
| 51.5 | 4-fluoro-3-methylbenzaldehyde | EtMgBr | 1-(4-fluoro-3-methylphenyl)propan-1-amine | 1. 89% 2. 168 |
| 51.6 | 4-phenoxybenzaldehyde | EtMgBr | 1-(4-phenoxyphenyl)propan-1-amine | 1. 20% 2. 228 |
| 51.8 | 3-fluoro-4-(trifluoromethyl)benzaldehyde | EtMgBr | 1-(3-fluoro-4-(trifluoromethyl)phenyl)propan-1-amine | 1. 36% 2. 222 |
| 51.10 | 5-methylfuran-2-carbaldehyde | allylMgBr | 1-(5-methylfuran-2-yl)but-3-en-1-amine | 1. 95% 2. 152.1 |

-continued

| Prep Ex. | Aldehyde | Grignard Reagent | Amine | 1. Yield 2. MH+ |
|---|---|---|---|---|
| 51.11 | 5-(hydroxymethyl)furan-2-carbaldehyde | EtMgBr | 1-(5-(hydroxymethyl)furan-2-yl)propan-1-amine | 1. 61% 2. 138.1 MH+ − H2O |
| 51.12 | 5-((dimethylamino)methyl)furan-2-carbaldehyde | EtMgBr | 1-(5-((dimethylamino)methyl)furan-2-yl)propan-1-amine | 1. 70% 2. 184.1 |
| 51.18 | 3,4-dimethylbenzaldehyde | EtMgBr | 1-(3,4-dimethylphenyl)propan-1-amine | 1. 42% 2. 147 [M − NH2]+ |
| 51.19 | 3,4-dichlorobenzaldehyde | EtMgBr | 1-(3,4-dichlorophenyl)propan-1-amine | 1. 67% 2. 204 |
| 51.20 | 3-chloro-4-fluorobenzaldehyde | EtMgBr | 1-(3-chloro-4-fluorophenyl)propan-1-amine | 1. 33% 2. 188 |

Preparative Examples 51.25-51.31

Following the procedure set forth in Example 34 but using the commercially available aldehydes and Grignard reagents listed in the Table below, the amine products were obtained.

| Prep Ex. | Aldehyde | Grignard Reagent | Amine | Yield (%) |
|---|---|---|---|---|
| 51.25 | 4-(diethylamino)benzaldehyde | EtMgBr | 1-(4-(diethylamino)phenyl)propan-1-amine | 20 |

-continued

| Prep Ex. | Aldehyde | Grignard Reagent | Amine | Yield (%) |
|---|---|---|---|---|
| 51.26 | ![5-methylfuran-2-carbaldehyde] | cyclopentyl-MgBr | cyclopentyl(5-methylfuran-2-yl)methanamine | 77 |
| 51.27 | (34.2) 4-chloro-furan-2-carbaldehyde | EtMgBr | 1-(4-chlorofuran-2-yl)propan-1-amine | 51 |
| 51.28 | (78.1) 3-methylisoxazole-5-carbaldehyde | PhMgBr | (3-methylisoxazol-5-yl)(phenyl)methanamine | 56 |
| 51.29 | (78.1) 3-methylisoxazole-5-carbaldehyde | cyclopentyl-MgBr | cyclopentyl(3-methylisoxazol-5-yl)methanamine | 54 |
| 51.30 | (34.12) 5-(trifluoromethyl)furan-2-carbaldehyde | EtMgBr | 1-(5-(trifluoromethyl)furan-2-yl)propan-1-amine | 80 |
| 51.31 | benzaldehyde | HC≡C—MgBr | 1-phenylprop-2-yn-1-amine | 10 |

Preparative Example 52

F₃C-C(=O)-thiophene → (Step A) → F₃C-C(=N-OH)-thiophene

-continued

F₃C-C(=N-OH)-thiophene → (Step B) → H₂N-CH(CF₃)-thiophene

Step A

A mixture of 2-(trifluoroacetyl)thiophene (2 mL, 15.6 mmol), hydroxylamine hydrochloride (2.2 g, 2 eq), diisopropylethylamine (5.5 mL, 2 eq) and MeOH (50 mL) was stirred at reflux for 48-72 hrs, then concentrated in vacuo. The residue was diluted with EtOAc, washed with 10% $KH_2PO_4$ and dried over $Na_2SO_4$ (anhydrous). Filtration and concentration afforded the desired oxime (2.9 g, 96%) which was used directly in Step B without further purification.

Step B

To a mixture of the product from Step A above in TFA (20 mL) was added Zn powder (3 g, 3 eq) portionwise over 30 min and stirred at room temperature overnight. The solid was filtered and the mixture reduced in vacuo. Aqueous NaOH (2 M) was added and the mixture was extracted several times with $CH_2Cl_2$. The organic phase was dried over anhydrous $Na_2SO_4$, filtered and concentrated to afford the desired product (1.4 g, 50%).

Preparative Examples 53-61

Following the procedure set forth in Preparative Example 52 but using the commercially available ketones listed in the Table below, the following amines were obtained.

| Prep Example | Ketone | Amine | 1. Yield (%) 2. $MH^+$ |
|---|---|---|---|
| 53 | | | 1. 11  2. 128 |
| 54 | | | 1. 33  2. 142 |
| 55 | | | 1. 49  2. 156 |
| 56 | | | 1. 5  2. 154 |
| 57 | | | 1. 47  2. 174 |
| 58 | | | 1. 71  2. 190 |
| 59 | | | 1. 78  2. 191 |
| 60 | | | 1. 80  2. 190 |
| 61 | | | 1. 9  2. 156 |

Preparative Example 62

To a cooled (0-5° C.) suspension of L-α-(2-thienyl)glycine (0.5 g) and $LiBH_4$ (2M in THF, 3.8 mL) in anhydrous THF (10 mL) was slowly added a THF (5 mL) solution of iodine (0.8 g). After stirring at room temperature for 15 min, the mixture was stirred at reflux overnight. After cooling to room temperature, MeOH was added dropwise until gas evolution ceased and after 30 min, the mixture was evaporated. The oily residue was stirred in 20 mL KOH for 4 hrs, diluted with brine and extracted with EtOAc.

The organic phase was dried over anhydrous $MgSO_4$, filtered and concentrated in vacuo to afford a crude mixture.

Purification by flash column chromatography (50% EtOAc/CH$_2$Cl$_2$, silica) afforded the product (0.3 g, 63%, MH$^+$=144).

Preparative Example 63

CeCl$_3$·7H$_2$O was dried at 140-150° C. for 22 hr. To this solid was added THF (80 mL, anhydrous) and after stirring for 2 hr, the suspension was cooled to −78° C. and to it was added methyl lithium over 30 min. After stirring for an additional 30 min 2-thiophenecarbonitrile dissolved in anhydrous THF (4.5 mL) was added and the resulting mixture stirred for an additional 4.5 hr at −78° C. Concentrated aqueous NH$_3$ (25 mL) was added and the mixture was warmed to room temperature and filtered through celite. The filtrate was extracted with dichloromethane, dried over anhydrous Na$_2$SO$_4$, filtered and concentrated in vacuo to afford a crude mixture. Purification by flash column chromatography (5% MeOH, CH$_2$Cl$_2$, silica) afforded the desired product (1.2 g, 62%).

Preparative Example 64

Step A

To a solution of (D)-valinol (4.16 g, 40.3 mmol) in CH$_2$Cl$_2$ (60 mL) at 0° C. was added MgSO$_4$ (20 g) followed by dropwise addition of 3-fluorobenzaldehyde (5.0 g, 40.3 mmol). The heterogenous solution was stirred at 0° C. for 2 h and was allowed to warm to room temperature and stir overnight (14 h). The mixture was filtered and the drying agent was washed with CH$_2$Cl$_2$ (2×10 mL). The filtrate was concentrated under reduced pressure to afford 8.4 g (100%) of an oil which was taken onto the next step without further purification.

Step B

To a solution of the imine (8.4 g, 40.2 mmol) from Step A in CH$_2$Cl$_2$ (60 mL) at room temperature was added Et$_3$N (6.2 mL, 44.5 mmol) followed by dropwise addition of TMSCl (5.7 mL, 44.5 mmol). The mixture was stirred for 6 h at room temperature whereupon the ppt that had formed was filtered off and washed with CH$_2$Cl$_2$ (2×10 mL). The combined filtrate was concentrated under reduced pressure and was taken up in Et$_2$O/hexane (1:1/150 mL). The precipitate was filtered off and the filtrate was concentrated under reduced pressure to afford 10.1 g (89%) of the protected imine as an oil. This material was taken onto the next step without further purification.

Step C

To a solution of EtI (4.0 g, 25.6 mmol) in Et$_2$O (40 mL) at −78° C. was added t-BuLi (30.1 mL, 51.2 mmol, 1.7 M in pentane) and the mixture was stirred for 10 min. The mixture was warmed to room temperature, stirred for 1 h, and was recooled to −40° C. A solution of the imine (6.0 g, 21.4 mmol) from Step B in Et$_2$O (30 mL) was added dropwise via addition funnel to afford a bright orange mixture. The reaction mixture was stirred for 1.5 h at −40° C. then 3M HCl (50 mL) was added and the mixture was allowed to warm to room temperature. Water (50 mL) was added and the layers were separated. The aqueous layer was extracted with Et$_2$O (2×30 mL) and the organic layers were combined and discarded. The aqueous layer was cooled to 0° C. and carefully treated with solid NaOH pellets until pH=12 was attained. The aqueous layer was extracted with Et$_2$O (3×30 mL) and the combined layers were washed with brine (1×30 mL). The organic layer was dried (Na$_2$SO$_4$), filtered, and concentrated under reduced pressure to afford 4.8 g (94% yield) of the amine as an oil. This material was taken on crude to the next step without further purification.

Step D

To a solution of amine (4.5 g, 18.8 mmol) from Step C in MeOH (80 mL) at room temperature was added MeNH$_2$ (25 mL, 40% in water) followed by addition of a solution of H$_5$IO$_6$ (14.0 g, 61.4 mmol) in H$_2$O (25 mL). The heterogenous mixture was stirred for 1.5 h (until the reaction was complete by TLC) and the precipitate was filtered off. The resulting filtrate was diluted with water (50 mL) and the mixture was extracted with Et$_2$O (4×60 mL). The combined organic layers were concentrated to a volume of ~30 mL whereupon 3M HCl (75 mL) was added. The mixture was stirred overnight (12 h at room temperature) after which the mixture was concentrated to remove the volatiles. The aqueous layer was extracted with Et$_2$O (3×40 mL) and the organic layers were discarded. The aqueous layer was cooled to 0° C. and was carefully treated with solid NaOH pellets until pH~12 was reached. The aqueous layer was extracted with Et$_2$O (3×60 mL) and the combined organic layers were dried (MgSO$_4$). The organic layer was concentrated under reduced pressure to afford 2.8 g (97% yield) of the desired amine as an oil [MH$^+$ 154]. This compound was proven to be >85% pure by $^1$H NMR and was used crude in the subsequent coupling step.

Preparative Examples 65-75.10J

Following the procedure set forth in Preparative Example 64 but using the prepared or commercially available aldehydes, amino alcohols, and organolithium reagents in the Table below, the optically pure amine products in the Table below were obtained.

| Prep Ex. | Aldehyde | Amino Alcohol | Organo lithium | Product | 1. Yield (%)<br>2. MH+ |
|---|---|---|---|---|---|
| 65 | 4-F-C6H4-CHO | | EtLi | | 1. 62<br>2. 154 |
| 66 | 4-F-C6H4-CHO | | EtLi | | 1. 70<br>2. 154 |
| 67 | 4-F-C6H4-CHO | | cyclopropyl-Li | | 1. 54<br>2. 166 |
| 68 | 4-F-C6H4-CHO | | cyclopropyl-Li | | 1. 67<br>2. 166 |
| 69 | 3-F-C6H4-CHO | | EtLi | | 1. 67<br>2. 154 |
| 70 | 2-thienyl-CHO | | EtLi | | 1. 42<br>2. 142 |
| 71 | 2-thienyl-CHO | | EtLi | | 1. 36<br>2. 142 |
| 72 | PhCHO | | cyclopropyl-Li | | 1. 62<br>2. 148 |

-continued

| Prep Ex. | Aldehyde | Amino Alcohol | Organo lithium | Product | 1. Yield (%)<br>2. MH+ |
|---|---|---|---|---|---|
| 73 | thiophene-2-carboxaldehyde | H2N—/—OH (isopropyl) | t-BuLi | amine-thiophene product | 1. 27<br>2. 256 |
| 74 | benzaldehyde | H2N—/—OH (isopropyl) | t-BuLi | amine-phenyl product | 1. 15<br>2. 164 |
| 75 | benzaldehyde | H2N—/—OH (isopropyl) | CF3CH2CH2Li | trifluoro-phenyl amine product | 1. 7<br>2. 204 |
| 75.1 | 5-methylfuran-2-carboxaldehyde | H2N—/—OH (isopropyl) | EtLi | ethyl-methylfuran amine | 1. 65<br>2. 123 [M – NH2]+ |
| 75.2 | 5-methylfuran-2-carboxaldehyde | H2N—/—OH (isopropyl, other stereo) | EtLi | ethyl-methylfuran amine | 1. 62<br>2. 123 [M – NH2]+ |
| 75.3 | 3-methylthiophene-2-carboxaldehyde | H2N—/—OH (isopropyl) | EtLi | ethyl-methylthiophene amine | 1. 93<br>2. 139 [M – NH2]+ |
| 75.4 | 3-methylthiophene-2-carboxaldehyde | H2N—/—OH (isopropyl) | tBuLi | t-Bu-methylthiophene amine | 1. 50<br>2. 167 [M – NH2]+ |
| 75.5 | (34.6) 4-methylthiophene-2-carboxaldehyde | H2N—/—OH (isopropyl) | tBuLi | t-Bu-methylthiophene amine | 1. 48<br>2. 167 [M – NH2]+ |

-continued

| Prep Ex. | Aldehyde | Amino Alcohol | Organo lithium | Product | 1. Yield (%)<br>2. MH+ |
|---|---|---|---|---|---|
| 75.6 | (34.6) | | EtLi | | 1. 97<br>2. 139 [M − NH$_2$]+ |
| 75.7 | (34.6) | | iPrLi | | 1. 87<br>2. 153 [M − NH$_2$]+ |
| 75.8 | (34.6) | | cyclopropyl-Li | | 1. 94<br>2. 151 [M − NH$_2$]+ |
| 75.9 | (34.8) | | EtLi | | 1. 75<br>2. 151 [M − NH$_2$]+ |
| 75.10 | (34.8) | | tBuLi | | 1. 30<br>2. 179 [M − NH$_2$]+ |
| 75.10A | (34.7) | | cyclopropyl-Li | | 1. 61<br>2. 135 [M − NH$_2$]+ |
| 75.10B | (34.19) | | EtLi | | 1. 24<br>2. 154 |

-continued

| Prep Ex. | Aldehyde | Amino Alcohol | Organo lithium | Product | 1. Yield (%) 2. MH+ |
|---|---|---|---|---|---|
| 75.10C | (34.18) | | EtLi | | 1. 32 2. 165 [M − NH₂]+ |
| 75.10D | (34.8) | | MeLi | | 1. 47 2. 137 [M − NH₂]+ |
| 75.10E | (34.8) | | iPrLi | | 1. 30 2. 165 [M − NH₂]+ |
| 75.10F | (34.8) | | cyclopropyl-Li | | 1. 67 2. 163.0 [M − NH₂]+ |
| 75.10G | (34.17) | | EtLi | | 1. 24 2. 165 [M − NH₂]+ |
| 75.10H | (34.15) | | EtLi | | 1. 70 2. 194 |

-continued

| Prep Ex. | Aldehyde | Amino Alcohol | Organo lithium | Product | 1. Yield (%)<br>2. MH+ |
|---|---|---|---|---|---|
| 75.10J | (34.16) | | EtLi | | 1. 54<br>2. 208 |

Preparative Examples 75.11-75.59

Following the procedure set forth in Preparative Example 64 but using the prepared or commercially available aldehydes, amino alcohols, and organolithium reagents in the Table below and carrying the amine on crude, the optically pure amine products in the Table below were obtained.

| Prep Ex. | Aldehyde | Amino Alcohol | Organo lithium | Product | Yield (%) |
|---|---|---|---|---|---|
| 75.11 | | | cyclopropyl-Li | | 52 |
| 75.12 | | | cyclopropyl-Li | | 50 |
| 75.13 | | | iPrLi | | 57 |
| 75.14 | | | iPrLi | | 54 |
| 75.15 | | | iPrLi | | 58 |
| 75.16 | | | cyclopropyl-Li | | 61 |

-continued

| Prep Ex. | Aldehyde | Amino Alcohol | Organo lithium | Product | Yield (%) |
|---|---|---|---|---|---|
| 75.17 | (5-methylthiophene-2-carbaldehyde) | (S)-2-amino-3-methylbutan-1-ol | EtLi | (1-(5-methylthiophen-2-yl)propyl)amine | 72 |
| 75.18 | (5-methylthiophene-2-carbaldehyde) | (S)-2-amino-3-methylbutan-1-ol | cyclopropyl-Li | cyclopropyl(5-methylthiophen-2-yl)methanamine | 68 |
| 75.19 | (5-methylthiophene-2-carbaldehyde) | (S)-2-amino-3-methylbutan-1-ol | iPrLi | 2-methyl-1-(5-methylthiophen-2-yl)propyl)amine | 77 |
| 75.20 | (5-methylthiophene-2-carbaldehyde) | (S)-2-amino-3-methylbutan-1-ol | t-BuLi | 2,2-dimethyl-1-(5-methylthiophen-2-yl)propyl)amine | 15 |
| 75.21 | (5-methylthiophene-2-carbaldehyde) | (S)-2-amino-3-methylbutan-1-ol | MeLi | 1-(5-methylthiophen-2-yl)ethylamine | 50 |
| 75.22 | 3-(benzyloxy)benzaldehyde | (S)-2-amino-3-methylbutan-1-ol | EtLi | 1-(3-(benzyloxy)phenyl)propylamine | 23 |
| 75.24 | biphenyl-3-carbaldehyde | (S)-2-amino-3-methylbutan-1-ol | EtLi | 1-(biphenyl-3-yl)propylamine | 20 |
| 75.27 | benzo[d][1,3]dioxole-5-carbaldehyde | (S)-2-amino-3-methylbutan-1-ol | EtLi | 1-(benzo[d][1,3]dioxol-5-yl)propylamine | 65 |

-continued

| Prep Ex. | Aldehyde | Amino Alcohol | Organo lithium | Product | Yield (%) |
|---|---|---|---|---|---|
| 75.28 | benzaldehyde | 2-amino-3-methylbutan-1-ol | iPrLi | (S)-2-methyl-1-phenylpropan-1-amine | 61 |
| 75.29 | 3,5-difluorobenzaldehyde | 2-amino-3-methylbutan-1-ol | EtLi | (S)-1-(3,5-difluorophenyl)propan-1-amine | 90 |
| 75.30 | 1-(benzo[d][1,3]dioxol-5-yl)-2-methylpropan-1-amine | 2-amino-3-methylbutan-1-ol | iPrLi | 1-(benzo[d][1,3]dioxol-5-yl)-2-methylpropan-1-amine | 62 |
| 75.31 | 3-fluorobenzaldehyde | 2-amino-3-methylbutan-1-ol | iPrLi | (S)-1-(3-fluorophenyl)-2-methylpropan-1-amine | 43 |
| 75.32 | benzo[d][1,3]dioxole-5-carbaldehyde | 2-amino-3-methylbutan-1-ol | cyclopropyl-Li | (benzo[d][1,3]dioxol-5-yl)(cyclopropyl)methanamine | 50 |
| 75.33 | 3-fluorobenzaldehyde | 2-amino-3-methylbutan-1-ol | cyclopropyl-Li | cyclopropyl(3-fluorophenyl)methanamine | 50 |
| 75.34 | 3-fluorobenzaldehyde | 2-amino-3-methylbutan-1-ol | tBuLi | 1-(3-fluorophenyl)-2,2-dimethylpropan-1-amine | 51 |
| 75.35 | 5-methylfuran-2-carbaldehyde | 2-amino-3-methylbutan-1-ol | MeLi | 1-(5-methylfuran-2-yl)ethan-1-amine | 51 |

| Prep Ex. | Aldehyde | Amino Alcohol | Organo lithium | Product | Yield (%) |
|---|---|---|---|---|---|
| 75.36 | thiazole-2-carbaldehyde | (S)-2-amino-3,3-dimethylbutan-1-ol | tBuLi | (R)-2,2-dimethyl-1-(thiazol-2-yl)propan-1-amine | 57 |
| 75.37 | 4,5-dimethylfuran-2-carbaldehyde | (S)-2-amino-3,3-dimethylbutan-1-ol | tBuLi | | 60 |
| 75.38 | 4,5-dimethylfuran-2-carbaldehyde | (S)-2-amino-3,3-dimethylbutan-1-ol | EtLi | | 73 |
| 75.39 | 5-methylfuran-2-carbaldehyde | (S)-2-amino-3,3-dimethylbutan-1-ol | MeLi | | 48 |
| 75.41 | 5-methylfuran-2-carbaldehyde | (S)-2-amino-3,3-dimethylbutan-1-ol | cyclopropyl-Li | | 52 |
| 75.42 | thiophene-3-carbaldehyde | (S)-2-amino-3,3-dimethylbutan-1-ol | EtLi | | 40 |
| 75.43 | thiophene-3-carbaldehyde | (S)-2-amino-3,3-dimethylbutan-1-ol | tBuLi | | 20 |
| 75.44 | 5-methylfuran-2-carbaldehyde | (S)-2-amino-3,3-dimethylbutan-1-ol | t-BuLi | | 79 |

-continued

| Prep Ex. | Aldehyde | Amino Alcohol | Organo lithium | Product | Yield (%) |
|---|---|---|---|---|---|
| 75.45 | 5-methylfuran-2-carbaldehyde | (S)-2-amino-3,3-dimethylbutan-1-ol | iPrLi | (S)-1-(5-methylfuran-2-yl)-2-methylpropan-1-amine | 55 |
| 75.46 | (75.57) 3-methylisoxazole-5-carbaldehyde | (S)-2-amino-3,3-dimethylbutan-1-ol | tBuLi | (S)-1-(3-methylisoxazol-5-yl)-2,2-dimethylpropan-1-amine | 39 |
| 75.47 | (75.57) 3-methylisoxazole-5-carbaldehyde | (S)-2-amino-3,3-dimethylbutan-1-ol | iPrLi | (S)-1-(3-methylisoxazol-5-yl)-2-methylpropan-1-amine | 55 |
| 75.48 | (75.57) 3-methylisoxazole-5-carbaldehyde | (S)-2-amino-3,3-dimethylbutan-1-ol | cyclopropyl-Li | (S)-cyclopropyl(3-methylisoxazol-5-yl)methanamine | 34 |
| 75.49 | (34.7) 4-methylfuran-2-carbaldehyde | (S)-2-amino-3,3-dimethylbutan-1-ol | EtLi | (S)-1-(4-methylfuran-2-yl)propan-1-amine | 61 |
| 75.50 | (34.7) 4-methylfuran-2-carbaldehyde | (S)-2-amino-3,3-dimethylbutan-1-ol | tBuLi | (S)-1-(4-methylfuran-2-yl)-2,2-dimethylpropan-1-amine | 25 |
| 75.51 | (34.2) 4-chlorofuran-2-carbaldehyde | (S)-2-amino-3,3-dimethylbutan-1-ol | iPrLi | (S)-1-(4-chlorofuran-2-yl)-2-methylpropan-1-amine | 33 |

-continued

| Prep Ex. | Aldehyde | Amino Alcohol | Organo lithium | Product | Yield (%) |
|---|---|---|---|---|---|
| 75.52 | (34.2) | | tBuLi | | 30 |
| 75.53 | (34.2) | | EtLi | | 39 |
| 75.54 | (34.2) | | cyclopropyl-Li | | 38 |
| 75.55 | | | EtLi | | 64 |
| 75.56 | | | EtLi | | 46 |
| 75.57 | (75.57) | | EtLi | | 62 |
| 75.58 | | | iPrLi | | 24 |
| 75.59 | (34.1) | | EtLi | | 70 |

-continued

| Prep Ex. | Aldehyde | Amino Alcohol | Organo lithium | Product | Yield (%) |
|---|---|---|---|---|---|
| 75.60 | benzo[1,3]dioxole-5-carbaldehyde | (S)-2-amino-3-methylbutan-1-ol | t-BuLi | (S)-1-(benzo[1,3]dioxol-5-yl)-2,2-dimethylpropylamine | 60 |
| 75.61 | 4,5-dimethylfuran-2-carbaldehyde | (S)-2-amino-3-methylbutan-1-ol | iPrLi | (S)-1-(4,5-dimethylfuran-2-yl)-2-methylpropylamine | 60 |
| 75.62 | benzofuran-2-carbaldehyde | (S)-2-amino-3-methylbutan-1-ol | t-BuLi | (S)-1-(benzofuran-2-yl)-2,2-dimethylpropylamine | 57 |
| 75.63 | benzofuran-2-carbaldehyde | (S)-2-amino-3-methylbutan-1-ol | EtLi | (S)-1-(benzofuran-2-yl)propylamine | 94 |
| 75.64 | furan-2-carbaldehyde | (S)-2-amino-3-methylbutan-1-ol | t-BuLi | (S)-1-(furan-2-yl)-2,2-dimethylpropylamine | 46 |
| 75.65 | 5-chlorofuran-2-carbaldehyde | (S)-2-amino-3-methylbutan-1-ol | t-BuLi | (S)-1-(5-chlorofuran-2-yl)-2,2-dimethylpropylamine | 60 |
| 75.66 | 5-methylthiophene-2-carbaldehyde | (S)-2-amino-3-methylbutan-1-ol | t-BuLi | (S)-2,2-dimethyl-1-(5-methylthiophen-2-yl)propylamine | 15 |

| Prep Ex. | Aldehyde | Amino Alcohol | Organo lithium | Product | Yield (%) |
|---|---|---|---|---|---|
| 75.67 | (5-formyl-3,4-dimethylfuran) | (2-amino-3-methylbutan-1-ol) | t-BuLi | (amine product, furan) | 60 |

Preparative Example 75.75

Step A

To a solution of aldehyde (2.5 g) in ether (50 ml) at 0° C. was added EtMgBr (4.56 ml) dropwise. The heterogenous mixture was stirred for 2 hr at 0° C. and then poured into a beaker of saturated ammonium chloride (25 ml), ice and $CH_2Cl_2$ (30 ml). After the biphasic mixture stirred for 10 min, the organic layer was separated, washed with brine, dried over $Na_2SO_4$, filtered, and concentrated in vacuo to afford the product (2.41 g, 95%)

Step B

To a solution of alcohol from Step A above (1 g) in toluene at room temperature was added DPPA. The mixture was cooled to 0° C. and DBU was added and let stir for 12 hr at room temperature. The layers were separated and the organic layer was washed with water, 1N HCl and dried over $Na_2SO_4$, filtered, and concentrated in vacuo. Purified by preparative plate chromatography (hexane/EtOAc 20/1) to give the product (840 mg, 75%).

Step C

To a solution of azide (730 mg) from Step B above in THF (7 ml) was added $PPh_3$ (1 g). The heterogenous solution was stirred for 12 hr, whereupon water (1.5 ml) was added. The mixture was refluxed overnight, cooled to room temperature and concentrated in vacuo. Ether and 1N HCl were added to the residue. The aqueous layer was cooled to 0° C., basified with NaOH pellets and extracted with ether. The ether layer was dried over $MgSO_4$, filtered, and concentrated in vacuo to afford the product (405 mg, 62%).

Step D

To a solution of azide in THF at −10° C. was added $LiAlH_4$ portionwise. The heterogenous solution was stirred at room temperature for 1 hr and then refluxed for 4 hr. The solution was cooled to 0° C. and water, 2M NaOH and ether were added to the reaction. The mixture was filtered through a celite pad. The filtrate was treated with 3N HCl. The aqueous layer was cooled to 0° C., basified with NaOH pellets and extracted with ether. The ether layer was dried over $MgSO_4$, filtered, and concentrated in vacuo to afford the product.

Preparative Example 75.76-75.90

Following a similar procedure set forth in Preparative Example 75.75, and using the reduction procedure indicated, the following amines were obtained.

| Prep Ex. | Aldehyde | Reducing Step | Product | % Yield |
|---|---|---|---|---|
| 75.76 | (furan-3-carbaldehyde) | D | (1-(furan-3-yl)propan-1-amine) | 43 |
| 75.77 | (benzofuran-2-carbaldehyde) | C | (1-(benzofuran-2-yl)propan-1-amine) | 36 |

| Prep Ex. | Aldehyde | Reducing Step | Product | % Yield |
|---|---|---|---|---|
| 75.78 | 5-chlorothiophene-2-carbaldehyde | D | 1-(5-chlorothiophen-2-yl)propan-1-amine | 32 |
| 75.79 | 5-ethylfuran-2-carbaldehyde | C | 1-(5-ethylfuran-2-yl)propan-1-amine | 42 |
| 75.80 | 1-(thiophen-3-yl)propan-1-amine (aldehyde shown as amine) | D | 1-(thiophen-3-yl)propan-1-amine | 56 |
| 75.81 | 4,5-dimethylfuran-2-carbaldehyde | D | 1-(4,5-dimethylfuran-2-yl)propan-1-amine | 35 |
| 75.82 | 5-bromofuran-2-carbaldehyde | C | 1-(5-bromofuran-2-yl)propan-1-amine | 13 |
| 75.83 | 5-(2-chlorophenyl)furan-2-carbaldehyde | C | 1-(5-(2-chlorophenyl)furan-2-yl)propan-1-amine | 42 |
| 75.84 | 5-(2-(trifluoromethyl)phenyl)furan-2-carbaldehyde | C | 1-(5-(2-(trifluoromethyl)phenyl)furan-2-yl)propan-1-amine | 39 |
| 75.85 | 5-(3-chlorophenyl)furan-2-carbaldehyde | C | 1-(5-(3-chlorophenyl)furan-2-yl)propan-1-amine | 26 |

-continued

| Prep Ex. | Aldehyde | Reducing Step | Product | % Yield |
|---|---|---|---|---|
| 75.86 | | C | | 25 |
| 75.87 | | C | | 14 |
| 75.88 | (34.14) | C | | 49 |
| 75.89 | (34.13) | C | | 34 |
| 75.90 | | C | | 44 |
| 75.92 | | C | | 74 |
| 75.93 | | C | | 81 |

Preparative Example 75.200

If one were to follow a similar procedure as that in Preparative Example 64, but using the aldehyde from Preparative Example 1004A and cyclopentyllithium instead of ethyllithium, the title aldehyde could be prepared.

Preparative Example 75.201

If one were to follow a similar procedure as in Preparative Example 75.200, but using 5-methylfuranaldehyde instead of the aldehyde from Preparative Example 1004A, the title aldehyde could be prepared.

Preparative Example 76

The desired compound was prepared according to methods previously described in *J. Med. Chem.* 1996, 39, 3319-3323 (the disclosure of which is incorporated herein by reference thereto).

Preparative Example 76.1

Step A

To a solution of amine from Preparative Example 75.90 (2.22 g) in $CH_2Cl_2$ (50 ml) at 0° C. was added TEA (3.03 ml) followed by $BOC_2O$ (2.85 g). The heterogenous mixture was allowed to stir at room temperature overnight. 10% Citric acid was added to the reaction and the layers were separated. The organic layer was washed with saturated sodium bicarbonate, brine and dried with $Na_2SO_4$, filtered, and concentrated in vacuo. The crude material was purified by flash column chromatography (Hex/EtOAc 10:1) to afford 2.7 g of an oil (81%).

Step B

Following the procedure from Preparative Example 13.4, Step A, but using the product from Step A above (450 mg) and 3-thiophene boronic acid (284 mg), the product was prepared (325 mg, 71%).

Step C

To the product from Step B (325 g) was added 4M HCl in dioxane (1.31 ml) and let stir for 1 hr. The reaction was concentrated in vacuo and taken up in $CH_2Cl_2$ and concentrated in vacuo again. This procedure was repeated 5 times to afford a semisolid (89%).

Preparative Example 76.2-76.3

Following the procedures set forth in Preparative Example 76.1, but using the commercially available boronic acids, the indicated amines were prepared.

| Prep Ex. | Boronic Acid | Product | Yield (%) |
|---|---|---|---|
| 76.2 | (pyridyl)B(OH)₂ | ClH·H₂N-(furan-pyridyl) | 70 |

-continued

| Prep Ex. | Boronic Acid | Product | Yield (%) |
|---|---|---|---|
| 76.3 | (HO)₂B-[3,5-dimethylisoxazole] | [1-(4-(3,5-dimethylisoxazol-4-yl)furan-2-yl)propyl]amine·HCl·H₂N | 35 |

Preparative Example 76.10

Step A

Step B

Step C

Step D

Step A

The product from Preparative Example 75.75, Step A (2.5 g) was reacted via the Preparative Example 13.11, Step B to give the ketone (1.93 g, 78%).

Step B

To a solution of ketone from Step A above (500 mg) in THF (5 ml) at 0° C. was added S-2-methyl-CBS-oxazaborolidine (0.98 ml) dropwise followed by $BH_3 \cdot Me_2S$ (1.48 ml). The mixture was stirred at 0° C. for 2 hr and was allowed to warm to room temperature and stir overnight. The mixture was cooled to 0° C. and treated with MeOH (10 ml). After stirring for 20 min, the reaction was concentrated in vacuo. The residue was dissolved in $CH_2Cl_2$ and washed with 1M HCl, saturated sodium bicarbonate, water and brine, dried over $Na_2SO_4$, filtered, and concentrated in vacuo. The crude material was purified by preparative plate chromatography (Hex/EtOAc 4:1) to afford 650 mg of an oil (89%).

Step C

The chiral alcohol from Step B above was reacted via the Preparative Example 75.75 Step B to give the azide.

Step D

The azide from Step C above was reacted via the Preparative Example 75.75 Step C to give the amine product.

Preparative Example 76.11

The desired compound was prepared as in Preparative Example 76.10, but using the R-2-methyloxazaborolidine in step B.

Preparative Example 77

The desired compound was prepared according to methods previously described in *J. Med. Chem.* 1996, 39, 3319-3323 (the disclosure of which is incorporated herein by reference thereto).

Preparative Example 78

The desired compound was prepared according to methods previously described in *Chem. Pharm. Bull.* 1991, 39, 181-183 (the disclosure of which is incorporated herein by reference thereto).

Preparative Example 78.1

The desired compound was prepared according to methods previously described in J. Organometallic Chem. 1998, 567, 31-37 (the disclosure of which is incorporated herein by reference thereto).

Preparative Example 79

The desired compound was prepared according to methods previously described in *Chem. Pharm. Bull.* 1991, 39, 181-183 (the disclosure of which is incorporated herein by reference thereto).

Preparative Example 80

The desired compound was prepared according to methods previously described in (a) *Synthesis* 1987, 998-1001, (b) *Synthesis* 1996, 641-646, and (c) *J. Med. Chem.* 1991, 34, 2176-2186 (the disclosures of each reference being incorporated herein by reference thereto).

Preparative Example 81

The desired compound was prepared according to methods previously described in (a) *Synthesis* 1987, 998-1001, (b) *Synthesis* 1996, 641-646 and (c) *J. Med. Chem.* 1991, 34, 2176-2186 (the disclosures of each reference being incorporated herein by reference thereto).

Preparative Example 82

The desired compound was prepared according to methods previously described in *J. Med. Chem.* 1988, 31, 2176-2186 (the disclosure of which is incorporated herein by reference thereto).

Preparative Example 83

To a solution of carboxylic acid (1.5 g, 7.89 mmol) in $H_2O$/acetone (1:10/12 mL total) at 0° C. was added $Et_3N$ (1.43 mL, 10.3 mmol) followed by addition of ethyl chloroformate (0.83 mL, 8.68 mmol). The resulting mixture was stirred for 30 min after which a solution of $NaN_3$ (0.77 g, 11.8 mmol) in $H_2O$ (2 mL) was added dropwise. The resultant heterogenous mixture was stirred for 1 h at 0° C., then cold water (5 mL) and $Et_2O$ (10 mL) were added. The layers were separated and the aqueous layer was extracted with $Et_2O$ (2×10 mL). The organic layers were combined, toluene (20 mL) was added, and the organic layers were dried ($MgSO_4$) and concentrated under reduced pressure to a volume of 20 mL. t-BuOH (5 mL) was added and the mixture was refluxed for 12 h. The mixture was concentrated under reduced pressure and the crude residue was taken up in 3M HCl (30 mL) and was heated at reflux for 12 h. The mixture was cooled to room temperature and extracted with $Et_2O$ (3×15 mL). The aqueous layer was cooled to 0° C. and solid NaOH pellets were added until pH~12 was reached. The aqueous layer was extracted with $Et_2O$ (3×30 mL) and the combined organic layers were dried ($MgSO_4$) and concentrated under reduced pressure to afford 0.78 g (61% yield) of an oil [$MH^+$ 162]. This material was used without further purification.

Preparative Example 84

The corresponding cyclopropyl analog was prepared according to the procedure outlined in Preparative Example 83.

Preparative Example 85

The corresponding cyclohexyl analog was prepared according to the procedure outlined in Preparative Example 83.

Preparative Example 86

The desired compound was prepared according to methods previously described in *J. Org. Chem.* 1978, 43, 892-898 (the disclosure of which is incorporated herein by reference thereto).

Preparative Example 88.2

Step A

2-Methylthiophene (3 g) was dissolved in THF and cooled to −40° C. N-butyllithium (2.5M in hexane, 12.24 ml) added dropwise and let stir at 40° C. for 30 min. CuBr.(CH$_3$)$_2$S (6.29 g) added and let warm to −25° C. where the trifluoroaceticanhydride (4.32 ml) was added. The reaction was stirred at −15° C. over the weekend. The reaction was quenched with saturated ammonium chloride and extracted with EtOAc. The organic layer washed with brine, dried with MgSO$_4$, filtered and concentrated in vacuo to give 4.59 g of an oil (78%).

Step B

The product from Step A (4.58 g), hydroxylamine hydrochloride (3 g), sodium acetate (4.4 g), EtOH (75 ml) and H$_2$O (7.5 ml) were combined and heated to 75° C. overnight. The reaction was concentrated in vacuo, taken up 1N HCl, extracted with ether, dried with MgSO$_4$, filtered and concentrated in vacuo to give 4.58 g of the product (93%, MH+=210).

Step C

The product from Step B above (4.5 g) was dissolved in TFA (40 ml) and cooled to 0° C. Zn powder (4.2 g) was added portionwise and let reaction warm to room temperature and stir overnight. The reaction was concentrated in vacuo, taken up in 1N NaOH, extracted with ether, dried with MgSO$_4$, filtered and concentrated in vacuo to give 3.43 g of the product (80%).

Preparative Example 89

To a solution of KH (0.45 g, 11.3 mmol) in THF (15 mL) at room temperature was added amine hydrochloride (0.85 g, 5.1 mmol) portionwise to afford a heterogenous reaction mixture. The mixture was allowed to stand overnight (12 h) and MeI (0.32 mL, 5.1 mmol) was added dropwise. The mixture was stirred for 6 h after which the mixture was carefully poured into cold brine (125 mL). The mixture was extracted with Et$_2$O (3×25 mL) and the organic layers were combined. The organic layer was dried (Na$_2$SO$_4$), filtered, and concentrated under reduced pressure to afford the crude product as an oil. This material was carried on crude to the coupling step without further purification or characterization.

Preparative Example 89.1

To a solution of KH (1.1 g) in THF (20 ml) at room temperature was added (R)-2-amino-1-butanol 48 ml) dropwise to afford a heterogenous mixture. The mixture was allowed to stand overnight (18 hr) and then MeI (1.59 ml) was added dropwise. The mixture was stirred for 4 hr after which brine was added. Extracted with ether, dried with K$_2$CO$_3$, filtered and concentrated in vacuo to afford 1.75 g of an oil.

Preparative Example 89.2

To a solution of KH (1.1 g) in THF (20 ml) at room temperature was added (S)-2-amino-1-butanol 48 ml) dropwise to afford a heterogenous mixture. The mixture was allowed to stand overnight (18 hr) and then MeI (1.59 ml) was added dropwise. The mixture was stirred for 4 hr after which brine was added. Extracted with ether, dried with K$_2$CO$_3$, filtered and concentrated in vacuo to afford 1.75 g of an oil.

Preparative Example 90

The corresponding cis analog was prepared in an analogous fashion utilizing the procedure described in Preparative Example 89. This material was also used without further purification.

Preparative Example 91

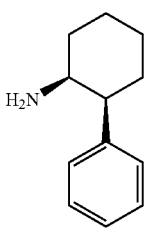

The desired compound was prepared according to methods previously described in *J. Org. Chem.* 1987, 52, 4437-4444 (the disclosure of which is incorporated herein by reference thereto).

Preparative Example 92

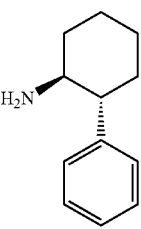

The desired compound was prepared according to methods previously described in *Bull. Chem. Soc. Jpn.* 1962, 35, 11-16 (the disclosure of which is incorporated herein by reference thereto).

Preparative Example 93

The desired amine was prepared from the corresponding ketone according to standard methods previously described in (a) *Synthesis* 1987, 998-1001, (b) *Synthesis* 1996, 641-646 and (c) *J. Med. Chem.* 1991, 34, 2176-2186 (the disclosures of each being incorporated herein by reference thereto).

Preparative Example 94

The desired amine was prepared from the corresponding ketone according to standard methods previously described in (a) *Synthesis* 1987, 998-1001, (b) *Synthesis* 1996, 641-646 and (c) *J. Med. Chem.* 1991, 34, 2176-2186 (the disclosures of each being incorporated herein by reference thereto).

Preparative Example 95

Step A

Lithium hexamethyldisilylazide (34 mL, 1M in THF) was added dropwise to a −78° C. THF (20 mL) solution of isobutyronitrile (2.8 mL). After 40 min, cyclopropyl-methylbromide (5 g) was added and the mixture warmed to and stirred at 25° C. overnight. After cooling to 0° C., 1M HCl (aq) was added and the mixture was extracted with diethyl ether, dried over anhydrous $Na_2SO_4$, filtered and concentrated in vacuo at 0° C. to give the desired product (4.5 g).

Step B

Methyl Lithium (17 mL, 1.4 M in $Et_2O$) was added to the product from Step A above (1.5 g) in $Et_2O$ (anhydrous) at 0° C. The mixture was stirred at 0-25° C. overnight, then diluted with 3M HCl (aq), extracted with $CH_2Cl_2$, dried over anhydrous $Na_2SO_4$, filtered, concentrated in vacuo at 0° C. and used directly in Step C.

Step C

The product from Step B above was added to a slurry of $NaBH_4$ (1.4 g) in isopropanol (50 mL) at 0° C., then the mixture was stirred at reflux for 8 hr and at room temperature for 48 hrs. Water was added and the mixture was stirred for 30 min, then extracted with diethyl ether, dried over anhydrous $Na_2SO_4$, filtered and concentrated in vacuo. The residue was diluted with $CH_2Cl_2$ and extracted with 3M HCl. The organic phase was discarded and the aqueous phase was basified with NaOH (aq) and extracted with $CH_2Cl_2$. Drying over anhydrous $Na_2SO_4$, filtering, and concentration in vacuo gave the desired compound (0.5 g).

Preparative Example 96

Step A

2-Thiophenecarbonyl chloride (2.0 mL, 18.7 mmol) was dissolved in 100 mL dichloromethane. After addition of diisopropylethylamine (4.1 mL, 23.4 mmol) and Boc-piperazine (3.66 g, 19.7 mmol), the mixture was stirred for 4 h at room temperature. The resulting mixture was put into water (500 mL) and acidified with 3N HCl to pH~1. Extraction with dichloromethane (2×100 mL) and drying over sodium sulfate resulted in sufficiently pure product that was used in the next step without any further purification. $^1$H NMR (300 MHz, $d_6$-DMSO) 1.60 (s, 9H), 3.29 (dd, 4H), 3.69 (dd, 4H), 7.23 (dd, 1H), 7.49 (d, 1H), 7.79 (d, 1H).

Step B

The crude material from Step A was dissolved in trifluoroacetic acid/dichloromethane (75 mL, 4/1). After stirring for 2 h, the reaction mixture was put drying over sodium sulfate resulted in sufficiently pure product that was used in Step C without any further purification. $^1$H NMR (300 MHz, $d_6$-DMSO) 2.81 (dd, 4H), 3.63 (dd, 4H), 7.21 (dd, 1H), 7.46 (d, 1H), 7.82 (d, 1H).

Step C

The crude material (3.50 g, 17.8 mmol) from Step B was dissolved in dichloromethane (100 mL). After addition of diisopropylethylamine (18.7 mL, 107 mmol), 3-nitrosalicylic acid (3.3 g, 18.0 mmol), and PyBrOP (10.4 g, 22.3 mmol), the resulting mixture was stirred over night at room temperature before being put into 1N sodium hydroxide (200 mL). Extraction with dichloromethane (2×200 mL) removed all PyBrOP by-products. The aqueous phase was acidified with 3N HCl and subsequently extracted with dichloromethane (3×100 mL). The combined organic phases of the acidic extraction were dried over sodium sulfate, concentrated, and finally purified by column chromatography (dichloromethane/methanol=10/1) to yield the desired product (2.31 g, 34% over 3 steps). $^1$H NMR (300 MHz, $d_6$-DMSO) 3.30-3.90 (m, 8H), 7.10-8.20 (m, double signals due to E/Z-isomers, 6H), 10.82 (s, 1H).

Step D

The nitro-compound (2.3 g, 6.4 mmol) from Step C was dissolved in methanol (50 mL) and stirred with 10% Pd/C under a hydrogen gas atmosphere over night. The reaction mixture was filtered through Celite and washed thoroughly with methanol. Finally, the filtrate was concentrated in vacuo and purified by column chromatography (dichloromethane/methanol=10/1) to yield the desired product (1.78 g, 84%). $^1$H NMR (300 MHz, $d_6$-DMSO) 3.30-3.90 (m, 8H), 7.22 (m, 2H), 7.55 (d, 1H), 7.71 (d, 1H), 7.88 (d, 1H), 8.15 (d, 1H), 10.85 (bs, 1H).

Preparative Example 97

Step A

Picolinic acid (3.0 g, 24.3 mmol) was suspended in $SOCl_2$ (15 mL). After addition of dimethylformamide (5 drops), the reaction mixture was stirred for 4 hours. Evaporation of the solvent yielded the corresponding acid chloride as HCl-salt. Without any further purification, the solid was suspended in 120 mL dichloromethane. After addition of diisopropylethylamine (12.7 mL, 73 mmol) and Boc-piparazine (4.8 g, 25.5 mmol), the reaction was stirred over night at room temperature. The resulting mixture was put into water (500 mL) and extracted with dichloromethane (2×100 mL). Drying over sodium sulfate resulted in sufficiently pure product that was used in Step B without any further purification. $^1$H NMR (300

MHz, d$_6$-DMSO) 1.63 (s, 9H), 3.21 (dd, 4H), 3.61 (dd, 4H), 7.57 (dd, 1H), 7.63 (d, 1H), 7.98 (dd, 1H), 8.70 (d, 1H).

Step B

The crude material from Step A was dissolved in trifluoroacetic acid/dichloromethane (75 mL, 4/1). After stirring for 2 days, the reaction mixture was put into 1N sodium hydroxide (400 mL). Extraction with dichloromethane (2×100 mL) and drying over sodium sulfate resulted in sufficiently pure product that was used in Step C without any further purification. $^1$H NMR (300 MHz, d$_6$-DMSO) 2.77 (dd, 2H), 2.83 (dd, 1H), 3.38 (dd, 2H), 3.64 (dd, 1H), 7.58 (dd, 1H), 7.62 (d, 1H), 8.00 (dd, 1H), 8.67 (d, 1H).

Step C

The crude material (1.35 g, 7.06 mmol) from Step B was dissolved in dichloromethane (50 mL). After addition of diisopropylethylamine (3.7 mL, 21.2 mmol), 3-nitrosalicylic acid (1.36 g, 7.41 mmol), and PyBrOP (3.62 g, 7.77 mmol), the resulting mixture was stirred over night at room temperature before being put into 1N sodium hydroxide (300 mL). Extraction with dichloromethane (2×100 mL) removed any PyBrOP products. The aqueous phase was acidified with 3N HCl. Adjustment of the pH with saturated sodium carbonate solution to almost neutral crushed the desired compound out of solution. The aqueous phase was subsequently extracted with dichloromethane (3×100 mL). The combined organic layers of the neutral extraction were dried over sodium sulfate, concentrated, and finally purified by column chromatography (dichloromethane/methanol=20/1) to yield the desired product (1.35 g, 16% over 3 steps). $^1$H NMR (300 MHz, d$_6$-DMSO) 3.30-3.95 (m, 8H), 7.22 (m, 1H), 7.61 (m, 1H), 7.73 (d, 2H), 8.03 (m, 1H), 8.17 (m, 1H), 8.69 (m, 1H), 10.82 (s, 1H).

Step D

The nitro-compound (1.35 g, 3.79 mmol) from Step C was dissolved in methanol (60 mL) and stirred with 10% Pd/C under a hydrogen gas atmosphere over night. The reaction mixture was filtered through Celite and washed thoroughly with methanol. Finally, the filtrate was concentrated in vacuo and purified by column chromatography (dichloromethane/methanol=20/1) to yield the desired product (1.10 g, 89%). $^1$H NMR (300 MHz, d$_6$-DMSO) 3.50-3.85 (m, 8H), 6.47 (dd 1H), 6.74 (m, 2H), 7.59 (dd, 1H), 7.71 (d, 1H), 8.04 (dd, 1H), 8.68 (d, 1H).

Preparative Example 98

Step A

1-Methyl-2-pyrrolecarboxylic acid (2.5 g, 20.0 mmol) was dissolved in dichloromethane (50 mL). After addition of PyBrOP (16.3 g, 35.0 mmol), diisopropylethylamine (14.0 mL, 73.0 mmol) and Boc-piparazine (5.5 g, 30.0 mmol), the reaction was stirred over night at room temperature before being put into 1N sodium hydroxide (200 mL). Extraction with dichloromethane (2×100 mL) removed all PyBrOP by-products. The aqueous phase was acidified with 3N HCl. Adjustment of the pH with saturated sodium carbonate solution to almost neutral precipitated the desired compound. The aqueous phase was subsequently extracted with dichloromethane (3×100 mL). The combined organic phases of the neutral extraction were dried over sodium sulfate. Removal of the solvent resulted in sufficiently pure product that was used in Step B without any further purification. $^1$H NMR (300 MHz, d$_6$-DMSO) 1.59 (s, 9H) 3.21 (dd, 4H), 3.61 (dd, 4H), 3.74 (s, 3H), 6.11 (dd, 1H), 6.33 (d, 1H), 7.01 (d, 1H).

Step B

The crude material from Step A was dissolved in trifluoroacetic acid/dichloromethane (75 mL, 4/1). After stirring for 3 h, the reaction mixture was put into 1N sodium hydroxide (400 mL). Extraction with dichloromethane (3×100 mL) and drying over sodium sulfate resulted in sufficiently pure product that was used in Step C without any further purification. $^1$H NMR (300 MHz, d$_6$-DMSO) 2.79 (dd, 4H), 3.62 (dd, 4H), 3.76 (s, 3H), 6.11 (dd, 1H), 6.37 (d, 1H), 6.96 (d, 1H).

Step C

The crude material (3.15 g, 16.3 mmol) from Step B was dissolved in dichloromethane (100 mL). After addition of diisopropylethylamine (8.5 mL, 49.0 mmol), 3-nitrosalicylic acid (3.13 g, 17.1 mmol), and PyBrOP (9.11 g, 19.6 mmol), the resulting mixture was stirred over night at room temperature before being put into 1N sodium hydroxide (400 mL). Extraction with dichloromethane (2×100 mL) removed all PyBrOP products. The aqueous phase was then carefully acidified with 3N HCl until the color of the solution changes from orange to yellow and the desired compound crashed out of solution. The aqueous phase was subsequently extracted with dichloromethane (3×100 mL). The combined organic layers of the acidic extraction were dried over sodium sulfate and concentrated in vacuo to yield the desired product. $^1$H NMR (300 MHz, d$_6$-DMSO) 3.35-3.85 (m, 8H), 3.79 (s, 3H), 6.13 (dd, 1H), 6.45 (d, 1H), 7.01 (s, 1H), 7.22 (dd, 1H), 7.70 (d, 1H), 8.16 (d, 1H), 10.83 (s, 2H).

Step D

The crude nitro-compound from Step C was suspended in methanol (60 mL) and stirred with 10% Pd/C under a hydrogen gas atmosphere over night. The reaction mixture was filtered through Celite and washed thoroughly with methanol. The filtrate was concentrated in vacuo and purified by column chromatography (dichloromethane/methanol=10/1) to yield the desired product (2.61 g, 40% for 4 steps). $^1$H NMR (300 MHz, d$_6$-DMSO) 3.45-4.80 (m, 8H), 3.79 (s, 3H), 6.17 (dd, 1H), 6.45 (m, 2H), 6.78 (m, 2H), 7.01 (d, 1H).

Preparative Example 99

Step A

2-Bromopyridine N-oxide hydrochloride (1.13 g, 5.37 mmol) and Boc-piperazine (1.50 g, 8.06 mmol) were heated to 80° C. in pyridine (10 mL) over night. The reaction mixture was put into water (300 mL) and then extracted with dichloromethane (2×100 mL). The combined organic phases were dried over sodium sulfate, concentrated, and finally purified by column chromatography (dichloromethane/methanol=10/1) to yield the desired product (500 mg, 33%).

$^1$H NMR (300 MHz, d-CDCl$_3$) 1.60 (s, 9H), 3.46 (dd, 4H), 3.78 (dd, 4H), 6.99 (m, 2H), 7.37 (dd, 1H), 8.33 (d, 1H).

Step B

The purified product (500 mg, 1.79 mmol) was stirred for 30 min with 4N HCl/dioxane (15 mL). Evaporation of the solvent yielded the crude amine (465 mg) as multiple HCl-salt which was used in Step C without any further purification.

$^1$H NMR (300 MHz, d$_6$-DMSO) 3.38 (m, 4H), 4.81 (m, 4H), 7.34 (dd, 1H), 7.55 (d, 1H), 7.86 (dd, 1H), 8.55 (d, 1H).

Step C

The crude material (370 mg, 1.48 mmol) from Step B was suspended in dichloromethane (20 mL). After addition of diisopropylethylamine (2.6 mL, 14.8 mmol), 3-nitrosalicylic acid (406 mg, 2.22 mmol), and PyBrOP (1.21 g, 2.59 mmol), the mixture was stirred over night at room temperature before being put into 1N sodium hydroxide (50 mL). Extraction with dichloromethane (2×50 mL) removed all PyBrOP products. The aqueous phase was then carefully acidified (pH~4-5) with 3N HCl and extracted with dichloromethane (3×50 mL). The combined organic layers of the acidic extraction were dried over sodium sulfate, concentrated in vacuo and purified by column chromatography (dichloromethane/methanol=10/1) to yield the desired product (330 mg, 65%).

LCMS calculated: 344.1, found: (M+1)$^+$ 345.1

Step D

Sodium hydrosulfite (1.05 g) was dissolved in water (3.0 mL) to yield a 1.5N solution. Addition of dioxane (3.0 mL) was followed by injection of conc. ammonium hydroxide (0.60 mL, yields a 1.0N concentration). After addition of the nitro-compound (100 mg, 0.29 mmol), the reaction mixture was stirred for 0.5 h. Subsequently, the solvent was removed and the residue suspended in dichloromethane/methanol (10/1). Filtration through Celite removed most of the salts. Final purification by column chromatography (dichloromethane/methanol=5/1) yielded the desired product (68 mg, 75%).

LCMS calculated: 314.14, found: (M+1)$^+$ 315.1

Preparative Example 100

Step A

4-Bromopyridine hydrochloride (3.0 g, 15.4 mmol) was dissolved in water (15 mL). After addition of N-benzylpiperazine (14.8 mL, 85.0 mmol) and 500 mg copper sulfate, the reaction mixture was heated overnight to 140° C. The resulting product was extracted with ether (5×75 mL), dried over sodium sulfate and concentrated. Final purification by column chromatography (dichloromethane/methanol/ $NH_4OH$=10/1/0.1) yielded the desired product (2.16 g, 55%). $^1$H NMR (300 MHz, d-CDCl$_3$) 2.68 (dd, 4H), 3.45 (dd, 4H), 6.76 (d, 2H), 7.40 (m, 5H), 8.38 (d, 2H).

Step B

The benzylamine (2.16 g, 8.54 mmol) from Step A, ammonium formate (2.71 g, 43.0 mmol) and Pd(C) (10%, 1.0 g) was suspended in methanol (50 mL) and refluxed for 3 h. The palladium was filtered off and the filtrate was concentrated. The sufficiently pure product was used in Step C without any further purification. $^1$H NMR (300 MHz, d-CDCl$_3$) 2.48 (bs, 1H), 3.13 (dd, 4H), 3.41 (dd, 4H), 7.78 (d, 2H), 8.39 (d, 2H).

Step C

The crude material (1.15 g, 7.06 mmol) from Step B was dissolved in dichloromethane (50 mL). After addition of diisopropylethylamine (4.7 mL, 42.4 mmol), 3-nitrosalicylic acid (1.94 g, 10.6 mmol), and PyBrOP (5.78 g, 12.3 mmol), the resulting mixture was stirred over night at room temperature before being put into 1N sodium hydroxide (300 mL). Extraction with dichloromethane (2×100 mL) removed all PyBrOP products. The aqueous phase was carefully acidified to pH~5-6 with 3N HCl and extracted with dichloromethane (3×100 mL). The combined organic layers of the neutral extraction were dried over sodium sulfate, concentrated, and finally purified by column chromatography (dichloromethane/methanol/$NH_4OH$=10/1/0.1) to yield the desired product (850 mg, 37% for 2 steps).

Step D

The nitro-compound (850 mg, 2.59 mmol) from Step C was dissolved in methanol (40 mL) and stirred with 10% Pd/C under a hydrogen gas atmosphere over night. The reaction mixture was filtered through Celite and washed thoroughly with methanol. Finally, the filtrate was concentrated in vacuo and purified by column chromatography (dichloromethane/methanol/$NH_4OH$=10/1/0.1) to yield the desired product (650 g, 84%). $^1$H NMR (300 MHz, d$_6$-DMSO) 3.40-3.75 (bm, 8H), 6.49 (dd, 1H), 6.76 (m, 2H), 6.93 (d, 2H), 8.28 (d, 2H).

Preparative Example 101

Step 1

N,N'-Dibenzyl-ethane-1,2-diamine (20 mL, 0.0813 mol), triethylamine (22.66 mL, 0.1626 mol) and benzene (100 mL) were combined in a round bottom flask. A solution of 2,3-dibromo-propionic acid ethyl ester (11.82 mL, 0.0813 mol) in benzene (50 mL) was added dropwise. The solution was refluxed over night and monitored by TLC (20% ethyl acetate/hexane). The reaction was cooled to room temperature, then filtered and washed with benzene. The filtrate was concentrated then purified by column chromatography (15% ethyl acetate/hexane). The product was isolated as an oil (25.42 g, 0.0752 mol, 92%). MS: calculated: 338.20, found: 339.2

$^1$H NMR (300 MHz, CDCl$_3$) 1.23 (t, 3H), 2.48 (m, 3H), 2.62 (m, 1H), 2.73 (m, 1H), 3.07 (m, 1H), 3.30 (m, 1H), 3.42 (d, 1H), 3.56 (m, 2H), 3.91 (d, 1H), 4.17 (m, 2H), 7.27 (m, 10H).

Step 2

In a Parr shaker vessel, the ester (25.43 g, 0.075 mol) and methanol (125 mL) were combined. The vessel was purged with argon and palladium catalyst (5% on carbon, 2.5 g) was added. The system was shaken under an atmosphere of hydrogen overnight. TLC (20% ethyl acetate/hexane) indicated that reaction was complete. The reaction mixture was filtered through a pad of Celite and washed with methanol. The filtrate was concentrated and the product isolated as a solid (11.7 g, 0.074 mol, 98%).

MS: calculated: 158.11, found: 159.2 $^1$H NMR (300 MHz, CDCl$_3$) 1.27 (t, 3H), 2.70 (m, 4H), 2.96 (m, 1H), 3.13 (dd, 1H), 3.43 (dd, 1H), 4.18 (m, 2H).

Preparative Example 102

Piperazine-2-carboxylic acid ethyl ester (3.11 g, 0.0197 mol), diisopropylethylamine (5.15 mL, 0.0296 mol) and methylene chloride (200 mL) were combined in a round bottom flask. While stirring at room temperature, a solution of N,N-dimethylcarbamoyl chloride (1.81 mL, 0.0197 mol) in methylene chloride (20 mL) was added dropwise. The reaction was stirred for one hour. After this time the reaction was concentrated and carried on to the next step without further purification. (99% yield).

MS: calculated: 229.14, found: 230.1 $^1$H NMR (300 MHz, CDCl$_3$) 1.30 (t, 3H), 2.85 (s, 6H), 3.10 (m, 3H), 3.31 (m, 2H), 3.60 (m, 2H), 4.21 (q, 2H).

Preparative Example 103-104

Following the procedure described for Preparative Example 102, the Products listed in the table below were prepared using the commercially available chloride shown and piperazine-2-carboxylic acid ethyl ester from Preparative Example 101.

| Ex-ample | Chloride | Product | 1. Yield (%) 2. (M + 1)+ |
|---|---|---|---|
| 103 | methanesulfonyl chloride | N-methylsulfonyl piperazine-2-carboxylic acid ethyl ester | 1. 99 2. 237.1 |
| 104 | furan-2-carbonyl chloride | 1-(furan-2-carbonyl) piperazine-2-carboxylic acid ethyl ester | 1. 62 2. 253.1 |

Preparative Example 105

Step 1

3-Nitrosalicylic acid (3.61 g, 0.0197 g), DCC (2.03 g, 0.0099 mol) and ethyl acetate (130 mL) were combined in a round bottom flask and stirred for 15 min. 4-Dimethylcarbamoyl-piperazine-2-carboxylic acid ethyl ester (4.51 g, 0.0197 g) was added, and the reaction was stirred for 72 hours. The reaction mixture was concentrated then dissolved in dichloromethane. The organic phase was washed once with 0.1N sodium hydroxide. The aqueous phase was back extracted once with dichloromethane. The aqueous phase was acidified and wash three times with ethyl acetate. The aqueous phase was concentrated and purified by column chromatography (5% methanol/DCM).

MS: calculated: 394.15, found: 395.0 $^1$H NMR (300 MHz, CDCl$_3$) 1.32 (t, 3H), 2.86 (m, 7H), 3.15 (m, 1H), 3.51 (m, 4H), 4.24 (m, 3H), 7.15 (m, 1H), 7.66 (m, 1H), 8.20 (m, 1H), 10.86 (bs, 1H).

Step 2

4-Dimethylcarbamoyl-1-(2-hydroxy-3-nitro-benzoyl)-piperazine-2-carboxylic acid ethyl ester (0.80 g, 0.002 mol) and methanol (50 mL) were combined in a round bottom flask. The system was purged with argon. To the solution was added 5% palladium on carbon (~100 mg). The flask was purged with hydrogen and stirred overnight. The reaction was filtered through a pad of celite and washed with methanol. The material was concentrated then purified by column chromatography (6% methanol/DCM). Isolated product (0.74 g, 0.002 mol, 100%).

MS: calculated: 364.17, found: 365.1 $^1$H NMR (300 MHz, CDCl$_3$) 1.27 (t, 3H), 2.85 (m, 8H), 3.18 (1H), 3.45 (m, 3H), 4.19 (m, 3H), 3.90 (m, 3H)

Step 3

1-(3-Amino-2-hydroxy-benzoyl)-4-dimethylcarbamoyl-piperazine-2-carboxylic acid ethyl ester (0.74 g, 0.002 mol) was suspended in a solution of dioxane (10 mL) and water (10 mL). Lithium hydroxide (0.26 g, 0.0061 mol) was added and the mixture stirred for two hours. The solution was acidified to pH=6 with 3N HCl then extracted with butanol. The extracts were combined, dried over sodium sulfate and concentrated.

MS: calculated: 336.14, found: 337.1 $^1$H NMR (300 MHz, CD$_3$OD) 2.86 (m, 7H), 3.23 (m, 3H), 3.54 (m, 3H), 6.92 (m, 2H), 7.23 (m, 1H).

Preparative Example 106-107

Following the procedure described for Example 105, the Products listed in the table below were prepared using the amine from the Preparative Example indicated and 3-nitro-salacylic acid.

| Example | Aniline | Product | 1. Yield (%) 2. (M + 1)+ 3. Note |
|---|---|---|---|
| 106 | 103 | sulfonyl piperazine product | 1. 91 2. Not observed 3. Rainey nickel used in Step 2 |
| 107 | 104 | furan-2-carbonyl piperazine product | 1. 24 2. 360.0 3. For Step 1 used PyBrop/DIEA in DCM |

Preparative Example 108

Step A

3-Nitrosalicylic acid (1.0 g, 5.5 mmol) was dissolved in ethyl acetate (20 mL). 1,3-Dicyclohexylcarbodiimide (0.568 g, 2.8 mmol) was added and the mixture was stirred for approximately 10 minutes and cooled to 0° C. During this time a precipitate formed. Azetidine (0.39 mL, 5.8 mmol) was added and the reaction was stirred overnight and allowed to warm to room temperature. After this time the reaction was cooled to 0° C. and filtered. The collected solid was washed with chilled ethyl acetate. The filtrate was concentrated and purified by column chromatography (80% EtOAc/Hex) to give the product (476 mg, 39.0%).

$^1$H NMR (300 MHz, CDCl$_3$) δ2.40 (m, 2H), 4.38 (m, 4H), 6.97 (m, 1H), 7.62 (d, 1H), 8.12 (d, 1H), 12.88 (m, 1H) ppm.

Step B

The nitro compound (0.48 g, 2.1 mmol) from Preparative Example 32 Step A was dissolved in methanol (25 ml) and stirred with 10% Pd/C under a hydrogen gas atmosphere overnight. The reaction mixture was filtered through celite, the filtrate concentrated in vacuo to give the product (344 mg, 90%). $^1$H NMR (300 MHz, CDCl$_3$) δ2.52 (m, 2H), 4.57 (bs, 4H), 6.75 (m, 1H), 6.90 (m, 2H), 12.71 (bs, 1H) ppm.

Preparative Example 109

In essentially the same manner as described in Preparative Example 108 above, the morpholino-amine product was obtained.

Preparative Example 110

Piperazine (4.9 g, 0.057 mol) was dissolved in dichloromethane (100 mL). N,N'-Dimethylcarbamoyl chloride (1.0 mL, 0.011 mol) was added dropwise to the solution at room temperature. The reaction was stirred for one hour. After this time 1N potassium hydroxide (200 mL) was added. The layers were separated and the aqueous layer was extracted three times with dichloromethane. The organic fractions were combined and dried over sodium sulfate. Filtration and concentration provided the product, without further purification, as an oil (1.16 g, 13%).

$^1$H NMR (CDCl$_3$, 300 MHz) 1.95 (s, 1H), 2.83 (s, 6H), 2.86 (m, 4H), 3.20 (m, 4H). MS: calculated: 157.12, found: 158.1.

Preparative Example 111

Piperazine (4.9 g, 0.057 mol) was dissolved in 1N HCl (100 mL). A solution of phenylsulfonylchloride (1.45 mL, 0.011 mol) in acetonitrile (25 mL) was added dropwise to the solution at room temperature. The reaction was stirred for 30 minutes. After this time the reaction was extracted two times with ethyl acetate. The solution was then made basic with 1N potassium hydroxide and extracted three times with dichloromethane. The dichloromethane fractions were combined and dried over magnesium sulfate. Filtration and concentration provided the product, without further purification, as a solid (1.22 g, 9.4%).

$^1$H NMR (CDCl$_3$, 300 MHz) 2.94 (m, 8H), 7.56 (m, 3H), 7.76 (m, 2H). MS: calculated: 226.08, found: 227.1.

Preparative Example 112

Piperazine (4.9 g, 0.057 mol) was dissolved in dichloromethane (100 mL). Methanesulfonyl chloride (0.85 mL, 0.011 mol) was added dropwise to the solution at room temperature. The reaction was stirred for 30 minutes. After this time 1N potassium hydroxide (200 mL) was added. The layers were separated and the aqueous layer was extracted three times with dichloromethane. The organic fractions were combined and dried over sodium sulfate. Filtration and concentration provided the product, without further purification, as a solid (1.07 g, 11%).

$^1$H NMR (CDCl$_3$, 300 MHz) 1.75 (s, 1H), 2.78 (s, 3H), 2.97 (m, 4H), 3.20 (m, 4H). MS: calculated: 164.06, found: 165.1.

Preparative Example 113

Step A

Boc-Piperazine (3.0 g, 0.0161 mol) was dissolved in dichloromethane (100 mL). Propylisocyanate (1.51 mL, 0.0161 mol) was added to the solution at room temperature. The reaction was stirred for over night. After this time the reaction was diluted with 1N potassium hydroxide (200 mL) and extracted six times with dichloromethane. The organic fractions were combined and dried over magnesium sulfate. Filtration and concentration provided the product as a solid.

Step B

The product of Step A above, was dissolved in a 30% trifluoroacetic acid/dichloromethane solution and stirred overnight. After this time a 1N potassium hydroxide solution (200 mL) was added to the reaction. The aqueous layer was extracted a total of six times with dichloromethane. The organic fractions were combined and dried over sodium sulfate. Filtration and concentration provided the product (1.37 g, 50%).

$^1$H NMR (CDCl$_3$, 300 MHz) 0.92 (t, 3H), 1.52 (m, 2H), 2.89 (m, 4H), 3.01 (s, 1H), 3.18 (m, 2H), 3.37 (m, 4H), 4.61 (bs, 1H). MS: calculated: 171.14, found: 172.0.

Preparative Example 114

Piperazine (4.9 g, 0.0569 mol) was dissolved in 1N HCl (70 mL). A solution of phenylchloroformate (1.43 mL, 0.0114 mol) in acetonitrile (25 mL) was added dropwise to the solution at room temperature. The reaction was stirred for 30 minutes. After this time the reaction was extracted two times with ethyl acetate. The solution was then made basic with 1N potassium hydroxide and extracted three times with dichloromethane. The dichloromethane fractions were combined and dried over magnesium sulfate. Filtration and concentration provided the product, without further purification, as a solid (2.12 g, 18%).

$^1$H NMR (CDCl$_3$, 300 MHz) 1.78 (s, 1H), 2.91 (m, 4H), 3.59 (m, 4H), 7.11 (2H), 7.19 (m, 1H), 7.36 (m, 2H). MS: calculated: 206.24, found: 207.1.

Preparative Example 115-117

Following the procedure described for Example 112, the Products listed in the table below were prepared using the commercially available chloroformate shown and piperazine.

| Example | Chloroformat | Product | 1. Yield (%) 2. (M + 1)$^+$ |
|---|---|---|---|
| 115 | | | 1. 54 2. 144.9 |
| 116 | | | 1. 17 2. 173.0 |
| 117 | | | 1. 69 2. 173.0 |

Preparative Example 118

Step A

Boc-Piperazine (3.01 g, 0.0161 mol) was dissolved in dichloromethane (100 mL) along with diisopropylethylamine (5.61 mL, 0.0322 mol). Benzoylchloride (1.87 mL, 0.0161 mol) was added dropwise to the solution at room temperature. The reaction was stirred for several hours. After this time the reaction was concentrated and the product was purified by column chromatography (10% MeOH/DCM). Boc-Protected product was isolated as a solid (5.21 g).

$^1$H NMR (CDCl$_3$, 300 MHz) 1.47 (s, 9H), 3.45 (m, 8H), 7.41 (m, 5H). MS: calculated: 290.16, found: 290.8.

Step B

The product from Step A above, was dissolved in a 50% trifluoroacetic acid/dichloromethane solution and stirred overnight. After this time the reaction was diluted with 1N potassium hydroxide (200 mL) and the organic layer was separated. The aqueous phase was then extracted six times with dichloromethane. The organic fractions were combined and dried over magnesium sulfate. Filtration and concentration provided product (2.93 g).

$^1$H NMR (CDCl$_3$, 300 MHz) 1.92 (s, 1H), 2.87 (m, 4H), 3.52 (m, 4H), 7.39 (s, 5H). MS: calculated: 190.11, found: 191.1.

Preparative Example 119

Step A

Boc-Piperazine (3.0 g, 0.0161 mol) was dissolved in dichloromethane (100 mL) along with diisopropylethylamine (3.1 mL, 0.0177 mol). N,N'-dimethylsulfamoyl chloride (1.73 mL, 0.0161 mol) was added dropwise to the solution at room temperature. The reaction was stirred for several hours. After this time the reaction was diluted with water (100 mL). The layers were separated and the aqueous layer was extracted six times with dichloromethane. The organic fractions were combined and dried over magnesium sulfate. Filtration and concentration provided the product, without further purification, as a solid (4.53 g).

$^1$H NMR (CDCl$_3$, 300 MHz) 1.47 (s, 9H), 2.84 (s, 6H), 3.21 (m, 4H), 3.48 (m, 4H). MS: calculated: 293.14, found: 194.1 (M-Boc)$^+$.

Step B

The product from Step A above, was dissolved in a 30% trifluoroacetic acid/dichloromethane solution and stirred overnight. After this time the reaction was diluted with water and 1N potassium hydroxide was used to make the aqueous layer slightly basic. The aqueous layer was extracted a total of seven times with dichloromethane. The organic fractions were combined and dried over sodium sulfate. Filtration and concentration provided the product (2.96 g).

$^1$H NMR (CDCl$_3$, 300 MHz) 2.03 (s, 1H), 2.83 (s, 6H), 2.92 (m, 4H), 3.23 (m, 4H). MS: calculated: 193.09, found: 194.1.

Preparative Example 120

Step A

In essentially the same manner as that described in Preparative Example 105, Step 1, using 3-nitrobenzoic acid instead of 3-nitrosalicylic acid, the methyl ester product was prepared.

Step B

The methyl ester (1.79 g, 6.1 mmol) from Step A above, was dissolved in dioxane/water (20 mL/15 mL) at room temperature. Lithium hydroxide (0.258 g, 6.2 mmol) was added to the solution. After a few hours more lithium hydroxide was added (0.128 g, 3.0 mmol) and the reaction was stirred for another hour. After this time the reaction was concentrated and then taken up in water. The solution was extracted two times with ether. The aqueous phase was then acidified and extracted three times with ethyl acetate. The organic fractions were then dried over sodium sulfate, filtered and concentrated. Product was isolated by column chromatography (95% EtOAc/Hex, 0.05% HOAc) to give the product (1.66 g, 98%).

$^1$H NMR (300 MHz, CDCl$_3$) 1.49 (m, 2H), 1.68 (m, 1H), 1.82 (m, 2H), 2.44 (m, 1H) 3.32 (m, 1H), 3.58 (m, 1H), 5.57 (m, 1H), 7.65 (m, 1H), 7.80 (m, 1H), 8.32 (m, 2H), 10.04 (bs, 1 Hppm).

Step C

The nitro compound was dissolved in an excess of methanol (20 mL) and covered by a blanket of argon. 5% Palladium on carbon was added (catalytic) and a hydrogen balloon was attached to the flask. The atmosphere of the system was purged under vacuum and replaced with hydrogen. This step was repeated for a total of three times. The reaction was then stirred under hydrogen overnight. After this time the balloon was removed and the solution was filtered through celite followed by several rinses with methanol. The filtrate was concentrated and dried on the vacuum line to provide the desired aniline product (1.33 g, 90%).

$^1$H NMR (300 MHz, CDCl$_3$) 1.40 (m, 2H), 1.50 (m, 1H), 1.68 (m, 2H), 2.33 (m, 1H) 3.18 (m, 1H), 3.62 (m, 1H), 5.39 (m, 1H), 6.12 (bs, 2H), 6.75 (m, 2H), 7.12 (m, 1H) ppm.

Mass Spectra, calculated: 248, found: 249.1 (M+1)$^+$

Preparative Examples 121-123

Following the procedure described in Preparative Example 120, but using the commercially available amine and benzoic acid indicated, the intermediate products in the table below were obtained.

| Ex. | Carboxylic Acid | Amine | Product | 1. Yield (%)<br>2. (M + 1)+<br>3. Note |
|---|---|---|---|---|
| 121 | 3-nitrosalicylic acid | (R)-pyrrolidine-2-carboxylic acid methyl ester·HCl | coupled product | 1. 21<br>2. 251.0 |
| 122 | 3-nitrosalicylic acid | pyrrolidine-2-carboxylic acid methyl ester·HCl | coupled product | 1. 21<br>2. 265.0<br>3. Skipped step B |
| 123 | 3-nitrosalicylic acid | pyrrolidine-2-carboxamide·HCl | coupled product | 1. 15<br>2. 264.0<br>3. Skipped step B |

Preparative Example 124

Step A

3-Nitrosalicylic acid (500 mg, 2.7 mmol), 1,3-dicyclohexylcarbodiimide (DCC) (563 mg) and ethyl acetate (10 mL) were combined and stirred for 10 min. (R)-(−)-2-pyrrolidinemethanol (0.27 mL) was added and the resulting suspension was stirred at room temperature overnight. The solid was filtered off and the filtrate was either concentrated down and directly purified or washed with 1N NaOH. The aqueous phase was acidified and extracted with EtOAc. The resulting organic phase was dried over anhydrous MgSO$_4$, filtered and concentrated in vacuo. Purification of the residue by preparative plate chromatography (silica gel, 5% MeOH/CH$_2$Cl$_2$ saturated with AcOH) gave the desired compound (338 mg, 46%, MH$^+$=267).

Step B

The product from Step A above was stirred with 10% Pd/C under a hydrogen gas atmosphere overnight. The reaction mixture was filtered through celite, the filtrate concentrated in vacuo, and the resulting residue purified by column chromatography (silica gel, 4% MeOH/CH$_2$Cl$_2$ saturated with NH$_4$OH) to give the product (129 mg, 43%, MH+=237).

Preparative Examples 125-145

Following the procedure described for Preparative Example 124, but using the commercially available amine or the amine from the Preparative Example indicated and 3-nitrosalicylic acid, the products in the table below were obtained.

| Ex. | Amine Comm. Avail./ From Prep. Ex. | Product | 1. Yield (%) 2. (M + 1)+ |
|---|---|---|---|
| 125 | | | 1. 37 2. 298.1 |
| 126 | | | 1. 31 2. 310.1 |
| 127 | | | 1. 68 2. 294.1 |
| 128 | | | 1. 54 2. 365.9 |
| 129 | | | 1. 45 2. 316.1 |
| 130 | 110 | | 1. 59 2. 293.1 |
| 131 | 111 | | 1. 32 2. 362.0 |

| | | | |
|---|---|---|---|
| 132 | 114 | (phenyl carbamate piperazine benzamide, 2-OH, 3-NH₂) | 1. 36  2. 342.0 |
| 133 | 112 | (methylsulfonyl piperazine benzamide, 2-OH, 3-NH₂) | 1. 65  2. 300.0 |
| 134 | (N-isopropyl acetamide piperazine) | (N-isopropyl acetamide piperazine benzamide, 2-OH, 3-NH₂) | 1. 48  2. 321.1 |
| 135 | (2-pyrimidinyl piperazine) | (2-pyrimidinyl piperazine benzamide, 2-OH, 3-NH₂) | 1. 50  2. 300.1 |
| 136 | (2-pyridyl piperazine) | (2-pyridyl piperazine benzamide, 2-OH, 3-NH₂) | 1. 56  2. 299.2 |
| 137 | 115 | (methyl carbamate piperazine benzamide, 2-OH, 3-NH₂) | 1. 79  2. 280.1 |
| 138 | 116 | (propyl carbamate piperazine benzamide, 2-OH, 3-NH₂) | 1. 64  2. 307.1 |
| 139 | (cyclohexyl piperazine) | (cyclohexyl piperazine benzamide, 2-OH, 3-NH₂) | 1. 73  2. 304.2 |

| # | | | |
|---|---|---|---|
| 140 | (acetyl piperazine) | (acetyl piperazinyl-carbonyl-aminophenol) | 1. 34  2. 264.0 |
| 141 | 117 | (isopropyl carbamate piperazinyl-carbonyl-aminophenol) | 1. 40  2. 307.1 |
| 142 | 113 | (propyl urea piperazinyl-carbonyl-aminophenol) | 1. 91  2. 307.1 |
| 143 | 118 | (benzoyl piperazinyl-carbonyl-aminophenol) | 1. 9.0  2. 326.0 |
| 144 | 119 | (dimethylsulfamoyl piperazinyl-carbonyl-aminophenol) | 1. 42  2. 329.0 |
| 145 | (N-methyl piperazine) | (N-methyl piperazinyl-carbonyl-aminophenol) | 1. 6.5  2. 236.1 |

Preparative Example 146

Step A

To a solution of tosylaziridine (*J. Am. Chem. Soc.* 1998, 120, 6844-6845, the disclosure of which is incorporated herein by reference thereto) (0.5 g, 2.1 mmol) and Cu(acac)$_2$ (55 mg, 0.21 mmol) in THF (5 mL) at 0° C. was added PhMgBr (3.5 ml, 3.0 M in THF) diluted with THF (8 mL) dropwise over 20 min. The resulting solution was allowed to gradually warm to rt and was stirred for 12 h. Sat. aq. NH$_4$Cl (5 mL), was added and the mixture was extracted with Et$_2$O (3×15 mL). The organic layers were combined, washed with brine (1×10 mL), dried (MgSO$_4$) and concentrated under reduced pressure. The crude residue was purified by preparative TLC eluting with hexane/EtOAc (4:1) to afford 0.57 g (86% yield) of a solid. The purified tosylamine was taken on directly to the next step.

Step B

To a solution of tosylamine (0.55 g, 1.75 mmol) in $NH_3$ (20 mL) at −78° C. was added sodium (0.40 g, 17.4 mmol). The resulting solution was stirred at −78° C. for 2 h whereupon the mixture was treated with solid $NH_4Cl$ and allowed to warm to rt. Once the $NH_3$ had boiled off, the mixture was partitioned between water (10 mL) and $CH_2Cl_2$ (10 mL). The layers were separated and the aqueous layer was extracted with $CH_2Cl_2$ (2×10 mL). The organic layers were combined,), dried ($NaSO_4$), and concentrated under reduced pressure to a volume of ~20 mL. 4N HCl in dioxane (5 mL) was added and the mixture was stirred for 5 min. The mixture was concentrated under reduced pressure and the resultant crude residue was recrystallized from $EtOH/Et_2O$ to afford 0.30 g (87% yield) of a solid.

Preparative Examples 147-156.10

Following the procedure set forth in Preparative Example 146 but using the requisite tosylaziridines and Grignard reagents listed in the Table below, the following racemic amine hydrochloride products were obtained.

| Prep Ex. | Tosyl aziridine | Grignard Reagent | Amine hydrochloride | Yield (%) |
|---|---|---|---|---|
| 147 | cyclopentane-NTs | MeMgBr | cyclopentyl-Me, $NH_2 \cdot HCl$ | 19 |
| 148 | cyclopentane-NTs | EtMgBr | cyclopentyl-Et, $NH_2 \cdot HCl$ | 56 |
| 149 | cyclopentane-NTs | n-PrMgBr | cyclopentyl-nPr, $NH_2 \cdot HCl$ | 70 |
| 150 | cyclopentane-NTs | i-PrMgCl | cyclopentyl-iPr, $NH_2 \cdot HCl$ | 41 |
| 151 | cyclopentane-NTs | BnMgCl | cyclopentyl-Bn, $NH_2 \cdot HCl$ | 61 |
| 152 | cyclohexane-NTs | MeMgBr | cyclohexyl-Me, $NH_2 \cdot HCl$ | 61 |
| 153 | cyclohexane-NTs | EtMgBr | cyclohexyl-Et, $NH_2 \cdot HCl$ | 66 |
| 154 | cyclohexane-NTs | n-PrMgBr | cyclohexyl-nPr, $NH_2 \cdot HCl$ | 80 |
| 155 | cyclohexane-NTs | i-PrMgBr | cyclohexyl-iPr, $NH_2 \cdot HCl$ | 27 |

-continued

| Prep Ex. | Tosyl aziridine | Grignard Reagent | Amine hydrochloride | Yield (%) |
|---|---|---|---|---|
| 156 | cyclohexane-fused aziridine-NTs | BnMgCl | 2-benzylcyclohexan-1-amine·HCl | 79 |
| 156.1 | cyclopentane-fused aziridine-NTs | cyclopentyl-MgBr | 2-cyclopentylcyclopentan-1-amine | 52 |
| 156.2 | cyclohexane-fused aziridine-NTs | cyclopentyl-MgBr | 2-cyclopentylcyclohexan-1-amine | 49 |
| 156.3 | ethyl-substituted TsN-aziridine | cyclohexyl-MgBr | 1-cyclohexyl-2-aminobutane | 61 |
| 156.4 | ethyl-substituted TsN-aziridine (other stereo) | cyclohexyl-MgBr | 1-cyclohexyl-2-aminobutane | 57 |
| 156.5 | ethyl-substituted TsN-aziridine | cyclopentyl-MgBr | 1-cyclopentyl-2-aminobutane | 64 |
| 156.6 | ethyl-substituted TsN-aziridine (other stereo) | cyclopentyl-MgBr | 1-cyclopentyl-2-aminobutane | 64 |
| 156.7 | methyl-substituted TsN-aziridine | cyclopentyl-MgBr | 1-cyclopentyl-2-aminopropane | 45 |
| 156.8 | methyl-substituted TsN-aziridine | cyclohexyl-MgBr | 1-cyclohexyl-2-aminopropane | 23 |
| 156.9 | methyl-substituted TsN-aziridine | cyclopentyl-MgBr | 1-cyclopentyl-2-aminopropane | 40 |
| 156.10 | methyl-substituted TsN-aziridine | cyclohexyl-MgBr | 1-cyclohexyl-2-aminopropane | 15 |

Preparative Example 156.11

Step A

To a solution of the amine (118 mg) from Preparative Example 148 in $CH_2Cl_2$ (10 ml) was added triethylamine (120 ul), R-Mandelic Acid (164 mg), DCC (213 mg) and DMAP (8.8 mg) and let stir for 40 hr. The mixture was diluted with $CH_2Cl_2$ and washed with saturated ammonium chloride, dried over $Na_2SO_4$, filtered, and concentrated in vacuo. The crude material was purified by preparative plate chromatography (Hex/EtOAc 4:1) to afford both isomers (A, 86 mg, 45%) (B, 90 mg, 48%).

Step B

To isomer B (90 mg) from above in dioxane (5 ml) was added 6M $H_2SO_4$ (5 ml). The reaction was heated to 80° C. over the weekend. 2M NaOH added to basify the reaction and extracted with ether. Ether layer washed with brine, dried over $Na_2SO_4$, filtered, and concentrated in vacuo. The residue was stirred in 4N HCl in dioxane for 30 min, concentrated in vacuo and recrystallized in EtOH/ether to afford 55 mg of product (98%).

Step C

Isomer A (86 mg) was reacted following the procedure set forth in Step B above to give the amine salt.

Preparative Example 156.12

The above nitro compound was reduced following the Preparative Example 2, Step B.

Preparative Example 156.13

To a solution of 1,2-phenylenediame (1.5 g) in $CH_2Cl_2$ (30 ml) at 0° C. was added TEA (2.91 ml), followed by dropwise addition of $MeSO_2Cl$ (1.07 ml). The mixture was allowed to warm to room temperature and stir overnight. 1M HCl added and the layers were separated. The aqueous layer was adjusted to pH=11 with solid NaOH, extracted with $CH_2Cl_2$. The basified aqueous layer was then neutralized using 3N HCl and extracted with $CH_2Cl_2$, dried with $Na_2SO_4$, filtered, and concentrated in vacuo to give 1.8 g of product (71%).

Preparative Example 156.14

The above compound was prepared using the procedure set forth in Preparative Example 156.13, but using $PhSO_2Cl$.

Preparative Example 156.15

The nitro compound was reduced following a similar procedure as in Preparative Example 2, Step B.

Preparative Example 156.16

363

Step A

The known acid (410 mg) above (*J. Med. Chem.* 1996, 34, 4654, the disclosure of which is incorporated herein by reference thereto.) was reacted following the procedure set forth in Preparative Example 2, Step A to yield 380 mg of an oil (80%).

Step B

The amide (200 mg) from above was reacted following the procedure set forth in Preparative Example 2, Step B to yield 170 mg of an oil (100%).

Preparative Example 156.17

Step A

To a solution of ketone (500 mg) in EtOH/water (3:1, 4 ml) at room temperature was added hydroxylamine hydrochloride (214 mg) followed by NaOH to afford a heterogenous mixture. The reaction was not complete so another equivalent of hydroxylamine hydrochloride was added and refluxed overnight. The reaction was cooled to 0° C. and treated with 3N HCl and extracted with $CH_2Cl_2$, washed with brine, dried over $Na_2SO_4$, filtered, and concentrated in vacuo to give 500 mg of product (92%).

Step B

To a solution of oxime (300 mg) in THF (5 ml) at 0° C. was added $LiAlH_4$ (266 mg) portionwise. The heterogenous solution was stirred at room temperature for 14 hr and then refluxed for 8 hr. The solution was cooled to 0° C. and water, 2M NaOH, water and ether were added to the reaction. The mixture was filtered through a celite pad. The filtrate was treated with 3N HCl. The aqueous layer was cooled to 0° C., basified with NaOH pellets and extracted with ether. The ether layer was dried over $MgSO_4$, filtered, and concentrated in vacuo to afford the product (143 mg, 69%).

Preparative Example 156.18

364

Step A

Methoxyacetic acid (14 mL) in $CH_2Cl_2$ (120 mL) and cooled in an ice-water bath was treated with DMF (0.9 mL) and oxalyl chloride (21 mL). After stirring at RT overnight, the mixture was concentrated in vacuo and redissolved in $CH_2Cl_2$ (120 mL). N-methyl-N-methoxylamine (20 g) was added and the mixture stirred at RT overnight. Filtration and concentration in vacuo afforded the desired amide (21 g, 89%).

Step B

To a solution of the above amide (260 mg) in THF (5 ml) at −78° C. was added a solution of 2-thienyllithium (1M in THF, 2.15 ml). The solution was stirred for 2 hr at −78° C. and warmed to −20° C. for an additional 2 hr. The reaction was quenched with saturated ammonium chloride and extracted with $CH_2Cl_2$, washed with brine, dried over $Na_2SO_4$, filtered, and concentrated in vacuo to give 250 mg of product (82%).

Step C

The ketone from above (250 mg) was reacted via the procedure set forth in Preparative Example 156.17 Steps A and B to yield 176 mg of the amine (79%).

Preparative Example 156.19

Step A

To a solution of 3-chlorothiophene (1.16 ml) in ether (20 ml) at −10° C. was added n-BuLi (2.5M in hexane, 5 ml). After solution was stirred at −10° C. for 20 min, propionaldehyde (0.82 ml) in ether (20 ml) was added dropwise and let warm to room temperature slowly. The reaction was quenched with saturated ammonium chloride and extracted with $CH_2Cl_2$, washed with brine, dried over $Na_2SO_4$, filtered, and concentrated in vacuo to give 1.37 g of product (62%).

Step B

The alcohol from Step A above was reacted via the procedures set forth in Preparative Example 75.75, Steps B and C to give the amine Preparative Example 156.20

Step A

To a solution of magnesium metal (360 mg) in THF (15 ml) at 0° C. was added 2-bromothiophene (1.45 ml) in THF (10 ml) dropwise over 20 min. The solution was warmed to room temperature for 3 hr, recooled to 0° C. whereupon a solution of cyclopropylacetonitrile (1 g) in ether (30 ml) was added dropwise via a syringe and let warm to room temperature and stir overnight. 3M HCl was added and washed with $CH_2Cl_2$. The aqueous layer was basified with NaOH pellets and extracted with ether, dried with $Na_2SO_4$, filtered, and concentrated in vacuo to give 625 mg of product (68%).

Step B

The ketone was reacted via the procedure set forth in Preparative Example 156.17 Step A to give the oxime.

Step C

The oxime from above was reacted via the procedure set forth in Preparative Example 156.17 Step B to give the amine.

Preparative Example 156.21

Step A

To a solution of $CH_3ONHCH_3$·HCl (780 mg) and acid chloride (1 g) in $CH_2Cl_2$ at 0° C. was added dry pyridine (1.35 ml) to afford a heterogenous mixture The solution was warmed to room temperature and stirred overnight. 1M HCl was added to the reaction and the organic layer was separated, washed with brine, dried with $Na_2SO_4$, filtered, and concentrated in vacuo to give 1 g of product (85%).

Step B

To a solution of EtI (614 ul) in ether (5 ml) at −78° C. was added t-BuLi (1.7M in pentane, 9 ml) dropwise. The mixture was warmed to room temperature for 1 hr, cooled to −78° C. where the amide (1 g) from Step A in THF (4 ml) was added and allowed to warm to 0° C. for 2 hr. 1M HCl was added to the reaction and extracted with $CH_2Cl_2$, washed with brine, dried with $Na_2SO_4$, filtered, and concentrated in vacuo to give 500 mg of product (63%).

Step C

To a solution of ketone (800 mg) in THF/water (10:1, 20 ml) at 0° C. was added sodium borohydride (363 mg) portionwise. The solution was stirred for 2 hr at 0° C. The mixture was concentrated in vacuo, the residue was dissolved in $CH_2Cl_2$, washed with 1N NaOH and brine, dried with $Na_2SO_4$, filtered, and concentrated in vacuo to give 560 mg of product (69%).

Step D

The alcohol from above was reacted via the procedures set forth in Preparative Example 75.75, Steps B and C to give the amine (176 mg, 59%).

Preparative Example 156.22

Step A

Cyclopropylacetonitrile (12 mmol) in $Et_2O$ (50 mL) at 0° C. was treated with PhMgBr (14 mmol) and the mixture was stirred for 2 hrs at 0° C., then at RT overnight. Hydrochloric acid (3 M) was added, and after stirring for an additional 12 hrs, the mixture was extracted with $CH_2Cl_2$, washed with brine, dried over $Na_2SO_4$, filtered and concentrated in vacuo to give the desired ketone (1.34 g, 70%).

Step B

Following the procedures set forth in Preparative Example 156.20 Steps B and C, the amine was prepared.

Preparative Example 156.23

The above amine was prepared using the procedures set forth in WO 98/11064 (the disclosure of which is incorporated herein by reference thereto.

Preparative Example 157

Step A

By taking the known carboxylic acid (*J. Med. Chem.* 1996, 39, 4654-4666, the disclosure of which is incorporated herein by reference thereto) and subjecting it to the conditions outlined in Preparative Example 112, the product can be prepared.

Step B

Following a similar procedure used in Preparative Example 2, Step A, except using dimethylamine and the compound from Step A above, the product can be prepared.

Step C

Following a similar procedure used in Preparative Example 2, Step B, except using the compound from Step B above, the product can be prepared.

Preparative Example 158

Following a similar procedure used in Preparative Example 157, Steps A-C, except using trifluoromethylsulfonylchloride in Step A above, the product can be prepared.

Preparative Example 500.1

Step A

By using the nitro-amide from Preparative Example 13.3, Step A, the amidine structure can be prepared following a similar procedure to that in *Tetrahedron Lett.*, 2000, 41 (11), 1677-1680 (the disclosure of which is incorporated herein by reference thereto).

Step B

By using the product from Step A and the procedure set forth in Preparative Example 2, Step B, one could obtain the desired amine-amidine.

Alternate Preparative Example 500.2

Step A

By treating the nitro-amide from Preparative Example 13.3, Step B with $POCl_3$ and subsequently $MeNH_2$, according to procedures known in the art, one would obtain the desired compound.

Step B

By treating the product from Step A according to the procedure set forth in Preparative Example 13.3, Step E, one could obtain the desired compound.

Step C

By using the product from Step B and the procedure set forth in Preparative Example 2 Step B, one would obtain the desired compound.

Preparative Example 500.3

Step A

By following a similar procedure as that described in *Zh. Obshch. Khim.*, 27, 1957, 754, 757 (the disclosure of which is incorporated herein by reference thereto), but instead using 2,4-dichlorophenol and dimethylphosphinic chloride, one would obtain the desired compound.

Step B

By following a similar procedure as that described in *J. Organomet. Chem.*; 317, 1986, 11-22 (the disclosure of which is incorporated herein by reference thereto), one would obtain the desired compound.

Step C

By following a similar procedure as that described in *J. Amer. Chem. Soc.*, 77, 1955, 6221 (the disclosure of which is incorporated herein by reference thereto), one would obtain the desired compound.

Step D

By following a similar procedure as that described in *J. Med. Chem.*, 27, 1984, 654-659 (the disclosure of which is incorporated herein by reference thereto), one would obtain the desired compound.

Alternate Preparative Example 500.4

Step A

By following a similar procedure as that described in *Phosphorous, Sulfur Silicon Relat. Elem.*; EN; 61, 12, 1991, 119-129 (the disclosure of which is incorporated herein by reference thereto), but instead using 4-chlorophenol, one would obtain the desired compound.

Step B

By using a similar procedure as that in *Phosphorous, Sulfur Silicon Relat. Elem.*; EN; 61, 12, 1991, 119-129 (the disclosure of which is incorporated herein by reference thereto), but instead using MeMgBr, the desired compound could be prepared.

Step C

By following a similar procedure as that described in *J. Amer. Chem. Soc.*, 77, 1955, 6221 (the disclosure of which is incorporated herein by reference thereto), one would obtain the desired compound.

Step D

By following a similar procedure as that described in *J. Med. Chem.*, 27, 1984, 654-659 (the disclosure of which is incorporated herein by reference thereto), one would obtain the desired compound.

Preparative Example 500.5

By following a similar procedure as that set forth in *J. Org. Chem.* 1998, 63, 2824-2828 (the disclosure of which is incorporated herein by reference thereto), but using CH$_3$CCMgBr, one could obtain the desired compound.

Preparative Example 500.6

Step A
By following the procedure set forth in Preparative Example 13.1, Step B using 3-methoxythiophene, one could obtain the desired product.

Step B
By using the product from step A and following the procedure set forth in Preparative Example 13.19, Step E, the desired compound could be obtained.

Step C
By using the product from Step B and following the procedure set forth in Preparative Example 13.29, Step D, one could obtain the desired compound.

Step D
By using the product from Step C and following the procedure set forth in Preparative Example 13.3, Step B, the desired compound could be obtained.

Step, E
By treating the product from Step D with n-BuLi at –78° C. in THF and quenching the resulting anion with $CO_2$ according to standard literature procedure, one could obtain the desired compound following aqueous acid work up.

Step, F
By using the product from Step E and the procedure set forth in Preparative Example 13.19, Step C, one could obtain the desired compound.

Step G
By using the product from step F and following the procedure set forth in Preparative Example 13.19, Step E, the desired compound could be obtained.

Step H
By using the product from Step G and following the procedure set forth in Preparative Example 2, Step B, the desired compound could be obtained.

Preparative Example 500.7

Step A
If one were to use a similar procedure to that used in Preparative Example 13.3 Step B, except using the hydroxy acid from *Bioorg. Med. Chem. Lett.* 6(9), 1996, 1043 (the disclosure of which is incorporated herein by reference thereto), one would obtain the desired methoxy compound.

Step B
If one were to use a similar procedure to that used in Preparative Example 13.19 Step B, except using the product from Step A above, one would obtain the desired compound.

Step C
If one were to use a similar procedure to that used in *Synth. Commun.* 1980, 10, p. 107 (the disclosure of which is incorporated herein by reference thereto), except using the product from Step B above and t-butanol, one would obtain the desired compound.

Step D
If one were to use a similar procedure to that used in *Synthesis*, 1986, 1031 (the disclosure of which is incorporated herein by reference thereto), except using the product from Step C above, one would obtain the desired sulfonamide compound.

Step E

If one were to use a similar procedure to that used in Preparative Example 13.19 Step E, except using the product from Step D above, one would obtain the desired compound.

Preparative Example 500.8

Step A

Step B

Preparative Example 500.9

Step A

If one were to treat the product from Step C of Example 1125 with BuLi (2.2 eq.) in THF followed by quenching of the reaction mixture with N,N,-dimethylsulfamoyl chloride (1.1 eq.) then one would obtain

Step B

If one were to use the product of Step A above and follow Step E of Preparative Example 500.7, then one would obtain the title compound.

Step A

To a solution of 3-methoxythiophene (3 g) in dichloromethane (175 mL) at −78° C. was added chlorosulfonic acid (8.5 mL) dropwise. The mixture was stirred for 15 min at −78° C. and 1.5 h at room temp. Afterwards, the mixture was poured carefully into crushed ice, and extracted with dichloromethane. The extracts were washed with brine, dried over magnesium sulfate, filtered through a 1-in silica gel pad. The filtrate was concentrated in vacuo to give the desired compound (4.2 g).

Step B

The product from Step A above (4.5 g) was dissolved in dichloromethane (140 mL) and added with triethylamine (8.8 mL) followed by diethyl amine in THF (2M, 21 mL). The resulting mixture was stirred at room temperature overnight.

The mixture was washed with brine and saturated bicarbonate (aq) and brine again, dried over sodium sulfate, filtered through a 1-in silica gel pad. The filtrate was concentrated in vacuo to give the desired compound (4.4 g).

Step C

The product from Step B above (4.3 g) was dissolved in dichloromethane (125 mL) and cooled in a −78° C. bath. A solution of boron tribromide (1.0 M in dichloromethane, 24.3 mL) was added. The mixture was stirred for 4 h while the temperature was increased slowly from −78° C. to 10° C. $H_2O$ was added, the two layers were separated, and the aqueous layer was extracted with dichloro-methane. The combined organic layer and extracts were washed with brine, dried over magnesium sulfate, filtered, and concentrated in vacuo to give 3.96 g of the desired hydroxy-compound.

Step D

The product from step C above (3.96 g) was dissolved in 125 mL of dichloromethane, and added with potassium carbonate (6.6 g) followed by bromine (2 mL). The mixture was stirred for 5 h at room temperature, quenched with 100 mL of $H_2O$. The aqueous mixture was adjusted to pH~5 using a 0.5N hydrogen chloride aqueous solution, and extracted with dichloromethane. The extracts were washed with brine, dried over sodium sulfate, and filtered through a celite pad. The filtrate was concentrated in vacuo to afford 4.2 g of the desired bromo-compound.

Step E

The product from Step D (4.2 g) was dissolved in 100 mL of acetone and added with potassium carbonate (10 g) followed by iodomethane (9 mL). The mixture was heated to reflux and continued for 3.5 h. After cooled to room temperature, the mixture was filtered through a Celite pad. The filtrate was concentrated in vacuo to a dark brown residue, which was purified by flash column chromatography eluting with dichloromethane-hexanes (1:1, v/v) to give 2.7 g of the desired product.

Step F

The product from step E (2.7 g) was converted to the desired imine compound (3 g), following the similar procedure to that of Preparative Example 13.19 step D.

Step G

The imine product from step F (3 g) was dissolved in 80 mL of dichloromethane and cooled in a −78° C. bath. A solution of boron tribromide (1.0 M in dichloromethane, 9.2 mL) was added dropwise. The mixture was stirred for 4.25 h from −78° C. to 5° C. $H_2O$ (50 mL) was added, and the layers were separated. The aqueous layer was extracted with dichloromethane. The organic layer and extracts were combined, washed with brine, and concentrated to an oily residue. The residue was dissolved in 80 mL of methanol, stirred with sodium acetate (1.5 g) and hydroxyamine hydrochloride (0.95 g) at room temperature for 2 h. The mixture was poured into an aqueous mixture of sodium hydroxide (1.0 M aq, 50 mL) and ether (100 mL). The two layers were separated. The aqueous layer was washed with ether three times. The combined ether washings were re-extracted with $H_2O$ once. The aqueous layers were combined, washed once with dichloromethane, adjusted to pH~6 using 3.0 M and 0.5 M hydrogen chloride aqueous solutions, and extracted with dichloromethane. The organic extracts were combined, washed with brine, dried over sodium sulfate, and concentrated in vacuo to give 1.2 g of desired amine compound.

Preparative Example 600

Step A

Following the procedure set forth in Preparative Example 13.19 Step D, the imine was prepared from the known bromoester (1.0 g) to yield 1.1 g (79%) as a yellow solid.

Step B

The product of Step A (0.6 g) was reacted following the procedure set forth in Preparative Example 13.19 Step E to give the amine product 0.19 g (64%).

Step C

The product of Step B (1.0 g) was reacted following the procedure set forth in Preparative Example 13.19 Step B to give the acid as yellow solid 0.9 g (94%).

Step D

The product of Step C (0.35 g) was reacted following the procedure set forth in Preparative Example 13.19 Step E to give the amino acid as yellow solid 0.167 g (93%).

Preparative Example 601

Step A

To a solution of 2-methyl furan (1.72 g) in ether was added BuLi (8.38 mL) at −78° C. and stirred at room temperature for half an hour. The reaction mixture again cooled to −78° C. and quenched with cyclopropyl amide 1 and stirred for two hours at −78° C. and slowly warmed to room temperature. The reaction mixture stirred for three hours at room temperature and quenched with the addition of saturated ammonium chloride solution. The mixture was taken to a separatory funnel, washed with water, brine and dried over anhydrous sodium sulfate. Filtration and removal of solvent afforded the crude ketone, which was purified by using column chromatography to afford the ketone 3.0 g (87%) as a pale yellow oil.

Step B

To a solution of ketone (1.0 g) from Step A above in THF (5.0 mL) at 0° C. was added R-methyl oxazoborolidine (1.2 Ml, 1M in toluene) dropwise followed by addition of a solution of borane complexed with dimethyl sulfide (1.85 mL, 2M in THF). The reaction mixture was stirred for 30 minutes at 0° C. and than at room temperature for one hour. The reaction mixture was cooled to 0° C. and MeOH was added carefully. The mixture was stirred for 20 minutes and was concentrated under reduced pressure. The residue was extracted with ether, washed with water, 1M HCl (10 mL), saturated sodium bicarbonate (10.0 mL) water and brine. The organic layer was dried over anhydrous sodium sulfate, filtered and removal of solvent afforded the crude alcohol which was purified by silica gel chromatography to afford the pure alcohol 0.91 g (91%) as yellow oil.

Preparative Example 601.A

Step A

If one were to follow the procedure set forth in Preparative Example 601, but using the cyclopentylamide instead of the cyclopropylamide (prepared according to standard procedures), then one would obtain the desired alcohol.

Step B

If one were to follow the procedure set forth in Preparative Example 13.25, but instead using the alcohol from Step A above, then one would obtain the title amine.

Preparative Example 601.B

Step A

If one were to follow the procedure set forth in Preparative Example 601.A, but using 4-isopropylfuran instead of 5-methylfuran, then one would obtain the desired alcohol.

Step B

If one were to follow the procedure set forth in Preparative Example 13.25, but instead using the alcohol from Step A above, then one would obtain the title amine.

Preparative Example 602

Step A

An equimolar mixture of 2-methylfuran (1.0 g) and anhydride (2.6 g) was mixed with $SnCl_4$ (0.05 mL) and heated at 100° C. for 3 hours. After cooling the reaction mixture, water (10 mL) was added, followed by saturated sodium carbonate solution until it becomes alkaline. The reaction mixture was extracted with ether several times and the combined ether layer was washed with water, brine and dried over anhydrous sodium sulfate. Filtration and removal of solvent afforded the crude ketone, which was purified by using silica gel chromatography to afford the ketone 0.9 g (43%) as a yellow oil.

Step B

The title alcohol was obtained following a similar procedure set forth in the Preparative Example 601.

Preparative Example 603

To a solution of 5-methyl furan-2-aldehyde (1.0 g) and 3-bromo-3,3-difluoropropene (2.24 g) in DMF (30 mL) was added indium powder (1.66 g) and lithium iodide (50.0 mg). The reaction mixture was stirred over night, diluted with water and extracted with ether. The ether layer was washed with water, brine and purified by silica gel chromatography to afford the pure alcohol 2.8 g (92%).

Preparative Examples 603A and 603D

If one were to follow the procedure of Preparative Example 64, using the aldehydes, amino alcohols and organolithiums in the Table below, then the optically pure amine Products in the Table below would be obtained.

| Prep. Ex. | Aldehyde | Amino Alcohol | Organolithium | Product |
|---|---|---|---|---|
| 603A | (see Preparative Example 1004B) | | iPrLi | |
| 603B | | | tBuLi | |
| 603C | | | tBuLi | |

Preparative Examples 604-611

Following a similar procedure set forth in Preparative Examples 13.25 or 601 the following Alcohols were prepared.

| Prep Ex | Furan | Electrophile | Alcohol | Yield |
|---|---|---|---|---|
| 604 | | CHO | | 86% |
| 605 | | F, COOEt | | 69% |
| 606 | | cyclopropyl-C(O)N(Me)OMe | | 84% |
| 607 | | cyclopropyl-C(O)N(Me)OMe | | 82% |
| 608 | | F, COOEt | | 60% |
| 609 | | F, COOEt | | 65% |
| 610 | | F,F -C(O)N(Me)OMe | | 82% |
| 611 | | OHC-CF$_3$ | | 89% |

Preparative Examples 620-631

Following a similar procedure to that set forth in Preparative Example 13.25 the following Amines were prepared from the corresponding Alcohols.

| Prep Ex | ALCOHOL | AMINE | % YIELD |
|---|---|---|---|
| 620 | | | 28 |
| 621 | | | 58 |

-continued

| Prep Ex | ALCOHOL | AMINE | % YIELD |
|---|---|---|---|
| 622 | | | 69 |
| 623 | | | 81 |
| 624 | | | 82 |
| 625 | | | 45 |
| 626 | | | 57 |

-continued

| Prep Ex | ALCOHOL | AMINE | % YIELD |
|---|---|---|---|
| 627 | | | 58 |
| 628 | | | 54 |
| 629 | | | 53 |
| 630 | | | 50 |
| 631 | | | 82% |

Preparative Example 1001

Step A

Oxalyl chloride (3 mL, 34.27 mmol) was added dropwise to a mixture of 2-methoxy-6-(trifluoromethyl)benzoic acid (1.5 g, 6.81 mmol) (prepared according to known method, see: EP0897904B1), N,N-dimethylformamide (0.3 mL), and dichloromethane (40 mL) with stirring at rt. The reaction mixture was stirred overnight. Evaporation of solvent and excess oxalyl chloride and drying under vacuum afforded 2-methoxy-6-(trifluoromethyl)benzoyl chloride as a solid, which was used without purification.

Step B

A solution of 2-methoxy-6-(trifluoromethyl)benzoyl chloride (ca. 6.81 mmol) from Step A above in dichloromethane (20 mL) was added dropwise to a mixture of 4-(dimethylamino)pyridine (42 mg, 0.34 mmol), triethylamine (2.8 mL, 20.09 mmol), and 2 M dimethylamine solution in tetrahydrofuran (7 mL, 14 mmol), and dichloromethane (30 mL) with stirring at rt. The reaction mixture was stirred overnight. A mixture of dichloromethane and water was added. The organic phase was separated, washed with 1N HCl solution, water, and saturated sodium bicarbonate solution and concentrated. The residue was purified by column chromatography (ethyl acetate:hexanes, 3:1 v/v) to give the product as a white solid (1.24 g, 74% over two steps).

Step C

A mixture of the amide from Step B above (1.8 g, 7.28 mmol), carbon tetrachloride (25 mL), and iron powder (305 mg, 5.46 mmol) was cooled to 0° C. Bromine (0.94 mL, 18.34 mmol) was added dropwise with stirring. After addition, the mixture was stirred at rt for 1 h and at 50° C. for 3 h. The mixture was cooled to rt, diluted with dichloromethane, and slowly poured to a cold 10% NaHSO$_3$ solution. After stirring at rt for 0.5 h, the organic layer was separated and concentrated to give the product as a white solid (2.26 g, 95%).

Step D

Concentrated sulfuric acid (10 mL) was added dropwise to a flask charged with the bromide from Step C above (600 mg, 1.84 mmol) at 0° C. with stirring. A mixture of nitric acid (0.2 mL, 4.76 mmol) and concentrated sulfuric acid (0.3 mL) was then added dropwise. After addition, the mixture was stirred at rt for 3 h. The mixture was added to ice-water, neutralized with 15% NaOH solution to pH 7, and extracted with dichloromethane. The organic layer was concentrated to give the product as a white solid (621 mg, 91%). mp 92° C., m/e 371 (MH$^+$).

Step E

A solution of the compound from Step D above (1.2 g, 3.23 mmol) in dichloromethane (50 mL) was cooled to −75° C. 1M BBr$_3$ solution in dichloromethane (7.5 mL, 7.5 mmol) was added dropwise with stirring. The mixture was stirred at −75° C. for 2 h. The mixture was added to ice-water. After stirring at rt for 0.5 h, the mixture was extracted with dichloromethane. The organic was concentrated and the residue was purified by column chromatography (dichloromethane-methanol, 9:1 v/v) to give the product as a yellow solid (1.05 g, 91%). m/e 357 (MH$^+$).

Step F

A mixture of the compound from Step E above (1.08 g, 3.02 mmol), methanol (30 mL), and 10% Pd—C (250 mg) was subjected to hydrogenation at 50 psi at rt for 6 h. The mixture was filtered through a layer of Celite. The filtrate was concentrated to give the title compound as a pale yellow solid (930 mg, 96%). mp 132° C., m/e 249.

Preparative Example 1002

Step A

To a cooled (−70° C.) etherial (45 mL dry) solution of 3-bromothiophene (3.8 mL) was added BuLi (30 mL of 1.6M in hexane) dropwise, and the mixture was stirred at −70° C. for 20 min. Acetophenone (4.6 mL) in ether (6 mL) was added dropwise with stirring at −70° C. After 3 hrs, the mixture was warmed to RT and sat. NH$_4$Cl (aq) was added and the mixture was extracted with ether. The organic phase was dried (Na$_2$SO$_4$) and concentrated in vacuo to give the title compound which was used in Step B without further purification.

Step B

The crude product from Step A above was stirred with oxalic acid (0.375 g) at 70° C. under reduced pressure for 3 hr, then cooled to RT and extracted with ether. The organic phase was dried (Na$_2$SO$_4$) and concentrated in vacuo to give the product as a pale yellow liquid (5.7 g, 78% for Steps A-B).

Step C

To the product from Step B above (4.2 g) diluted with dichloromethane (30 mL) and containing triethylsilane (6 mL) was added TFA (3 mL) in dichloromethane (7.5 mL). After stirring at RT for 10 min, the mixture was concentrated in vacuo to give the product as a colorless liquid (4.61 g, 80%).

Step D

To an etherial (3.5 mL dry) solution of the thiophene product (1.5 g) from Step C above was added BuLi (3.2 mL of 2.5M), and the mixture was heated at reflux for 15 min, cooled to RT, and DMF (0.8 mL) in ether (3.5 mL) was added dropwise. After stirring for 30 min, sat. NH$_4$Cl (aq) was added and the mixture was extracted with ether. The organic phase was dried (Na$_2$SO$_4$) and concentrated in vacuo to give the title compound (1.71 g, 98%).

Preparative Example 1003

Step A

The aldehyde (0.50 g) was combined with ethylene glycol (1 mL), benzene (40 mL) and pTSA monohydrate (30 mg) and stirred at reflux for 20 hr. Cool to room temperature, add EtOAc and sat. NaHCO$_3$ (aq) solution, separate the organic phase, concentrate in vacuo, and purify by silica gel chromatography (EtOAc-Hex, 1:4) to give a colorless liquid (60 mg)

Step B

The product from Step A above (0.607 g) was stirred at 45° C. overnight with 1N NaOH (aq), then cooled to room temperature, acidified with 3N HCl and extracted with EtOAc. Washing with brine and concentration in vacuo gave a solid (5.0 g).

Step C

Following a similar procedure as that used in Preparative Example 1, except using the product from Step B above and dimethylamine in THF (2M), the product was obtained (1.21 g crude).

Step D

The product from Step C above was dissolved in THF and stirred with 0.3N HCl (aq) and stirred at RT for 4 hr. Concentration in vacuo gave a pale yellow oil (1.1 g, 67%).

Preparative Example 1004

Step A

To a cooled (−78° C.) solution of methoxybenzofuran-2-carboxylic acid (1 g) was added DIBAL (30 mL, 1M in THF). After stirring for 20 min, the mixture was warmed to RT and stirred for 4 hr, then poured into sat. NH$_4$Cl (aq) (35 mL). After stirring at RT for 20 min, 6M HCl (aq) was added and the mixture was extracted with EtOAc, the organic phase dried and then concentrated in vacuo. Purification by silica gel chromatography (EtOAc-hexane, 3:7) afforded the alcohol as a solid (0.4 g, 97%).

Step B

A mixture of the product from Step A above (0.9 g), EtOAc (50 mL) and MnO2 (5.2 g) was stirred at RT for 22 h, then filtered and concentrated in vacuo. The solid was redissolved in EtOAc (50 mL), MnO2 (5.2 g) was added and the mixture was stirred for 4 additional hrs. Filtration, concentration and silica gel purification (EtOAc-Hexane, 1:3) gave the title compound as a solid (0.60 g, 67%).

Preparative Example 1004A

Step A

To a stirred solution of potassium t-butoxide (2.5 g) in HMPA (20 ml) was added 2-nitropropane (2 ml) dropwise. After 5 min, a solution of methyl-5-nitro-2-furoate (3.2 g) in HMPA (8 ml) was added to the mixture and stirred for 16 hr. Water was added and the aqueous mixture was extracted with EtOAc. The EtOAc layer was washed with water, dried with MgSO$_4$, filtered and concentrated in vacuo. The crude material was purified by flash column chromatography (Hex/EtOAc, 6:1) to yield 3.6 g of product (90%).

Step B

To a solution of product from Step A (3.6 g) in toluene (16 ml) was added tributyltin hydride (5.4 ml) followed by AIBN (555 mg). The mixture was heated to 85° C. for 3.5 hr. After cooling, the mixture was separated by flash column chromatography (Hex/EtOAc, 7:1) to afford 2.06 g of product (73%).

Step C

To a solution of product from Step B (2.05 g) in THF (60 ml) at 0° C. was added a solution of LAH (1M in ether, 12.8 ml). The reaction was stirred at room temperature for 30 min. Water and 1M NaOH was added until a precipitate formed, diluted with EtOAc, stirred for 30 min and then filtered through a celite pad. The organic filtrate was concentrated in vacuo to give 1.56 g of product (93%).

Step D

To a solution of product from Step C (2.15 g) in CH$_2$Cl$_2$ (100 ml) was added Dess-Martin oxidant (7.26 g) in CH$_2$Cl$_2$ (45 ml) and stirred for 30 min. The mixture was diluted with ether (200 ml). The organic layer was washed with 1N NaOH, water and brine, dried with MgSO$_4$, filtered and concentrated in vacuo to give oil and solid. The material was extracted with ether and filtered. Some solid crystallized out from the filtrate, filtered again, and the filtrate was concentrated in vacuo to give 2.19 g of product.

Preparative Example 1004B

Step A

To a suspension of 5-bromo-2-furoic acid (15 g) in CH$_2$Cl$_2$ (275 ml) at room temperature was added oxalyl chloride (6.9 ml) followed by a catalytic amount of N,N'-dimethylformamide ((0.3 ml). The mixture was stirred for 1 hr, whereupon, EtOH (20 ml) and TEA (22 ml) were added and then let stir overnight. The mixture was concentrated in vacuo and extracted with hexanes and hexanes/CH$_2$Cl$_2$. The extracts were concentrated in vacuo to give an oil (17.2 g, 93%).

Step B

The product from Step A (17.2 g), aluminum trichloride (19.52 g) and carbon disulfide (150 ml) were combined in a flask. A solution of n-octadecyl bromide (24.4 g) in carbon-disulfide (50 ml) was added dropwise over 45 min. The reaction was stirred for 2.5 hr, whereupon, 300 ml of crushed ice and water were added. The layers were separated and the organic layer was washed with saturated sodium bicarbonate, water, and brine. The organic layer was dried with Na₂SO₄ and concentrated in vacuo. The crude material was purified by flash column chromatography (hexanes/CH₂Cl₂, 3:1) to yield 7.91 g of product (37%).

Step C

To the product from step B (7.9 g) in THF (140 ml) at −10° C. was added a solution of LAH (1M in THF, 28.5 ml). The solution was stirred for 2.5 hrs at 15° C. Water and 1M NaOH were added carefully to the mixture, followed by EtOAc and let stir for 1.5 hr. The reaction was filtered through a silica pad and the filtrate was concentrated in vacuo to yield 6.48 g of crude product (100%).

Step D

The product from Step C (6.32 g) was dissolved in THF (140 ml) and cooled to −78° C. A solution of t-BuLi (2.5M in hexanes, 22 ml) was added dropwise and let stir for 15 min. An excess of water (70 ml) was then added and let the reaction stir another hour. CH₂Cl₂ (300 ml) and brine (50 ml) were added and the layers were separated. The organic layer was dried with Na₂SO₄ and concentrated in vacuo to give 5.33 g of crude product.

Step E

To a solution of the product from Step D (5.33 g) in CH₂Cl₂ (100 ml) was added a solution of Dess-Martin periodinane in CH₂Cl₂ (15 wt %, 12.6 g). The mixture was stirred for 1.5 hr and then diluted with ether (400 ml) and washed with 1N NaOH, water and brine. The organic layer was dried with Na₂SO₄ and filtered through a magnesium sulfate/silica pad. The filtrate was concentrated in vacuo and purified via flash column chromatography (hex/EtOAc, 50:1, 25:1) to yield 3.06 g of an oil (74%).

Preparative Example 1005

Following a similar procedure as that described in Preparative Example 1004, except using 5-chlorobenzofuran-2-carboxylic acid (1.5 g), the title compound was obtained (solid, 0.31 g, 24%).

Preparative Example 1006

Step A

The sulfonyl chloride from Preparative Example 13.29 Step A (1.5 g) was stirred with AlCl3 and benzene for 15 min at 20° C. Treatment with NaOH, extraction with Et₂O, concentration in vacuo, and purification by column chromatography (silica, hexane-EtOAc, 5:2) gave the phenylsulfone (1.5 g, 84%, MH⁺=255).

Step B

Following similar procedures as those used in Preparative Example 13.29 Steps C-G, except using the sulfone from Step A above, the title compound was prepared (0.04 g, 27%, MH⁺=256).

Preparative Example 1030

Step A

The product of Preparative Example 34.18 Step B (2 g, 8 mmol) was stirred with morpholine (0.9 mL, 10.29 mmol) and K₂CO₃ (2.2 g, 15.9 mmol) in 50 mL of acetone at RT to obtain the morpholinobutylfuran derivative (1.22 g, 73%).

Step B

Following a similar procedure as that in Preparative Example 34.18 Step D, but using the product (1.2 g) from Step A above, the title aldehyde was prepared (0.9 g, 66%, 1:0.7 regioisomeric mixture).

Preparative Example 1030-A

Following a similar procedure as that in Preparative Example 1030 Steps A-B, but using N-methylpiperazine instead of morpholine, the title aldehyde could be prepared.

Preparative Example 1030-B

Following a similar procedure as in Preparative Example 1030 Steps A-B, but using N,N-dimethylamine instead of morpholine, the title aldehyde could be prepared.

Preparative Example 1031

A solution of 5-bromobenzofuran (950 mg, 4.82 mmol) in anhydrous ether (12 mL) was cooled to −78° C. 1.7 M tert-BuLi solution in pentane (6 ml, 10.2 mmol) was added dropwise under argon. After addition, the mixture was stirred at −78° C. for 20 min, followed by addition of a mixture of DMF (0.8 mL) and ether (1 mL). The mixture was allowed to warm to rt and stirred for 0.5 h. Ethyl acetate was added. The mixture was poured to saturated ammonium chloride solution. The organic layer was separated and concentrated. The residue was purified by column chromatography (ethyl acetate-hexanes, 1:5 v/v) to give the title compound as a pale yellow solid (490 mg, 70%).

Preparative Examples 1040-1054

Following the procedure set forth in Preparative Example 64 but using the commercially available (or prepared) aldehyde, aminoalcohols, and organolithium reagents in the Table below, the optically pure amine products in the Table below were obtained.

| Prep. Ex. | Aldehyde | Amino Alcohol | Organo-lithium | Product | 1. Yield (%)<br>2. (M + 1)+ |
|---|---|---|---|---|---|
| 1040 | | | EtLi | | 1. 24%<br>2. 267 |

-continued

| Prep. Ex. | Aldehyde | Amino Alcohol | Organo-lithium | Product | 1. Yield (%) 2. $(M+1)^+$ |
|---|---|---|---|---|---|
| 1041 | benzofuran-2-carbaldehyde | (S)-2-amino-3-methylbutan-1-ol | EtLi | | 1. 94% 2. 176 (m/e) |
| 1042 | 4-(1-phenylethyl)thiophene-2-carbaldehyde | (S)-2-amino-3-methylbutan-1-ol | EtLi | | 1. 67% 2. 229 (M − 16) |
| 1043 | 4,5-dimethylfuran-2-carbaldehyde | (S)-2-amino-3-methylbutan-1-ol | i-PrLi | | 1. 60% 2. 151 [M − 16] |
| 1044 | 4-(dimethylcarbamoyl)-5-methylfuran-2-carbaldehyde | (S)-2-amino-3-methylbutan-1-ol | EtLi | | 1. 74% 2. 194 (M − 16) |
| 1045 | 4-(sec-butyl)furan-2-carbaldehyde | (S)-2-amino-3-methylbutan-1-ol | EtLi | | 1. 33% 2. 165 [M − NH2]+ |
| 1046 | 4-(pentan-3-yl)furan-2-carbaldehyde | (S)-2-amino-3-methylbutan-1-ol | EtLi | | 1. 31 2. 179 [M − NH2]+ |
| 1047 | 5-chlorofuran-2-carbaldehyde | (S)-2-amino-3-methylbutan-1-ol | t-BuLi | | 1. 31% 2. 188 |

| Prep. Ex. | Aldehyde | Amino Alcohol | Organo-lithium | Product | 1. Yield (%) 2. (M + 1)+ |
|---|---|---|---|---|---|
| 1048 | furan-2-carbaldehyde | (S)-2-amino-3-methylbutan-1-ol | t-BuLi | t-Bu furyl amine | 1. 10% 2. 154 |
| 1049 | 5-ethylfuran-2-carbaldehyde | (S)-2-amino-3-methylbutan-1-ol | EtLi | ethyl (5-ethylfuran-2-yl) amine | 1. 73% 2. 137 [M − NH2]+ |
| 1051 | 2,2-difluorobenzo[d][1,3]dioxole-5-carbaldehyde | (S)-2-amino-3-methylbutan-1-ol | t-BuLi | t-Bu (2,2-difluorobenzodioxol-5-yl) amine | 1. 17% |
| 1054 | benzofuran-2-carbaldehyde | (S)-2-amino-3-methylbutan-1-ol | t-BuLi | t-Bu benzofuran-2-yl amine | 1. 79% 2. 151 (M − 16) |

Preparative Examples 1100-1126

Following the procedure set forth in Preparative Example 34 but using the commercially available aldehydes and Grignard/Organolithium reagents listed in the Table below, the amine products were obtained.

| Prep. Ex. | Aldehyde | Organo-metallic Reagent | Product | 1. Yield (%) 2. (M + 1)+ |
|---|---|---|---|---|
| 1100 | 4-(dimethylamino)benzaldehyde | t-BuLi | t-Bu (4-NMe2-phenyl) amine | 1. 83% 2. 190 (M − 16) |
| 1101 | benzofuran-5-carbaldehyde | t-BuLi | t-Bu benzofuran-5-yl amine | 1. 46% 2. 204 |

-continued

| Prep. Ex. | Aldehyde | Organo-metallic Reagent | Product | 1. Yield (%) 2. (M + 1)+ |
|---|---|---|---|---|
| 1102 | 2-methoxybenzaldehyde | t-BuLi | 1-(2-methoxyphenyl)-2,2-dimethylpropylamine | 1. 48% 2. 194 |
| 1103 | 4-methoxybenzamide | t-BuLi | 1-(4-methoxyphenyl)-2,2-dimethylpropylamine | 1. 51% 2. 194 |
| 1104 | 5-chlorobenzofuran-2-carbaldehyde | t-BuLi | 1-(5-chlorobenzofuran-2-yl)-2,2-dimethylpropylamine | 1. 12% 2. 238 |
| 1105 | 5-methoxybenzofuran-2-carbaldehyde | t-BuLi | 1-(5-methoxybenzofuran-2-yl)-2,2-dimethylpropylamine | 1. 39% 2. 234 |
| 1106 | 3-methoxybenzaldehyde | t-BuLi | 1-(3-methoxyphenyl)-2,2-dimethylpropylamine | 1. 44% 2. 194 (m/e) |
| 1107 | 1-methylpyrrole-2-carbaldehyde | t-BuLi | 1-(1-methylpyrrol-2-yl)-2,2-dimethylpropylamine | 1. 57% 2. 150 (M − 16) |
| 1108 | 3,4-dimethoxybenzaldehyde | t-BuLi | 1-(3,4-dimethoxyphenyl)-2,2-dimethylpropylamine | 1. 31% 2. 224 |

-continued

| Prep. Ex. | Aldehyde | Organo-metallic Reagent | Product | 1. Yield (%) 2. (M + 1)+ |
|---|---|---|---|---|
| 1109 | 2,5-dimethoxybenzaldehyde | t-BuLi | amine product | 1. 11% 2. 224 |
| 1110 | 2,3-dimethoxybenzaldehyde | t-BuLi | amine product | 1. 57% 2. 224 |
| 1111 | 3,5-dimethoxybenzaldehyde | t-BuLi | amine product | 1. 21% 2. 224 |
| 1112 | benzaldehyde | c-Pentyl-Li | amine product | 1. 58% 2. 190 |
| 1113 | 3-OCF3-benzaldehyde | t-BuLi | amine product | 1. 20% 2. 248 |
| 1114 | 3-CF3-benzaldehyde | t-BuLi | amine product | 1. 24% 2. 232 |

-continued

| Prep. Ex. | Aldehyde | Organometallic Reagent | Product | 1. Yield (%) 2. (M + 1)+ |
|---|---|---|---|---|
| 1115 | benzo[1,4]dioxine-6-carbaldehyde | EtLi | 1-(2,3-dihydrobenzo[1,4]dioxin-6-yl)propylamine | 1. 32% 2. 177 (M − NH2) |
| 1116 | benzo[1,4]dioxine-6-carbaldehyde | t-BuLi | 1-(2,3-dihydrobenzo[1,4]dioxin-6-yl)-2,2-dimethylpropylamine | 1. 26% 2. 205 (M − NH2) |
| 1117 | 4-dimethylaminobenzaldehyde | t-BuLi | 1-(4-dimethylaminophenyl)-2,2-dimethylpropylamine | 1. 50% 2. 190 (M − NH2) |
| 1118 | 3,5-difluorobenzaldehyde | t-BuLi | 1-(3,5-difluorophenyl)-2,2-dimethylpropylamine | 1. 29% 2. 200 |
| 1119 | 3,5-dichlorobenzaldehyde | t-BuLi | 1-(3,5-dichlorophenyl)-2,2-dimethylpropylamine | 1. 28% 2. 232 |
| 1120 | 3,5-dimethoxybenzaldehyde | t-BuLi | 1-(3,5-dimethoxyphenyl)-2,2-dimethylpropylamine | 1. 76% 2. 224 |

-continued

| Prep. Ex. | Aldehyde | Organo-metallic Reagent | Product | 1. Yield (%) 2. (M + 1)+ |
|---|---|---|---|---|
| 1121 | | t-BuLi | | 1. 40% 2. 206 |
| 1122 | | t-BuLi | | 1. 38% 2. 236 |
| 1123 | | t-BuLi | | 1. 70% 2. 192 |
| 1124 | | t-BuLi | | 1. 81% 2. 204 |
| 1125 | | t-BuLi | | 33% |
| 1126 | | t-BuLi | | 50% |

Preparative Examples 1200A-1203A

Following the procedure set forth in Preparative Example 13.29 but using the commercially available amines, the hydroxyaminothiophene products listed in the Table below were obtained.

| Prep. Ex. | Amine | Product | 1. Yield (%) <br> 2. $(M + 1)^+$ |
|---|---|---|---|
| 1200A | [piperazinyl-pyrimidine amine structure] | [sulfonyl thiophene product structure] | 1. 3% <br> 2. 342 |
| 1201A | [morpholine structure] | [morpholine sulfonyl thiophene product] | 1. 41% <br> 2. 265 |
| 1202A | [N-methyl-N-ethylamine structure] | [N-methyl-N-ethyl sulfonyl thiophene product] | 1. 17% <br> 2. 237 |
| 1203A | [N-methyl-N-isopropylamine structure] | [N-methyl-N-isopropyl sulfonyl thiophene product] | 1. 1% |

Preparative Example 1300

[reaction scheme showing conversion of benzyl-ethyl sulfonamide thiophene to ethyl sulfonamide thiophene]

The title compound from Preparative Example 13.32 (0.35 g) was treated with concentrated sulfuric acid (3 mL) for 6 hrs, then poured on ice, and the pH adjusted to 4 with NaOH. Extraction with EtOAc, and drying of the organic phase over $Na_2SO_4$ gave the title compound (159 mg, 64%, $MH^+$=223).

Preparative Example 1301

[reaction scheme: methyl furan carboxaldehyde → Step A → fluoro-hydroxy intermediate → Step B]

Step A
Following the procedure set forth in Preparative Example 605 but using the commercially available fluoroisopropylester, the alcohol product was obtained (1.2 g, 84%, M-OH=155).

Step B
Following the procedure set forth in Preparative Example 625 but using the alcohol from Step A above, the amine product was obtained (350 mg, 35%, M-NH2=155).

Preparative Example 1302

Step A
Following a similar procedure as that used in Preparative Example 13.29 Step B, except using the commercially available arylsulfonylchloride (0.15 g) and diethylamine (2.2 eq), the dimethylsulfonamide was obtained (0.12 g, 71%, MH$^+$=323).

Step B
Following a similar procedure as that used in Preparative Example 13.29 Step C, except using the product from Step A above (0.12 g), the phenol was obtained (0.112 g, 98%).

Step C
Following a similar procedure as that used in Preparative Example 10.55 Step C, except using the product from Step B above (0.112 g), the title compound was obtained (0.1 g, 99%, MH$^+$=245).

Preparative Example 1303

Following a similar procedure as that used in Preparative Example 1302 Steps A-C, except using piperidine in Step A (0.078 g) instead of diethylamine, the title compound was obtained (0.070 g, 35%, MH$^+$=257).

Preparative Example 1304

Following a similar procedure as that used in Preparative Example 1302 Steps A-C, except using dimethylamine (2M in THF) in Step A instead of diethylamine, the title compound was obtained (1.92 g, 72%, MH$^+$=217).

Preparative Example 1305

Step A

Following a similar procedure as that used in Preparative Example 1302 Step A, except using the phenethylamine indicated (4.99 g), the product was obtained (5.96 g, 86%, MH+=210).

Step B

The compound from Step A above (5.0 g) was added to 30 g of PPA at 150° C. and the resulting mixture stirred for 20 min, before being poured on ice and extracted with dichloromethane. The organic phase was dried over MgSO4, concentrated in vacuo and purified by silica gel chromatography (EtOAc:MeOH, 95:5) to give the product (0.5 g, 9%).

Step C

Following a similar procedure as that used in Preparative Example 13.3 Step D, except using the compound from Step B above (0.14 g), the product was obtained (0.18 g, 87%, MH$^+$=256).

Step D

Following a similar procedure as that used in Preparative Example 11 Step B, except using the compound from Step C above (0.18 g), the product was obtained (0.17 g).

Step E

Following a similar procedure as that used in Preparative Example 13.3 Step B, except using the compound from Step D above (0.17 g), the product was obtained (0.17 g, 95%, MH$^+$=315).

Step F

Following a similar procedure as that used in Preparative Example 13.29 Step C, except using the product from Step E above (0.17 g), the nitrophenol was obtained (0.165 g, 99%, MH$^+$=303).

Step G

Following a similar procedure as that used in Preparative Example 10.55 Step C, except using the product from Step F above (0.165 g), the title compound was obtained (0.128 g, 86%, MH$^+$=193).

Preparative Example 1306

Step A

Following a similar procedure as that used in Preparative Example 11 Step B, except using the lactam (0.179 g), the title compound was obtained (0.25 g, 25%).

Step B

Following a similar procedure as that used in Preparative Example 13.29 Step C, except using the product from Step A above (0.055 g), the phenol was obtained (0.045 g, 99%).

Step C

Following a similar procedure as that used in Preparative Example 10.55 Step C, except using the product from Step B above (0.045 g), the title compound was obtained (0.022 g, 57%, MH$^+$=179).

Preparative Example 1307

Following a similar procedure as that used in Preparative Example 2, except using 3(R)-hydroxypyrrolidine HCl (1.36 g), the title compound was obtained (2.25 g, 89%).

Preparative Example 1308

Following a similar procedure as that used in Preparative Example 2, except using morpholine, the title compound was obtained (3.79 g).

Preparative Example 1309

Step A

Following a similar procedure as that used in Preparative Example 13.29 Step B, except using the commercially available nitrophenylsulfonylchloride and diethylamine (2.2 eq), the dimethylsulfonamide was obtained (90%, MH+=231).

Step B

Following a similar procedure as that used in Preparative Example 10.55 Step C, except using the product from Step B above, the title compound was obtained (45%, MH+=201).

Preparative Example 1310

Step A

Following a similar procedure as that used in Preparative Example 13.29 Step B, except using the commercially available nitrobenzoylchloride and the commercially available amine indicated, the benzamide was obtained (13%, MH+=253).

Step B

Following a similar procedure as that used in Preparative Example 10.55 Step C, except using the product from Step A above, the title compound was obtained (94%, MH+=223).

Preparative Example 1311

Step A

To a benzene (20 mL) solution of methoxythiophenesulfonylchloride (1.5 g) was added AlCl₃ (2.0 g) at RT. After 15 min, the mixture was added to 0.1N HCl (aq) with stirring, then extracted with Et₂O. Washing the organic phase with bring, drying over MgSO₄, concentration in vacuo and purification by silica gel chromatography (Hexane:EtOAc, 5:2) gave the title compound (1.5 g, 84%).

Step B

Following a similar procedure as that used in Preparative Example 13.29 Steps C-G, except using the product from Step A above, the title compound was obtained (3%, MH+=380).

Preparative Example 1312

Step A
Following a similar procedure as that used in Preparative Example 1311 Step A, except using the commercially available sulfonylchloride, the diphenylsulfone was obtained (880 mg, 80%).

Step B
Following a similar procedure as that used in Preparative Example 11 Step B, except using the product from Step A above, the title compound was obtained (0.90 g, 97%).

Step C
Following a similar procedure as that used in Preparative Example 10.55 Step C, except using the product from Step B above (0.16 g), the title compound was obtained (0.106 g, 95%).

Preparative Example 1313

Step A
Following a similar procedure as that used in Preparative Example 1311 Step A, except using the commercially available phenol (2 g), the nitroacid was obtained (~13 mmol).

Step B
Oxallyl chloride (3.5 mL) and two drops of DMF was added to the product from Step A above (~13 mmol) dissolved in dichloromethane (100 mL). After stirring at RT overnight, the mixture was concentrated in vacuo, diluted with dichloromethane (50 mL), cooled to 0° C. Dimethylamine in THF (20 mL of 2N) and TEA (8 mL) were added. After 3 hr of stirring, the mixture was concentrated in vacuo, aq NaOH (1M) was added, and the mixture was extracted with dichloromethane. The pH of the aq layer was adjusted to pH=2 using 6N HCl (aq), and extracted with dichloromethane. The combined organic extracts were washed with brine, dried, concentrated in vacuo, and the product purified by silica gel chromatography (700 mL dichloromethane/20 mL MeOH/1 mL AcOH) to give the title compound (800 mg, 27% for two steps).

Step C
Following a similar procedure as that used in Preparative Example 10.55 Step C, except using the product from Step B above (780 mg), the title compound was obtained (0.46 g, 68%).

Preparative Example 1314

Step A

Methyl-4-bromo-3-hydroxy-2-thiophenecarboxylate (20 g, 84.36 mmol) was dissolved in 400 mL of acetone. Potassium carbonate (58 g, 420.3 mmol) was added followed by iodomethane (45 mL, 424 mmol). The resulting mixture was heated at reflux for 4.5 h. After cooling, the mixture was filtered through a thin Celite pad, rinsing with methylene chloride. The filtrate was concentrated in vacuo to give 22.5 g of methyl-4-bromo-3-methoxy-2-thiophenecarboxylate (crude, 100%, MH$^+$=251.0) as a dark green solid.

Step B

The product from Step A above (22.5 g, 84.36 mmol) was dissolved in 60 mL of tetrahydrofuran and added with 125 mL of a 1.0 M NaOH aqueous solution. The mixture was stirred at room temperature for 4 d, then washed with ether (60 mL×2), acidified to pH~2 using a 1.0 M HCl aqueous solution. Solids were precipitated out after acidification, and collected by filtration. The solid was dissolved in methylene chloride-ethyl acetate (~4:1, v/v). The organic solution was washed with H$_2$O and brine, dried with Na$_2$SO$_4$, and concentrated in vacuo to a light yellow solid, further dried on high vacuum, yielding 17.95 g of 4-bromo-3-methoxy-2-thiophene carboxylic acid (90%, MH$^+$=237.0).

Step C

The carboxylic acid (3.26 g, 13.75 mmol) available from Step B above was treated with 30 mL of concentrated sulfuric acid. The mixture was sealed in a one-neck round bottom flask, and heated at 65° C. for 4.5 h. After cooled to room temperature, the mixture was poured into 200 mL of crushed ice, and extracted with methylene chloride (100 mL×3). The organic extracts were combined, washed successively with H$_2$O (50 mL×2), sat. NaHCO$_3$ (50 mL×3), and brine (50 mL). The organic solution was dried with Na$_2$SO$_4$, and concentrated in vacuo to a dark brown oil, which was purified by flash column chromatography (biotage, SiO$_2$ column) using hexanes-methylene chloride (3:1, v/v) as eluents. Removal of solvents afforded 1.83 g of 3-bromo-4-methoxy thiophene (69%) as a light yellow oil.

Step D

To a stirred solution of 3-bromo-4-methoxythiophene (550 mg, 2.85 mmol), prepared in Step C above, in 30 mL of methylene chloride at −78° C. was added dropwise along the inside wall of the flask chlorosulfonic acid (0.48 mL, 7.21 mmol). The mixture was stirred at −78° C. for 10 min, continued at room temperature for 1 h, and filtered through a 1-in silica gel pad, rinsing with methylene chloride. The filtrate was concentrated in vacuum to give 270 mg of 4-bromo-3-methoxy-2-thiophene sulfonylchloride (33%) as a light yellow oil.

Step E

To a stirred solution of thiophene sulfonylchloride (270 mg, 0.926 mmol) prepared in Step D above in 15 mL of methylene chloride at room temperature was added triethylamine followed by N-methyl-tertbutylamine (0.25 mL, 2.094 mmol). After 20 h, the mixture was diluted with 50 mL of methylene chloride, and washed with H$_2$O and brine. The organic solution was dried over Na$_2$SO$_4$, filtered, and concentrated to an oily residue, which was purified by preparative TLC (methylene chloride as eluent) to afford 73 mg of the titled bromo-sulfonamide (23%) as a near colorless oil.

Step F

A one-neck round bottom flask was charged with bromosulfonamide (73 mg, 0.2133 mmol, from Step E above), palladium acetate (5 mg, 0.0223 mmol), binap (0.03212 mmol), cesium carbonate (139 mg, 0.4266 mmol), and benzophenonimine (0.06 mL, 0.358 mmol). The mixture was evacuated via house vacuum, and refilled with nitrogen. A 3 mL of anhydrous toluene was added. The mixture was evacuated again, refilled with nitrogen, and heated at reflux for 2.5 d. After cooled to room temperature, methylene chloride (50 mL) was added, the mixture was filtered through a Celite pad, rinsing with methylene chloride. The filtrated was concentrated in vacuo to give 205 mg (crude, MH$^+$=443.1) of the desired imine product as a dark brown oil, used in next step without purification.

Step G

The imine from Step F above (205 mg, crude, 0.2133 mmol) was dissolved in 5 mL of methanol, and added with sodium acetate (81 mg, 0.9873 mmol) followed by hydroxylamine hydrochloride (68 mg, 0.98 mmol). The mixture was stirred at room temperature for 6.5 h, quenched with the addition of 10 mL of a 1.0 M NaOH aqueous solution. The aqueous mixture was extracted with methylene chloride (30 mL×3). The extracts were combined, washed with brine, dried by Na$_2$SO$_4$, and concentrated in vacuo to a dark yellow oil, which was purified by preparative TLC (methylene chloride—methanol=100:1, v/v) to give 34 mg (57% over two steps, MH$^+$=279.0) of methoxy-thiophenesulfonamide amine as a light yellow oil, solidified on standing.

Step H

To a stirred suspension of sodium hydride (60%, 45 mg, 1.13 mmol) in 3 mL of anhydrous N,N'-dimethylformamide (DMF) was added dropwise ethanethiol (0.1 mL, 1.34 mmol). After 10 min, the mixture tured into a clear solution, and 1 mL of this solution was taken up in a syringe and added dropwise to a stirred solution of methoxy-thiophenesulfonamide amine in 1 mL of DMF. The mixture was heated up to 95° C., and continued for 3.5 h. After cooling, the mixture was poured into 20 mL of a 1.0 M NaOH aqueous solution. The aqueous mixture was washed with methylene chloride (30 mL×3). The organic washings were combined, re-extracted with a 1.0 M NaOH aqueous solution (15 mL) and H$_2$O (15 mL). The aqueous layer and aqueous extracts were combined, adjusted to pH~6 using a 1.0 M HCl aqueous solution, and extracted with methylene chloride (75 mL×3). The organic extracts were washed with brine, dried (Na$_2$SO$_4$), and concentrated in vacuo to a dark yellow oil. This oil was dissolved in ethyl acetate (50 mL), washed with H$_2$O (10 mL×2) and brine (10 mL). The organic solution was dried (Na$_2$SO$_4$), and concentrated in vacuo to afford 36 mg (100%, MH$^+$=265.0) of hydroxyl-thiophene sulfonamide amine as a yellow oil.

Preparative Example 1315

Step A

Following the procedures described in Preparative Example 1314 Step E, 4-bromo-3-methoxy-2-thiophene-sulfonyl chloride (190 mg, 0.65 mmol, available from Step D, Preparative Example 1314) was converted to the titled tert-butyl sulfonamide (56 mg, 26%, MH$^+$=328.1) upon treatment of triethylamine (0.28 mL, 2.0 mmol) and tert-butylamine (0.15 mL, 1.43 mmol) in 10 mL of methylene chloride.

Step B tert-Butyl sulfonamide (98 mg, 0.3 mmol) available from Step A above was converted to the imine product (296 mg, crude, MH$^+$=429.1) by using the procedure described in Step F of Preparative Example 1314.

Step C

The imine product (296 mg, crude, ~0.3 mmol) was transformed to the desired thiophene-amine (23 mg, 30% over two steps, MH$^+$=265.0) by using the procedure described in Step G of Preparative Example 1314.

Step D

If one were to apply the procedure set forth in Step H of Preparative Example 1314, but using the thiophene amine available from Step C above, one would obtain the titled hydroxyl thiophene sulfonamide amine.

Preparative Example 1316

Step A

Following the procedures set forth in Preparative example 13.29 Step B through F, but using diethylamine, 3-methoxy-2-thiophenesulfonyl chloride (available from Step A, Preparative example 13.29) was converted to titled diethylsulfonamido thiophene imine (MH$^+$=429.1)

Step B

Thiophene-imine (1.5 g, 3.5 mmol), available from Step A above, was dissolved in 30 mL of CH$_2$Cl$_2$, and added with potassium carbonate (1.2 g, 8.70 mmol) followed by drop wise addition of bromine (0.32 mL, 6.25 mmol). After stirred for 2 d, H$_2$O was added. The two layers were separated. The aqueous layer was extracted with CH$_2$Cl$_2$ (50 mL×2). The organic layers were combined, washed with a 10% Na$_2$S$_2$O$_3$ aqueous solution (40 mL×2) and brine (40 mL), dried over Na$_2$SO$_4$, and concentrated in vacuo to a dark brown oil. This oil was separated by preparative TLC (CH$_2$Cl$_2$ as eluent), to give 0.96 g (54%) of the desired bromo-imine as a bright yellow oil (M$^+$=507, M+2=509)

Step C

Bromo-imine (0.95 g, 1.87 mmol), available from Step B above, was dissolved in 15 mL of anhydrous THF, cooled in a −78° C. bath, and treated with a 2.5 M solution of n-butyl lithium in hexanes (1.2 mL, 3.0 mmol) drop wise along the side wall of the flask. After 30 min, Iodomethane (0.35 mL, 5.62 mmol) was added drop wise. Reaction was continued for 5 h, during which time the cooling bath was allowed to warm slowly to 0° C. The mixture was quenched by H$_2$O (25 mL), and extracted with CH$_2$Cl$_2$ (50 mL×2). The organic extracts were washed with brine, dried with Na$_2$SO$_4$, and concentrated in vacuo to give 0.93 g (crude, >100%) of the desired methylated imine as a dark yellow oil (MH$^+$=443.1)

Step D

The crude methyl-imine (0.93 g), prepared in step C above, was converted to the methyl-hydroxyl-amine (0.21 g, 41%, MH$^+$=265.0) by using the procedures described in Step G of Preparative Example 13.29.

Preparative Examples 1203-1234

Following a similar procedure set forth in Preparative Example 22 but using the commercially available or prepared amine from the Preparative Example indicated in the Table below, the following thiadiazoledioxide intermediates were obtained.

| Prep Ex | Amine/Aniline | Product | 1. Yield (%) 2. (M + 1)$^+$ |
|---|---|---|---|
| 1203 | | | 1. 99% 2. 395.0 |
| 1205 | | | 1. 33% 2. 382.1 |
| 1206 | | | 1. 71% 2. 445.1 |
| 1207 | | | 1. 85% 2. 369.1 |

-continued

| Prep Ex | Amine/Aniline | Product | 1. Yield (%) 2. (M + 1)+ |
|---|---|---|---|
| 1209 | | | 1. 69% 2. 363.0 |
| 1210 | | | 1. 92% 2. 405.0 (M + Na) |
| 1211 | | | 1. 45% 2. 403.0 |
| 1212 | | | 1. 85% 2. 442.8 |
| 1216 | | | 1. 50% 2. 389.0 |
| 1217 | | | 1. 67% 2. 339.0 |
| 1218 | | | 1. 87% 2. 370.9 |

-continued

| Prep Ex | Amine/Aniline | Product | 1. Yield (%) 2. (M + 1)+ |
|---|---|---|---|
| 1219 | | | 1. 70% 2. 404.0 |
| 1220 | | | 1. 83% 2. 419.0 |
| 1221 | | | 1. 99% 2. 383.1 |
| 1222 | | | 1. 99% 2. 405.0 |

-continued

| Prep Ex | Amine/Aniline | Product | 1. Yield (%) 2. (M + 1)+ |
|---|---|---|---|
| 1223 | | | 1. 69% 2. 473.0 |
| 1224 | | | 1. 99% 2. 461.0 |
| 1225 | | | 1. 99% 2. 314 |
| 1226 | | | 1. 99% 2. 354 |
| 1227 | | | 1. 92% 2. 300 |

-continued

| Prep Ex | Amine/Aniline | Product | 1. Yield (%) 2. (M + 1)+ |
|---|---|---|---|
| 1228 | | | 1. 99% 2. 342 |
| 1229 | | | 1. 99% 2. 300 |
| 1230 | | | 1. 99% 2. 286 |
| 1231 | | | 1. 99% 2. 300 |
| 1232 | | | used crude |
| 1233 | | | 1. 92% 2. 396 |

-continued

| Prep Ex | Amine/Aniline | Product | 1. Yield (%) 2. (M + 1)+ |
|---|---|---|---|
| 1234 | [structure: 3-amino-2-hydroxy-N,N,4-trimethylbenzamide] | [structure: thiadiazoledioxide-OMe product] | used crude |

Example 1

[structure of Example 1 starting material with OMe] → [structure of Example 1 product with isopropylamine]

The thiadiazole intermediate from Preparative Example 22 (65 mg, 0.2 mmol), isopropylamine (17 ul, 0.2 mmol) and DIEA (100 ul) were combined in MeOH (2 ml) and stirred overnight at room temperature. The reaction was purified by liquid chromatography to yield product (22 mg, 31%, MH+=31%).

Examples 2-71

Following a similar procedure set forth in Example 1 but using the commercially available (or prepared amine) and the thiadiazoledioxide intermediate from the Preparative Example(s) indicated in the Table below and stirring the reaction mixtures at room temperature up to reflux, the following thiadiazoledioxide products were obtained.

| Ex. | Prep Ex of Thiadiazole Intermediate and Amine | Product | 1. Yield 2. MH+ |
|---|---|---|---|
| 2 | 22 and H₂N-cyclopentyl | [cyclopentylamino thiadiazoledioxide product] | 1. 43 2. 379.9 |
| 3 | 22 and H₂N-cyclohexyl | [cyclohexylamino thiadiazoledioxide product] | 1. 54 2. 393.9 |

-continued

| Ex. | Prep Ex of Thiadiazole Intermediate and Amine | Product | 1. Yield 2. MH+ |
|---|---|---|---|
| 4 | 22 and aniline | (structure) | 1. 18 2. 387.9 |
| 5 | 22 and (S)-1-phenylpropylamine | (structure) | 1. 55 2. 430 |
| 6 | 22 and (S)-1-(5-methylfuran-2-yl)propylamine | (structure) | 1. 58 2. 433.8 |
| 7 | 22 and sec-butylamine | (structure) | 1. 14 2. 367.9 |
| 8 | 22 and 3-methylbutan-2-amine | (structure) | 1. 34 2. 381.9 |
| 9 | 22 and (S)-1-phenylpropylamine | (structure) | 1. 43 2. 429.8 |

-continued

| Ex. | Prep Ex of Thiadiazole Intermediate and Amine | Product | 1. Yield 2. MH+ |
|---|---|---|---|
| 10 | 22 and | | 1. 47 2. 415.8 |
| 11 | 22 and | | 1. 32% 2. 381.9 |
| 12 | 22 and | | 1. 27 2. 514.9 |
| 13 | 22 and | | 1. 24 2. 441.8 |
| 14 | 22 and | | 1. 42 2. 427.9 |

-continued

| Ex. | Prep Ex of Thiadiazole Intermediate and Amine | Product | 1. Yield 2. MH+ |
|---|---|---|---|
| 15 | 22 and (propyl-4-isopropylfuran-2-yl methanamine) | | 1. 33 2. 461.7 |
| 16 | 22 and (1-(4-chlorofuran-2-yl)propan-1-amine) | | 1. 12 2. 453.7 |
| 17 | 22 and (cyclopropyl(4-methylthiophen-2-yl)methanamine) | | 1. 29 2. 461.4 |
| 18 | 22 and (1-(4-phenylfuran-2-yl)propan-1-amine) | | 1. 44 2. 495.7 |

| Ex. | Prep Ex of Thiadiazole Intermediate and Amine | Product | 1. Yield 2. MH+ |
|---|---|---|---|
| 19 | 22 and (structure: H₂N-CH(CF₃)-(5-methylfuran-2-yl)) | (product structure) | 1. 40 2. 473.8 |
| 20 | 22 and (structure: H₂N-CH(CF₃)-phenyl) | (product structure) | 1. 34 2. 469.9 |
| 21 | 22 and (structure: H₂N-CH(CF₃)-benzo[1,3]dioxol-5-yl) | (product structure) | 1. 31 2. 513.8 |
| 22 | 22 and (structure: H₂N-CH(cyclopropyl)-(4-isopropylfuran-2-yl)) | (product structure) | 1. 30 2. 496.0 (M + Na)⁺ |

-continued

| Ex. | Prep Ex of Thiadiazole Intermediate and Amine | Product | 1. Yield 2. MH+ |
|---|---|---|---|
| 23 | 22 and [structure: (S)-1-(4-isopropylfuran-2-yl)-2,2-dimethylpropan-1-amine] | [structure: thiadiazole dioxide bis-amine product with 2-hydroxy-N,N-dimethylbenzamide and (4-isopropylfuran-2-yl)-tert-butyl group] | 1. 23 2. 489.9 |
| 24 | 22 and [structure: (S)-1-(benzo[d][1,3]dioxol-5-yl)propan-1-amine] | [structure: thiadiazole dioxide product with benzodioxole propyl group] | 1. 55 2. 473.8 |
| 25 | 22 and [structure: (S)-1-(4-isopropylfuran-2-yl)ethan-1-amine] | [structure: thiadiazole dioxide product with 4-isopropylfuran ethyl group] | 1. 4 2. 447.8 |
| 26 | 22 and [structure: 1-(4-(thiophen-3-yl)furan-2-yl)propan-1-amine] | [structure: thiadiazole dioxide product with 4-(thiophen-3-yl)furan propyl group] | 1. 8 2. 501.8 |

| Ex. | Prep Ex of Thiadiazole Intermediate and Amine | Product | 1. Yield 2. MH+ |
|---|---|---|---|
| 27 | 22 and (cyclopropyl-(5-methylfuran-2-yl)methylamine) | | 1. 18 2. 482.0 (M + Na)+ |
| 28 | 22 and (cyclopropyl-(5-methylfuran-2-yl)methylamine, opposite enantiomer) | | 1. 42 2. 467.9 (M + Na)+ |
| 29 | 22 and (1-(5-methylthiophen-2-yl)ethylamine) | | 1. 24% 2. 435.8 |
| 30 | 22 and (2-methyl-1-(5-methylthiophen-2-yl)propylamine) | | 1. 51 2. 463.8 |

-continued

| Ex. | Prep Ex of Thiadiazole Intermediate and Amine | Product | 1. Yield 2. MH+ |
|---|---|---|---|
| 31 | 22 and | | 1. 52 2. 475.8 |
| 32 | 22 and | | 1. 32 2. 477.8 |
| 33 | 22 and | | 1. 58 2. 449.7 |
| 34 | 22 and | | 1. 50 2. 483.9 (M + Na)+ |

-continued

| Ex. | Prep Ex of Thiadiazole Intermediate and Amine | Product | 1. Yield 2. MH+ |
|---|---|---|---|
| 35 | 22 and | | 1. 33 2. 447.8 |
| 36 | 22 and | | 1. 53 2. 449.8 |
| 37 | 22 and | | 1. 15 2. 459.8 |
| 38 | 23.2 and | | 1. 34 2. 430.0 |
| 39 | 23.1 and | | 1. 13 2. 403.8 |

-continued

| Ex. | Prep Ex of Thiadiazole Intermediate and Amine | Product | 1. Yield 2. MH+ |
|---|---|---|---|
| 40 | 23.1 and (4-cyano-2-hydroxyaniline) | | 1. 28 2. 383.8 |
| 41 | 23.1 and (2-hydroxyaniline) | | 1. 42 2. 358.8 |
| 42 | 23.1 and (4-amino-3-hydroxy-N,N-dimethylthiophene-2-carboxamide) | | 1. 19 2. 435.8 |
| 43 | 23.1 and (4-amino-3-hydroxybenzoic acid) | | 1. 34 2. 402.8 |
| 44 | 23.1 and (3-amino-2-hydroxybenzonitrile) | | 1. 23 2. 383.8 |

-continued

| Ex. | Prep Ex of Thiadiazole Intermediate and Amine | Product | 1. Yield 2. MH+ |
|---|---|---|---|
| 45 | 23.1 and 4-fluoro-2-hydroxyaniline | | 1. 30 2. 376.8 |
| 46 | 23.1 and 3-amino-2-hydroxy-N-methylbenzamide | | 1. 35 2. 415.8 |
| 47 | 23.1 and 3-amino-2-hydroxybenzamide | | 1. 25 2. 401.8 |
| 48 | 23.1 and 4-amino-3-hydroxy-N,N-dimethylthiophene-2-sulfonamide | | 1. 13 2. 471.7 |
| 49 | 23.1 and 2-amino-3-hydroxy-6-methylpyridine | | 1. 10 2. 373.9 |

| Ex. | Prep Ex of Thiadiazole Intermediate and Amine | Product | 1. Yield 2. MH+ |
|---|---|---|---|
| 50 | 23.5 and 3-amino-2-hydroxybenzonitrile | (structure with thiadiazole-S-dioxide, 3-cyano-2-hydroxyanilino, and (R)-1-(benzo[d][1,3]dioxol-5-yl)-2,2,2-trifluoroethylamino groups) | 1. 15 2. 467.7 |
| 51 | 23.4 and 3-amino-2-hydroxybenzonitrile | (structure with thiadiazole-S-dioxide, 3-cyano-2-hydroxyanilino, and (R)-1-(furan-2-yl)-2,2,2-trifluoroethylamino groups) | 1. 21 2. 413.8 |
| 52 | 23.3 and 3-amino-2-hydroxybenzonitrile | (structure with thiadiazole-S-dioxide, 3-cyano-2-hydroxyanilino, and pentan-3-ylamino groups) | 1. 16 2. 336.9 |
| 53 | 23.6 and 3-amino-2-hydroxybenzonitrile | (structure with thiadiazole-S-dioxide, 3-cyano-2-hydroxyanilino, and (S)-1-(5-methylfuran-2-yl)propylamino groups) | 1. 29 2. 774.6 (dimer) |
| 54 | 23.6 and 2-amino-5-nitrophenol | (structure with thiadiazole-S-dioxide, 4-nitro-2-hydroxyanilino, and 1-(5-methylfuran-2-yl)propylamino groups) | 1. 20 2. 814.4 (dimer) |

-continued

| Ex. | Prep Ex of Thiadiazole Intermediate and Amine | Product | 1. Yield 2. MH+ |
|---|---|---|---|
| 55 | 23.8 and | | 1. 1 2. 539.9 |
| 56 | 23.8 and | | 1. 9 2. 567.9 |
| 57 | 23.1 and | | 1. 11 2. 443.9 |
| 58 | 23.1 and | | 1. 14 2. 509.8 |
| 59 | 23.1 and | | 1. 15 2. 471.7 |

US 7,691,856 B2

-continued

| Ex. | Prep Ex of Thiadiazole Intermediate and Amine | Product | 1. Yield 2. MH+ |
|---|---|---|---|
| 60 | 23.1 and (3-amino-2-hydroxyphenyl)(4-methylpiperazin-1-yl)methanone | thiadiazole dioxide product | 1. 41 2. 485.0 |
| 61 | 23.1 and (3-amino-2-hydroxyphenyl)(morpholin-4-yl)methanone | thiadiazole dioxide product | 1. 33 2. 471.9 |
| 62 | 23.1 and 1-(3-amino-2-hydroxybenzoyl)piperidine-4-carboxylic acid | thiadiazole dioxide product | 1. 21 2. 514.0 |
| 63 | 23.1 and (3S)-1-(3-amino-2-hydroxybenzoyl)piperidine-3-carboxylic acid | thiadiazole dioxide product | 1. 11 2. 513.9 |
| 64 | 23.7 and 3-amino-2-hydroxybenzonitrile | thiadiazole dioxide product with isopropylfuryl group | 1. 34 2. 415.7 |

| Ex. | Prep Ex of Thiadiazole Intermediate and Amine | Product | 1. Yield 2. MH+ |
|---|---|---|---|
| 65 | 23.7 and 13.29 | | 1. 31 2. 503.7 |
| 66 | 23.8 and | | 1. 22 2. 511.7 |
| 67 | 22 and | | 1. 33 2. 539.8 |
| 68 | 22 and | | 1. 24 2. 469.9 |

-continued

| Ex. | Prep Ex of Thiadiazole Intermediate and Amine | Product | 1. Yield 2. MH+ |
|---|---|---|---|
| 69 | 23.1 and (piperidine-N-C(O)-phenyl with OH and NH₂) | (thiadiazole dioxide product with piperidine amide, OH, and (S)-1-phenylethylamine) | 1. 12 2. 470.0 |
| 70 | 23.1 and (pyrrolidine-N-C(O)-phenyl with OH and NH₂) | (thiadiazole dioxide product with pyrrolidine amide, OH, and (S)-1-phenylethylamine) | 1. 20 2. 456.0 |
| 71 | 23.9 and aniline (H₂N-phenyl) | (thiadiazole dioxide with O₂N-phenyl-OH and phenylamino) | 1. 8 2. 361.9 |
| 72 | 22 and 75.60 | (thiadiazole dioxide with N,N-dimethylbenzamide-OH and (S)-1-(benzo[d][1,3]dioxol-5-yl)-2,2-dimethylpropylamine) | 1. 48 2. 502.1 |

Examples 100-188

If one were to follow a procedure similar to that set forth in Example 2, but using the commercially available (or prepared amine) and the thiadiazoledioxide intermediate from the Preparative Example(s) indicated in the Table below and stirring the reaction mixtures at room temperature up to reflux, the thiadiazoledioxide products in the Table below could be obtained.

| Ex. | Prep Ex of Thiadiazole dioxide Intermediate | Amine | Product |
|---|---|---|---|
| 100 | 22 | H₂N-C(CH₃)₃ | 3-{[4-(tert-butylamino)-1,1-dioxido-1,2,5-thiadiazol-3-yl]amino}-2-hydroxy-N,N-dimethylbenzamide |
| 101 | 22 | 2-aminopyridine | 2-hydroxy-N,N-dimethyl-3-{[1,1-dioxido-4-(pyridin-2-ylamino)-1,2,5-thiadiazol-3-yl]amino}benzamide |
| 103 | 22 | (R)-1-phenylethylamine | 2-hydroxy-N,N-dimethyl-3-{[1,1-dioxido-4-((1R)-1-phenylethylamino)-1,2,5-thiadiazol-3-yl]amino}benzamide |
| 104 | 22 | (cyclopropyl)(phenyl)methanamine | 3-{[4-(cyclopropyl(phenyl)methylamino)-1,1-dioxido-1,2,5-thiadiazol-3-yl]amino}-2-hydroxy-N,N-dimethylbenzamide |
| 105 | 22 | (R)-2,2-dimethyl-1-phenylpropan-1-amine | 2-hydroxy-N,N-dimethyl-3-{[1,1-dioxido-4-((1R)-2,2-dimethyl-1-phenylpropylamino)-1,2,5-thiadiazol-3-yl]amino}benzamide |
| 106 | 22 | (R)-1-(thiophen-2-yl)propan-1-amine | 2-hydroxy-N,N-dimethyl-3-{[1,1-dioxido-4-((1R)-1-(thiophen-2-yl)propylamino)-1,2,5-thiadiazol-3-yl]amino}benzamide |

-continued

| Ex. | Prep Ex of Thiadiazole dioxide Intermediate | Amine | Product |
|---|---|---|---|
| 107 | 22 | | |
| 108 | 22 | | |
| 109 | 22 | | |
| 110 | 22 | | |
| 111 | 22 | | |
| 112 | 22 | | |

-continued

| Ex. | Prep Ex of Thiadiazole dioxide Intermediate | Amine | Product |
|---|---|---|---|
| 113 | 22 | | |
| 114 | 22 | | |
| 115 | 22 | | |
| 116 | 22 | | |
| 117 | 22 | | |
| 118 | 22 | | |

-continued

| Ex. | Prep Ex of Thiadiazole dioxide Intermediate | Amine | Product |
|---|---|---|---|
| 119 | 22 | | |
| 120 | 22 | | |
| 121 | 22 | | |
| 122 | 22 | | |
| 123 | 22 | | |

-continued

| Ex. | Prep Ex of Thiadiazole dioxide Intermediate | Amine | Product |
|---|---|---|---|
| 124 | 22 | | |
| 125 | 22 | | |
| 126 | 22 | | |
| 127 | 22 | | |
| 128 | 22 | | |

-continued

| Ex. | Prep Ex of Thiadiazole dioxide Intermediate | Amine | Product |
|---|---|---|---|
| 129 | 22 | | |
| 130 | 22 | | |
| 131 | 22 | | |
| 132 | 22 | | |
| 134 | 23.32 | | |

-continued

| Ex. | Prep Ex of Thiadiazole dioxide Intermediate | Amine | Product |
|---|---|---|---|
| 135 | 23.32 | 13.19 | |
| 136 | 23.6 | 13.19 | |
| 137 | 23.31 | 13.19 | |
| 138 | 23.6 | 13.29 | |
| 139 | 23.39 | | |

-continued

| Ex. | Prep Ex of Thiadiazole dioxide Intermediate | Amine | Product |
|---|---|---|---|
| 140 | 23.39 | | |
| 141 | 23.39 | | |
| 142 | 23.39 | | |
| 143 | 23.39 | | |
| 144 | 23.39 | | |
| 145 | 23.39 | | |

-continued

| Ex. | Prep Ex of Thiadiazole dioxide Intermediate | Amine | Product |
|---|---|---|---|
| 146 | 23.39 | | |
| 147 | 23.39 | | |
| 148 | 23.6 | 500.1 or 500.2 | |
| 149 | 23.32 | 500.1 or 500.2 | |
| 150 | 23.6 | | |
| 151 | 23.38 | | |

-continued

| Ex. | Prep Ex of Thiadiazole dioxide Intermediate | Amine | Product |
|---|---|---|---|
| 152 | 23.37 | 3 | (structure) |
| 153 | 23.32 | 13.32-A | (structure) |
| 154 | 23.33 | 13.32-A | (structure) |
| 155 | 23.31 | 13.32-A | (structure) |
| 156 | 23.34 | 13.32-A | (structure) |

-continued

| Ex. | Prep Ex of Thiadiazole dioxide Intermediate | Amine | Product |
|---|---|---|---|
| 157 | 23.40 | | |
| 158 | 23.40 | | |
| 159 | 23.40 | | |
| 160 | 23.41 | | |
| 161 | 23.41 | | |

-continued

| Ex. | Prep Ex of Thiadiazole dioxide Intermediate | Amine | Product |
|---|---|---|---|
| 162 | 23.41 | | |
| 163 | 23.41 | | |
| 164 | 23.42 | | |
| 165 | 23.42 | | |
| 166 | 23.42 | | |

-continued

| Ex. | Prep Ex of Thiadiazole dioxide Intermediate | Amine | Product |
|---|---|---|---|
| 167 | 23.40 | | |
| 168 | 23.41 | | |
| 169 | 23.42 | | |
| 170 | 22 | | |
| 171 | 23.8 | | |

-continued

| Ex. | Prep Ex of Thiadiazole dioxide Intermediate | Amine | Product |
|---|---|---|---|
| 172 | 23.8 | | |
| 173 | 23.8 | | |
| 174 | 23.8 | | |
| 175 | 23.8 | | |
| 176 | 23.8 | | |

-continued

| Ex. | Prep Ex of Thiadiazole dioxide Intermediate | Amine | Product |
|---|---|---|---|
| 177 | 23.32 | 13.32-A | |
| 178 | 23.32 | | |
| 179 | 23.30 | 15 | |
| 180 | 23.32 | 15 | |
| 181 | 23.33 | 15 | |

-continued

| Ex. | Prep Ex of Thiadiazole dioxide Intermediate | Amine | Product |
|---|---|---|---|
| 182 | 23.30 | 500.3 or 500.4 | |
| 183 | 23.32 | 500.3 or 500.4 | |
| 184 | 23.33 | 500.3 or 500.4 | |
| 185 | 23.30 | 500.1 or 500.2 | |
| 186 | 23.32 | 500.1 or 500.2 | |

-continued

| Ex. | Prep Ex of Thiadiazole dioxide Intermediate | Amine | Product |
|---|---|---|---|
| 187 | 23.33 | 500.1 or 500.2 | *(structure)* |
| 188 | 23.32 | 13.71 | *(structure)* |

Example 200

*(reaction scheme)*

The thiazoleoxide from Preparative Example 22.1 (55 mg, 0.17 mmol) was added to R-2-phenylpropylamine (0.024 mL, 0.17 mmol) in methanol (2 ml) with diiospropylethylamine (100 μL). The reaction mixture was microwaved at 100 W for 4 hr then purified by preparative HPLC. Concentration of desired fractions gave the pure product (12.4 mg, 18%). MH$^+$=413.9.

Example 201

*(reaction scheme)*

The thiadiazoleoxide from Preparative Example 22.2 (56 mg, 0.2 mmol) was added to 2-amino-6-cyanophenol (27 mg, 0.2 mmol) in methanol (2 ml) with diiospropylethylamine (100 μL). The reaction mixture was microwaved at 100 W for 24 hr then purified by preparative HPLC. Concentration of desired fractions gave the pure product (11 mg, 15%). MH$^+$=367.9.

Example 201A

To a solution of the Thiadiazole mono-oxide intermediate from Preparative Example 22.1 (100 mg, 0.3086 mmol) and the Furyl amine from Preparative Example 75.1 (43 mg, 0.3086 mmol) in methanol (2 mL) was added sodium trifluoro acetate (84 mg, 0.6172 mmol), followed by drop wise addition of diisopropylethylamine (80 mg, 0.6172 mmol). The reaction mixture was stirred over night at room temperature, solvents were removed under reduced pressure and the product was purified by preparative thin layer chromatography using Dichloromethane-Methanol (20:1) to afford the compound as a white solid. (Yield: 98 mg, 74%, m.p=140° C.)

Examples 201.1-201.9

Following a similar procedure to that set forth in Example 201, but using the amine and the thiadiazoleoxide intermediate from the Preparative Example indicated in the Table below, the thiadiazoleoxide products in the Table below were prepared.

| Ex. | Prep Ex (Thiadiazole oxide Intermediate) | Prep Ex (Amine) | Product | 1. Yield 2. mp (° C.) 3. MH+ |
|---|---|---|---|---|
| 201.1 | 22.1 | 75.9 | | 1. 9% 2. 110 3. 446 |
| 201.2 | 22.1 | 75.49 | | 1. 6% 2. 107 3. 418 |

-continued

| Ex. | Prep Ex (Thiadiazole oxide Intermediate) | Prep Ex (Amine) | Product | 1. Yield 2. mp (° C.) 3. MH+ |
|---|---|---|---|---|
| 201.3 | 23.9 | 64.1 | | 1. 32% 2. 156 3. 440 |
| 201.4 | 22.1 | 64.4 | | 1. 50% 2. 171 3. 380 |
| 201.5 | 22.1 | 64.3 | | 1. 49% 2. 171 3. 380 |
| 201.6 | 22.1 | 75.92 | | 1. 25% 2. 102 3. 482 |
| 201.7 | 23.3 | 75.1 | | 1. 9% 2. 145 3. 460 |

-continued

| Ex. | Prep Ex (Thiadiazole oxide Intermediate) | Prep Ex (Amine) | Product | 1. Yield 2. mp (° C.) 3. MH+ |
|---|---|---|---|---|
| 201.8 | 22.1 | 623 | | 1. 31% 2. 60 3. 444 |
| 201.9 | 22.1 | 75.61 | | 1. 37% 2. 172 3. 446 |

Examples 202-245 f one were to follow a procedure similar to that set forth in Example 201A, but using the commercially available (or prepared amine) and the thiadiazoleoxide intermediate from the Preparative Example(s) indicated in the Table below and stirring the reaction mixtures at room temperature up to reflux, the thiadiazoleoxide products in the Table below could be obtained.

| Ex. | Prep Ex of Thiadiazole oxide Intermediate | Amine | Product |
|---|---|---|---|
| 202 | 22.1 | | |
| 203 | 22.1 | | |

| Ex. | Prep Ex of Thiadiazole oxide Intermediate | Amine | Product |
|---|---|---|---|
| 204 | 22.1 | | |
| 205 | 22.1 | | |
| 206 | 22.1 | | |
| 207 | 22.1 | | |
| 208 | 22.3 | | |

| Ex. | Prep Ex of Thiadiazole oxide Intermediate | Amine | Product |
|---|---|---|---|
| 209 | 22.3 | | |
| 210 | 22.3 | | |
| 211 | 22.3 | | |
| 212 | 22.3 | | |
| 213 | 22.3 | | |

-continued

| Ex. | Prep Ex of Thiadiazole oxide Intermediate | Amine | Product |
|---|---|---|---|
| 214 | 22.4 | | |
| 215 | 22.4 | | |
| 216 | 22.4 | | |
| 217 | 22.4 | | |
| 218 | 22.4 | | |

-continued

| Ex. | Prep Ex of Thiadiazole oxide Intermediate | Amine | Product |
|---|---|---|---|
| 219 | 22.4 | | |
| 220 | 22.5 | | |
| 221 | 22.5 | | |
| 222 | 22.5 | | |
| 223 | 22.5 | | |

-continued

| Ex. | Prep Ex of Thiadiazole oxide Intermediate | Amine | Product |
|---|---|---|---|
| 224 | 22.5 | | |
| 225 | 22.5 | | |
| 226 | 22.6 | | |
| 227 | 22.6 | | |
| 228 | 22.6 | | |

| Ex. | Prep Ex of Thiadiazole oxide Intermediate | Amine | Product |
|---|---|---|---|
| 229 | 22.6 | | |
| 230 | 22.6 | | |
| 231 | 22.6 | | |
| 232 | 22.7 | | |
| 233 | 22.7 | | |

| Ex. | Prep Ex of Thiadiazole oxide Intermediate | Amine | Product |
|---|---|---|---|
| 234 | 22.7 | | |
| 235 | 22.7 | | |
| 236 | 22.7 | | |
| 237 | 22.7 | | |
| 238 | 22.1 | | |

-continued

| Ex. | Prep Ex of Thiadiazole oxide Intermediate | Amine | Product |
|---|---|---|---|
| 239 | 22.1 | 2-bromoaniline | thiadiazole 1-oxide linked to 2-hydroxy-N,N-dimethylbenzamide and 2-bromophenylamine |
| 240 | 22.3 | aniline | 6-bromo-2-hydroxy-N,N-dimethylbenzamide linked via thiadiazole 1-oxide to anilino group |
| 241 | 22.3 | 2-bromoaniline | 6-bromo-2-hydroxy-N,N-dimethylbenzamide linked via thiadiazole 1-oxide to 2-bromoanilino group |
| 241.1 | 22.4 | aniline | 6-chloro-2-hydroxy-N,N-dimethylbenzenesulfonamide linked via thiadiazole 1-oxide to anilino group |
| 241.2 | 22.4 | 2-bromoaniline | 6-chloro-2-hydroxy-N,N-dimethylbenzenesulfonamide linked via thiadiazole 1-oxide to 2-bromoanilino group |

-continued

| Ex. | Prep Ex of Thiadiazole oxide Intermediate | Amine | Product |
|---|---|---|---|
| 241.3 | 22.5 | aniline | 3-{[4-(phenylamino)-1-oxido-1,2,5-thiadiazol-3-yl]amino}-2-hydroxy-N,N-dimethylbenzenesulfonamide |
| 241.4 | 22.5 | 2-bromoaniline | 3-{[4-(2-bromophenylamino)-1-oxido-1,2,5-thiadiazol-3-yl]amino}-2-hydroxy-N,N-dimethylbenzenesulfonamide |
| 242 | 22.6 | aniline | thiophene-based analog with N,N-dimethylsulfonamide and phenylamino-thiadiazole oxide |
| 243 | 22.6 | 2-bromoaniline | thiophene-based analog with N,N-dimethylsulfonamide and 2-bromophenylamino-thiadiazole oxide |
| 244 | 22.7 | aniline | thiophene-based analog with N,N-diethylsulfonamide and phenylamino-thiadiazole oxide |
| 245 | 22.7 | 2-bromoaniline | thiophene-based analog with N,N-diethylsulfonamide and 2-bromophenylamino-thiadiazole oxide |

Examples 246-373

If one were to follow a procedure similar to that set forth in Example 201A, but using the amines from the Preparative Examples indicated in the Table below (or the commercially available amines indicated in the Table below), and the thiadiazoleoxide intermediates from the Preparative Examples indicated in the Table below and stirring the reaction mixtures at room temperature up to reflux, the thiadiazoleoxide products in the Table below could be obtained.

| Ex. | Prep. Ex. (Thiadiazole oxide Intermediate) | Prep. Ex. (Amine) | Product |
| --- | --- | --- | --- |
| 246 | 22.25 | 75.44 | |
| 248 | 22.23 | 74 | |
| 249 | 22.23 | 75.44 | |
| 251 | 22.24 | 74 | |

-continued

| Ex. | Prep. Ex. (Thiadiazole oxide Intermediate) | Prep. Ex. (Amine) | Product |
|---|---|---|---|
| 252 | 22.24 | 75.44 | |
| 254 | 22.26 | 75.44 | |
| 255 | 22.1 | H₂N–C(CH₃)₃ (commercially available) | |
| 256 | 22.1 | H₂N-cyclohexyl (commercially available) | |
| 257 | 22.1 | 75.66 | |

-continued

| Ex. | Prep. Ex. (Thiadiazole oxide Intermediate) | Prep. Ex. (Amine) | Product |
|---|---|---|---|
| 258 | 22.1 | 75.30 | |
| 259 | 22.1 | 75.50 | |
| 260 | 22.1 | 603D | |
| 262 | 22.1 | 75.10 | |
| 263 | 22.1 | 75.10E | |

-continued

| Ex. | Prep. Ex. (Thiadiazole oxide Intermediate) | Prep. Ex. (Amine) | Product |
|---|---|---|---|
| 264 | 22.29 | 75.44 | |
| 265 | 22.39 | 603C | |
| 266 | 22.30 | 75.44 | |
| 267 | 22.6 | 75.1 | |
| 268 | 22.6 | 75.9 | |
| 269 | 22.39 | 75.44 | |

-continued

| Ex. | Prep. Ex. (Thiadiazole oxide Intermediate) | Prep. Ex. (Amine) | Product |
|---|---|---|---|
| 270 | 22.6 | 75.61 | |
| 271 | 23.9 | 75.44 | |
| 272 | 22.27 | 75.44 | |
| 273 | 22.28 | 75.10 | |
| 274 | 22.28 | 75.61 | |
| 275 | 22.31 | 75.44 | |

-continued

| Ex. | Prep. Ex. (Thiadiazole oxide Intermediate) | Prep. Ex. (Amine) | Product |
|---|---|---|---|
| 276 | 22.32 | 75.61 | |
| 277 | 22.32 | 75.10 | |
| 278 | 22.32 | 75.44 | |
| 279 | 22.32 | 75.9 | |
| 280 | 22.32 | 75.60 | |

-continued

| Ex. | Prep. Ex. (Thiadiazole oxide Intermediate) | Prep. Ex. (Amine) | Product |
|---|---|---|---|
| 281 | 22.32 | 75.30 | |
| 282 | 22.32 | 75.52 | |
| 283 | 22.47 | 75.60 | |
| 284 | 22.34 | 75.52 | |
| 285 | 22.48 | 75.44 | |
| 286 | 22.1 | 75.67 | |

-continued

| Ex. | Prep. Ex. (Thiadiazole oxide Intermediate) | Prep. Ex. (Amine) | Product |
|---|---|---|---|
| 287 | 22.36 | 75.44 | |
| 289 | 22.41 | 75.44 | |
| 291 | 22.32 | 75.201 | |
| 292 | 22.32 | 75.200 | |
| 293 | 22.47 | 75.201 | |
| 294 | 22.47 | 75.200 | |

-continued

| Ex. | Prep. Ex. (Thiadiazole oxide Intermediate) | Prep. Ex. (Amine) | Product |
|---|---|---|---|
| 295 | 22.4 | 75.201 | |
| 296 | 22.4 | 75.200 | |
| 297 | 22.45 | 75.201 | |
| 298 | 22.45 | 75.200 | |
| 299 | 22.46 | 75.201 | |

-continued

| Ex. | Prep. Ex. (Thiadiazole oxide Intermediate) | Prep. Ex. (Amine) | Product |
|---|---|---|---|
| 300 | 22.46 | 75.200 | |
| 301 | 22.39 | 75.201 | |
| 302 | 22.39 | 75.200 | |
| 303 | 22.39 | 601.A | |
| 304 | 22.39 | 601.B | |

-continued

| Ex. | Prep. Ex. (Thiadiazole oxide Intermediate) | Prep. Ex. (Amine) | Product |
|---|---|---|---|
| 305 | 22.1 | 75.93 | |
| 306 | 22.1 | 64.11 | |
| 307 | 22.48 | 75.1 | |
| 308 | 22.37 | 75.9 | |
| 309 | 22.50 | 51.26 | |
| 310 | 22.51 | 75.9 | |

-continued

| Ex. | Prep. Ex. (Thiadiazole oxide Intermediate) | Prep. Ex. (Amine) | Product |
|---|---|---|---|
| 311 | 22.16 | 75.1 | |
| 312 | 22.51 | 51.26 | |
| 313 | 22.38 | 75.1 | |
| 314 | 22.7 | 75.61 | |
| 315 | 22.7 | 75.10 | |

-continued

| Ex. | Prep. Ex. (Thiadiazole oxide Intermediate) | Prep. Ex. (Amine) | Product |
|---|---|---|---|
| 316 | 22.7 | 75.10E | |
| 317 | 22.7 | 603A | |
| 318 | 22.7 | 603B | |
| 319 | 22.7 | 603C | |

-continued

| Ex. | Prep. Ex. (Thiadiazole oxide Intermediate) | Prep. Ex. (Amine) | Product |
|---|---|---|---|
| 320 | 22.19 | 75.10 | |
| 321 | 22.19 | 75.10E | |
| 322 | 22.19 | 603A | |
| 323 | 22.19 | 603B | |

-continued

| Ex. | Prep. Ex. (Thiadiazole oxide Intermediate) | Prep. Ex. (Amine) | Product |
|---|---|---|---|
| 324 | 22.19 | 603C | |
| 325 | 22.20 | 75.10 | |
| 326 | 22.20 | 75.10E | |
| 327 | 22.20 | 603A | |

-continued

| Ex. | Prep. Ex. (Thiadiazole oxide Intermediate) | Prep. Ex. (Amine) | Product |
|---|---|---|---|
| 328 | 22.20 | 603B | |
| 329 | 22.20 | 603C | |
| 330 | 22.21 | 75.10 | |
| 331 | 22.21 | 75.10E | |

-continued

| Ex. | Prep. Ex. (Thiadiazole oxide Intermediate) | Prep. Ex. (Amine) | Product |
|---|---|---|---|
| 332 | 22.21 | 75.10E | |
| 333 | 22.21 | 603A | |
| 334 | 22.21 | 603B | |
| 335 | 22.21 | 603C | |
| 336 | 22.19 | 75.61 | |

-continued

| Ex. | Prep. Ex. (Thiadiazole oxide Intermediate) | Prep. Ex. (Amine) | Product |
|---|---|---|---|
| 337 | 22.20 | 75.61 | |
| 338 | 22.21 | 75.61 | |
| 339 | 22.22 | 75.61 | |
| 340 | 22.22 | 75.10 | |
| 341 | 22.22 | 75.10E | |

-continued

| Ex. | Prep. Ex. (Thiadiazole oxide Intermediate) | Prep. Ex. (Amine) | Product |
|---|---|---|---|
| 342 | 22.22 | 603A | |
| 343 | 22.22 | 603B | |
| 344 | 22.22 | 603C | |
| 345 | 22.1 | 74 | |

-continued

| Ex. | Prep. Ex. (Thiadiazole oxide Intermediate) | Prep. Ex. (Amine) | Product |
|---|---|---|---|
| 346 | 22.1 | 75.45 | |
| 347 | 22.1 | 75.1 | |
| 348 | 22.1 | 75.44 | |
| 349 | 22.39 | 75.1 | |
| 350 | 22.47 | 64.2 | |

-continued

| Ex. | Prep. Ex. (Thiadiazole oxide Intermediate) | Prep. Ex. (Amine) | Product |
|---|---|---|---|
| 351 | 22.47 | 75.1 | |
| 352 | 22.1 | 51.26 | |
| 353 | 22.41 | H₂N— (commercially available) | |
| 354 | 22.1 | 13.18 | |
| 355 | 22.1 | 75.60 | |

-continued

| Ex. | Prep. Ex. (Thiadiazole oxide Intermediate) | Prep. Ex. (Amine) | Product |
|---|---|---|---|
| 356 | 22.1 | H₂N-benzo[d][1,3]dioxol-5-amine (commercially available) | (structure) |
| 357 | 22.1 | 75.29 | (structure) |
| 358 | 22.1 | 72 | (structure) |
| 359 | 22.1 | 75.34 | (structure) |
| 360 | 22.1 | 75.62 | (structure) |

-continued

| Ex. | Prep. Ex. (Thiadiazole oxide Intermediate) | Prep. Ex. (Amine) | Product |
|---|---|---|---|
| 361 | 22.39 | 75.61 | |
| 362 | 22.39 | H₂N-CH(CH₃)-phenyl (commercially available) | |
| 363 | 22.42 | H₂N-CH(CH₃)-phenyl (commercially available) | |
| 364 | 22.43 | H₂N-CH(CH₃)-phenyl (commercially available) | |
| 365 | 22.1 | 75.63 | |

-continued

| Ex. | Prep. Ex. (Thiadiazole oxide Intermediate) | Prep. Ex. (Amine) | Product |
|---|---|---|---|
| 366 | 22.44 | (commercially available) | |
| 367 | 22.1 | (commercially available) | |
| 368 | 22.1 | 75.27 | |
| 369 | 22.1 | 64.6* (commercially available) | |
| 370 | 22.46 | 64.1* (commercially available) | |

-continued

| Ex. | Prep. Ex. (Thiadiazole oxide Intermediate) | Prep. Ex. (Amine) | Product |
|---|---|---|---|
| 371 | 22.45 | 75.1 | |
| 372 | 22.47 | 75.61 | |
| 373 | 22.1 | 75.19 | |
| 374 | 22.39 | 75.19 | |

-continued

| Ex. | Prep. Ex. (Thiadiazole oxide Intermediate) | Prep. Ex. (Amine) | Product |
|---|---|---|---|
| 375 | 22.46 | 75.9 | |
| 376 | 22.52 | 75.9 | |
| 377 | 22.52 | 75.44 | |
| 378 | 22.46 | 75.10E | |

-continued

| Ex. | Prep. Ex. (Thiadiazole oxide Intermediate) | Prep. Ex. (Amine) | Product |
|---|---|---|---|
| 379 | 22.52 | 75.10E | |
| 380 | 22.5 | 75.9 | |
| 381 | 22.4 | 75.9 | |
| 382 | 22.39 | 75.10E | |

-continued

| Ex. | Prep. Ex. (Thiadiazole oxide Intermediate) | Prep. Ex. (Amine) | Product |
|---|---|---|---|
| 383 | 22.46 | 75.61 | |
| 384 | 22.52 | 75.61 | |
| 385 | 22.5 | 75.61 | |
| 386 | 22.4 | 75.61 | |

-continued

| Ex. | Prep. Ex. (Thiadiazole oxide Intermediate) | Prep. Ex. (Amine) | Product |
|---|---|---|---|
| 387 | 22.7 | 75.10E | |
| 388 | 22.7 | 75.9 | |
| 389 | 22.22 | 75.9 | |
| 390 | 22.22 | 75.44 | |

-continued

| Ex. | Prep. Ex. (Thiadiazole oxide Intermediate) | Prep. Ex. (Amine) | Product |
|---|---|---|---|
| 391 | 22.53 | 75.9 | |
| 392 | 22.53 | 75.10E | |
| 393 | 22.53 | 75.44 | |
| 394 | 22.53 | 75.61 | |

Examples 2001-2113

Following a similar procedure as that set forth in Example 1 but using the commercially available or prepared amine from the Preparative Example indicated in the Table below, the following thiadiazoledioxide products were obtained.

| Ex | Amine & Prep Ex of intermediate | Product | 1. Yield (%)<br>2. $(M+1)^+$ |
|---|---|---|---|
| 2001 | (structure) & 22 | (structure) | 1. 33%<br>2. 539.8 |
| 2002 | (structure) & 22 | (structure) | 1. 72%<br>2. 461.0 |
| 2003 | (structure) & 22 | (structure) | 1. 45%<br>2. 497.9 |
| 2004 | (structure) & 22 | (structure) | 1. 37%<br>2. 447.9 |
| 2005 | (structure) & 22 | (structure) | 1. 5%<br>2. 497.9 |

-continued

| Ex | Amine & Prep Ex of intermediate | Product | 1. Yield (%) 2. $(M+1)^+$ |
|---|---|---|---|
| 2006 | H₂N-C(CMe₃)-(5-methylfuran-2-yl) & 1203 | F₃C-substituted product with 5-methylfuran | 1. 59% 2. 529.9 |
| 2007 | H₂N-CH(iPr)-(4,5-dimethylfuran-2-yl) & 22 | product with 4,5-dimethylfuran | 1. 64% 2. 461.7 |
| 2008 | H₂N-CH(CMe₃)-(2-methoxyphenyl) & 22 | product with 2-methoxyphenyl | 1. 55% 2. 487.9 |
| 2009 | H₂N-CH(CMe₃)-(3-methoxyphenyl) & 22 | product with 3-methoxyphenyl | 1. 14% 2. 488.0 |
| 2010 | H₂N-CH(Et)-(benzofuran-2-yl) & 22 | product with benzofuran-2-yl | 1. 24% 2. 469.9 |

-continued

| Ex | Amine & Prep Ex of intermediate | Product | 1. Yield (%) 2. (M + 1)+ |
|---|---|---|---|
| 2011 | (amine with H2N-CH(tBu)- attached to 4-methoxyphenyl) & 22 | (product: 3-NH-thiadiazole-1,1-dioxide linked to benzamide with OH, NMe2, and CH(tBu)-4-methoxyphenyl) | 1. 14% 2. 488.9 |
| 2012 | (amine with H2N-CH(tBu)- attached to 5-methoxybenzofuran-2-yl) & 22 | (product with 5-methoxybenzofuran) | 1. 10% 2. 527.8 |
| 2013 | (amine with H2N-CH(iPr)- attached to 4,5-dimethylfuran-2-yl) & 1203 | (product with CF3 substituent and 4,5-dimethylfuran) | 1. 14% 2. 529.8 |
| 2014 | (amine with H2N-CH(tBu)- attached to 5-chlorobenzofuran-2-yl) & 22 | (product with 5-chlorobenzofuran) | 1. 32% 2. 531.8 |
| 2015 | (amine with H2N-CH(tBu)- attached to 4,5-dimethylfuran-2-yl) & 22 | (product with 4,5-dimethylfuran) | 1. 6% 2. 498 |

-continued

| Ex | Amine & Prep Ex of intermediate | Product | 1. Yield (%) 2. (M + 1)+ |
|---|---|---|---|
| 2016 | (amine with prep ex 22) | | 1. 6% 2. 504.9 |
| 2017 | (amine with prep ex 22) | | 1. 8% 2. 458.2 |
| 2018 | (amine with prep ex 22) | · CF₃CO₂H | 1. 92% 2. 501.0 |
| 2019 | (amine with prep ex 1224) | | 1. 75% 2. 596.2 |
| 2020 | (amine with prep ex 1205) | | 1. 33% 2. 517.2 |

-continued

| Ex | Amine & Prep Ex of intermediate | Product | 1. Yield (%) <br> 2. $(M+1)^+$ |
|---|---|---|---|
| 2021 | & 1206 | | 1. 71% <br> 2. 580.2 |
| 2022 | & 1207 | | 1. 85% <br> 2. 504.2 |
| 2023 | 22 & | | 1. 92% <br> 2. 518.2 |
| 2024 | 22 & | | 1. 69% <br> 2. 418.1 |
| 2025 | 22 & | | 1. 86% <br> 2. 518.2 |
| 2026 | 1206 & | | 1. 75% <br> 2. 552.2 |

-continued

| Ex | Amine & Prep Ex of intermediate | Product | 1. Yield (%) 2. (M + 1)+ |
|---|---|---|---|
| 2027 | 22 & | | 1. 83% 2. 518.2 |
| 2028 | 1207 & | | 1. 79% 2. 516.1 |
| 2029 | 1224 & | | 1. 75% 2. 568.2 |
| 2031 | & 1207 | | 1. 92% 2. 476.1 |
| 2032 | & 1209 | | 1. 39% 2. 497.7 |

-continued

| Ex | Amine & Prep Ex of intermediate | Product | 1. Yield (%) 2. (M + 1)+ |
|---|---|---|---|
| 2033 | & 1209 | | 1. 46% 2. 509.8 |
| 2034 | & 1210 | | 1. 89% 2. 489.9 |
| 2035 | & 1209 | | 1. 13% 2. 469.6 |
| 2036 | & 1211 | | 1. 36% 2. 509.5 |
| 2037 | & 1212 | | 1. 48% 2. 577.7 |
| 2038 | & 23.1 | | 1. 12% 2. 470.0 |
| 2039 | & 23.8 | | 1. 1% 2. 539.8 |

-continued

| Ex | Amine & Prep Ex of intermediate | Product | 1. Yield (%)<br>2. (M + 1)⁺ |
|---|---|---|---|
| 2040 | & 23.1 | | 1. 19%<br>2. 456.0 |
| 2041 | & 1216 | | 1. 73%<br>2. 523.7 |
| 2042 | & 1217 | | 1. 23%<br>2. 442.0 |
| 2043 | & 1216 | | 1. 38%<br>2. 495.6 |
| 2044 | & 1209 | | 1. 25%<br>2. 497.6 |
| 2045 | & 23.1 | | 1. 4%<br>2. 466.0 |

-continued

| Ex | Amine & Prep Ex of intermediate | Product | 1. Yield (%)<br>2. (M + 1)+ |
|---|---|---|---|
| 2046 | & 23.1 | | 1. 33%<br>2. 471.9 |
| 2047 | & 23.8 | | 1. 9%<br>2. 567.9 |
| 2049 | & 1207 | | 1. 28%<br>2. 526.0<br>(M + Na) |
| 2050 | & 22 | | 1. 17%<br>2. 410.0 |
| 2051 | & 1218 | | 1. 43%<br>2. 505.8 |

-continued

| Ex | Amine & Prep Ex of intermediate | Product | 1. Yield (%) 2. $(M+1)^+$ |
|---|---|---|---|
| 2052 | & 1219 | | 1. 45% 2. 539.0 |
| 2053 | & 23.8 | | 1. 22% 2. 511.6 |
| 2054 | & 1220 | | 1. 55% 2. 531.9 |
| 2055 | & 1221 | | 1. 46% 2. 517.9 |

-continued

| Ex | Amine & Prep Ex of intermediate | Product | 1. Yield (%) 2. (M + 1)+ |
|---|---|---|---|
| 2056 | & 1222 | | 1. 38% 2. 517.9 |
| 2057 | & 23.8 | | 1. 1% 2. 539.8 |
| 2058 | & 22 | | 1. 23% 2. 396.0 |
| 2059 | & 1205 | | 1. 41% 2. 485.0 |

-continued

| Ex | Amine & Prep Ex of intermediate | Product | 1. Yield (%) 2. (M + 1)+ |
|---|---|---|---|
| 2060 | & 1223 | | 1. 55% 2. 608.0 |
| 2062 | & 23.1 | | 1. 11% 2. 513.9 |
| 2063 | & 22 | | 1. 5% 2. 461.7 |
| 2064 | & 23.1 | | 1. 21% 2. 514.0 |

-continued

| Ex | Amine & Prep Ex of intermediate | Product | 1. Yield (%) 2. (M + 1)+ |
|---|---|---|---|
| 2065 | & 1225 | | 1. 41% 2. 532 |
| 2066 | & 1225 | | 1. 48% 2. 546 |
| 2067 | & 1226 | | 1. 23% 2. 586 |
| 2068 | & 1226 | | 1. 58% 2. 572 |
| 2069 | & 1227 | | 1. 43% 2. 518 |
| 2070 | & 1228 | | 1. 28% 2. 560 |

-continued

| Ex | Amine & Prep Ex of intermediate | Product | 1. Yield (%) 2. (M + 1)⁺ |
|---|---|---|---|
| 2071 | & 1229 | | 1. 69% 2. 518 |
| 2072 | & 23.7 | | 1. 27% 2. 532 |
| 2073 | & 1230 | | 1. 23% 2. 504 |
| 2074 | & 1231 | | 1. 44% 2. 518 |
| 2075 | & 1225 | | 1. 48% 2. 546 |
| 2076 | & 22 | | 1. 48% 2. 502 |

-continued

| Ex | Amine & Prep Ex of intermediate | Product | 1. Yield (%) 2. (M + 1)+ |
|---|---|---|---|
| 2077 | & 22 | | 1. 24% 2. 476 |
| 2078 | & 22 | | 1. 22% 2. 448 |
| 2079 | & 22 | | 1. 28% 2. 482 |
| 2080 | & 22 | | 1. 38% 2. 528 |
| 2081 | & 22 | | 1. 27% 2. 488 |

-continued

| Ex | Amine & Prep Ex of intermediate | Product | 1. Yield (%)<br>2. $(M+1)^+$ |
|---|---|---|---|
| 2082 | (cyclopropyl-benzodioxole amine) & 22 | (product structure) | 1. 29%<br>2. 486 |
| 2083 | (isopropyl-3-fluorophenyl amine) & 22 | (product structure) | 1. 36%<br>2. 462 |
| 2084 | (tert-butyl-benzofuran amine) & 22 | (product structure) | 1. 40%<br>2. 498 |
| 2085 | (propyl-difluorobenzodioxole amine) & 22 | (product structure) | 1. 67%<br>2. 510 |

-continued

| Ex | Amine & Prep Ex of intermediate | Product | 1. Yield (%) 2. (M + 1)+ |
|---|---|---|---|
| 2086 | & 22 | | 1. 71% 2. 542 |
| 2087 | & 22 | | 1. 58% 2. 526 |
| 2088 | & 22 | | 1. 70% 2. 476 |
| 2089 | & 22 | | 1. 42% 2. 548 |

-continued

| Ex | Amine & Prep Ex of intermediate | Product | 1. Yield (%)<br>2. $(M + 1)^+$ |
|---|---|---|---|
| 2090 | (3,5-dimethoxyphenyl neopentylamine) & 22 | (product structure) | 1. 47%<br>2. 518 |
| 2091 | (3,5-difluorophenyl neopentylamine) & 22 | (product structure) | 1. 37%<br>2. 494 |
| 2092 | (3,5-dichlorophenyl neopentylamine) & 22 | (product structure) | 1. 39%<br>2. 526 |
| 2093 | (3,5-dimethylphenyl neopentylamine) & 22 | (product structure) | 1. 34%<br>2. 486 |

-continued

| Ex | Amine & Prep Ex of intermediate | Product | 1. Yield (%) 2. (M + 1)+ |
|---|---|---|---|
| 2094 | & 22 | | 1. 48% 2. 500 |
| 2095 | & 22 | | 1. 38% 2. 530 |
| 2096 | & 22 | | 1. 21% 2. 514 |
| 2097 | & 1232 | | 1. 13% 2. 649 |

-continued

| Ex | Amine & Prep Ex of intermediate | Product | 1. Yield (%) 2. (M + 1)+ |
|---|---|---|---|
| 2098 | & 1233 | | 1. 49% 2. 517 |
| 2099 | & 1233 | | 1. 22% 2. 567 |
| 2100 | & 1233 | | 1. 40% 2. 571 |
| 2101 | & 23.8 | | 1. 15% 2. 582 |
| 2102 | & 1209 | | 1. 15% 2. 538 |

-continued

| Ex | Amine & Prep Ex of intermediate | Product | 1. Yield (%) 2. (M + 1)⁺ |
|---|---|---|---|
| 2103 | & 23.8 | | 1. 9% 2. 568 |
| 2104 | & 22 | | 1. 29% 2. 538 |
| 2105 | & 1234 | | 1. 15% 2. 476 |
| 2106 | & 22 | | 1. 11% 2. 476 |
| 2107 | & 22 | | 1. 26% 2. 466 |

-continued

| Ex | Amine & Prep Ex of intermediate | Product | 1. Yield (%) 2. (M + 1)+ |
|---|---|---|---|
| 2108 | & 22 | | 1. 25% 2. 470 |
| 2109 | & 22 | | 1. 34% 2. 448 |
| 2110 | & 22 | | 1. 24% 2. 480 |
| 2111 | & 22 | | 1. 17% 2. 516 |
| 2112 | & 22 | | 1. 22% 2. 498 |

| Ex | Amine & Prep Ex of intermediate | Product | 1. Yield (%) 2. (M + 1)+ |
|---|---|---|---|
| 2113 | (structure with H₂N-CH(tBu)-benzofuran) & 22 | (product structure) | 1. 30% 2. 516 |

While the present invention has been described in conjunction with specific embodiments set forth above, many alternatives, modifications and variations thereof will be apparent to those of ordinary skill in the art. All such alternatives, modifications and variations are intended to fall within the spirit and scope of the present invention.

What is claimed is:

1. A compound of the formula:

(IA)

and the pharmaceutically acceptable salts and solvates thereof, wherein:

A is selected from the group consisting of:

-continued wherein the above rings of said A groups are substituted with 1 to 6 substituents each independently selected from the group consisting of: $R^9$ groups, provided that when $R^9$ is $R^{13}$ then $R^{13}$ is not H;

(3)

wherein one or both of the above rings of said A groups are substituted with 1 to 6 substituents each independently selected from the group consisting of: $R^9$ groups, provided that when $R^9$ is $R^{13}$ then $R^{13}$ is not H;

(4)

wherein the above phenyl rings of said A groups are substituted with 1 to 3 substituents each independently selected from the group consisting of: $R^9$ groups, provided that when $R^9$ is $R^{13}$ then $R^{13}$ is not H; and (5)

B is selected from the group consisting of n is 0;

$R^2$ is selected from the group consisting of: hydrogen, OH, —C(O)OH, —SH, —SO$_2$NR$^{13}$R$^{14}$, —NHC(O)R$^{13}$, —NHSO$_2$NR$^{13}$R$^{14}$, —NHSO$_2$R$^{13}$, —NR$^{13}$R$^{14}$, —C(O)NR$^{13}$R$^{14}$, —C(O)NHOR$^{13}$, —C(O)NR$^{13}$OH, —S(O$_2$)OH, —OC(O)R$^{13}$, an unsubstituted heterocyclic acidic functional group, and a substituted heterocyclic acidic functional group; wherein there are 1 to 6 substituents on said substituted heterocyclic acidic functional group each substituent being independently selected from the group consisting of: $R^9$ groups, and wherein the heterocyclic acidic functional group is selected from the group consisting of pyrrole, imidazole, triazole, and tetrazole;

each $R^3$ and $R^4$ is independently selected from the group consisting of: hydrogen, cyano, halogen, alkyl, alkoxy, cycloalkyl substituted with 1 to 4 alkyl groups wherein each alkyl group is independently selected, unsubstituted cycloalkyl, —OH, —CF$_3$, —OCF$_3$, —NO$_2$, —C(O)R$^{13}$, —C(O)OR$^{13}$, —C(O)NHR$^{17}$, —C(O)NR$^{13}$R$^{14}$, —SO$_{(t)}$NR$^{13}$R$^{14}$, —SO$_{(t)}$R$^{13}$, —C(O)

NR$^{13}$OR$^{14}$, unsubstituted or substituted aryl, unsubstituted or substituted heteroaryl,

[structures: phosphine oxide with R$^{31}$, R$^{31}$; amidine with R$^{13}$, R$^{14}$, R$^{30}$; and oxime ether with OR$^{13}$, R$^{14}$]

wherein there are 1 to 6 substituents on said substituted aryl group and each substituent is independently selected from the group consisting of: R$^9$ groups; and wherein there are 1 to 6 substituents on said substituted heteroaryl group and each substituent is independently selected from the group consisting of: R$^9$ groups; or R$^3$ is and R$^4$ taken together with the carbons atoms to which they are bonded to in the phenyl B substituent

[structure: phenyl ring with R$^2$, R$^3$, R$^4$, R$^5$, R$^6$ substituents]

form a fused ring of the formula:

[structure: fused ring system with Z$^1$, R$^{13}$-N, C=O, R$^2$, R$^5$, R$^6$]

or

[structure: fused ring with Z$^2$, R$^{13}$-N-C(=O), R$^2$, R$^5$, R$^6$]

wherein Z$^1$ or Z$^2$ is an unsubstituted or substituted saturated heterocyclic ring, said ring Z$^1$ or Z$^2$ optionally containing one additional heteroatom selected from the group consisting of: O, S and NR$^{18}$; wherein there are 1 to 3 substituents on said ring Z$^1$ or Z$^2$, and each substituent is independently selected from the group consisting of: alkyl, aryl, hydroxy, hydroxyalkyl, alkoxy, alkoxyalkyl, arylalkyl, fluoroalkyl, cycloalkyl, cycloalkylalkyl, heteroaryl, heteroarylalkyl, amino, —C(O)OR$^{15}$, —C(O)NR$^{15}$R$^{16}$, —SO$_t$NR$^{15}$R$^{16}$, —C(O)R$^{15}$, —SO$_2$R$^{15}$ provided that R$^{15}$ is not H, —NHC(O)NR$^{15}$R$^{16}$, —NHC(O)OR$^{15}$, halogen, and a heterocycloalkenyl group;

each R$^5$ and R$^6$ are the same or different and are independently selected from the group consisting of hydrogen, halogen, alkyl, alkoxy, —CF$_3$, —OCF$_3$, —NO$_2$, —C(O)R$^{13}$, —C(O)OR$^{13}$, —C(O)NR$^{13}$R$^{14}$, —SO$_{(t)}$NR$^{13}$R$^{14}$, —C(O)NR$^{13}$OR$^{14}$, cyano, unsubstituted or substituted aryl, and unsubstituted or substituted heteroaryl group; wherein there are 1 to 6 substituents on said substituted aryl group and each substituent is independently selected from the group consisting of: R$^9$ groups; and wherein there are 1 to 6 substituents on said substituted heteroaryl group and each substituent is independently selected from the group consisting of: R$^9$ groups;

each R$^7$ and R$^8$ is independently selected from the group consisting of: H, unsubstituted or substituted alkyl, unsubstituted or substituted aryl, unsubstituted or substituted heteroaryl, unsubstituted or substituted arylalkyl, unsubstituted or substituted heteroarylalkyl, unsubstituted or substituted cycloalkyl, unsubstituted or substituted cycloalkylalkyl, —CO$_2$R$^{13}$, —CONR$^{13}$R$^{14}$, alkynyl, alkenyl, and cycloalkenyl; and wherein there are one or more substituents on said substituted R$^7$ and R$^8$ groups, wherein each substitutent is independently selected from the group consisting of:
a) halogen,
b) —CF$_3$,
c) —COR$^{13}$,
d) —OR$^{13}$,
e) —NR$^{13}$R$^{14}$,
f) —NO$_2$,
g) —CN,
h) —SO$_2$OR$^{13}$,
i) —Si(alkyl)$_3$, wherein each alkyl is independently selected,
j) —Si(aryl)$_3$, wherein each aryl is independently selected,
k) —(R$^{13}$)$_2$R$^{14}$Si, wherein each R$^{13}$ is independently selected,
l) —CO$_2$R$^{13}$,
m) —C(O)NR$^{13}$R$^{14}$,
n) —SO$_2$NR$^{13}$R$^{14}$,
o) —SO$_2$R$^{13}$,
p) —OC(O)R$^{13}$,
q) —OC(O)NR$^{13}$R$^{14}$,
r) —NR$^{13}$C(O)R$^{14}$, and
s) —NR$^{13}$CO$_2$R$^{14}$;

R$^{8a}$ is selected from the group consisting of: hydrogen, alkyl, cycloalkyl and cycloalkylalkyl;

each R$^9$ is independently selected from the group consisting of:
a) —R$^{13}$,
b) halogen,
c) —CF$_3$,
d) —COR$^{13}$,
e) —OR$^{13}$,
f) —NR$^{13}$R$^{14}$,
g) —NO$_2$,
h) —CN,
i) —SO$_2$R$^{13}$,
j) —SO$_2$NR$^{13}$R$^{14}$,
k) —NR$^{13}$COR$^{14}$,
l) —CONR$^{13}$R$^{14}$
m) —NR$^{13}$CO$_2$R$^{14}$,
n) —CO$_2$R$^{13}$,
o)

[structure: tetrazole ring attached via squiggly bond, with NH]

p) alkyl substituted with one or more —OH groups,
q) alkyl substituted with one or more —NR$^{13}$R$^{14}$ group, and
r) —N(R$^{13}$)SO$_2$R$^{14}$;

each $R^{10}$ and $R^{11}$ is independently selected from the group consisting of $R^{13}$, halogen, —$CF_3$, —$OCF_3$, —$NR^{13}R^{14}$, —$NR^{13}C(O)NR^{13}R^{14}$, —OH, —$C(O)OR^{13}$, —SH, —$SO_{(t)}NR^{13}R^{14}$, —$SO_2R^{13}$, —$NHC(O)R^{13}$, —$NHSO_2NR^{13}R^{14}$, —$NHSO_2R^{13}$, —$C(O)NR^{13}R^{14}$, —$C(O)NR^{13}OR^{14}$, —$OC(O)R^{13}$ and cyano;

$R^{12}$ is selected from the group consisting of: hydrogen, —$C(O)OR^{13}$, unsubstituted or substituted aryl, unsubstituted or substituted heteroaryl, unsubstituted or substituted arylalkyl, unsubstituted or substituted cycloalkyl, unsubstituted or substituted alkyl, unsubstituted or substituted cycloalkylalkyl, and unsubstituted or substituted heteroarylalkyl group; wherein there are 1 to 6 substituents on the substituted $R^{12}$ groups and each substituent is independently selected from the group consisting of: $R^9$ groups;

each $R^{13}$ and $R^{14}$ is independently selected from the group consisting of: H, unsubstituted or substituted alkyl, unsubstituted or substituted aryl, unsubstituted or substituted heteroaryl, unsubstituted or substituted arylalkyl, unsubstituted or substituted heteroarylalkyl, unsubstituted or substituted cycloalkyl, unsubstituted or substituted cycloalkylalkyl, unsubstituted or substituted heterocyclic, unsubstituted or substituted fluoroalkyl, and unsubstituted or substituted heterocycloalkylalkyl (wherein "heterocyloalkyl" means heterocyclic); wherein there are 1 to 6 substituents on said substituted $R^{13}$ and $R^{14}$ groups and each substituent is independently selected from the group consisting of: alkyl, —$CF_3$, —OH, alkoxy, aryl, arylalkyl, fluoroalkyl, cycloalkyl, cycloalkylalkyl, heteroaryl, heteroarylalkyl, —$N(R^{40})_2$, —$C(O)OR^{15}$, —$C(O)NR^{15}R^{16}$, —$S(O)_t NR^{15}R^{16}$, —$C(O)R^{15}$, —$SO_2R^{15}$ provided that $R^{15}$ is not H, halogen, and —$NHC(O)NR^{15}R^{16}$; or $R^{13}$ and $R^{14}$ taken together with the nitrogen they are attached to in the groups —$C(O)NR^{13}R^{14}$ and —$SO_2NR^{13}R^{14}$ form an unsubstituted or substituted saturated heterocyclic ring, said ring optionally containing one additional heteroatom selected from the group consisting of: O, S and $NR^{18}$; wherein there are 1 to 3 substituents on the substituted cyclized $R^{13}$ and $R^{14}$ groups and each substituent is independently selected from the group consisting of: alkyl, aryl, hydroxy, hydroxyalkyl, alkoxy, alkoxyalkyl, arylalkyl, fluoroalkyl, cycloalkyl, cycloalkylalkyl, heteroaryl, heteroarylalkyl, amino, —$C(O)OR^{15}$, —$C(O)NR^{15}R^{16}$, —$SO_tNR^{15}R^{16}$, —$C(O)R^{15}$, —$SO_2R^{15}$ provided that $R^{15}$ is not H, —$NHC(O)NR^{15}R^{16}$, —$NHC(O)OR^{15}$, halogen, and a heterocycloalkenyl group;

each $R^{15}$ and $R^{16}$ is independently selected from the group consisting of: H, alkyl, aryl, arylalkyl, cycloalkyl and heteroaryl;

$R^{17}$ is selected from the group consisting of: —$SO_2$alkyl, —$SO_2$aryl, —$SO_2$cycloalkyl, and —$SO_2$heteroaryl;

$R^{18}$ is selected from the group consisting of: H, alkyl, aryl, heteroaryl, —$C(O)R^{19}$, —$SO_2R^{19}$ and —$C(O)NR^{19}R^{20}$;

each $R^{19}$ and $R^{20}$ is independently selected from the group consisting of: alkyl, aryl and heteroaryl;

$R^{30}$ is selected from the group consisting of: alkyl, cycloalkyl, —CN, —$NO_2$, or —$SO_2R^{15}$ provided that $R^{15}$ is not H;

each $R^{31}$ is independently selected from the group consisting of: unsubstituted or substituted alkyl, unsubstituted or substituted aryl, unsubstituted or substituted heteroaryl and unsubstituted or substituted cycloalkyl; wherein there are 1 to 6 substituents on said substituted $R^{31}$ groups and each substituent is independently selected from the group consisting of: alkyl, halogen and —$CF_3$;

each $R^{40}$ is independently selected from the group consisting of: H, alkyl and cycloalkyl;

g is 1 or 2; and t is 0, 1 or 2.

2. The compound of claim 1 wherein A is selected from the group consisting of:

(1) unsubstituted or substituted:

3. The compound of claim 1 wherein substituent A is:

wherein the furan ring is unsubstituted or substituted with 1 or 2 alkyl groups wherein each alkyl group is independently selected, $R^7$ is selected from the group consisting of: —$CF_3$, alkyl and cycloalkyl, and $R^8$ is H.

4. The compound of claim 1 wherein substituent A is:

wherein the furan ring is substituted with 1 or 2 alkyl groups independently selected from the group consisting of methyl, ethyl and isopropyl, $R^7$ is selected from the group consisting of: ethyl, isopropyl and t-butyl, and $R^8$ is H.

5. The compound of claim 1 wherein A is selected from the group consisting of:

-continued

-continued

6. The compound of claim 1 wherein A is selected from the group consisting of:

-continued

7. The compound of claim 1 wherein substituent A is selected from the group consisting of:

8. The compound of claim 1 wherein B is selected from the group consisting of:

9. The compound of claim 1 wherein B is selected from the group consisting of:

10. The compound of claim 1 wherein B is selected from the group consisting of:

11. The compound of claim 1 wherein B is selected from the group consisting of:

12. The compound of claim 1 wherein B is

13. The compound of claim 1 wherein B is:

wherein $R^2$ is —OH.

14. The compound of claim 1 wherein B is:

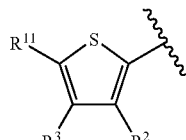

wherein $R^2$ is —OH, and $R^{13}$ and $R^{14}$ are independently selected from the group consisting of H and alkyl.

15. The compound of claim 1 wherein B is

[structure with $R^{11}$, S, $R^3$, $R^2$]

16. The compound of claim 15 wherein $R^{11}$ is H.
17. The compound of claim 16 wherein $R^2$ is —OH.
18. The compound of claim 17 wherein $R^3$ is —C(O)NR$^{13}$R$^{14}$.
19. The compound of claim 17 wherein $R^3$ is —S(O)$_t$NR$^{13}$R$^{14}$.
20. The compound of claim 1 wherein B is:

[structure with $R^{11}$, S, $R^3$, $R^2$]

wherein $R^2$ is —OH, $R^3$ is —C(O)NR$^{13}$R$^{14}$, $R^{11}$ is H or methyl, and $R^{13}$ and $R^{14}$ are independently selected from the group consisting of: H, alkyl, unsubstituted cycloalkyl, substituted cycloalkyl, unsubstituted heteroaryl and substituted heteroaryl.

21. The compound of claim 1 wherein B is:

[structure with $R^{11}$, S, $R^3$, $R^2$]

wherein $R^2$ is —OH, $R^3$ is —S(O)$_t$NR$^{13}$R$^{14}$, $R^{11}$ is H or methyl, and $R^{13}$ and $R^{14}$ are independently selected from the group consisting of H, alkyl, unsubstituted cycloalkyl and substituted cycloalkyl.

22. The compound of claim 1 wherein B is:

[structure with $R^{11}$, S, $R^3$, $R^2$]

23. The compound of claim 22 in $R^{11}$ is H.
24. The compound of claim 23 wherein $R^2$ is —OH.
25. The compound of claim 24 wherein $R^3$ is —C(O)NR$^{13}$R$^{14}$.
26. The compound of claim 24 wherein $R^3$ is —S(O)$_t$NR$^{13}$R$^{14}$.

27. The compound of claim 1 wherein B is:

[structure with $R^{11}$, S, $R^3$, $R^2$]

wherein $R^2$ is —OH, $R^3$ is —C(O)NR$^{13}$R$^{14}$, $R^{11}$ is H, and $R^{13}$ and $R^{14}$ are independently selected from the group consisting of: H, alkyl, unsubstituted heteroaryl and substituted heteroaryl.

28. The compound of claim 1 wherein B is:

[structure with $R^{11}$, S, $R^3$, $R^2$]

wherein $R^2$ is —OH, $R^3$ is —S(O)$_t$NR$^{13}$R$^{14}$, $R^{11}$ is H, and $R^{13}$ and $R^{14}$ are independently selected from the group consisting of H and alkyl.

29. The compound of claim 1 wherein:
(1) substituent A in formula IA is selected from the group consisting of:

[four structures with $R^7$, $R^8$, $R^9$]

and wherein the above rings are unsubstituted, or the above rings are substituted with 1 to 3 substituents independently selected from the group consisting of: F, Cl, Br, alkyl, cycloalkyl, and —CF$_3$; $R^7$ is selected from the group consisting of: H, —CF$_3$, —CF$_2$CH$_3$, methyl, ethyl, isopropyl, cyclopropyl and t-butyl; and $R^8$ is H; and (2) substituent B in formula IA is selected from the group consisting of:

[two structures]

and wherein:
$R^2$ is selected from the group consisting of: H, OH, —NHC(O)R$^{13}$ and —NHSO$_2$R$^{13}$;
$R^3$ is selected from the group consisting of: —C(O)NR$^{13}$R$^{14}$, —SO$_2$NR$^{13}$R$^{14}$, —NO$_2$, cyano, and —SO$_2$R$^{13}$;
$R^4$ is selected from the group consisting of: H, —NO$_2$, cyano, alkyl, halogen and —CF$_3$;

$R^5$ is selected from the group consisting of: H, —CF$_3$, —NO$_2$, halogen and cyano;

$R^6$ is selected from the group consisting of: H, alkyl and —CF$_3$;

$R^{11}$ is selected from the group consisting of: H, halogen and alkyl; and each $R^{13}$ and $R^{14}$ is independently selected from the group consisting of: H, unsubstituted alkyl.

30. The compound of claim 1 wherein:

(1) substituent A in formula IA is selected from the group consisting of:

[structures]

(2) substituent B in formula IA is selected from the group consisting of:

[structures]

wherein:

$R^2$ is —OH;

$R^3$ is selected from the group consisting of: —SO$_2$NR$^{13}$R$^{14}$ and —CONR$^{13}$R$^{14}$;

$R^4$ is selected form the group consisting of: H, Br, —CH$_3$, ethyl and —CF$_3$;

$R^5$ is selected from the group consisting of: H and cyano;

$R^6$ is selected from the group consisting of: H, —CH$_3$ and —CF$_3$;

$R^{11}$ is H; and $R^{13}$ and $R^{14}$ are independently selected from the group consisting of H and methyl.

31. The compound of claim 1 wherein substituent A is selected from the group consisting of:

[structures]

and substituent B is selected from the group consisting of:

[structure]

32. The compound of claim 1 wherein substituent A is selected from the group consisting of:

and substituent B is selected from the group consisting of:

33. The compound of claim 1 wherein g is 1.
34. The compound of claim 1 wherein g is 2.
35. The compound of claim 31 wherein g is 1.
36. The compound of claim 32 wherein g is 2.
37. A sodium, potassium, calcium, aluminum, gold, silver, N-methylglucamine, hydrochloric, sulfuric, phosphoric, acetic, citric, oxalic, malonic, salicylic, malic, fumaric, succinic, ascorbic, maleic, or methanesulfonic salt of a compound of claim 1.
38. A sodium salt of a compound of claim 1.
39. A calcium salt of a compound of claim 1.
40. A compound selected from the group consisting of:

647

648

-continued

-continued

-continued

-continued

-continued

-continued

-continued

[chemical structures]

pharmaceutically acceptable salts thereof, and pharmaceutically acceptable solvates thereof.

41. The compound of claim 40 selected from the group consisting of:

(a1)

(a2)

(a3)

(a4)

(a5)

-continued (a18), (a20), (a21), (a22), (a23), (a24), (a25), (a26), (a27), (a28)

-continued (a29), (a30), (a31), (a32), (a33), (a34), (a35), (a36), (a37)

-continued (a38)

(a39)

(a40)

(a41)

(a41a)

-continued (a42)

(a43)

(a44)

(a45)

-continued (a46), (a47), (a48), (a49), (a50), (a51), (a52), (a20)

pharmaceutically acceptable salts thereof, and pharmaceutically acceptable solvates thereof.

42. The compound of claim 41 selected from the group consisting of compounds of the formula:

(a21), (a22), (a23), (a24), (a25), (a26), (a27), (a28), (a29), (a30)

-continued (a31)
(a32)
(a33)
(a34)
(a35)

-continued (a36)
(a37)
(a38)
(a39)
(a40)

-continued

-continued (a49)

(a50)

(a51)

(a52)

the pharmaceutically acceptable salts thereof, and the pharmaceutically acceptable solvates thereof.

43. The compound of claim 41 having the formula:

or a pharmaceutically acceptable salt or solvate thereof.

44. The compound of claim 41 having the formula:

or a pharmaceutically acceptable salt or solvate thereof.

45. The compound of claim 41 having the formula:

or a pharmaceutically acceptable salt or solvate thereof.

46. The compound of claim 42 having the formula:

or a pharmaceutically acceptable salt or solvate thereof.

47. The compound of claim 41 having the formula:

or a pharmaceutically acceptable salt or solvate thereof.

48. The compound of claim 41 having the formula:

or a pharmaceutically acceptable salt or solvate thereof.

49. The compound of claim 41 having the formula:

or a pharmaceutically acceptable salt or solvate thereof.

50. The compound of claim 41 having the formula:

or a pharmaceutically acceptable salt or solvate thereof.

51. The compound of claim 41 having the formula:

or a pharmaceutically acceptable salt or solvate thereof.

52. The compound of claim 41 having the formula:

or a pharmaceutically acceptable salt or solvate thereof.

53. The compound of claim 41 having the formula:

or a pharmaceutically acceptable salt or solvate thereof.

54. The compound of claim 41 having the formula:

or a pharmaceutically acceptable salt or solvate thereof.

55. The compound of claim 41 having the formula:

or a pharmaceutically acceptable salt or solvate thereof.

56. The compound of claim 41 having the formula:

or a pharmaceutically acceptable salt or solvate thereof.

57. The compound of claim 41 having the formula:

or a pharmaceutically acceptable salt or solvate thereof.

58. The compound of claim 41 having the formula:

or a pharmaceutically acceptable salt or solvate thereof.

59. The compound of claim 41 having the formula:

or a pharmaceutically acceptable salt or solvate thereof.

60. The compound of claim 41 having the formula:

or a pharmaceutically acceptable salt or solvate thereof.

61. The compound of claim 40 having the formula:

or a pharmaceutically acceptable salt or solvate thereof.

62. The compound of claim 40 having the formula:

or a pharmaceutically acceptable salt or solvate thereof.

63. The compound of claim 40 having the formula:

or a pharmaceutically acceptable salt or solvate thereof.

64. The compound of claim 40 having the formula:

or a pharmaceutically acceptable salt or solvate thereof.

65. A pharmaceutical composition comprising at least one compound of claim 1, or a pharmaceutically acceptable salt or solvate thereof, in combination with a pharmaceutically acceptable carrier.

66. A pharmaceutical composition comprising at least one compound of claim 41, or a pharmaceutically acceptable salt or solvate thereof, in combination with a pharmaceutically acceptable carrier.

67. A compound selected from the group consisting of:

687 688

-continued

-continued

-continued

-continued 693 694

-continued 695                                    696

-continued                             -continued

697

-continued

698

-continued

-continued

-continued

703

-continued

704

-continued

-continued

707

708

-continued

709

-continued

710

-continued 711 712

-continued

-continued 717                                                             718

-continued                                                      -continued

719

-continued

720

-continued

-continued

723 -continued

724 -continued

-continued

727 -continued

728 -continued

729

-continued

730

-continued

731

-continued

732

-continued